US012702332B2

United States Patent
Rao

(10) Patent No.: US 12,702,332 B2
(45) Date of Patent: Aug. 11, 2026

(54) SYSTEMS, DEVICES, AND METHODS FOR ANALYTE MONITORING

(71) Applicant: ABBOTT DIABETES CARE INC., Alameda, CA (US)

(72) Inventor: Vivek S. Rao, Alameda, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 713 days.

(21) Appl. No.: 18/092,579

(22) Filed: Jan. 3, 2023

(65) Prior Publication Data

US 2023/0301561 A1 Sep. 28, 2023

Related U.S. Application Data

(60) Provisional application No. 63/296,262, filed on Jan. 4, 2022.

(51) Int. Cl.
*A61B 5/145* (2006.01)
*A61B 5/00* (2006.01)

(52) U.S. Cl.
CPC ...... *A61B 5/14546* (2013.01); *A61B 5/14503* (2013.01); *A61B 5/6848* (2013.01)

(58) Field of Classification Search
CPC ............ A61B 5/14546; A61B 5/14503; A61B 5/6848; A61B 5/14532
See application file for complete search history.

(56) References Cited

U.S. PATENT DOCUMENTS

| | | | |
|---|---|---|---|
| 2,402,306 | A | 6/1946 | Turkel |
| 2,752,918 | A | 7/1956 | Uytenbogaart |
| 3,123,790 | A | 3/1964 | Tyler |
| 3,132,123 | A | 5/1964 | Harris, Jr. et al. |
| 3,173,200 | A | 3/1965 | Dunmire et al. |
| 3,211,001 | A | 10/1965 | Petit |
| 3,260,656 | A | 7/1966 | Ross, Jr. |
| 3,517,670 | A | 6/1970 | Speelman |
| 3,522,807 | A | 8/1970 | Millenbach |
| 3,581,062 | A | 5/1971 | Aston |
| 3,653,841 | A | 4/1972 | Klein |
| 3,670,727 | A | 6/1972 | Reiterman |
| 3,719,564 | A | 3/1973 | Lilly, Jr. et al. |
| 3,776,832 | A | 12/1973 | Oswin et al. |
| 3,837,339 | A | 9/1974 | Aisenberg et al. |

(Continued)

FOREIGN PATENT DOCUMENTS

| | | |
|---|---|---|
| AU | 2003259741 | 2/2004 |
| CA | 2291105 | 12/1998 |

(Continued)

OTHER PUBLICATIONS

AU, 2007309066 Examiner's Report, Jul. 12, 2012

(Continued)

*Primary Examiner* — Christian Jang
(74) *Attorney, Agent, or Firm* — ONE LLP

(57) ABSTRACT

Systems, devices and methods are provided for inserting at least a portion of an in vivo analyte sensor for sensing an analyte level in a bodily fluid of a subject. In particular, disclosed herein are various embodiments of applicators, and components thereof, designed to reduce trauma to tissue of a sensor insertion site and to increase the likelihood of a successful sensor insertion.

18 Claims, 42 Drawing Sheets

(56) References Cited

U.S. PATENT DOCUMENTS 3,926,760 A 12/1975 Allen et al.
3,949,388 A 4/1976 Fuller
3,960,497 A 6/1976 Acord et al.
3,972,320 A 8/1976 Kalman
3,979,274 A 9/1976 Newman
4,008,717 A 2/1977 Kowarski
4,016,866 A 4/1977 Lawton
4,033,330 A 7/1977 Willis et al.
4,036,749 A 7/1977 Anderson
4,055,175 A 10/1977 Clemens et al.
4,059,406 A 11/1977 Fleet
4,076,596 A 2/1978 Connery et al.
4,098,574 A 7/1978 Dappen
4,100,048 A 7/1978 Pompei et al.
4,120,292 A 10/1978 LeBlanc, Jr. et al.
4,129,128 A 12/1978 McFarlane
4,151,845 A 5/1979 Clemens
4,168,205 A 9/1979 Danninger et al.
4,172,770 A 10/1979 Semersky et al.
4,178,916 A 12/1979 McNamara
4,203,446 A 5/1980 Hofert et al.
4,206,755 A 6/1980 Klein
4,224,125 A 9/1980 Nakamura et al.
4,240,438 A 12/1980 Updike et al.
4,240,889 A 12/1980 Yoda et al.
4,245,634 A 1/1981 Albisser et al.
4,247,297 A 1/1981 Berti et al.
4,294,258 A 10/1981 Bernard
4,305,401 A 12/1981 Reissmueller et al.
4,308,981 A 1/1982 Miura
4,327,725 A 5/1982 Cortese et al.
4,340,458 A 7/1982 Lerner et al.
4,344,438 A 8/1982 Schultz
4,349,728 A 9/1982 Phillips et al.
4,352,960 A 10/1982 Dormer et al.
4,353,888 A 10/1982 Sefton
4,356,074 A 10/1982 Johnson
4,365,637 A 12/1982 Johnson
4,366,033 A 12/1982 Richter et al.
4,373,527 A 2/1983 Fischell
4,375,399 A 3/1983 Havas et al.
4,384,586 A 5/1983 Christiansen
4,390,621 A 6/1983 Bauer
4,392,849 A 7/1983 Petre et al.
4,401,122 A 8/1983 Clark, Jr.
4,404,066 A 9/1983 Johnson
4,418,148 A 11/1983 Oberhardt
4,425,920 A 1/1984 Bourland et al.
4,427,004 A 1/1984 Miller et al.
4,427,770 A 1/1984 Chen et al.
4,431,004 A 2/1984 Bessman et al.
4,436,094 A 3/1984 Cerami
4,440,175 A 4/1984 Wilkins
4,441,968 A 4/1984 Emmer et al.
4,450,842 A 5/1984 Zick et al.
4,458,686 A 7/1984 Clark, Jr.
4,461,691 A 7/1984 Frank
4,464,170 A 8/1984 Clemens et al.
4,469,110 A 9/1984 Slama
4,477,314 A 10/1984 Richter et al.
4,478,976 A 10/1984 Goertz et al.
4,484,987 A 11/1984 Gough
4,494,950 A 1/1985 Fischell
4,509,531 A 4/1985 Ward
4,522,690 A 6/1985 Venkatasetty
4,524,114 A 6/1985 Samuels et al.
4,526,661 A 7/1985 Steckhan et al.
4,527,240 A 7/1985 Kvitash
4,534,356 A 8/1985 Papadakis
4,538,616 A 9/1985 Rogoff
4,543,955 A 10/1985 Schroeppel
4,545,382 A 10/1985 Higgins et al.
4,552,840 A 11/1985 Riffer
4,553,541 A 11/1985 Burns
4,560,534 A 12/1985 Kung et al.
4,571,292 A 2/1986 Liu et al.
4,573,994 A 3/1986 Fischell et al.
4,581,336 A 4/1986 Malloy et al.
4,592,745 A 6/1986 Rex et al.
4,595,011 A 6/1986 Phillips
4,619,754 A 10/1986 Niki et al.
4,619,793 A 10/1986 Lee
4,622,966 A 11/1986 Beard
4,627,445 A 12/1986 Garcia et al.
4,627,842 A 12/1986 Katz
4,627,908 A 12/1986 Miller
4,633,878 A 1/1987 Bombardieri
4,637,403 A 1/1987 Garcia et al.
4,639,062 A 1/1987 Taniguchi et al.
4,650,547 A 3/1987 Gough
4,654,197 A 3/1987 Lilja et al.
4,655,880 A 4/1987 Liu
4,655,885 A 4/1987 Hill et al.
4,663,824 A 5/1987 Kenmochi
4,665,906 A 5/1987 Jervis
4,671,288 A 6/1987 Gough
4,675,346 A 6/1987 Lin et al.
4,679,562 A 7/1987 Luksha
4,680,268 A 7/1987 Clark, Jr.
4,682,602 A 7/1987 Prohaska
4,684,245 A 8/1987 Goldring
4,684,537 A 8/1987 Graetzel et al.
4,685,463 A 8/1987 Williams
4,685,466 A 8/1987 Rau
4,690,675 A 9/1987 Katz
4,698,057 A 10/1987 Joishy
4,703,324 A 10/1987 White
4,703,756 A 11/1987 Gough et al.
4,711,245 A 12/1987 Higgins et al.
4,711,247 A 12/1987 Fishman
4,717,673 A 1/1988 Wrighton et al.
4,721,601 A 1/1988 Wrighton et al.
4,721,677 A 1/1988 Clark, Jr.
4,726,378 A 2/1988 Kaplan
4,726,716 A 2/1988 McGuire
4,729,672 A 3/1988 Takagi
4,731,726 A 3/1988 Allen, III
4,749,985 A 6/1988 Corsberg
4,755,173 A 7/1988 Konopka
4,757,022 A 7/1988 Shults et al.
4,758,323 A 7/1988 Davis et al.
4,759,371 A 7/1988 Franetzki
4,759,828 A 7/1988 Young et al.
4,764,416 A 8/1988 Ueyama et al.
4,776,944 A 10/1988 Janata et al.
4,777,953 A 10/1988 Ash et al.
4,779,618 A 10/1988 Mund et al.
4,781,683 A 11/1988 Wozniak et al.
4,781,798 A 11/1988 Gough
4,784,736 A 11/1988 Lonsdale et al.
4,785,868 A 11/1988 Koenig, Jr.
4,795,707 A 1/1989 Niiyama et al.
4,796,634 A 1/1989 Huntsman et al.
4,805,624 A 2/1989 Yao et al.
4,813,424 A 3/1989 Wilkins
4,815,469 A 3/1989 Cohen et al.
4,817,603 A 4/1989 Turner et al.
4,818,994 A 4/1989 Orth et al.
4,820,399 A 4/1989 Senda et al.
4,822,337 A 4/1989 Newhouse et al.
4,830,959 A 5/1989 McNeil et al.
4,832,797 A 5/1989 Vadgama et al.
RE32,947 E 6/1989 Dormer et al.
4,840,893 A 6/1989 Hill et al.
4,847,785 A 7/1989 Stephens
4,848,351 A 7/1989 Finch
4,852,025 A 7/1989 Herpichböhm
4,854,322 A 8/1989 Ash et al.
4,856,648 A 8/1989 Krueger
4,865,038 A 9/1989 Rich et al.
4,871,351 A 10/1989 Feingold
4,871,440 A 10/1989 Nagata et al.
4,874,500 A 10/1989 Madou et al.
4,890,620 A 1/1990 Gough

(56) References Cited

U.S. PATENT DOCUMENTS 4,894,137 A 1/1990 Takizawa et al.
4,895,147 A 1/1990 Bodicky et al.
4,897,162 A 1/1990 Lewandowski et al.
4,897,173 A 1/1990 Nankai et al.
4,909,908 A 3/1990 Ross et al.
4,911,794 A 3/1990 Parce et al.
4,917,800 A 4/1990 Lonsdale et al.
4,919,141 A 4/1990 Zier et al.
4,919,767 A 4/1990 Vadgama et al.
4,921,199 A 5/1990 Villaveces
4,923,586 A 5/1990 Katayama et al.
4,924,879 A 5/1990 O'Brien
4,925,268 A 5/1990 Iyer et al.
4,927,516 A 5/1990 Yamaguchi et al.
4,934,369 A 6/1990 Maxwell
4,935,105 A 6/1990 Churchouse
4,935,345 A 6/1990 Guibeau et al.
4,938,860 A 7/1990 Wogoman
4,944,299 A 7/1990 Silvian
4,950,378 A 8/1990 Nagara
4,953,552 A 9/1990 DeMarzo
4,954,129 A 9/1990 Giuliani et al.
4,969,468 A 11/1990 Byers et al.
4,970,145 A 11/1990 Bennetto et al.
4,974,929 A 12/1990 Curry
4,985,142 A 1/1991 Laycock et al.
4,986,271 A 1/1991 Wilkins
4,988,341 A 1/1991 Columbus et al.
4,994,167 A 2/1991 Shults et al.
4,995,402 A 2/1991 Smith et al.
5,000,180 A 3/1991 Kuypers et al.
5,001,054 A 3/1991 Wagner
5,002,054 A 3/1991 Ash et al.
5,006,110 A 4/1991 Garrison et al.
5,013,161 A 5/1991 Zaragoza et al.
5,019,974 A 5/1991 Beckers
5,035,860 A 7/1991 Kleingeld et al.
5,036,860 A 8/1991 Leigh et al.
5,047,044 A 9/1991 Smith et al.
5,050,612 A 9/1991 Matsumura
5,051,688 A 9/1991 Murase et al.
5,055,171 A 10/1991 Peck
5,058,592 A 10/1991 Whisler
5,067,957 A 11/1991 Jervis
5,068,536 A 11/1991 Rosenthal
5,070,535 A 12/1991 Hochmair et al.
5,082,550 A 1/1992 Rishpon et al.
5,082,786 A 1/1992 Nakamoto
5,086,246 A 2/1992 Dymond et al.
5,089,112 A 2/1992 Skotheim et al.
5,095,904 A 3/1992 Seligman et al.
5,101,814 A 4/1992 Palti
5,106,365 A 4/1992 Hernandez
5,108,564 A 4/1992 Szuminsky et al.
5,108,889 A 4/1992 Smith et al.
5,109,850 A 5/1992 Blanco et al.
5,120,420 A 6/1992 Nankai et al.
5,122,925 A 6/1992 Inpyn
5,124,661 A 6/1992 Zelin et al.
5,126,034 A 6/1992 Carter et al.
5,133,856 A 7/1992 Yamaguchi et al.
5,135,003 A 8/1992 Souma
5,135,004 A 8/1992 Adams et al.
5,140,985 A 8/1992 Schroeder et al.
5,141,868 A 8/1992 Shanks et al.
5,161,532 A 11/1992 Joseph
5,162,407 A 11/1992 Turner
5,165,407 A 11/1992 Wilson et al.
5,173,165 A 12/1992 Schmid et al.
5,174,291 A 12/1992 Schoonen et al.
5,190,041 A 3/1993 Palti
5,190,546 A 3/1993 Jervis
5,192,416 A 3/1993 Wang et al.
5,193,545 A 3/1993 Marsoner et al.
5,198,367 A 3/1993 Aizawa et al.
5,202,261 A 4/1993 Musho et al.
5,204,264 A 4/1993 Kaminer et al.
5,205,297 A 4/1993 Montecalvo et al.
5,205,920 A 4/1993 Oyama et al.
5,208,154 A 5/1993 Weaver et al.
5,209,229 A 5/1993 Gilli
5,217,595 A 6/1993 Smith et al.
5,228,449 A 7/1993 Christ et al.
5,229,282 A 7/1993 Yoshioka et al.
5,231,988 A 8/1993 Wernicke et al.
5,234,835 A 8/1993 Nestor et al.
5,238,729 A 8/1993 Debe
5,243,696 A 9/1993 Carr et al.
5,245,314 A 9/1993 Kah et al.
5,246,867 A 9/1993 Lakowicz et al.
5,250,439 A 10/1993 Musho et al.
5,251,126 A 10/1993 Kahn et al.
5,262,035 A 11/1993 Gregg et al.
5,262,305 A 11/1993 Heller et al.
5,264,103 A 11/1993 Yoshioka et al.
5,264,104 A 11/1993 Gregg et al.
5,264,105 A 11/1993 Gregg et al.
5,264,106 A 11/1993 McAleer et al.
5,267,963 A 12/1993 Bachynsky
5,271,815 A 12/1993 Wong
5,279,294 A 1/1994 Anderson
5,284,156 A 2/1994 Schramm et al.
5,285,792 A 2/1994 Sjoquist et al.
5,286,362 A 2/1994 Hoenes et al.
5,286,364 A 2/1994 Yacynych et al.
5,288,636 A 2/1994 Pollmann et al.
5,289,497 A 2/1994 Jackobson et al.
5,293,546 A 3/1994 Tadros et al.
5,293,877 A 3/1994 O'Hara et al.
5,299,571 A 4/1994 Mastrototaro
5,305,008 A 4/1994 Turner et al.
5,318,583 A 6/1994 Rabenau et al.
5,320,098 A 6/1994 Davidson
5,320,715 A 6/1994 Berg
5,320,725 A 6/1994 Gregg et al.
5,322,063 A 6/1994 Allen et al.
5,333,615 A 8/1994 Craelius et al.
5,337,747 A 8/1994 Neftel
5,340,722 A 8/1994 Wolfbeis et al.
5,342,789 A 8/1994 Chick et al.
5,352,348 A 10/1994 Young et al.
5,356,420 A 10/1994 Czernecki et al.
5,356,786 A 10/1994 Heller et al.
5,360,404 A 11/1994 Novacek et al.
5,368,028 A 11/1994 Palti
5,372,133 A 12/1994 Hogen Esch
5,372,427 A 12/1994 Padovani et al.
5,376,251 A 12/1994 Kaneko et al.
5,378,628 A 1/1995 Gratzel et al.
5,379,238 A 1/1995 Stark
5,384,547 A 1/1995 Lynk et al.
5,387,327 A 2/1995 Khan
5,390,670 A 2/1995 Centa et al.
5,390,671 A 2/1995 Lord et al.
5,391,250 A 2/1995 Cheney, II et al.
5,394,877 A 3/1995 Orr et al.
5,395,504 A 3/1995 Saurer et al.
5,400,782 A 3/1995 Beaubiah
5,400,794 A 3/1995 Gorman
5,402,780 A 4/1995 Faasse, Jr.
5,407,431 A 4/1995 Botich et al.
5,408,999 A 4/1995 Singh et al.
5,410,326 A 4/1995 Goldstein
5,411,647 A 5/1995 Johnson et al.
5,425,361 A 6/1995 Fenzlein et al.
5,425,868 A 6/1995 Pedersen
5,431,160 A 7/1995 Wilkins
5,431,921 A 7/1995 Thombre
5,437,999 A 8/1995 Diebold et al.
5,438,983 A 8/1995 Falcone
5,462,051 A 10/1995 Oka et al.
5,462,645 A 10/1995 Albery et al.
5,469,846 A 11/1995 Khan
5,472,317 A 12/1995 Field et al.

(56) References Cited

U.S. PATENT DOCUMENTS 5,482,473 A 1/1996 Lord et al.
5,484,403 A 1/1996 Yoakum et al.
5,489,414 A 2/1996 Schreiber et al.
5,491,474 A 2/1996 Suni et al.
5,494,562 A 2/1996 Maley et al.
5,496,453 A 3/1996 Uenoyama et al.
5,497,772 A 3/1996 Schulman et al.
5,499,243 A 3/1996 Hall
5,507,288 A 4/1996 Bocker et al.
5,509,410 A 4/1996 Hill et al.
5,514,718 A 5/1996 Lewis et al.
5,516,832 A 5/1996 Kennan et al.
5,527,288 A 6/1996 Gross et al.
5,531,878 A 7/1996 Vadgama et al.
5,532,686 A 7/1996 Urbas et al.
5,533,977 A 7/1996 Metcalf et al.
5,536,259 A 7/1996 Utterberg
5,543,326 A 8/1996 Heller et al.
5,544,196 A 8/1996 Tiedmann, Jr. et al.
5,545,191 A 8/1996 Mann et al.
5,549,568 A 8/1996 Sheilds
5,551,427 A 9/1996 Altman
5,555,190 A 9/1996 Derby et al.
5,558,638 A 9/1996 Evers et al.
5,560,357 A 10/1996 Faupei et al.
5,562,713 A 10/1996 Silvian
5,564,434 A 10/1996 Halperin et al.
5,565,085 A 10/1996 Ikeda et al.
5,567,302 A 10/1996 Song et al.
5,568,806 A 10/1996 Cheney, II et al.
5,569,186 A 10/1996 Lord et al.
5,571,022 A 11/1996 Schaarschmidt
5,575,563 A 11/1996 Chiu et al.
5,581,206 A 12/1996 Chevallier et al.
5,582,184 A 12/1996 Erickson et al.
5,582,697 A 12/1996 Ikeda et al.
5,582,698 A 12/1996 Flaherty et al.
5,584,813 A 12/1996 Livingston et al.
5,586,553 A 12/1996 Halili et al.
5,589,326 A 12/1996 Deng et al.
5,593,852 A 1/1997 Heller et al.
5,596,150 A 1/1997 Arndt et al.
5,597,378 A 1/1997 Jervis
5,600,301 A 2/1997 Robinson, III
5,601,435 A 2/1997 Quy
5,609,575 A 3/1997 Larson et al.
5,613,978 A 3/1997 Harding
5,617,851 A 4/1997 Lipkovker
5,623,933 A 4/1997 Amano et al.
5,626,566 A 5/1997 Petersen et al.
5,628,310 A 5/1997 Rao et al.
5,628,324 A 5/1997 Sarbach
5,628,890 A 5/1997 Carter et al.
5,632,557 A 5/1997 Simons
5,634,468 A 6/1997 Platt et al.
5,636,640 A 6/1997 Staehlin
5,638,832 A 6/1997 Singer et al.
5,640,954 A 6/1997 Pfeiffer et al.
5,651,869 A 7/1997 Yoshioka et al.
5,653,239 A 8/1997 Pompei et al.
5,659,454 A 8/1997 Vermesse
5,660,163 A 8/1997 Schulman et al.
5,665,071 A 9/1997 Wyrick
5,665,222 A 9/1997 Heller et al.
5,669,543 A 9/1997 Ueno
5,669,890 A 9/1997 Grimm
5,670,031 A 9/1997 Hintsche et al.
5,673,322 A 9/1997 Pepe et al.
5,680,858 A 10/1997 Hansen et al.
5,682,233 A 10/1997 Brinda
5,695,623 A 12/1997 Michel et al.
5,707,502 A 1/1998 McCaffrey et al.
5,708,247 A 1/1998 McAleer et al.
5,711,001 A 1/1998 Bussan et al.
5,711,297 A 1/1998 Iliff et al.
5,711,861 A 1/1998 Ward et al.
5,711,862 A 1/1998 Sakoda et al.
5,724,030 A 3/1998 Urbas et al.
5,726,646 A 3/1998 Bane et al.
5,733,044 A 3/1998 Rose et al.
5,733,259 A 3/1998 Valcke et al.
5,733,262 A 3/1998 Paul
5,733,313 A 3/1998 Barreras, Sr. et al.
5,735,285 A 4/1998 Albert et al.
5,738,220 A 4/1998 Geszler
5,741,211 A 4/1998 Renirie et al.
5,743,262 A 4/1998 Lepper, Jr. et al.
5,746,217 A 5/1998 Erickson et al.
5,746,697 A 5/1998 Swedlow et al.
5,748,103 A 5/1998 Flach et al.
5,749,656 A 5/1998 Boehm et al.
5,749,907 A 5/1998 Mann
5,758,290 A 5/1998 Nealon et al.
5,766,131 A 6/1998 Kondo et al.
5,770,028 A 6/1998 Maley et al.
5,771,001 A 6/1998 Cobb
5,771,891 A 6/1998 Gozani
5,772,586 A 6/1998 Heinonen et al.
5,778,879 A 7/1998 Ota et al.
5,779,665 A 7/1998 Mastrototaro et al.
5,786,439 A 7/1998 Van Antwerp et al.
5,791,344 A 8/1998 Schulman et al.
5,798,961 A 8/1998 Heyden et al.
5,800,420 A 9/1998 Gross et al.
5,804,047 A 9/1998 Karube et al.
5,807,375 A 9/1998 Gross et al.
5,814,020 A 9/1998 Gross
5,820,551 A 10/1998 Hill et al.
5,820,570 A 10/1998 Erickson et al.
5,820,622 A 10/1998 Gross et al.
5,822,715 A 10/1998 Worthington et al.
5,823,802 A 10/1998 Bartley
5,827,184 A 10/1998 Netherly et al.
5,830,064 A 11/1998 Bradish et al.
5,833,603 A 11/1998 Kovacs et al.
5,840,020 A 11/1998 Heinonen et al.
5,842,983 A 12/1998 Abel et al.
5,851,197 A 12/1998 Marano et al.
5,856,758 A 1/1999 Joffe et al.
5,858,001 A 1/1999 Tsals et al.
5,865,804 A 2/1999 Bachynsky
5,871,494 A 2/1999 Simons et al.
5,875,186 A 2/1999 Belanger et al.
5,879,311 A 3/1999 Duchon et al.
5,885,211 A 3/1999 Eppstein et al.
5,891,049 A 4/1999 Cyrus et al.
5,899,855 A 5/1999 Brown
5,899,856 A 5/1999 Schoendorfer et al.
5,914,026 A 6/1999 Blubaugh, Jr. et al.
5,918,603 A 7/1999 Brown
5,919,141 A 7/1999 Money et al.
5,921,963 A 7/1999 Erez et al.
5,924,979 A 7/1999 Swedlow et al.
5,925,021 A 7/1999 Castellano et al.
5,931,814 A 8/1999 Alex et al.
5,931,868 A 8/1999 Gross
5,935,224 A 8/1999 Svancarek et al.
5,938,679 A 8/1999 Freeman et al.
5,942,979 A 8/1999 Luppino
5,948,006 A 9/1999 Mann
5,951,485 A 9/1999 Cyrus et al.
5,951,492 A 9/1999 Douglas et al.
5,951,521 A 9/1999 Mastrototaro et al.
5,951,582 A 9/1999 Thorne et al.
5,954,643 A 9/1999 Van Antwerp
5,954,685 A 9/1999 Tierny
5,957,854 A 9/1999 Besson et al.
5,961,451 A 10/1999 Reber et al.
5,964,718 A 10/1999 Duchon et al.
5,964,993 A 10/1999 Blubaugh, Jr. et al.
5,965,380 A 10/1999 Heller et al.
5,971,922 A 10/1999 Arita et al.
5,971,941 A 10/1999 Simons et al.
5,972,199 A 10/1999 Heller et al.

(56) References Cited

U.S. PATENT DOCUMENTS 5,987,353 A 11/1999 Khatchatrian et al.
5,993,411 A 11/1999 Choi
5,995,860 A 11/1999 Sun et al.
5,997,501 A 12/1999 Gross et al.
6,001,067 A 12/1999 Shults et al.
6,004,278 A 12/1999 Botich et al.
6,017,335 A 1/2000 Burnham
6,022,315 A 2/2000 Iliff
6,022,368 A 2/2000 Gavronsky et al.
6,024,699 A 2/2000 Surwit et al.
6,026,321 A 2/2000 Miyata et al.
6,027,459 A 2/2000 Shain et al.
6,028,413 A 2/2000 Brockmann
6,032,064 A 2/2000 Devlin et al.
6,036,924 A 3/2000 Simons et al.
6,048,352 A 4/2000 Douglas et al.
6,049,727 A 4/2000 Crothall
6,052,565 A 4/2000 Ishikura et al.
6,054,194 A 4/2000 Kane
6,056,718 A 5/2000 Funderburk et al.
6,059,946 A 5/2000 Yukawa et al.
6,066,243 A 5/2000 Anderson et al.
6,068,399 A 5/2000 Tseng
6,071,294 A 6/2000 Simons et al.
6,071,391 A 6/2000 Gotoh et al.
6,083,710 A 7/2000 Heller et al.
6,085,342 A 7/2000 Marholev et al.
6,088,605 A 7/2000 Griffith et al.
6,088,608 A 7/2000 Schulman et al.
6,091,975 A 7/2000 Daddona et al.
6,091,976 A 7/2000 Pfeiffer et al.
6,091,987 A 7/2000 Thompson
6,093,172 A 7/2000 Funderburk et al.
6,096,364 A 8/2000 Bok et al.
6,097,480 A 8/2000 Kaplan
6,099,484 A 8/2000 Douglas et al.
6,102,896 A 8/2000 Roser
6,103,033 A 8/2000 Say et al.
6,106,484 A 8/2000 Terwilliger
6,117,290 A 9/2000 Say et al.
6,119,028 A 9/2000 Schulman et al.
6,120,676 A 9/2000 Heller et al.
6,121,009 A 9/2000 Heller et al.
6,121,611 A 9/2000 Lindsay et al.
6,122,351 A 9/2000 Schlueter, Jr. et al.
6,129,666 A 10/2000 DeLuca et al.
6,130,623 A 10/2000 MacLellan et al.
6,132,449 A 10/2000 Lum et al.
6,134,461 A 10/2000 Say et al.
6,141,573 A 10/2000 Kurnik et al.
6,143,164 A 11/2000 Heller et al.
6,144,837 A 11/2000 Quy
6,144,871 A 11/2000 Saito et al.
6,144,922 A 11/2000 Douglas et al.
6,149,626 A 11/2000 Bachynsky et al.
6,157,850 A 12/2000 Diab et al.
6,159,147 A 12/2000 Lichter et al.
6,159,181 A 12/2000 Crossman et al.
6,161,095 A 12/2000 Brown
6,162,611 A 12/2000 Heller et al.
6,168,606 B1 1/2001 Levin et al.
6,175,752 B1 1/2001 Say et al.
6,186,982 B1 2/2001 Gross et al.
6,192,891 B1 2/2001 Gravel et al.
6,197,040 B1 3/2001 LeVaughn et al.
6,198,946 B1 3/2001 Shin et al.
6,200,265 B1 3/2001 Walsh et al.
6,203,495 B1 3/2001 Bardy et al.
6,212,416 B1 4/2001 Ward et al.
6,213,972 B1 4/2001 Butterfield et al.
6,219,574 B1 4/2001 Cormier et al.
6,223,283 B1 4/2001 Chaiken et al.
6,231,531 B1 5/2001 Lum et al.
6,233,471 B1 5/2001 Berner et al.
6,237,394 B1 5/2001 Harris et al.
6,248,067 B1 6/2001 Causey, III et al.
6,254,536 B1 7/2001 DeVito
6,254,586 B1 7/2001 Mann et al.
6,264,810 B1 7/2001 Stol et al.
6,270,455 B1 8/2001 Brown
6,275,717 B1 8/2001 Gross et al.
6,283,761 B1 9/2001 Joao
6,283,982 B1 9/2001 Levaughn et al.
6,284,478 B1 9/2001 Heller et al.
6,291,200 B1 9/2001 LeJeune et al.
6,293,925 B1 9/2001 Safabash et al.
6,294,997 B1 9/2001 Paratore et al.
6,295,506 B1 9/2001 Heinonen et al.
6,298,255 B1 10/2001 Cordero et al.
6,299,347 B1 10/2001 Pompei
6,299,757 B1 10/2001 Feldman et al.
6,302,866 B1 10/2001 Marggi
6,304,766 B1 10/2001 Colvin, Jr.
6,306,104 B1 10/2001 Cunningham et al.
6,306,141 B1 10/2001 Jervis
6,309,884 B1 10/2001 Cooper et al.
6,314,317 B1 11/2001 Willis
6,329,161 B1 12/2001 Heller et al.
6,331,244 B1 12/2001 Lewis et al.
6,336,269 B1 1/2002 Eldridge et al.
6,338,790 B1 1/2002 Feldman et al.
6,341,232 B1 1/2002 Conn et al.
6,348,640 B1 2/2002 Navot et al.
6,359,270 B1 3/2002 Bridson
6,359,444 B1 3/2002 Grimes
6,360,888 B1 3/2002 McIvor et al.
6,364,890 B1 4/2002 Lum et al.
6,366,794 B1 4/2002 Moussy et al.
6,368,141 B1 4/2002 Van Antwerp et al.
6,368,274 B1 4/2002 Van Antwerp et al.
6,368,339 B1 4/2002 Amplatz
6,377,828 B1 4/2002 Chaiken et al.
6,377,829 B1 4/2002 Al-Ali
6,377,894 B1 4/2002 Deweese et al.
6,379,301 B1 4/2002 Worthington et al.
6,387,048 B1 5/2002 Schulman et al.
6,400,974 B1 6/2002 Lesho
6,405,066 B1 6/2002 Essenpreis et al.
6,409,740 B1 6/2002 Kuhr et al.
6,413,393 B1 7/2002 Van Antwerp et al.
6,416,471 B1 7/2002 Kumar et al.
6,418,332 B1 7/2002 Mastrototaro et al.
6,418,346 B1 7/2002 Nelson et al.
6,424,847 B1 7/2002 Mastrototaro et al.
6,427,088 B1 7/2002 Bowman, IV et al.
6,433,743 B1 8/2002 Massy et al.
6,435,017 B1 8/2002 Nowicki, Jr. et al.
6,437,679 B1 8/2002 Roques
6,438,414 B1 8/2002 Conn et al.
6,440,068 B1 8/2002 Brown et al.
6,442,413 B1 8/2002 Silver
6,445,374 B2 9/2002 Albert et al.
6,451,025 B1 9/2002 Jervis
6,458,109 B1 10/2002 Henley et al.
6,461,496 B1 10/2002 Feldman et al.
6,471,689 B1 10/2002 Joseph et al.
6,472,220 B1 10/2002 Simons et al.
6,478,736 B1 11/2002 Mault
6,482,176 B1 11/2002 Wich
6,484,045 B1 11/2002 Holker et al.
6,484,046 B1 11/2002 Say et al.
6,493,069 B1 12/2002 Nagashimada et al.
6,494,830 B1 12/2002 Wessel
6,496,729 B2 12/2002 Thompson
6,497,655 B1 12/2002 Linberg et al.
6,503,381 B1 1/2003 Gotoh et al.
6,510,344 B1 1/2003 Halpern
6,514,460 B1 2/2003 Fendrock
6,514,689 B2 2/2003 Han et al.
6,514,718 B2 2/2003 Heller et al.
6,520,326 B2 2/2003 McIvor et al.
6,522,927 B1 2/2003 Bishay et al.
6,533,805 B1 3/2003 Jervis
6,537,242 B1 3/2003 Palmer

(56) References Cited

U.S. PATENT DOCUMENTS

| | | | |
|---|---|---|---|
| 6,540,891 | B1 | 4/2003 | Stewart et al. |
| 6,544,212 | B2 | 4/2003 | Galley et al. |
| 6,546,268 | B1 | 4/2003 | Ishikawa et al. |
| 6,549,796 | B2 | 4/2003 | Sohrab |
| 6,551,494 | B1 | 4/2003 | Heller et al. |
| 6,551,496 | B1 | 4/2003 | Moles et al. |
| 6,554,795 | B2 | 4/2003 | Bagaoisan et al. |
| 6,554,798 | B1 | 4/2003 | Mann et al. |
| 6,558,320 | B1 | 5/2003 | Causey, III et al. |
| 6,558,321 | B1 | 5/2003 | Burd et al. |
| 6,558,351 | B1 | 5/2003 | Steil et al. |
| 6,560,471 | B1 | 5/2003 | Heller et al. |
| 6,561,975 | B1 | 5/2003 | Pool et al. |
| 6,561,978 | B1 | 5/2003 | Conn et al. |
| 6,562,001 | B2 | 5/2003 | Lebel et al. |
| 6,564,105 | B2 | 5/2003 | Starkweather et al. |
| 6,565,509 | B1 | 5/2003 | Say et al. |
| 6,571,128 | B2 | 5/2003 | Lebel et al. |
| 6,572,542 | B1 | 6/2003 | Houben et al. |
| 6,572,566 | B2 | 6/2003 | Effenhauser |
| 6,574,490 | B2 | 6/2003 | Abbink et al. |
| 6,574,510 | B2 | 6/2003 | Von Arx et al. |
| 6,575,895 | B1 | 6/2003 | Blair |
| 6,576,101 | B1 | 6/2003 | Heller et al. |
| 6,577,899 | B2 | 6/2003 | Lebel et al. |
| 6,579,231 | B1 | 6/2003 | Phipps |
| 6,579,690 | B1 | 6/2003 | Bonnecaze et al. |
| 6,584,335 | B1 | 6/2003 | Haar et al. |
| 6,585,644 | B2 | 7/2003 | Lebel et al. |
| 6,589,229 | B1 | 7/2003 | Connelly et al. |
| 6,591,125 | B1 | 7/2003 | Buse et al. |
| 6,592,745 | B1 | 7/2003 | Feldman et al. |
| 6,595,919 | B2 | 7/2003 | Berner et al. |
| 6,600,997 | B2 | 7/2003 | Deweese et al. |
| 6,602,268 | B2 | 8/2003 | Kuhr et al. |
| 6,603,995 | B1 | 8/2003 | Carter |
| 6,604,050 | B2 | 8/2003 | Trippel et al. |
| 6,605,200 | B1 | 8/2003 | Mao et al. |
| 6,605,201 | B1 | 8/2003 | Mao et al. |
| 6,607,509 | B2 | 8/2003 | Bobroff et al. |
| 6,607,543 | B2 | 8/2003 | Purcell et al. |
| 6,608,562 | B1 | 8/2003 | Kimura et al. |
| 6,610,012 | B2 | 8/2003 | Mault |
| 6,611,206 | B2 | 8/2003 | Eshelman et al. |
| 6,613,015 | B2 | 9/2003 | Sandstrom et al. |
| 6,616,819 | B1 | 9/2003 | Liamos et al. |
| 6,618,934 | B1 | 9/2003 | Feldman et al. |
| 6,627,154 | B1 | 9/2003 | Goodman et al. |
| 6,631,281 | B1 | 10/2003 | Kastle |
| 6,633,772 | B2 | 10/2003 | Ford et al. |
| 6,635,014 | B2 | 10/2003 | Starkweather et al. |
| 6,635,167 | B1 | 10/2003 | Batman et al. |
| 6,637,611 | B2 | 10/2003 | Luch |
| 6,641,533 | B2 | 11/2003 | Causey, III et al. |
| 6,645,359 | B1 | 11/2003 | Bhullar et al. |
| 6,648,821 | B2 | 11/2003 | Lebel et al. |
| 6,650,471 | B2 | 11/2003 | Doi |
| 6,654,625 | B1 | 11/2003 | Say et al. |
| 6,656,114 | B1 | 12/2003 | Poulson et al. |
| 6,658,396 | B1 | 12/2003 | Tang et al. |
| 6,659,948 | B2 | 12/2003 | Lebel et al. |
| 6,662,439 | B1 | 12/2003 | Bhullar |
| 6,666,849 | B1 | 12/2003 | Marshall et al. |
| 6,668,196 | B1 | 12/2003 | Villegas et al. |
| 6,671,534 | B2 | 12/2003 | Putz |
| 6,675,030 | B2 | 1/2004 | Ciurczak et al. |
| 6,676,290 | B1 | 1/2004 | Lu |
| 6,676,816 | B2 | 1/2004 | Mao et al. |
| 6,682,546 | B2 | 1/2004 | Amplatz |
| 6,687,546 | B2 | 2/2004 | Lebel et al. |
| 6,689,056 | B1 | 2/2004 | Kilcoyne et al. |
| 6,694,191 | B2 | 2/2004 | Starkweather et al. |
| 6,695,860 | B1 | 2/2004 | Ward et al. |
| 6,698,269 | B2 | 3/2004 | Baber et al. |
| 6,699,188 | B2 | 3/2004 | Wessel |
| 6,702,857 | B2 | 3/2004 | Brauker et al. |
| 6,706,159 | B2 | 3/2004 | Moerman et al. |
| 6,721,582 | B2 | 4/2004 | Trepagnier et al. |
| 6,730,025 | B1 | 5/2004 | Platt |
| 6,730,072 | B2 | 5/2004 | Shawgo et al. |
| 6,730,200 | B1 | 5/2004 | Stewart et al. |
| 6,731,976 | B2 | 5/2004 | Penn et al. |
| 6,733,446 | B2 | 5/2004 | Lebel et al. |
| 6,735,183 | B2 | 5/2004 | O'Toole et al. |
| 6,735,479 | B2 | 5/2004 | Fabian et al. |
| 6,736,957 | B1 | 5/2004 | Forrow et al. |
| 6,740,075 | B2 | 5/2004 | Lebel et al. |
| 6,741,877 | B1 | 5/2004 | Shults et al. |
| 6,743,635 | B2 | 6/2004 | Neel et al. |
| 6,746,582 | B2 | 6/2004 | Heller et al. |
| 6,748,445 | B1 | 6/2004 | Darcey et al. |
| 6,749,740 | B2 | 6/2004 | Liamos et al. |
| 6,758,810 | B2 | 7/2004 | Lebel et al. |
| 6,758,835 | B2 | 7/2004 | Close et al. |
| 6,764,581 | B1 | 7/2004 | Forrow et al. |
| 6,767,440 | B1 | 7/2004 | Bhullar et al. |
| 6,770,030 | B1 | 8/2004 | Schaupp et al. |
| 6,773,671 | B1 | 8/2004 | Lewis et al. |
| 6,781,522 | B2 | 8/2004 | Sleva et al. |
| 6,790,178 | B1 | 9/2004 | Mault et al. |
| 6,804,558 | B2 | 10/2004 | Haller et al. |
| 6,804,561 | B2 | 10/2004 | Stover |
| 6,809,653 | B1 | 10/2004 | Mann et al. |
| 6,810,290 | B2 | 10/2004 | Lebel et al. |
| 6,811,533 | B2 | 11/2004 | Lebel et al. |
| 6,811,534 | B2 | 11/2004 | Bowman, IV et al. |
| 6,813,519 | B2 | 11/2004 | Lebel et al. |
| 6,814,844 | B2 | 11/2004 | Bhullar et al. |
| 6,830,551 | B1 | 12/2004 | Uchigaki et al. |
| 6,837,858 | B2 | 1/2005 | Cunningham et al. |
| 6,837,885 | B2 | 1/2005 | Koblish et al. |
| 6,837,988 | B2 | 1/2005 | Leong et al. |
| 6,849,052 | B2 | 2/2005 | Uchigaki et al. |
| 6,850,790 | B2 | 2/2005 | Berner et al. |
| 6,850,859 | B1 | 2/2005 | Schuh |
| 6,854,882 | B2 | 2/2005 | Chen |
| 6,862,465 | B2 | 3/2005 | Shults et al. |
| 6,873,268 | B2 | 3/2005 | Lebel et al. |
| 6,878,112 | B2 | 4/2005 | Linberg et al. |
| 6,881,551 | B2 | 4/2005 | Heller et al. |
| 6,892,085 | B2 | 5/2005 | McIvor et al. |
| 6,893,545 | B2 | 5/2005 | Gotoh et al. |
| 6,895,263 | B2 | 5/2005 | Shin et al. |
| 6,895,265 | B2 | 5/2005 | Silver |
| 6,923,763 | B1 | 8/2005 | Kovatchev et al. |
| 6,923,764 | B2 | 8/2005 | Aceti et al. |
| 6,925,393 | B1 | 8/2005 | Kalatz et al. |
| 6,931,327 | B2 | 8/2005 | Goode, Jr. et al. |
| 6,932,892 | B2 | 8/2005 | Chen |
| 6,932,894 | B2 | 8/2005 | Mao et al. |
| 6,936,006 | B2 | 8/2005 | Sabra |
| 6,937,222 | B2 | 8/2005 | Numao |
| 6,940,403 | B2 | 9/2005 | Kail, IV |
| 6,941,163 | B2 | 9/2005 | Ford et al. |
| 6,942,518 | B2 | 9/2005 | Liamos et al. |
| 6,950,708 | B2 | 9/2005 | Bowman IV et al. |
| 6,954,662 | B2 | 10/2005 | Freger et al. |
| 6,958,705 | B2 | 10/2005 | Lebel et al. |
| 6,959,211 | B2 | 10/2005 | Rule et al. |
| 6,960,192 | B1 | 11/2005 | Flaherty et al. |
| 6,968,294 | B2 | 11/2005 | Gutta et al. |
| 6,971,274 | B2 | 12/2005 | Olin |
| 6,971,999 | B2 | 12/2005 | Py et al. |
| 6,973,706 | B2 | 12/2005 | Say et al. |
| 6,974,437 | B2 | 12/2005 | Lebel et al. |
| 6,975,893 | B2 | 12/2005 | Say et al. |
| 6,983,867 | B1 | 1/2006 | Fugere |
| 6,990,366 | B2 | 1/2006 | Say et al. |
| 6,997,907 | B2 | 2/2006 | Safabash et al. |
| 6,998,247 | B2 | 2/2006 | Monfre et al. |
| 6,999,854 | B2 | 2/2006 | Roth |
| 7,003,336 | B2 | 2/2006 | Holker et al. |
| 7,003,340 | B2 | 2/2006 | Say et al. |
| 7,003,341 | B2 | 2/2006 | Say et al. |

(56) References Cited

U.S. PATENT DOCUMENTS 7,005,857 B2 2/2006 Stiene et al.
7,009,511 B2 3/2006 Mazar et al.
7,010,356 B2 3/2006 Jog et al.
7,015,817 B2 3/2006 Copley et al.
7,016,713 B2 3/2006 Gardner et al.
7,020,508 B2 3/2006 Stivoric et al.
7,022,072 B2 4/2006 Fox et al.
7,022,219 B2 4/2006 Mansouri et al.
7,024,236 B2 4/2006 Ford et al.
7,024,245 B2 4/2006 Lebel et al.
7,025,743 B2 4/2006 Mann et al.
7,025,774 B2 4/2006 Freeman et al.
7,027,848 B2 4/2006 Robinson et al.
7,027,859 B1 4/2006 McNichols et al.
7,027,931 B1 4/2006 Jones et al.
7,029,444 B2 4/2006 Shin et al.
7,041,057 B1 5/2006 Faupel et al.
7,041,068 B2 5/2006 Freeman et al.
7,041,468 B2 5/2006 Drucker et al.
7,043,305 B2 5/2006 Kenknight et al.
7,046,153 B2 5/2006 Oja et al.
7,052,483 B2 5/2006 Wojcik
7,056,302 B2 6/2006 Douglas
7,058,453 B2 6/2006 Nelson et al.
7,060,031 B2 6/2006 Webb et al.
7,073,246 B2 7/2006 Bhullar et al.
7,074,307 B2 7/2006 Simpson et al.
7,081,195 B2 7/2006 Simpson et al.
7,082,334 B2 7/2006 Boute et al.
7,097,637 B2 8/2006 Triplett et al.
7,098,803 B2 8/2006 Mann et al.
7,108,778 B2 9/2006 Simpson et al.
7,110,803 B2 9/2006 Shults et al.
7,113,821 B1 9/2006 Sun et al.
7,118,667 B2 10/2006 Lee
7,120,483 B2 10/2006 Russel et al.
7,123,950 B2 10/2006 Mannheimer
7,124,027 B1 10/2006 Ernst et al.
7,125,382 B2 10/2006 Zhou et al.
7,131,984 B2 11/2006 Sato et al.
7,134,999 B2 11/2006 Brauker et al.
7,136,689 B2 11/2006 Shults et al.
7,144,384 B2 12/2006 Gorman et al.
7,146,202 B2 12/2006 Ward et al.
7,154,398 B2 12/2006 Chen et al.
7,155,290 B2 12/2006 Von Arx et al.
7,167,818 B2 1/2007 Brown
7,169,600 B2 1/2007 Hoss et al.
7,171,274 B2 1/2007 Starkweather et al.
7,174,199 B2 2/2007 Berner et al.
7,179,226 B2 2/2007 Crothall et al.
7,183,102 B2 2/2007 Monfre et al.
7,190,988 B2 3/2007 Say et al.
7,192,450 B2 3/2007 Brauker et al.
7,198,606 B2 4/2007 Boecker et al.
7,203,549 B2 4/2007 Schommer et al.
7,207,974 B2 4/2007 Safabash et al.
7,220,387 B2 5/2007 Flaherty et al.
7,223,276 B2 5/2007 List et al.
7,225,535 B2 6/2007 Feldman et al.
7,226,442 B2 6/2007 Sheppard et al.
7,226,978 B2 6/2007 Tapsak et al.
7,228,162 B2 6/2007 Ward et al.
7,228,182 B2 6/2007 Healy et al.
7,237,712 B2 7/2007 DeRocco et al.
7,267,665 B2 9/2007 Steil et al.
7,276,029 B2 10/2007 Goode, Jr. et al.
7,276,146 B2 10/2007 Wilsey
7,276,147 B2 10/2007 Wilsey
7,278,983 B2 10/2007 Ireland et al.
7,286,894 B1 10/2007 Grant et al.
7,287,318 B2 10/2007 Bhullar et al.
7,291,497 B2 11/2007 Holmes et al.
7,295,867 B2 11/2007 Berner et al.
7,297,151 B2 11/2007 Boecker et al.
7,299,082 B2 11/2007 Feldman et al.
7,310,544 B2 12/2007 Brister et al.
7,318,816 B2 1/2008 Bobroff et al.
7,324,012 B2 1/2008 Mann et al.
7,324,850 B2 1/2008 Persen et al.
7,329,239 B2 2/2008 Safabash et al.
7,335,294 B2 2/2008 Heller et al.
7,340,287 B2 3/2008 Mason et al.
7,340,309 B2 3/2008 Miazga et al.
7,344,500 B2 3/2008 Talbot et al.
7,347,819 B2 3/2008 Lebel et al.
7,354,420 B2 4/2008 Steil et al.
7,364,592 B2 4/2008 Carr-Brendel et al.
7,366,556 B2 4/2008 Brister et al.
7,379,765 B2 5/2008 Petisce et al.
7,381,184 B2 6/2008 Funderburk et al.
7,384,397 B2 6/2008 Zhang et al.
7,386,937 B2 6/2008 Bhullar et al.
7,387,010 B2 6/2008 Sunshine et al.
7,399,277 B2 7/2008 Saidara et al.
7,400,111 B2 7/2008 Batman et al.
7,401,111 B1 7/2008 Batman et al.
7,402,153 B2 7/2008 Steil et al.
7,404,796 B2 7/2008 Ginsberg
7,407,493 B2 8/2008 Cane
7,408,132 B2 8/2008 Wambsganss et al.
7,416,541 B2 8/2008 Yuzhakov et al.
7,419,573 B2 9/2008 Gundel
7,424,318 B2 9/2008 Brister et al.
7,429,255 B2 9/2008 Thompson
7,433,727 B2 10/2008 Ward
7,448,996 B2 11/2008 Khanuja et al.
7,455,663 B2 11/2008 Bikovsky
7,460,898 B2 12/2008 Brister et al.
7,462,264 B2 12/2008 Heller et al.
7,467,003 B2 12/2008 Brister et al.
7,468,125 B2 12/2008 Kraft et al.
7,471,972 B2 12/2008 Rhodes et al.
7,476,827 B1 1/2009 Bhullar et al.
7,481,819 B2 1/2009 Koeppel et al.
7,492,254 B2 2/2009 Bandy et al.
7,494,465 B2 2/2009 Brister et al.
7,497,827 B2 3/2009 Brister et al.
7,499,002 B2 3/2009 Blasko et al.
7,519,408 B2 4/2009 Rasdal et al.
7,545,272 B2 6/2009 Goodnow et al.
7,547,281 B2 6/2009 Hayes et al.
7,565,197 B2 7/2009 Haubrich et al.
7,568,619 B2 8/2009 Todd et al.
7,569,030 B2 8/2009 Lebel et al.
7,574,266 B2 8/2009 Dudding et al.
7,582,059 B2 9/2009 Funderburk et al.
7,583,990 B2 9/2009 Goode, Jr. et al.
7,585,287 B2 9/2009 Bresina et al.
7,591,801 B2 9/2009 Brauker et al.
7,599,726 B2 10/2009 Goode, Jr. et al.
7,602,310 B2 10/2009 Mann et al.
7,604,178 B2 10/2009 Stewart
7,604,592 B2 10/2009 Freeman et al.
7,613,491 B2 11/2009 Boock et al.
7,615,007 B2 11/2009 Shults et al.
7,618,369 B2 11/2009 Hayter et al.
7,632,228 B2 12/2009 Brauker et al.
7,635,594 B2 12/2009 Holmes et al.
7,637,868 B2 12/2009 Saint et al.
7,640,048 B2 12/2009 Dobbles et al.
7,643,798 B2 1/2010 Ljung
7,651,596 B2 1/2010 Petisce et al.
7,651,845 B2 1/2010 Doyle, III et al.
7,653,425 B2 1/2010 Hayter et al.
7,654,956 B2 2/2010 Brister et al.
7,657,297 B2 2/2010 Simpson et al.
7,659,823 B1 2/2010 Killian et al.
7,660,615 B2 2/2010 VanAntwerp et al.
7,666,149 B2 2/2010 Simons et al.
7,668,596 B2 2/2010 Von Arx et al.
7,682,338 B2 3/2010 Griffin
7,697,967 B2 4/2010 Stafford
7,699,775 B2 4/2010 Desai et al.

(56) References Cited

U.S. PATENT DOCUMENTS

| | | | |
|---|---|---|---|
| 7,699,807 | B2 | 4/2010 | Faust et al. |
| 7,701,052 | B2 | 4/2010 | Borland et al. |
| 7,711,402 | B2 | 5/2010 | Shults et al. |
| 7,713,574 | B2 | 5/2010 | Brister et al. |
| 7,715,893 | B2 | 5/2010 | Kamath et al. |
| 7,727,147 | B1 | 6/2010 | Osorio et al. |
| 7,729,737 | B2 | 6/2010 | Ward |
| 7,731,657 | B2 | 6/2010 | Stafford |
| 7,731,691 | B2 | 6/2010 | Cote et al. |
| 7,736,310 | B2 | 6/2010 | Taub et al. |
| 7,736,344 | B2 | 6/2010 | Moberg et al. |
| 7,741,734 | B2 | 6/2010 | Joannopoulos et al. |
| 7,763,042 | B2 | 7/2010 | Iio et al. |
| 7,766,829 | B2 | 8/2010 | Sloan et al. |
| 7,768,387 | B2 | 8/2010 | Fennell et al. |
| 7,771,352 | B2 | 8/2010 | Shults et al. |
| 7,774,145 | B2 | 8/2010 | Brauker et al. |
| 7,775,444 | B2 | 8/2010 | DeRocco et al. |
| 7,778,680 | B2 | 8/2010 | Goode, Jr. et al. |
| 7,779,332 | B2 | 8/2010 | Karr et al. |
| 7,780,827 | B1 | 8/2010 | Bhullar et al. |
| 7,782,192 | B2 | 8/2010 | Jeckelmann et al. |
| 7,783,333 | B2 | 8/2010 | Brister et al. |
| 7,791,467 | B2 | 9/2010 | Mazar et al. |
| 7,792,562 | B2 | 9/2010 | Shults et al. |
| 7,811,231 | B2 | 10/2010 | Jin et al. |
| 7,813,809 | B2 | 10/2010 | Strother et al. |
| 7,822,454 | B1 | 10/2010 | Alden et al. |
| 7,826,981 | B2 | 11/2010 | Goode, Jr. et al. |
| 7,831,310 | B2 | 11/2010 | Lebel et al. |
| 7,833,151 | B2 | 11/2010 | Khait et al. |
| 7,833,170 | B2 | 11/2010 | Matsumoto et al. |
| 7,837,633 | B2 | 11/2010 | Conway et al. |
| 7,842,046 | B1 | 11/2010 | Nakao |
| 7,846,132 | B2 | 12/2010 | Gravesen et al. |
| 7,850,652 | B2 | 12/2010 | Liniger et al. |
| 7,860,574 | B2 | 12/2010 | Von Arx et al. |
| 7,866,026 | B1 | 1/2011 | Wang et al. |
| 7,867,244 | B2 | 1/2011 | Lathrop et al. |
| 7,873,299 | B2 | 1/2011 | Berner et al. |
| 7,882,611 | B2 | 2/2011 | Shah et al. |
| 7,883,464 | B2 | 2/2011 | Stafford |
| 7,883,473 | B2 | 2/2011 | LeVaughn et al. |
| 7,885,697 | B2 | 2/2011 | Brister et al. |
| 7,889,069 | B2 | 2/2011 | Fifolt et al. |
| 7,896,844 | B2 | 3/2011 | Thalmann et al. |
| 7,899,511 | B2 | 3/2011 | Shults et al. |
| 7,899,545 | B2 | 3/2011 | John |
| 7,905,833 | B2 | 3/2011 | Brister et al. |
| 7,912,655 | B2 | 3/2011 | Power et al. |
| 7,912,674 | B2 | 3/2011 | Killoren Clark et al. |
| 7,914,450 | B2 | 3/2011 | Goode, Jr. et al. |
| 7,914,460 | B2 | 3/2011 | Melker et al. |
| 7,916,013 | B2 | 3/2011 | Stevenson |
| 7,920,906 | B2 | 4/2011 | Goode, Jr. et al. |
| 7,920,907 | B2 | 4/2011 | McGarraugh et al. |
| 7,938,797 | B2 | 5/2011 | Estes |
| 7,941,200 | B2 | 5/2011 | Weinart et al. |
| 7,946,984 | B2 | 5/2011 | Brister et al. |
| 7,946,985 | B2 | 5/2011 | Mastrototaro et al. |
| 7,955,258 | B2 | 6/2011 | Goscha et al. |
| 7,955,297 | B2 | 6/2011 | Radmer et al. |
| 7,970,448 | B2 | 6/2011 | Shults et al. |
| 7,970,449 | B2 | 6/2011 | Ward |
| 7,972,296 | B2 | 7/2011 | Braig et al. |
| 7,974,672 | B2 | 7/2011 | Shults et al. |
| 7,976,467 | B2 | 7/2011 | Young et al. |
| 7,978,063 | B2 | 7/2011 | Baldus et al. |
| 7,985,203 | B2 | 7/2011 | Haueter et al. |
| 7,985,222 | B2 | 7/2011 | Gall et al. |
| 7,996,158 | B2 | 8/2011 | Hayter et al. |
| 7,999,674 | B2 | 8/2011 | Kamen |
| 8,000,918 | B2 | 8/2011 | Fjield et al. |
| 8,005,524 | B2 | 8/2011 | Brauker et al. |
| 8,010,174 | B2 | 8/2011 | Goode, Jr. et al. |
| 8,010,256 | B2 | 8/2011 | Oowada |
| 8,016,774 | B2 | 9/2011 | Freeman et al. |
| 8,028,837 | B2 | 10/2011 | Gerstle et al. |
| 8,029,441 | B2 | 10/2011 | Mazza et al. |
| 8,029,442 | B2 | 10/2011 | Funderburk et al. |
| 8,072,310 | B1 | 12/2011 | Everhart |
| 8,090,445 | B2 | 1/2012 | Ginggen |
| 8,093,991 | B2 | 1/2012 | Stevenson et al. |
| 8,094,009 | B2 | 1/2012 | Allen et al. |
| 8,098,159 | B2 | 1/2012 | Batra et al. |
| 8,098,160 | B2 | 1/2012 | Howarth et al. |
| 8,098,161 | B2 | 1/2012 | Lavedas |
| 8,098,201 | B2 | 1/2012 | Choi et al. |
| 8,098,208 | B2 | 1/2012 | Ficker et al. |
| 8,102,021 | B2 | 1/2012 | Degani |
| 8,102,154 | B2 | 1/2012 | Bishop et al. |
| 8,102,263 | B2 | 1/2012 | Yeo et al. |
| 8,102,789 | B2 | 1/2012 | Rosar et al. |
| 8,103,241 | B2 | 1/2012 | Young et al. |
| 8,103,325 | B2 | 1/2012 | Swedlow et al. |
| 8,103,471 | B2 | 1/2012 | Hayter |
| 8,111,042 | B2 | 2/2012 | Bennett |
| 8,112,240 | B2 | 2/2012 | Fennell |
| 8,115,488 | B2 | 2/2012 | McDowell |
| 8,116,681 | B2 | 2/2012 | Baarman |
| 8,116,683 | B2 | 2/2012 | Baarman |
| 8,117,481 | B2 | 2/2012 | Anselmi et al. |
| 8,120,493 | B2 | 2/2012 | Burr |
| 8,124,452 | B2 | 2/2012 | Sheats |
| 8,130,093 | B2 | 3/2012 | Mazar et al. |
| 8,131,351 | B2 | 3/2012 | Kalgren et al. |
| 8,131,365 | B2 | 3/2012 | Zhang et al. |
| 8,131,565 | B2 | 3/2012 | Docks et al. |
| 8,132,037 | B2 | 3/2012 | Fehr et al. |
| 8,135,352 | B2 | 3/2012 | Langsweirdt et al. |
| 8,136,735 | B2 | 3/2012 | Arai et al. |
| 8,138,925 | B2 | 3/2012 | Downie et al. |
| 8,140,160 | B2 | 3/2012 | Pless et al. |
| 8,140,168 | B2 | 3/2012 | Olson et al. |
| 8,140,299 | B2 | 3/2012 | Siess |
| 8,140,312 | B2 | 3/2012 | Hayter et al. |
| 8,150,321 | B2 | 4/2012 | Winter et al. |
| 8,150,516 | B2 | 4/2012 | Levine et al. |
| 8,160,670 | B2 | 4/2012 | Quyang et al. |
| 8,160,900 | B2 | 4/2012 | Taub et al. |
| 8,172,805 | B2 | 5/2012 | Mogensen et al. |
| 8,175,673 | B2 | 5/2012 | Say et al. |
| 8,179,266 | B2 | 5/2012 | Hermle |
| 8,180,423 | B2 | 5/2012 | Mang et al. |
| 8,192,394 | B2 | 6/2012 | Estes et al. |
| 8,216,138 | B1 | 7/2012 | McGaraugh et al. |
| 8,221,332 | B2 | 7/2012 | Robbins et al. |
| 8,224,410 | B2 | 7/2012 | Hadvary et al. |
| 8,239,166 | B2 | 8/2012 | Hayter et al. |
| 8,255,026 | B1 | 8/2012 | Al-Ali |
| 8,260,558 | B2 | 9/2012 | Hayter et al. |
| 8,262,618 | B2 | 9/2012 | Scheurer |
| 8,282,549 | B2 | 10/2012 | Brauker et al. |
| 8,333,714 | B2 | 12/2012 | Stafford |
| 8,346,335 | B2 | 1/2013 | Harper et al. |
| 8,346,337 | B2 | 1/2013 | Heller et al. |
| 8,373,544 | B2 | 2/2013 | Pitt-Plady |
| 8,374,668 | B1 | 2/2013 | Hayter et al. |
| 8,376,945 | B2 | 2/2013 | Hayter et al. |
| 8,377,271 | B2 | 2/2013 | Mao et al. |
| 8,382,671 | B2 | 2/2013 | Anthony et al. |
| 8,398,664 | B2 | 3/2013 | Lamps et al. |
| 8,409,093 | B2 | 4/2013 | Bugler |
| 8,409,145 | B2 | 4/2013 | Raymond et al. |
| 8,439,838 | B2 | 5/2013 | Mogensen et al. |
| 8,444,560 | B2 | 5/2013 | Hayter et al. |
| 8,461,985 | B2 | 6/2013 | Fennell et al. |
| 8,469,986 | B2 | 6/2013 | Schraga |
| 8,512,243 | B2 | 8/2013 | Stafford |
| 8,515,518 | B2 | 8/2013 | Ouyang et al. |
| 8,515,519 | B2 | 8/2013 | Brister et al. |
| 8,538,512 | B1 | 9/2013 | Bibian et al. |
| 8,545,403 | B2 | 10/2013 | Peyser et al. |
| 8,560,038 | B2 | 10/2013 | Hayter et al. |

(56) References Cited

U.S. PATENT DOCUMENTS 8,562,567 B2 10/2013 Gundberg
8,571,808 B2 10/2013 Hayter
8,583,205 B2 11/2013 Budiman et al.
8,585,591 B2 11/2013 Sloan et al.
8,597,570 B2 12/2013 Terashima et al.
8,600,681 B2 12/2013 Hayter et al.
8,602,991 B2 12/2013 Stafford
8,612,163 B2 12/2013 Hayter et al.
8,615,282 B2 12/2013 Brister et al.
8,617,069 B2 12/2013 Bernstein et al.
8,617,071 B2 12/2013 Say et al.
8,622,903 B2 1/2014 Jin et al.
8,628,498 B2 1/2014 Safabach et al.
8,641,674 B2 2/2014 Bobroff et al.
8,652,043 B2 2/2014 Drucker et al.
8,682,408 B2 3/2014 Boock et al.
8,682,615 B2 3/2014 Hayter et al.
8,684,930 B2 4/2014 Feldman et al.
8,692,655 B2 4/2014 Zimman et al.
8,710,993 B2 4/2014 Hayter et al.
8,747,363 B2 6/2014 Nielsen et al.
8,750,955 B2 6/2014 Brister et al.
8,771,183 B2 7/2014 Sloan
8,797,163 B2 8/2014 Finkenzeller
8,808,515 B2 8/2014 Feldman et al.
8,834,366 B2 9/2014 Hayter et al.
8,845,536 B2 9/2014 Brauker et al.
8,870,822 B2 10/2014 Thalmann et al.
8,880,138 B2 11/2014 Cho
8,945,056 B2 2/2015 Iio et al.
8,961,413 B2 2/2015 Teller et al.
9,007,781 B2 4/2015 Moein et al.
9,014,774 B2 4/2015 Mao et al.
9,031,630 B2 5/2015 Hoss et al.
9,060,719 B2 6/2015 Hayter et al.
9,060,805 B2 6/2015 Goodnow et al.
9,066,697 B2 6/2015 Peyser et al.
9,101,302 B2 8/2015 Mace et al.
9,186,098 B2 11/2015 Lee et al.
9,215,992 B2 12/2015 Donnay et al.
9,241,631 B2 1/2016 Valdes et al.
9,259,175 B2 2/2016 Stafford
9,265,453 B2 2/2016 Curry et al.
9,289,179 B2 3/2016 Hayter et al.
9,295,786 B2 3/2016 Gottlieb et al.
9,357,951 B2 6/2016 Simpson et al.
9,398,872 B2 7/2016 Hayter et al.
9,402,544 B2 8/2016 Yee et al.
9,402,570 B2 8/2016 Pace et al.
9,439,586 B2 9/2016 Bugler
9,451,910 B2 9/2016 Brister et al.
9,474,479 B2 10/2016 Pusey et al.
9,480,421 B2 11/2016 Stafford
9,483,608 B2 11/2016 Hayter et al.
9,504,471 B2 11/2016 Vaitekunas et al.
9,558,325 B2 1/2017 Hayter et al.
9,566,384 B2 2/2017 Gymn et al.
9,636,068 B2 5/2017 Yee et al.
9,668,682 B2 6/2017 Brister et al.
9,743,876 B2 8/2017 Gelfand et al.
9,808,574 B2 11/2017 Yodfat et al.
9,814,414 B2 11/2017 Brister et al.
10,213,139 B2 2/2019 Rao et al.
10,292,632 B2 5/2019 Lee et al.
10,342,489 B2 7/2019 Stafford
10,772,547 B1 9/2020 Lee et al.
10,820,842 B2 11/2020 Harper
10,827,954 B2 11/2020 Hoss et al.
10,874,338 B2 12/2020 Stafford
10,881,340 B2 1/2021 Curry et al.
10,881,341 B1 1/2021 Curry et al.
10,945,647 B2 3/2021 Mazza et al.
10,945,649 B2 3/2021 Lee et al.
10,952,653 B2 3/2021 Harper
10,959,654 B2 3/2021 Curry et al.
10,966,644 B2 4/2021 Stafford
10,973,443 B2 4/2021 Funderburk et al.
10,980,461 B2 4/2021 Simpson et al.
11,000,213 B2 5/2021 Kamath et al.
11,000,216 B2 5/2021 Curry et al.
11,006,870 B2 5/2021 Yee et al.
11,006,871 B2 5/2021 Yee et al.
11,013,440 B2 5/2021 Lee et al.
11,051,724 B2 7/2021 Pace et al.
11,064,917 B2 7/2021 Simpson et al.
11,116,430 B2 9/2021 Funderburk et al.
11,141,084 B2 10/2021 Funderburk et al.
11,166,656 B2 11/2021 Yee et al.
11,179,068 B2 11/2021 Pace et al.
11,197,625 B1 12/2021 Schleicher et al.
11,202,591 B2 12/2021 Yee et al.
11,213,229 B2 1/2022 Yee et al.
11,246,519 B2 2/2022 Donnay et al.
11,266,335 B2 3/2022 Donnay et al.
11,298,056 B2 4/2022 Harper
11,298,058 B2 4/2022 Stafford
11,510,625 B2 11/2022 Gray et al.
2001/0016682 A1 8/2001 Berner et al.
2001/0034479 A1 10/2001 Ring et al.
2001/0037060 A1 11/2001 Thompson et al.
2001/0037366 A1 11/2001 Webb et al.
2001/0039387 A1 11/2001 Rutynowski et al.
2001/0044608 A1 11/2001 Odell et al.
2001/0047127 A1 11/2001 New et al.
2001/0056262 A1 12/2001 Cabiri et al.
2002/0002344 A1 1/2002 Douglas et al.
2002/0010390 A1 1/2002 Guice et al.
2002/0013522 A1 1/2002 Lav et al.
2002/0013538 A1 1/2002 Teller
2002/0016534 A1 2/2002 Trepagnier et al.
2002/0016568 A1 2/2002 Lebel et al.
2002/0019022 A1 2/2002 Dunn et al.
2002/0019584 A1 2/2002 Schulze et al.
2002/0019586 A1 2/2002 Teller et al.
2002/0019606 A1 2/2002 Lebel et al.
2002/0022855 A1 2/2002 Bobroff et al.
2002/0023852 A1 2/2002 Mclvor et al.
2002/0029058 A1 3/2002 LeVaughn et al.
2002/0032386 A1 3/2002 Sackner et al.
2002/0039026 A1 4/2002 Stroth et al.
2002/0042090 A1 4/2002 Heller et al.
2002/0045808 A1 4/2002 Ford et al.
2002/0049482 A1 4/2002 Fabian et al.
2002/0050250 A1 5/2002 Peterson et al.
2002/0055711 A1 5/2002 Lavi et al.
2002/0057993 A1 5/2002 Maisey et al.
2002/0065454 A1 5/2002 Lebel et al.
2002/0066764 A1 6/2002 Perry et al.
2002/0072720 A1 6/2002 Hague et al.
2002/0072784 A1 6/2002 Sheppard et al.
2002/0074162 A1 6/2002 Su et al.
2002/0076966 A1 6/2002 Carron et al.
2002/0077599 A1 6/2002 Wojcik
2002/0082487 A1 6/2002 Kollias et al.
2002/0084196 A1 7/2002 Liamos et al.
2002/0091796 A1 7/2002 Higginson et al.
2002/0093969 A1 7/2002 Lin et al.
2002/0095076 A1 7/2002 Krausman et al.
2002/0103499 A1 8/2002 Perez et al.
2002/0106709 A1 8/2002 Potts et al.
2002/0111832 A1 8/2002 Judge
2002/0117639 A1 8/2002 Paolini et al.
2002/0118528 A1 8/2002 Su et al.
2002/0119711 A1 8/2002 VanAntwerp et al.
2002/0120186 A1 8/2002 Keimel
2002/0124017 A1 9/2002 Mault
2002/0128594 A1 9/2002 Das et al.
2002/0130042 A1 9/2002 Moerman et al.
2002/0133066 A1 9/2002 Miller et al.
2002/0147135 A1 10/2002 Schnell
2002/0150959 A1 10/2002 Lejeune et al.
2002/0151770 A1 10/2002 Noll et al.
2002/0151796 A1 10/2002 Koulik
2002/0151816 A1 10/2002 Rich et al.

(56) References Cited

U.S. PATENT DOCUMENTS

2002/0154050 A1 10/2002 Krupp et al.
2002/0161288 A1 10/2002 Shin et al.
2002/0161290 A1 10/2002 Chance
2002/0161338 A1 10/2002 Peterson
2002/0164836 A1 11/2002 Ho
2002/0165462 A1 11/2002 Westbrook et al.
2002/0169369 A1 11/2002 Ward et al.
2002/0169439 A1 11/2002 Flaherty
2002/0169635 A1 11/2002 Shillingburg
2002/0183604 A1 12/2002 Gowda et al.
2002/0185128 A1 12/2002 Theobald
2002/0185130 A1 12/2002 Wright et al.
2002/0188748 A1 12/2002 Blackwell et al.
2002/0197522 A1 12/2002 Lawrence et al.
2002/0198444 A1 12/2002 Ughigaki et al.
2002/0198543 A1 12/2002 Burdulis et al.
2003/0004403 A1 1/2003 Drinan et al.
2003/0020477 A1 1/2003 Goldstein
2003/0023189 A1 1/2003 Kuo
2003/0023317 A1 1/2003 Brauker et al.
2003/0023461 A1 1/2003 Quintanilla et al.
2003/0028089 A1 2/2003 Galley et al.
2003/0028184 A1 2/2003 Lebel et al.
2003/0032077 A1 2/2003 Itoh et al.
2003/0032867 A1 2/2003 Crothall et al.
2003/0032874 A1 2/2003 Rhodes et al.
2003/0042137 A1 3/2003 Mao et al.
2003/0050546 A1 3/2003 Desai et al.
2003/0054428 A1 3/2003 Monfre et al.
2003/0055380 A1 3/2003 Flaherty
2003/0060692 A1 3/2003 Ruchti et al.
2003/0060753 A1 3/2003 Starkweather et al.
2003/0065308 A1 4/2003 Lebel et al.
2003/0069509 A1 4/2003 Matzinger et al.
2003/0069510 A1 4/2003 Semler
2003/0076792 A1 4/2003 Theimer
2003/0077642 A1 4/2003 Fritsch et al.
2003/0078481 A1 4/2003 McIvor et al.
2003/0078560 A1 4/2003 Miller et al.
2003/0083686 A1 5/2003 Freeman et al.
2003/0088166 A1 5/2003 Say et al.
2003/0097092 A1 5/2003 Flaherty
2003/0100040 A1 5/2003 Bonnecaze et al.
2003/0100821 A1 5/2003 Heller et al.
2003/0109775 A1 6/2003 O'Neil et al.
2003/0114897 A1 6/2003 Von Arx et al.
2003/0114898 A1 6/2003 Von Arx et al.
2003/0119457 A1 6/2003 Standke
2003/0125612 A1 7/2003 Fox et al.
2003/0130616 A1 7/2003 Steil et al.
2003/0134347 A1 7/2003 Heller et al.
2003/0135127 A1 7/2003 Sackner et al.
2003/0135333 A1 7/2003 Aceti et al.
2003/0144579 A1 7/2003 Buss
2003/0144581 A1 7/2003 Conn et al.
2003/0144608 A1 7/2003 Kojima et al.
2003/0153900 A1 8/2003 Aceti et al.
2003/0155656 A1 8/2003 Chiu et al.
2003/0168338 A1 9/2003 Gao et al.
2003/0176933 A1 9/2003 Lebel et al.
2003/0187338 A1 10/2003 Say et al.
2003/0188427 A1 10/2003 Say et al.
2003/0199744 A1 10/2003 Buse et al.
2003/0199790 A1 10/2003 Boecker et al.
2003/0199910 A1 10/2003 Boecker et al.
2003/0204290 A1 10/2003 Sadler et al.
2003/0208113 A1 11/2003 Mault et al.
2003/0208114 A1 11/2003 Ackerman
2003/0212317 A1 11/2003 Kovatchev et al.
2003/0212379 A1 11/2003 Bylund et al.
2003/0212579 A1 11/2003 Brown et al.
2003/0216621 A1 11/2003 Alpert et al.
2003/0216630 A1 11/2003 Jersey-Willuhn et al.
2003/0217966 A1 11/2003 Tapsak et al.
2003/0225361 A1 12/2003 Sabra
2003/0225373 A1 12/2003 Bobroff et al.
2003/0236489 A1 12/2003 Jacobson et al.
2004/0002682 A1 1/2004 Kovelman et al.
2004/0010207 A1 1/2004 Flaherty et al.
2004/0011671 A1 1/2004 Shults et al.
2004/0015131 A1 1/2004 Flaherty et al.
2004/0017300 A1 1/2004 Kotzin et al.
2004/0030226 A1 2/2004 Quy
2004/0030531 A1 2/2004 Miller et al.
2004/0030581 A1 2/2004 Levin et al.
2004/0034289 A1 2/2004 Teller et al.
2004/0039255 A1 2/2004 Simonsen et al.
2004/0039298 A1 2/2004 Abreu
2004/0040840 A1 3/2004 Mao et al.
2004/0045879 A1 3/2004 Shults et al.
2004/0054263 A1 3/2004 Moerman et al.
2004/0060818 A1 4/2004 Feldman et al.
2004/0061232 A1 4/2004 Shah et al.
2004/0063435 A1 4/2004 Sakamoto et al.
2004/0064068 A1 4/2004 DeNuzzio et al.
2004/0064133 A1 4/2004 Miller et al.
2004/0072357 A1 4/2004 Steine et al.
2004/0073266 A1 4/2004 Haefner et al.
2004/0078215 A1 4/2004 Dahlin et al.
2004/0096959 A1 5/2004 Steine et al.
2004/0100376 A1 5/2004 Lye et al.
2004/0105411 A1 6/2004 Boatwright et al.
2004/0106858 A1 6/2004 Say et al.
2004/0106859 A1 6/2004 Say et al.
2004/0106860 A1 6/2004 Say et al.
2004/0111017 A1 6/2004 Say et al.
2004/0116847 A1 6/2004 Wall
2004/0116865 A1 6/2004 Bengtsson
2004/0116866 A1 6/2004 Gorman et al.
2004/0117204 A1 6/2004 Mazar et al.
2004/0119169 A1 6/2004 Hanawa
2004/0122353 A1 6/2004 Shahmirian et al.
2004/0122489 A1 6/2004 Mazar et al.
2004/0133089 A1 7/2004 Kilcoyne et al.
2004/0133164 A1 7/2004 Funderburk et al.
2004/0133390 A1 7/2004 Osorio et al.
2004/0135571 A1 7/2004 Uutela et al.
2004/0135684 A1 7/2004 Steinthal et al.
2004/0138544 A1 7/2004 Ward et al.
2004/0138588 A1 7/2004 Saikley et al.
2004/0138688 A1 7/2004 Giraud
2004/0140211 A1 7/2004 Broy et al.
2004/0142403 A1 7/2004 Hetzel et al.
2004/0146909 A1 7/2004 Duong et al.
2004/0147872 A1 7/2004 Thompson
2004/0147996 A1 7/2004 Miazga et al.
2004/0152366 A1 8/2004 Schultz et al.
2004/0152622 A1 8/2004 Keith et al.
2004/0158207 A1 8/2004 Hunn et al.
2004/0162521 A1 8/2004 Bengtsson et al.
2004/0162678 A1 8/2004 Hetzel et al.
2004/0167801 A1 8/2004 Say et al.
2004/0171910 A1 9/2004 Moore-Steele
2004/0171921 A1 9/2004 Say et al.
2004/0176672 A1 9/2004 Silver et al.
2004/0186362 A1 9/2004 Brauker et al.
2004/0186365 A1 9/2004 Jin et al.
2004/0193020 A1 9/2004 Chiba et al.
2004/0193025 A1 9/2004 Steil et al.
2004/0193090 A1 9/2004 Lebel et al.
2004/0197846 A1 10/2004 Hockersmith et al.
2004/0199056 A1 10/2004 Husemann et al.
2004/0199059 A1 10/2004 Brauker et al.
2004/0204673 A1 10/2004 Flaherty
2004/0204687 A1 10/2004 Mogensen et al.
2004/0204744 A1 10/2004 Penner et al.
2004/0204868 A1 10/2004 Maynard et al.
2004/0206625 A1 10/2004 Bhullar et al.
2004/0206916 A1 10/2004 Colvin, Jr. et al.
2004/0210122 A1 10/2004 Sleburg
2004/0221057 A1 11/2004 Darcey et al.
2004/0223876 A1 11/2004 Kirollos et al.
2004/0223985 A1 11/2004 Dunfield et al.
2004/0225199 A1 11/2004 Evanyk et al.

(56) References Cited

U.S. PATENT DOCUMENTS

2004/0225262 A1 11/2004 Fathallah et al.
2004/0225338 A1 11/2004 Lebel et al.
2004/0236200 A1 11/2004 Say et al.
2004/0236251 A1 11/2004 Roe et al.
2004/0240426 A1 12/2004 Wu et al.
2004/0249253 A1 12/2004 Racchini et al.
2004/0249999 A1 12/2004 Connolly et al.
2004/0254433 A1 12/2004 Bandis et al.
2004/0254434 A1 12/2004 Goodnow et al.
2004/0258564 A1 12/2004 Charlton
2004/0260224 A1 12/2004 Binder et al.
2004/0267300 A1 12/2004 Mace
2005/0001024 A1 1/2005 Kusaka et al.
2005/0003470 A1 1/2005 Nelson et al.
2005/0004439 A1 1/2005 Shin et al.
2005/0004494 A1 1/2005 Perez et al.
2005/0006122 A1 1/2005 Burnette
2005/0010269 A1 1/2005 Lebel et al.
2005/0017864 A1 1/2005 Tsoukalis
2005/0027177 A1 2/2005 Shin et al.
2005/0027180 A1 2/2005 Goode, Jr. et al.
2005/0027181 A1 2/2005 Goode, Jr. et al.
2005/0027462 A1 2/2005 Goode, Jr. et al.
2005/0027463 A1 2/2005 Goode, Jr. et al.
2005/0031689 A1 2/2005 Shults et al.
2005/0033132 A1 2/2005 Shults et al.
2005/0038332 A1 2/2005 Saidara et al.
2005/0038465 A1 2/2005 Shraga
2005/0038680 A1 2/2005 McMahon
2005/0043598 A1 2/2005 Goode, Jr. et al.
2005/0049179 A1 3/2005 Davidson et al.
2005/0051427 A1 3/2005 Brauker et al.
2005/0051440 A1 3/2005 Simpson et al.
2005/0056552 A1 3/2005 Simpson et al.
2005/0065464 A1 3/2005 Talbot et al.
2005/0070774 A1 3/2005 Addison et al.
2005/0070819 A1 3/2005 Poux et al.
2005/0085872 A1 4/2005 Yanagihara et al.
2005/0090607 A1 4/2005 Tapsak et al.
2005/0090850 A1 4/2005 Thoes et al.
2005/0096511 A1 5/2005 Fox et al.
2005/0096512 A1 5/2005 Fox et al.
2005/0096516 A1 5/2005 Soykan et al.
2005/0096520 A1 5/2005 Maekawa et al.
2005/0096587 A1 5/2005 Santini, Jr. et al.
2005/0101912 A1 5/2005 Faust et al.
2005/0101932 A1 5/2005 Cote et al.
2005/0103624 A1 5/2005 Bhullar et al.
2005/0104457 A1 5/2005 Jordan et al.
2005/0106713 A1 5/2005 Phan et al.
2005/0112169 A1 5/2005 Brauker et al.
2005/0112544 A1 5/2005 Xu et al.
2005/0113648 A1 5/2005 Yang et al.
2005/0113653 A1 5/2005 Fox et al.
2005/0113886 A1 5/2005 Fischell et al.
2005/0114068 A1 5/2005 Chey et al.
2005/0115832 A1 6/2005 Simpson et al.
2005/0116683 A1 6/2005 Cheng et al.
2005/0121322 A1 6/2005 Say et al.
2005/0131346 A1 6/2005 Douglas
2005/0131347 A1 6/2005 Marano-Ford et al.
2005/0134731 A1 6/2005 Lee et al.
2005/0137488 A1 6/2005 Henry et al.
2005/0137530 A1 6/2005 Campbell et al.
2005/0143635 A1 6/2005 Kamath et al.
2005/0149066 A1 7/2005 Stafford
2005/0151976 A1 7/2005 Toma
2005/0154271 A1 7/2005 Rasdal et al.
2005/0154410 A1 7/2005 Conway et al.
2005/0159678 A1 7/2005 Taniike et al.
2005/0161346 A1 7/2005 Simpson et al.
2005/0165404 A1 7/2005 Miller
2005/0171442 A1 8/2005 Shirasaki et al.
2005/0173245 A1 8/2005 Feldman et al.
2005/0176136 A1 8/2005 Burd et al.
2005/0177398 A1 8/2005 Watanabe et al.
2005/0181010 A1 8/2005 Hunter et al.
2005/0182306 A1 8/2005 Sloan
2005/0182358 A1 8/2005 Heit et al.
2005/0187442 A1 8/2005 Cho et al.
2005/0187720 A1 8/2005 Goode, Jr. et al.
2005/0192494 A1 9/2005 Ginsberg
2005/0192557 A1 9/2005 Brauker et al.
2005/0195930 A1 9/2005 Spital et al.
2005/0197554 A1 9/2005 Polcha
2005/0197793 A1 9/2005 Baker, Jr.
2005/0199494 A1 9/2005 Say et al.
2005/0203360 A1 9/2005 Brauker et al.
2005/0204134 A1 9/2005 Von Arx et al.
2005/0214892 A1 9/2005 Kovatchev et al.
2005/0215871 A1 9/2005 Feldman et al.
2005/0221504 A1 10/2005 Petruno et al.
2005/0222518 A1 10/2005 Dib
2005/0222599 A1 10/2005 Czernecki et al.
2005/0236277 A9 10/2005 Imran et al.
2005/0236361 A1 10/2005 Ufer et al.
2005/0239154 A1 10/2005 Feldman et al.
2005/0239156 A1 10/2005 Drucker et al.
2005/0241957 A1 11/2005 Mao et al.
2005/0245795 A1 11/2005 Goode, Jr. et al.
2005/0245799 A1 11/2005 Brauker et al.
2005/0245839 A1 11/2005 Stivoric et al.
2005/0245844 A1 11/2005 Mace et al.
2005/0245904 A1 11/2005 Estes et al.
2005/0247319 A1 11/2005 Berger
2005/0251033 A1 11/2005 Scarantino et al.
2005/0261563 A1 11/2005 Zhou et al.
2005/0267325 A1 12/2005 Bouchier et al.
2005/0267327 A1 12/2005 Iizuka et al.
2005/0269214 A1 12/2005 Lee
2005/0277164 A1 12/2005 Drucker et al.
2005/0277912 A1 12/2005 John
2005/0281234 A1 12/2005 Kawamura et al.
2005/0283114 A1 12/2005 Bresina et al.
2005/0283208 A1 12/2005 Von Arx et al.
2005/0283209 A1 12/2005 Katoozi et al.
2005/0284758 A1 12/2005 Funke et al.
2005/0287620 A1 12/2005 Heller et al.
2006/0001538 A1 1/2006 Kraft et al.
2006/0001551 A1 1/2006 Kraft et al.
2006/0004270 A1 1/2006 Bedard et al.
2006/0004272 A1 1/2006 Shah et al.
2006/0004303 A1 1/2006 Weidenhaupt et al.
2006/0006141 A1 1/2006 Ufer et al.
2006/0009727 A1 1/2006 O'Mahony et al.
2006/0010098 A1 1/2006 Goodnow et al.
2006/0012464 A1 1/2006 Nitzan et al.
2006/0015020 A1 1/2006 Neale et al.
2006/0015024 A1 1/2006 Brister et al.
2006/0016700 A1 1/2006 Brister et al.
2006/0019327 A1 1/2006 Brister et al.
2006/0020186 A1 1/2006 Brister et al.
2006/0020187 A1 1/2006 Brister et al.
2006/0020188 A1 1/2006 Kamath et al.
2006/0020189 A1 1/2006 Brister et al.
2006/0020190 A1 1/2006 Kamath et al.
2006/0020191 A1 1/2006 Brister et al.
2006/0020192 A1 1/2006 Brister et al.
2006/0020300 A1 1/2006 Nghiem et al.
2006/0025662 A1 2/2006 Buse et al.
2006/0025663 A1 2/2006 Talbot et al.
2006/0029177 A1 2/2006 Cranford, Jr. et al.
2006/0030789 A1 2/2006 Allen
2006/0031094 A1 2/2006 Cohen et al.
2006/0036139 A1 2/2006 Brister et al.
2006/0036140 A1 2/2006 Brister et al.
2006/0036141 A1 2/2006 Kamath et al.
2006/0036142 A1 2/2006 Brister et al.
2006/0036143 A1 2/2006 Brister et al.
2006/0036144 A1 2/2006 Brister et al.
2006/0036145 A1 2/2006 Brister et al.
2006/0040402 A1 2/2006 Brauker et al.
2006/0040793 A1 2/2006 Martens et al.
2006/0041276 A1 2/2006 Chan

(56) References Cited

U.S. PATENT DOCUMENTS

| | | | |
|---|---|---|---|
| 2006/0042080 | A1 | 3/2006 | Say et al. |
| 2006/0047220 | A1 | 3/2006 | Sakata et al. |
| 2006/0049359 | A1 | 3/2006 | Busta et al. |
| 2006/0058588 | A1 | 3/2006 | Zdeblick |
| 2006/0064035 | A1 | 3/2006 | Wang et al. |
| 2006/0068208 | A1 | 3/2006 | Tapsak et al. |
| 2006/0079740 | A1 | 4/2006 | Silver et al. |
| 2006/0081469 | A1 | 4/2006 | Lee |
| 2006/0086624 | A1 | 4/2006 | Tapsak et al. |
| 2006/0091006 | A1 | 5/2006 | Wang et al. |
| 2006/0094944 | A1 | 5/2006 | Chuang |
| 2006/0095014 | A1 | 5/2006 | Ethelfeld |
| 2006/0116607 | A1 | 6/2006 | Nakamura et al. |
| 2006/0129173 | A1 | 6/2006 | Wilkinson |
| 2006/0129733 | A1 | 6/2006 | Solbelman |
| 2006/0135908 | A1 | 6/2006 | Liniger et al. |
| 2006/0142651 | A1 | 6/2006 | Brister et al. |
| 2006/0154642 | A1 | 7/2006 | Scannell |
| 2006/0155180 | A1 | 7/2006 | Brister et al. |
| 2006/0155210 | A1 | 7/2006 | Beckman et al. |
| 2006/0155317 | A1 | 7/2006 | List |
| 2006/0161194 | A1 | 7/2006 | Freeman et al. |
| 2006/0161664 | A1 | 7/2006 | Motoyama |
| 2006/0166629 | A1 | 7/2006 | Reggiardo |
| 2006/0173260 | A1 | 8/2006 | Gaoni et al. |
| 2006/0173406 | A1 | 8/2006 | Hayes et al. |
| 2006/0173444 | A1 | 8/2006 | Choy et al. |
| 2006/0181695 | A1 | 8/2006 | Sage, Jr. |
| 2006/0183984 | A1 | 8/2006 | Dobbles et al. |
| 2006/0183985 | A1 | 8/2006 | Brister et al. |
| 2006/0189851 | A1 | 8/2006 | Tvig et al. |
| 2006/0189863 | A1 | 8/2006 | Peyser et al. |
| 2006/0189939 | A1 | 8/2006 | Gonnelli et al. |
| 2006/0193375 | A1 | 8/2006 | Lee et al. |
| 2006/0195029 | A1 | 8/2006 | Shults et al. |
| 2006/0195133 | A1 | 8/2006 | Freeman et al. |
| 2006/0200020 | A1 | 9/2006 | Brister et al. |
| 2006/0200022 | A1 | 9/2006 | Brauker et al. |
| 2006/0200181 | A1 | 9/2006 | Fukuzawa et al. |
| 2006/0200970 | A1 | 9/2006 | Brister et al. |
| 2006/0200981 | A1 | 9/2006 | Bhullar et al. |
| 2006/0200982 | A1 | 9/2006 | Bhullar et al. |
| 2006/0202805 | A1 | 9/2006 | Schulman et al. |
| 2006/0202859 | A1 | 9/2006 | Mastrototaro et al. |
| 2006/0211921 | A1 | 9/2006 | Brauker et al. |
| 2006/0220839 | A1 | 10/2006 | Fifolt et al. |
| 2006/0222566 | A1 | 10/2006 | Brauker et al. |
| 2006/0222866 | A1 | 10/2006 | Nakamura et al. |
| 2006/0224108 | A1 | 10/2006 | Brauker et al. |
| 2006/0224109 | A1 | 10/2006 | Steil et al. |
| 2006/0224141 | A1 | 10/2006 | Rush et al. |
| 2006/0224171 | A1 | 10/2006 | Sakata et al. |
| 2006/0226985 | A1 | 10/2006 | Goodnow et al. |
| 2006/0229512 | A1 | 10/2006 | Petisce et al. |
| 2006/0233839 | A1 | 10/2006 | Jacquet |
| 2006/0247508 | A1 | 11/2006 | Fennell |
| 2006/0247710 | A1 | 11/2006 | Goetz et al. |
| 2006/0247895 | A1 | 11/2006 | Liamos et al. |
| 2006/0248398 | A1 | 11/2006 | Neel et al. |
| 2006/0253085 | A1 | 11/2006 | Geismar et al. |
| 2006/0253086 | A1 | 11/2006 | Moberg et al. |
| 2006/0258929 | A1 | 11/2006 | Goode, Jr. et al. |
| 2006/0258939 | A1 | 11/2006 | Pesach et al. |
| 2006/0258959 | A1 | 11/2006 | Sode |
| 2006/0264785 | A1 | 11/2006 | Dring et al. |
| 2006/0264888 | A1 | 11/2006 | Moberg et al. |
| 2006/0270922 | A1 | 11/2006 | Brauker et al. |
| 2006/0270923 | A1 | 11/2006 | Brauker et al. |
| 2006/0271013 | A1 | 11/2006 | Triplett et al. |
| 2006/0272652 | A1 | 12/2006 | Stocker et al. |
| 2006/0273759 | A1 | 12/2006 | Reggiardo |
| 2006/0276714 | A1 | 12/2006 | Holt et al. |
| 2006/0276724 | A1 | 12/2006 | Freeman et al. |
| 2006/0276771 | A1 | 12/2006 | Galley et al. |
| 2006/0281985 | A1 | 12/2006 | Ward et al. |
| 2006/0282042 | A1 | 12/2006 | Walters et al. |
| 2006/0287591 | A1 | 12/2006 | Ocvirk et al. |
| 2006/0287691 | A1 | 12/2006 | Drew |
| 2006/0290496 | A1 | 12/2006 | Peeters et al. |
| 2006/0293607 | A1 | 12/2006 | Alt et al. |
| 2007/0007133 | A1 | 1/2007 | Mang et al. |
| 2007/0010950 | A1 | 1/2007 | Abensour et al. |
| 2007/0016129 | A1 | 1/2007 | Liniger et al. |
| 2007/0016381 | A1 | 1/2007 | Kamath et al. |
| 2007/0017983 | A1 | 1/2007 | Frank et al. |
| 2007/0027381 | A1 | 2/2007 | Stafford |
| 2007/0027384 | A1 | 2/2007 | Brister et al. |
| 2007/0027385 | A1 | 2/2007 | Brister et al. |
| 2007/0027507 | A1 | 2/2007 | Burdett et al. |
| 2007/0030154 | A1 | 2/2007 | Aiki et al. |
| 2007/0032706 | A1 | 2/2007 | Kamath et al. |
| 2007/0032717 | A1 | 2/2007 | Brister et al. |
| 2007/0032718 | A1 | 2/2007 | Shults et al. |
| 2007/0033074 | A1 | 2/2007 | Nitzan et al. |
| 2007/0038044 | A1 | 2/2007 | Dobbles et al. |
| 2007/0045902 | A1 | 3/2007 | Brauker et al. |
| 2007/0049865 | A1 | 3/2007 | Radmer et al. |
| 2007/0055799 | A1 | 3/2007 | Koehler et al. |
| 2007/0056858 | A1 | 3/2007 | Chen et al. |
| 2007/0059196 | A1 | 3/2007 | Brister et al. |
| 2007/0060801 | A1 | 3/2007 | Neinast |
| 2007/0060814 | A1 | 3/2007 | Stafford |
| 2007/0060869 | A1 | 3/2007 | Tolle et al. |
| 2007/0066873 | A1 | 3/2007 | Kamath et al. |
| 2007/0068807 | A1 | 3/2007 | Feldman et al. |
| 2007/0071681 | A1 | 3/2007 | Gadkar et al. |
| 2007/0073129 | A1 | 3/2007 | Shah et al. |
| 2007/0078320 | A1 | 4/2007 | Stafford |
| 2007/0078321 | A1 | 4/2007 | Mazza et al. |
| 2007/0078322 | A1 | 4/2007 | Stafford |
| 2007/0078323 | A1 | 4/2007 | Reggiardo et al. |
| 2007/0088377 | A1 | 4/2007 | Levaughn et al. |
| 2007/0090511 | A1 | 4/2007 | Borland et al. |
| 2007/0093704 | A1 | 4/2007 | Brister et al. |
| 2007/0093754 | A1 | 4/2007 | Mogensen et al. |
| 2007/0093786 | A1 | 4/2007 | Goldsmith et al. |
| 2007/0095661 | A1 | 5/2007 | Wang et al. |
| 2007/0100218 | A1 | 5/2007 | Sweitzer et al. |
| 2007/0100222 | A1 | 5/2007 | Mastrototaro et al. |
| 2007/0106133 | A1 | 5/2007 | Satchwell et al. |
| 2007/0106135 | A1 | 5/2007 | Sloan et al. |
| 2007/0108048 | A1 | 5/2007 | Wang et al. |
| 2007/0110124 | A1 | 5/2007 | Shiraki et al. |
| 2007/0111196 | A1 | 5/2007 | Alarcon et al. |
| 2007/0123819 | A1 | 5/2007 | Mernoe et al. |
| 2007/0124002 | A1 | 5/2007 | Estes et al. |
| 2007/0129621 | A1 | 6/2007 | Kellogg et al. |
| 2007/0135696 | A1 | 6/2007 | Ward |
| 2007/0135774 | A1 | 6/2007 | Turner et al. |
| 2007/0149873 | A1 | 6/2007 | Say et al. |
| 2007/0149875 | A1 | 6/2007 | Ouyang et al. |
| 2007/0153705 | A1 | 7/2007 | Rosar et al. |
| 2007/0156033 | A1 | 7/2007 | Causey, III et al. |
| 2007/0156094 | A1 | 7/2007 | Safabash et al. |
| 2007/0163880 | A1 | 7/2007 | Woo et al. |
| 2007/0168224 | A1 | 7/2007 | Letzt et al. |
| 2007/0173706 | A1 | 7/2007 | Neinast et al. |
| 2007/0173709 | A1 | 7/2007 | Petisce et al. |
| 2007/0173710 | A1 | 7/2007 | Petisce et al. |
| 2007/0173711 | A1 | 7/2007 | Shah et al. |
| 2007/0173741 | A1 | 7/2007 | Deshmukh et al. |
| 2007/0173761 | A1 | 7/2007 | Kanderian et al. |
| 2007/0179349 | A1 | 8/2007 | Hoyme et al. |
| 2007/0179352 | A1 | 8/2007 | Randlov et al. |
| 2007/0179406 | A1 | 8/2007 | DeNuzzio et al. |
| 2007/0191701 | A1 | 8/2007 | Feldman et al. |
| 2007/0191702 | A1 | 8/2007 | Yodfat et al. |
| 2007/0197889 | A1 | 8/2007 | Brister et al. |
| 2007/0199818 | A1 | 8/2007 | Petyt et al. |
| 2007/0202562 | A1 | 8/2007 | Curry et al. |
| 2007/0203407 | A1 | 8/2007 | Hoss et al. |
| 2007/0203539 | A1 | 8/2007 | Stone et al. |
| 2007/0203966 | A1 | 8/2007 | Brauker et al. |
| 2007/0208244 | A1 | 9/2007 | Brauker et al. |

(56) References Cited

U.S. PATENT DOCUMENTS

2007/0208245 A1 9/2007 Brauker et al.
2007/0208246 A1 9/2007 Brauker et al.
2007/0213611 A1 9/2007 Simpson et al.
2007/0219480 A1 9/2007 Kamen et al.
2007/0219496 A1 9/2007 Kamen et al.
2007/0222609 A1 9/2007 Duron et al.
2007/0227911 A1 10/2007 Wang et al.
2007/0228071 A1 10/2007 Kamen et al.
2007/0231846 A1 10/2007 Cosentino et al.
2007/0232877 A1 10/2007 He
2007/0232878 A1 10/2007 Kovatchev et al.
2007/0232879 A1 10/2007 Brister et al.
2007/0232880 A1 10/2007 Siddiqui et al.
2007/0233013 A1 10/2007 Schoenberg et al.
2007/0235331 A1 10/2007 Simpson et al.
2007/0244368 A1 10/2007 Bayloff et al.
2007/0244379 A1 10/2007 Boock et al.
2007/0244383 A1 10/2007 Talbot et al.
2007/0244398 A1 10/2007 Lo et al.
2007/0249922 A1 10/2007 Peyser et al.
2007/0253021 A1 11/2007 Mehta et al.
2007/0255116 A1 11/2007 Mehta et al.
2007/0255125 A1 11/2007 Moberg et al.
2007/0255302 A1 11/2007 Koeppel et al.
2007/0255321 A1 11/2007 Gerber et al.
2007/0255348 A1 11/2007 Holtzclaw
2007/0255531 A1 11/2007 Drew
2007/0258395 A1 11/2007 Jollota et al.
2007/0270672 A1 11/2007 Hayter
2007/0282299 A1 12/2007 Hellwig
2007/0285238 A1 12/2007 Batra
2008/0004512 A1 1/2008 Funderburk et al.
2008/0004515 A1 1/2008 Jennewine et al.
2008/0004573 A1 1/2008 Kaufmann et al.
2008/0004601 A1 1/2008 Jennewine et al.
2008/0004904 A1 1/2008 Tran
2008/0009304 A1 1/2008 Fry
2008/0009692 A1 1/2008 Stafford
2008/0009805 A1 1/2008 Ethelfeld
2008/0017522 A1 1/2008 Heller et al.
2008/0018433 A1 1/2008 Pitt-Pladdy
2008/0021543 A1 1/2008 Shrivastava
2008/0021666 A1 1/2008 Goode, Jr. et al.
2008/0027296 A1 1/2008 Hadvary et al.
2008/0027474 A1 1/2008 Curry et al.
2008/0029391 A1 2/2008 Mao et al.
2008/0030369 A1 2/2008 Mann et al.
2008/0031941 A1 2/2008 Pettersson
2008/0033254 A1 2/2008 Kamath et al.
2008/0033268 A1 2/2008 Stafford
2008/0033273 A1 2/2008 Zhou et al.
2008/0033318 A1 2/2008 Mace et al.
2008/0039702 A1 2/2008 Hayter et al.
2008/0045824 A1 2/2008 Tapsak et al.
2008/0046038 A1 2/2008 Hill et al.
2008/0055070 A1 3/2008 Bange et al.
2008/0057484 A1 3/2008 Miyata et al.
2008/0058625 A1 3/2008 McGarraugh et al.
2008/0058626 A1 3/2008 Miyata et al.
2008/0058678 A1 3/2008 Miyata et al.
2008/0058773 A1 3/2008 John
2008/0058830 A1 3/2008 Cole et al.
2008/0059227 A1 3/2008 Clapp
2008/0060955 A1 3/2008 Goodnow
2008/0061961 A1 3/2008 John
2008/0062055 A1 3/2008 Cunningham et al.
2008/0064437 A1 3/2008 Chambers et al.
2008/0064937 A1 3/2008 McGarraugh et al.
2008/0064941 A1 3/2008 Funderburk et al.
2008/0064943 A1 3/2008 Talbot et al.
2008/0064944 A1 3/2008 VanAntwerp et al.
2008/0065646 A1 3/2008 Zhang et al.
2008/0066305 A1 3/2008 Wang et al.
2008/0067627 A1 3/2008 Boeck et al.
2008/0071156 A1 3/2008 Brister et al.
2008/0071157 A1 3/2008 McGarraugh et al.
2008/0071158 A1 3/2008 McGarraugh et al.
2008/0071328 A1 3/2008 Haubrich et al.
2008/0071580 A1 3/2008 Marcus
2008/0081977 A1 4/2008 Hayter et al.
2008/0083617 A1 4/2008 Simpson et al.
2008/0086042 A1 4/2008 Brister et al.
2008/0086044 A1 4/2008 Brister et al.
2008/0086273 A1 4/2008 Shults et al.
2008/0092638 A1 4/2008 Brenneman et al.
2008/0092911 A1 4/2008 Schulman et al.
2008/0097246 A1 4/2008 Stafford
2008/0097289 A1 4/2008 Steil et al.
2008/0097908 A1 4/2008 Dicks et al.
2008/0099332 A1 5/2008 Scott et al.
2008/0102441 A1 5/2008 Chen et al.
2008/0108942 A1 5/2008 Brister et al.
2008/0112848 A1 5/2008 Huffstodt et al.
2008/0114228 A1 5/2008 McCluskey et al.
2008/0114280 A1 5/2008 Stafford
2008/0119705 A1 5/2008 Patel et al.
2008/0119707 A1 5/2008 Stafford
2008/0119710 A1 5/2008 Reggiardo et al.
2008/0125636 A1 5/2008 Ward et al.
2008/0127052 A1 5/2008 Rostoker
2008/0129486 A1 6/2008 Jeckelmann et al.
2008/0133059 A1 6/2008 Trippel et al.
2008/0133702 A1 6/2008 Sharma et al.
2008/0139910 A1 6/2008 Mastrototaro et al.
2008/0146904 A1 6/2008 Hunn
2008/0148873 A1 6/2008 Wang
2008/0154205 A1 6/2008 Wojcik
2008/0154286 A1 6/2008 Abbott et al.
2008/0154513 A1 6/2008 Kovatchev et al.
2008/0161664 A1 7/2008 Mastrototaro et al.
2008/0161666 A1 7/2008 Feldman et al.
2008/0167543 A1 7/2008 Say et al.
2008/0167572 A1 7/2008 Stivoric et al.
2008/0167578 A1 7/2008 Bryer et al.
2008/0172205 A1 7/2008 Breton et al.
2008/0177149 A1 7/2008 Weinart et al.
2008/0177165 A1 7/2008 Blomquist et al.
2008/0179187 A1 7/2008 Ouyang
2008/0182537 A1 7/2008 Manku et al.
2008/0183060 A1 7/2008 Steil et al.
2008/0183061 A1 7/2008 Goode, Jr. et al.
2008/0183399 A1 7/2008 Goode, Jr. et al.
2008/0188731 A1 8/2008 Brister et al.
2008/0188796 A1 8/2008 Steil et al.
2008/0189051 A1 8/2008 Goode, Jr. et al.
2008/0194926 A1 8/2008 Goh et al.
2008/0194934 A1 8/2008 Ray et al.
2008/0194935 A1 8/2008 Brister et al.
2008/0194936 A1 8/2008 Goode, Jr. et al.
2008/0194937 A1 8/2008 Goode, Jr. et al.
2008/0194938 A1 8/2008 Brister et al.
2008/0195049 A1 8/2008 Thalmann et al.
2008/0195232 A1 8/2008 Carr-Brendel et al.
2008/0195967 A1 8/2008 Goode, Jr. et al.
2008/0197024 A1 8/2008 Simpson et al.
2008/0200788 A1 8/2008 Brister et al.
2008/0200789 A1 8/2008 Brister et al.
2008/0200791 A1 8/2008 Simpson et al.
2008/0200897 A1 8/2008 Hoss et al.
2008/0201325 A1 8/2008 Doniger et al.
2008/0208025 A1 8/2008 Shults et al.
2008/0208026 A1 8/2008 Noujaim et al.
2008/0208113 A1 8/2008 Damiano et al.
2008/0214481 A1 9/2008 Challoner et al.
2008/0214900 A1 9/2008 Fennell et al.
2008/0214910 A1 9/2008 Buck
2008/0214915 A1 9/2008 Brister et al.
2008/0214918 A1 9/2008 Brister et al.
2008/0215035 A1 9/2008 Yodfat et al.
2008/0228051 A1 9/2008 Shults et al.
2008/0228054 A1 9/2008 Shults et al.
2008/0234561 A1 9/2008 Roesicke et al.
2008/0234992 A1 9/2008 Ray et al.
2008/0235469 A1 9/2008 Drew

(56) References Cited

U.S. PATENT DOCUMENTS

| | | | |
|---|---|---|---|
| 2008/0242961 | A1 | 10/2008 | Brister et al. |
| 2008/0242962 | A1 | 10/2008 | Roesicke et al. |
| 2008/0242963 | A1 | 10/2008 | Essenpreis et al. |
| 2008/0243051 | A1 | 10/2008 | DeStefano |
| 2008/0252459 | A1 | 10/2008 | Butler et al. |
| 2008/0254544 | A1 | 10/2008 | Modzelewski et al. |
| 2008/0255434 | A1 | 10/2008 | Hayter et al. |
| 2008/0255437 | A1 | 10/2008 | Hayter |
| 2008/0255438 | A1 | 10/2008 | Saidara et al. |
| 2008/0255440 | A1 | 10/2008 | Eilerson et al. |
| 2008/0255808 | A1 | 10/2008 | Hayter |
| 2008/0256048 | A1 | 10/2008 | Hayter |
| 2008/0262300 | A1 | 10/2008 | Reynolds et al. |
| 2008/0262469 | A1 | 10/2008 | Brister et al. |
| 2008/0267823 | A1 | 10/2008 | Wang et al. |
| 2008/0269584 | A1 | 10/2008 | Shekalim |
| 2008/0269673 | A1 | 10/2008 | Butoi et al. |
| 2008/0269683 | A1 | 10/2008 | Bikovsky |
| 2008/0269687 | A1 | 10/2008 | Chong et al. |
| 2008/0269714 | A1 | 10/2008 | Mastrototaro et al. |
| 2008/0275313 | A1 | 11/2008 | Brister et al. |
| 2008/0275327 | A1 | 11/2008 | Faarbaek et al. |
| 2008/0278333 | A1 | 11/2008 | Fennell et al. |
| 2008/0281178 | A1 | 11/2008 | Chuang et al. |
| 2008/0281179 | A1 | 11/2008 | Fennell et al. |
| 2008/0283396 | A1 | 11/2008 | Wang et al. |
| 2008/0287755 | A1 | 11/2008 | Sass et al. |
| 2008/0287761 | A1 | 11/2008 | Hayter |
| 2008/0287762 | A1 | 11/2008 | Hayter |
| 2008/0287763 | A1 | 11/2008 | Hayter |
| 2008/0287764 | A1 | 11/2008 | Rasdal et al. |
| 2008/0287765 | A1 | 11/2008 | Rasdal et al. |
| 2008/0287766 | A1 | 11/2008 | Rasdal et al. |
| 2008/0288180 | A1 | 11/2008 | Hayter |
| 2008/0288204 | A1 | 11/2008 | Hayter et al. |
| 2008/0294024 | A1 | 11/2008 | Cosentino et al. |
| 2008/0294096 | A1 | 11/2008 | Uber et al. |
| 2008/0296155 | A1 | 12/2008 | Shults et al. |
| 2008/0300476 | A1 | 12/2008 | Stafford |
| 2008/0300572 | A1 | 12/2008 | Rankers et al. |
| 2008/0306368 | A1 | 12/2008 | Goode, Jr. et al. |
| 2008/0306434 | A1 | 12/2008 | Dobbles et al. |
| 2008/0306435 | A1 | 12/2008 | Kamath et al. |
| 2008/0306444 | A1 | 12/2008 | Brister et al. |
| 2008/0308523 | A1 | 12/2008 | Krulevitch et al. |
| 2008/0312518 | A1 | 12/2008 | Jina et al. |
| 2008/0312601 | A1 | 12/2008 | Cane |
| 2008/0312841 | A1 | 12/2008 | Hayter |
| 2008/0312842 | A1 | 12/2008 | Hayter |
| 2008/0312844 | A1 | 12/2008 | Hayter et al. |
| 2008/0312845 | A1 | 12/2008 | Hayter et al. |
| 2008/0312859 | A1 | 12/2008 | Skyggebjerg et al. |
| 2008/0319085 | A1 | 12/2008 | Wright et al. |
| 2008/0319295 | A1 | 12/2008 | Bernstein et al. |
| 2008/0319296 | A1 | 12/2008 | Bernstein et al. |
| 2008/0319414 | A1 | 12/2008 | Yodfat et al. |
| 2008/0319416 | A1 | 12/2008 | Yodfat et al. |
| 2009/0005659 | A1 | 1/2009 | Kollias et al. |
| 2009/0005665 | A1 | 1/2009 | Hayter et al. |
| 2009/0005666 | A1 | 1/2009 | Shin et al. |
| 2009/0005729 | A1 | 1/2009 | Hendrixson et al. |
| 2009/0006034 | A1 | 1/2009 | Hayter et al. |
| 2009/0006061 | A1 | 1/2009 | Thukral et al. |
| 2009/0006133 | A1 | 1/2009 | Weinart et al. |
| 2009/0012376 | A1 | 1/2009 | Agus |
| 2009/0012377 | A1 | 1/2009 | Jennewine et al. |
| 2009/0012379 | A1 | 1/2009 | Goode, Jr. et al. |
| 2009/0018424 | A1 | 1/2009 | Kamath et al. |
| 2009/0018425 | A1 | 1/2009 | Ouyang et al. |
| 2009/0020502 | A1 | 1/2009 | Bhullar et al. |
| 2009/0028824 | A1 | 1/2009 | Chiang et al. |
| 2009/0030293 | A1 | 1/2009 | Cooper et al. |
| 2009/0030294 | A1 | 1/2009 | Petisce et al. |
| 2009/0033482 | A1 | 2/2009 | Hayter et al. |
| 2009/0036747 | A1 | 2/2009 | Hayter et al. |
| 2009/0036758 | A1 | 2/2009 | Brauker et al. |
| 2009/0036760 | A1 | 2/2009 | Hayter |
| 2009/0036763 | A1 | 2/2009 | Brauker et al. |
| 2009/0036915 | A1 | 2/2009 | Karbowniczek et al. |
| 2009/0040022 | A1 | 2/2009 | Finkenzeller |
| 2009/0043181 | A1 | 2/2009 | Brauker et al. |
| 2009/0043182 | A1 | 2/2009 | Brauker et al. |
| 2009/0043525 | A1 | 2/2009 | Brauker et al. |
| 2009/0043541 | A1 | 2/2009 | Brauker et al. |
| 2009/0043542 | A1 | 2/2009 | Brauker et al. |
| 2009/0045055 | A1 | 2/2009 | Rhodes et al. |
| 2009/0048499 | A1 | 2/2009 | Glejbol |
| 2009/0048503 | A1 | 2/2009 | Dalal et al. |
| 2009/0048563 | A1 | 2/2009 | Ethelfeld et al. |
| 2009/0054737 | A1 | 2/2009 | Magar et al. |
| 2009/0054745 | A1 | 2/2009 | Jennewine et al. |
| 2009/0054747 | A1 | 2/2009 | Fennell |
| 2009/0054748 | A1 | 2/2009 | Feldman et al. |
| 2009/0054753 | A1 | 2/2009 | Robinson et al. |
| 2009/0054866 | A1 | 2/2009 | Teisen-Simony et al. |
| 2009/0055149 | A1 | 2/2009 | Hayter et al. |
| 2009/0058635 | A1 | 3/2009 | LaLonde et al. |
| 2009/0062633 | A1 | 3/2009 | Brauker et al. |
| 2009/0062635 | A1 | 3/2009 | Brauker et al. |
| 2009/0062767 | A1 | 3/2009 | Van Antwerp et al. |
| 2009/0063187 | A1 | 3/2009 | Johnson et al. |
| 2009/0063402 | A1 | 3/2009 | Hayter |
| 2009/0069658 | A1 | 3/2009 | Say et al. |
| 2009/0069750 | A1 | 3/2009 | Schraga |
| 2009/0076356 | A1 | 3/2009 | Simpson et al. |
| 2009/0076359 | A1 | 3/2009 | Peyser |
| 2009/0076360 | A1 | 3/2009 | Brister et al. |
| 2009/0076361 | A1 | 3/2009 | Kamath et al. |
| 2009/0082693 | A1 | 3/2009 | Stafford |
| 2009/0085768 | A1 | 4/2009 | Patel et al. |
| 2009/0085873 | A1 | 4/2009 | Betts et al. |
| 2009/0088614 | A1 | 4/2009 | Taub |
| 2009/0088787 | A1 | 4/2009 | Koike et al. |
| 2009/0093687 | A1 | 4/2009 | Telfort et al. |
| 2009/0099436 | A1 | 4/2009 | Brister et al. |
| 2009/0099521 | A1 | 4/2009 | Gravesen et al. |
| 2009/0102678 | A1 | 4/2009 | Mazza et al. |
| 2009/0105554 | A1 | 4/2009 | Stahmann et al. |
| 2009/0105560 | A1 | 4/2009 | Solomon |
| 2009/0105568 | A1 | 4/2009 | Bugler |
| 2009/0105569 | A1 | 4/2009 | Stafford |
| 2009/0105570 | A1 | 4/2009 | Sloan et al. |
| 2009/0105571 | A1 | 4/2009 | Fennell et al. |
| 2009/0105636 | A1 | 4/2009 | Hayter et al. |
| 2009/0108992 | A1 | 4/2009 | Shafer |
| 2009/0112123 | A1 | 4/2009 | Freeman et al. |
| 2009/0112478 | A1 | 4/2009 | Mueller, Jr. et al. |
| 2009/0118592 | A1 | 5/2009 | Klitgaard |
| 2009/0124877 | A1 | 5/2009 | Goode, Jr. et al. |
| 2009/0124878 | A1 | 5/2009 | Goode, Jr. et al. |
| 2009/0124879 | A1 | 5/2009 | Brister et al. |
| 2009/0124964 | A1 | 5/2009 | Leach et al. |
| 2009/0124979 | A1 | 5/2009 | Raymond et al. |
| 2009/0131768 | A1 | 5/2009 | Simpson et al. |
| 2009/0131769 | A1 | 5/2009 | Leach et al. |
| 2009/0131776 | A1 | 5/2009 | Simpson et al. |
| 2009/0131777 | A1 | 5/2009 | Simpson et al. |
| 2009/0131860 | A1 | 5/2009 | Nielsen |
| 2009/0137886 | A1 | 5/2009 | Shariati et al. |
| 2009/0137887 | A1 | 5/2009 | Shariati et al. |
| 2009/0143659 | A1 | 6/2009 | Li et al. |
| 2009/0143660 | A1 | 6/2009 | Brister et al. |
| 2009/0149728 | A1 | 6/2009 | Van Antwerp et al. |
| 2009/0150186 | A1 | 6/2009 | Cohen et al. |
| 2009/0150454 | A1 | 6/2009 | Gejdos et al. |
| 2009/0156919 | A1 | 6/2009 | Brister et al. |
| 2009/0156924 | A1 | 6/2009 | Shariati et al. |
| 2009/0163790 | A1 | 6/2009 | Brister et al. |
| 2009/0163791 | A1 | 6/2009 | Brister et al. |
| 2009/0163855 | A1 | 6/2009 | Shin et al. |
| 2009/0164190 | A1 | 6/2009 | Hayter |
| 2009/0164239 | A1 | 6/2009 | Hayter et al. |
| 2009/0164251 | A1 | 6/2009 | Hayter |
| 2009/0171182 | A1 | 7/2009 | Stafford |

(56) References Cited

U.S. PATENT DOCUMENTS

| | | | |
|---|---|---|---|
| 2009/0177068 | A1 | 7/2009 | Stivoric et al. |
| 2009/0178459 | A1 | 7/2009 | Li et al. |
| 2009/0182217 | A1 | 7/2009 | Li et al. |
| 2009/0189738 | A1 | 7/2009 | Hermle |
| 2009/0192366 | A1 | 7/2009 | Mensinger et al. |
| 2009/0192380 | A1 | 7/2009 | Shariati et al. |
| 2009/0192722 | A1 | 7/2009 | Shariati et al. |
| 2009/0192724 | A1 | 7/2009 | Brauker et al. |
| 2009/0192745 | A1 | 7/2009 | Kamath et al. |
| 2009/0192751 | A1 | 7/2009 | Kamath et al. |
| 2009/0198118 | A1 | 8/2009 | Hayter et al. |
| 2009/0198186 | A1 | 8/2009 | Mernoe et al. |
| 2009/0198215 | A1 | 8/2009 | Chong et al. |
| 2009/0203981 | A1 | 8/2009 | Brauker et al. |
| 2009/0204340 | A1 | 8/2009 | Feldman et al. |
| 2009/0204341 | A1 | 8/2009 | Brauker et al. |
| 2009/0210249 | A1 | 8/2009 | Rasch-Menges et al. |
| 2009/0212766 | A1 | 8/2009 | Olson et al. |
| 2009/0216100 | A1 | 8/2009 | Ebner et al. |
| 2009/0216103 | A1 | 8/2009 | Brister et al. |
| 2009/0216215 | A1 | 8/2009 | Thalmann et al. |
| 2009/0234200 | A1 | 9/2009 | Husheer |
| 2009/0240120 | A1 | 9/2009 | Mensinger et al. |
| 2009/0240121 | A1 | 9/2009 | Bickoff |
| 2009/0240128 | A1 | 9/2009 | Mensinger et al. |
| 2009/0240193 | A1 | 9/2009 | Mensinger et al. |
| 2009/0242399 | A1 | 10/2009 | Kamath et al. |
| 2009/0242425 | A1 | 10/2009 | Kamath et al. |
| 2009/0247855 | A1 | 10/2009 | Boock et al. |
| 2009/0247856 | A1 | 10/2009 | Boock et al. |
| 2009/0247857 | A1 | 10/2009 | Harper et al. |
| 2009/0247931 | A1 | 10/2009 | Damgaard-Sorenson |
| 2009/0253973 | A1 | 10/2009 | Bashan et al. |
| 2009/0259118 | A1 | 10/2009 | Feldman et al. |
| 2009/0259201 | A1 | 10/2009 | Hwang et al. |
| 2009/0259202 | A1 | 10/2009 | Leeflang et al. |
| 2009/0267765 | A1 | 10/2009 | Greene et al. |
| 2009/0270765 | A1 | 10/2009 | Ghesquire et al. |
| 2009/0277242 | A1 | 11/2009 | Crane et al. |
| 2009/0281406 | A1 | 11/2009 | McGarraugh et al. |
| 2009/0287073 | A1 | 11/2009 | Boock et al. |
| 2009/0287074 | A1 | 11/2009 | Shults et al. |
| 2009/0289796 | A1 | 11/2009 | Blumberg |
| 2009/0292184 | A1 | 11/2009 | Funderburk et al. |
| 2009/0292185 | A1 | 11/2009 | Funderburk et al. |
| 2009/0294277 | A1 | 12/2009 | Thomas et al. |
| 2009/0298182 | A1 | 12/2009 | Schulat et al. |
| 2009/0299152 | A1 | 12/2009 | Taub et al. |
| 2009/0299155 | A1 | 12/2009 | Yang et al. |
| 2009/0299156 | A1 | 12/2009 | Simpson et al. |
| 2009/0299162 | A1 | 12/2009 | Brauker et al. |
| 2009/0299167 | A1 | 12/2009 | Seymour |
| 2009/0299276 | A1 | 12/2009 | Brauker et al. |
| 2009/0299301 | A1 | 12/2009 | Gottleib et al. |
| 2010/0004597 | A1 | 1/2010 | Gryn et al. |
| 2010/0010324 | A1 | 1/2010 | Brauker et al. |
| 2010/0010329 | A1 | 1/2010 | Taub et al. |
| 2010/0010331 | A1 | 1/2010 | Brauker et al. |
| 2010/0010332 | A1 | 1/2010 | Brauker et al. |
| 2010/0014626 | A1 | 1/2010 | Fennell et al. |
| 2010/0016687 | A1 | 1/2010 | Brauker et al. |
| 2010/0016698 | A1 | 1/2010 | Rasdal et al. |
| 2010/0022855 | A1 | 1/2010 | Brauker et al. |
| 2010/0022863 | A1 | 1/2010 | Mogensen et al. |
| 2010/0022988 | A1 | 1/2010 | Wochner et al. |
| 2010/0025238 | A1 | 2/2010 | Gottlieb et al. |
| 2010/0030038 | A1 | 2/2010 | Brauker et al. |
| 2010/0030053 | A1 | 2/2010 | Goode, Jr. et al. |
| 2010/0030111 | A1 | 2/2010 | Perriere |
| 2010/0030484 | A1 | 2/2010 | Brauker et al. |
| 2010/0030485 | A1 | 2/2010 | Brauker et al. |
| 2010/0036215 | A1 | 2/2010 | Goode, Jr. et al. |
| 2010/0036216 | A1 | 2/2010 | Goode, Jr. et al. |
| 2010/0036222 | A1 | 2/2010 | Goode, Jr. et al. |
| 2010/0036223 | A1 | 2/2010 | Goode, Jr. et al. |
| 2010/0036225 | A1 | 2/2010 | Goode, Jr. et al. |
| 2010/0036281 | A1 | 2/2010 | Doi |
| 2010/0041971 | A1 | 2/2010 | Goode, Jr. et al. |
| 2010/0045465 | A1 | 2/2010 | Brauker et al. |
| 2010/0049014 | A1 | 2/2010 | Funderburk et al. |
| 2010/0049024 | A1 | 2/2010 | Saint et al. |
| 2010/0049129 | A1 | 2/2010 | Yokoi et al. |
| 2010/0057040 | A1 | 3/2010 | Hayter |
| 2010/0057041 | A1 | 3/2010 | Hayter |
| 2010/0057042 | A1 | 3/2010 | Hayter |
| 2010/0057044 | A1 | 3/2010 | Hayter |
| 2010/0057057 | A1 | 3/2010 | Hayter et al. |
| 2010/0063373 | A1 | 3/2010 | Kamath et al. |
| 2010/0069728 | A1 | 3/2010 | Funderburk et al. |
| 2010/0076283 | A1 | 3/2010 | Simpson et al. |
| 2010/0076379 | A1 | 3/2010 | Matusch |
| 2010/0081905 | A1 | 4/2010 | Bommakanti et al. |
| 2010/0081906 | A1 | 4/2010 | Hayter et al. |
| 2010/0081908 | A1 | 4/2010 | Dobbles et al. |
| 2010/0081910 | A1 | 4/2010 | Brister et al. |
| 2010/0081953 | A1 | 4/2010 | Syeda-Mahmood et al. |
| 2010/0087724 | A1 | 4/2010 | Brauker et al. |
| 2010/0094251 | A1 | 4/2010 | Estes et al. |
| 2010/0096259 | A1 | 4/2010 | Zhang et al. |
| 2010/0099970 | A1 | 4/2010 | Shults et al. |
| 2010/0099971 | A1 | 4/2010 | Shults et al. |
| 2010/0100113 | A1 | 4/2010 | Iio et al. |
| 2010/0105999 | A1 | 4/2010 | Dixon et al. |
| 2010/0106088 | A1 | 4/2010 | Yodfat et al. |
| 2010/0113897 | A1 | 5/2010 | Brenneman et al. |
| 2010/0119693 | A1 | 5/2010 | Tapsak et al. |
| 2010/0119881 | A1 | 5/2010 | Patel et al. |
| 2010/0121167 | A1 | 5/2010 | McGarraugh et al. |
| 2010/0121169 | A1 | 5/2010 | Petisce et al. |
| 2010/0137695 | A1 | 6/2010 | Yodfat et al. |
| 2010/0141656 | A1 | 6/2010 | Krieftewirth |
| 2010/0145229 | A1 | 6/2010 | Perez et al. |
| 2010/0145377 | A1 | 6/2010 | Lai et al. |
| 2010/0146300 | A1 | 6/2010 | Brown |
| 2010/0152548 | A1 | 6/2010 | Koski |
| 2010/0152554 | A1 | 6/2010 | Steine et al. |
| 2010/0152674 | A1 | 6/2010 | Kavazov et al. |
| 2010/0160757 | A1 | 6/2010 | Weinart et al. |
| 2010/0160759 | A1 | 6/2010 | Celentano et al. |
| 2010/0160760 | A1 | 6/2010 | Shults et al. |
| 2010/0161269 | A1 | 6/2010 | Kamath et al. |
| 2010/0168538 | A1 | 7/2010 | Keenan et al. |
| 2010/0168540 | A1 | 7/2010 | Kamath et al. |
| 2010/0168541 | A1 | 7/2010 | Kamath et al. |
| 2010/0168542 | A1 | 7/2010 | Kamath et al. |
| 2010/0168543 | A1 | 7/2010 | Kamath et al. |
| 2010/0168544 | A1 | 7/2010 | Kamath et al. |
| 2010/0168545 | A1 | 7/2010 | Kamath et al. |
| 2010/0168546 | A1 | 7/2010 | Kamath et al. |
| 2010/0168547 | A1 | 7/2010 | Kamath et al. |
| 2010/0168660 | A1 | 7/2010 | Galley et al. |
| 2010/0168677 | A1 | 7/2010 | Gabriel et al. |
| 2010/0174157 | A1 | 7/2010 | Brister et al. |
| 2010/0174158 | A1 | 7/2010 | Kamath et al. |
| 2010/0174163 | A1 | 7/2010 | Brister et al. |
| 2010/0174164 | A1 | 7/2010 | Brister et al. |
| 2010/0174165 | A1 | 7/2010 | Brister et al. |
| 2010/0174166 | A1 | 7/2010 | Brister et al. |
| 2010/0174167 | A1 | 7/2010 | Kamath et al. |
| 2010/0174168 | A1 | 7/2010 | Goode, Jr. et al. |
| 2010/0174266 | A1 | 7/2010 | Estes |
| 2010/0179399 | A1 | 7/2010 | Goode, Jr. et al. |
| 2010/0179400 | A1 | 7/2010 | Brauker et al. |
| 2010/0179401 | A1 | 7/2010 | Rasdal et al. |
| 2010/0179402 | A1 | 7/2010 | Goode, Jr. et al. |
| 2010/0179404 | A1 | 7/2010 | Kamath et al. |
| 2010/0179405 | A1 | 7/2010 | Goode, Jr. et al. |
| 2010/0179407 | A1 | 7/2010 | Goode, Jr. et al. |
| 2010/0179408 | A1 | 7/2010 | Kamath et al. |
| 2010/0179409 | A1 | 7/2010 | Kamath et al. |
| 2010/0185065 | A1 | 7/2010 | Goode, Jr. et al. |
| 2010/0185069 | A1 | 7/2010 | Brister et al. |
| 2010/0185070 | A1 | 7/2010 | Brister et al. |
| 2010/0185071 | A1 | 7/2010 | Simpson et al. |

(56) References Cited

U.S. PATENT DOCUMENTS

2010/0185072 A1 7/2010 Goode, Jr. et al.
2010/0185073 A1 7/2010 Goode, Jr. et al.
2010/0185074 A1 7/2010 Goode, Jr. et al.
2010/0185075 A1 7/2010 Brister et al.
2010/0185175 A1 7/2010 Kamen et al.
2010/0190435 A1 7/2010 Cook et al.
2010/0191082 A1 7/2010 Brister et al.
2010/0191087 A1 7/2010 Talbot et al.
2010/0191472 A1 7/2010 Doniger et al.
2010/0198033 A1 8/2010 Krulevitch et al.
2010/0198034 A1 8/2010 Thomas et al.
2010/0198035 A1 8/2010 Kamath et al.
2010/0198036 A1 8/2010 Kamath et al.
2010/0198042 A1 8/2010 Sloan et al.
2010/0198142 A1 8/2010 Sloan et al.
2010/0198314 A1 8/2010 Wei
2010/0204557 A1 8/2010 Kiaie et al.
2010/0204653 A1 8/2010 Gryn et al.
2010/0212583 A1 8/2010 Brister et al.
2010/0213057 A1 8/2010 Feldman et al.
2010/0213080 A1 8/2010 Celentano et al.
2010/0214104 A1 8/2010 Goode, Jr. et al.
2010/0217105 A1 8/2010 Yodfat et al.
2010/0217557 A1 8/2010 Kamath et al.
2010/0223013 A1 9/2010 Kamath et al.
2010/0223022 A1 9/2010 Kamath et al.
2010/0223023 A1 9/2010 Kamath et al.
2010/0228109 A1 9/2010 Kamath et al.
2010/0228111 A1 9/2010 Friman et al.
2010/0228497 A1 9/2010 Kamath et al.
2010/0230285 A1 9/2010 Hoss et al.
2010/0235439 A1 9/2010 Goodnow et al.
2010/0240975 A1 9/2010 Goode, Jr. et al.
2010/0240976 A1 9/2010 Goode, Jr. et al.
2010/0256471 A1 10/2010 Say et al.
2010/0259543 A1 10/2010 Tarassenko et al.
2010/0261987 A1 10/2010 Kamath et al.
2010/0262183 A1 10/2010 Abbott et al.
2010/0262201 A1 10/2010 He et al.
2010/0267161 A1 10/2010 Wu et al.
2010/0274107 A1 10/2010 Boock et al.
2010/0274111 A1 10/2010 Say et al.
2010/0274515 A1 10/2010 Hoss et al.
2010/0275108 A1 10/2010 Sloan et al.
2010/0280341 A1 11/2010 Boock et al.
2010/0286496 A1 11/2010 Simpson et al.
2010/0298684 A1 11/2010 Leach et al.
2010/0312176 A1 12/2010 Lauer et al.
2010/0313105 A1 12/2010 Nekoomaram et al.
2010/0317952 A1 12/2010 Budiman et al.
2010/0324392 A1 12/2010 Yee et al.
2010/0324403 A1 12/2010 Brister et al.
2010/0325868 A1 12/2010 Wang et al.
2010/0326842 A1 12/2010 Mazza et al.
2010/0331642 A1 12/2010 Bruce et al.
2010/0331644 A1 12/2010 Neale et al.
2010/0331647 A1 12/2010 Shah et al.
2010/0331648 A1 12/2010 Kamath et al.
2010/0331651 A1 12/2010 Groll
2010/0331653 A1 12/2010 Stafford
2010/0331656 A1 12/2010 Mensinger et al.
2010/0331657 A1 12/2010 Mensinger et al.
2011/0004085 A1 1/2011 Mensinger et al.
2011/0004276 A1 1/2011 Blair et al.
2011/0009727 A1 1/2011 Mensinger et al.
2011/0015509 A1 1/2011 Peyser
2011/0016691 A1 1/2011 Alden et al.
2011/0021889 A1 1/2011 Hoss et al.
2011/0022411 A1 1/2011 Hjelm et al.
2011/0024043 A1 2/2011 Boock et al.
2011/0024307 A1 2/2011 Simpson et al.
2011/0027127 A1 2/2011 Simpson et al.
2011/0027453 A1 2/2011 Boock et al.
2011/0027458 A1 2/2011 Boock et al.
2011/0028815 A1 2/2011 Simpson et al.
2011/0028816 A1 2/2011 Simpson et al.
2011/0031986 A1 2/2011 Bhat et al.
2011/0040163 A1 2/2011 Telson et al.
2011/0040256 A1 2/2011 Bobroff et al.
2011/0040263 A1 2/2011 Hordum et al.
2011/0046456 A1 2/2011 Hordum et al.
2011/0046467 A1 2/2011 Simpson et al.
2011/0046977 A1 2/2011 Goodnow et al.
2011/0054275 A1 3/2011 Stafford
2011/0054282 A1 3/2011 Nekoomaram et al.
2011/0060196 A1 3/2011 Stafford
2011/0060530 A1 3/2011 Fennell
2011/0070633 A1 3/2011 Matsumoto et al.
2011/0073475 A1* 3/2011 Kastanos ........... A61B 5/14865 204/403.01
2011/0077469 A1 3/2011 Blocker et al.
2011/0077490 A1 3/2011 Simpson et al.
2011/0077494 A1 3/2011 Doniger et al.
2011/0077659 A1 3/2011 Mandecki et al.
2011/0081726 A1 4/2011 Berman et al.
2011/0082484 A1 4/2011 Saravia et al.
2011/0087196 A1 4/2011 Hunn et al.
2011/0097090 A1 4/2011 Cao
2011/0106126 A1 5/2011 Love et al.
2011/0112696 A1 5/2011 Yodfat et al.
2011/0118579 A1 5/2011 Goode, Jr. et al.
2011/0118580 A1 5/2011 Goode, Jr. et al.
2011/0123971 A1 5/2011 Berkowitz et al.
2011/0124992 A1 5/2011 Brauker et al.
2011/0124997 A1 5/2011 Goode, Jr. et al.
2011/0125040 A1 5/2011 Crawford et al.
2011/0125410 A1 5/2011 Goode, Jr. et al.
2011/0130970 A1 6/2011 Goode, Jr. et al.
2011/0130971 A1 6/2011 Goode, Jr. et al.
2011/0130998 A1 6/2011 Goode, Jr. et al.
2011/0137257 A1 6/2011 Gymn et al.
2011/0137571 A1 6/2011 Power et al.
2011/0144465 A1 6/2011 Shults et al.
2011/0148905 A1 6/2011 Simmons et al.
2011/0152637 A1 6/2011 Kateraas et al.
2011/0152778 A1 6/2011 Gyrn
2011/0172510 A1 7/2011 Chickering, III et al.
2011/0178378 A1 7/2011 Brister et al.
2011/0178461 A1 7/2011 Chong et al.
2011/0184258 A1 7/2011 Stafford
2011/0184482 A1 7/2011 Eberman et al.
2011/0184752 A1 7/2011 Ray et al.
2011/0190603 A1 8/2011 Stafford
2011/0190614 A1 8/2011 Brister et al.
2011/0191044 A1 8/2011 Stafford
2011/0193704 A1 8/2011 Harper et al.
2011/0201910 A1 8/2011 Rasdal et al.
2011/0201911 A1 8/2011 Johnson et al.
2011/0208027 A1 8/2011 Wagner et al.
2011/0213225 A1* 9/2011 Bernstein ......... G01N 33/48792 600/309
2011/0218414 A1 9/2011 Kamath et al.
2011/0218490 A1 9/2011 Ocvirk et al.
2011/0230741 A1 9/2011 Liang et al.
2011/0231107 A1 9/2011 Brauker et al.
2011/0231140 A1 9/2011 Goode, Jr. et al.
2011/0231141 A1 9/2011 Goode, Jr. et al.
2011/0231142 A1 9/2011 Goode, Jr. et al.
2011/0253533 A1 10/2011 Shults et al.
2011/0257495 A1 10/2011 Hoss et al.
2011/0257521 A1 10/2011 Fraden
2011/0257895 A1 10/2011 Brauker et al.
2011/0263958 A1 10/2011 Brauker et al.
2011/0263959 A1 10/2011 Young et al.
2011/0264378 A1 10/2011 Breton et al.
2011/0270062 A1 11/2011 Goode, Jr. et al.
2011/0270158 A1 11/2011 Brauker et al.
2011/0275919 A1 11/2011 Petisce et al.
2011/0282327 A1 11/2011 Kellogg et al.
2011/0287528 A1 11/2011 Fern et al.
2011/0288574 A1 11/2011 Curry et al.
2011/0289497 A1 11/2011 Kiaie et al.
2011/0290645 A1 12/2011 Brister et al.
2011/0313543 A1 12/2011 Brauker et al.

(56) References Cited

U.S. PATENT DOCUMENTS

| | | | |
|---|---|---|---|
| 2011/0319729 | A1 | 12/2011 | Donnay et al. |
| 2011/0319733 | A1 | 12/2011 | Stafford |
| 2011/0319738 | A1 | 12/2011 | Woodruff et al. |
| 2011/0319739 | A1 | 12/2011 | Kamath et al. |
| 2011/0320130 | A1 | 12/2011 | Valdes et al. |
| 2012/0010642 | A1 | 1/2012 | Lee et al. |
| 2012/0035445 | A1 | 2/2012 | Boock et al. |
| 2012/0040101 | A1 | 2/2012 | Tapsak et al. |
| 2012/0046534 | A1 | 2/2012 | Simpson et al. |
| 2012/0078071 | A1 | 3/2012 | Bohm et al. |
| 2012/0088995 | A1 | 4/2012 | Fennell et al. |
| 2012/0095406 | A1 | 4/2012 | Gyrn et al. |
| 2012/0108934 | A1 | 5/2012 | Valdes et al. |
| 2012/0108983 | A1 | 5/2012 | Banet et al. |
| 2012/0116322 | A1 | 5/2012 | Brink et al. |
| 2012/0123385 | A1 | 5/2012 | Edwards et al. |
| 2012/0143135 | A1 | 6/2012 | Cole et al. |
| 2012/0165626 | A1 | 6/2012 | Irina et al. |
| 2012/0165640 | A1 | 6/2012 | Galley et al. |
| 2012/0173200 | A1 | 7/2012 | Breton et al. |
| 2012/0179113 | A1 | 7/2012 | Yokota et al. |
| 2012/0184909 | A1 | 7/2012 | Gyrn et al. |
| 2012/0190943 | A1* | 7/2012 | Donnay ........... A61B 5/150396 600/309 |
| 2012/0190989 | A1 | 7/2012 | Kaiser et al. |
| 2012/0197098 | A1 | 8/2012 | Donnay et al. |
| 2012/0197222 | A1 | 8/2012 | Donnay et al. |
| 2012/0245447 | A1 | 9/2012 | Karan et al. |
| 2012/0265042 | A1 | 10/2012 | Neinast et al. |
| 2012/0296327 | A1 | 11/2012 | Hutchins et al. |
| 2012/0303043 | A1 | 11/2012 | Donnay et al. |
| 2013/0035575 | A1 | 2/2013 | Mayou et al. |
| 2013/0047981 | A1 | 2/2013 | Bacon |
| 2013/0109940 | A1 | 5/2013 | Yang et al. |
| 2013/0111248 | A1 | 5/2013 | Ghesquiere et al. |
| 2013/0150691 | A1 | 6/2013 | Pace et al. |
| 2013/0184547 | A1 | 7/2013 | Taub et al. |
| 2013/0199312 | A1 | 8/2013 | Wilmer et al. |
| 2013/0225959 | A1 | 8/2013 | Bugler |
| 2013/0235166 | A1 | 9/2013 | Jones et al. |
| 2013/0253289 | A1 | 9/2013 | Hadvary et al. |
| 2013/0267811 | A1 | 10/2013 | Pryor et al. |
| 2013/0317323 | A1 | 11/2013 | Fujiwara et al. |
| 2014/0031655 | A1 | 1/2014 | Stafford |
| 2014/0121480 | A1 | 5/2014 | Budiman et al. |
| 2014/0148667 | A1 | 5/2014 | Boock et al. |
| 2014/0171771 | A1 | 6/2014 | Feldman et al. |
| 2014/0188053 | A1 | 7/2014 | Lundquist |
| 2014/0228760 | A1 | 8/2014 | Ethelfeld |
| 2014/0275907 | A1 | 9/2014 | Feldman et al. |
| 2015/0005601 | A1 | 1/2015 | Hoss et al. |
| 2015/0018643 | A1 | 1/2015 | Cole et al. |
| 2015/0025338 | A1 | 1/2015 | Lee et al. |
| 2015/0073238 | A1 | 3/2015 | Matsumoto et al. |
| 2015/0105644 | A1 | 4/2015 | Yang et al. |
| 2015/0141776 | A1 | 5/2015 | Hadvary et al. |
| 2015/0164545 | A1 | 6/2015 | Gyrn |
| 2015/0173661 | A1 | 6/2015 | Myles |
| 2015/0241407 | A1 | 8/2015 | Ou et al. |
| 2015/0326072 | A1 | 11/2015 | Petras et al. |
| 2016/0058342 | A1 | 3/2016 | Maiz-Aguinaga et al. |
| 2016/0058470 | A1 | 3/2016 | Peterson et al. |
| 2016/0058474 | A1 | 3/2016 | Peterson et al. |
| 2016/0128615 | A1 | 5/2016 | Curry et al. |
| 2016/0157759 | A1 | 6/2016 | Yang |
| 2016/0256106 | A1 | 9/2016 | Krasnow et al. |
| 2016/0331283 | A1* | 11/2016 | Rao .................... A61B 5/14503 |
| 2016/0331284 | A1 | 11/2016 | Pace |
| 2016/0338733 | A1 | 11/2016 | Shah et al. |
| 2016/0338734 | A1 | 11/2016 | Shah et al. |
| 2016/0354555 | A1 | 12/2016 | Gibson et al. |
| 2017/0112533 | A1 | 4/2017 | Schoonmaker et al. |
| 2017/0112534 | A1 | 4/2017 | Schoonmaker et al. |
| 2017/0127985 | A1 | 5/2017 | Thompson et al. |
| 2017/0128011 | A1 | 5/2017 | Frey et al. |
| 2017/0165451 | A1 | 6/2017 | Frey et al. |
| 2017/0188908 | A1 | 7/2017 | Hoss et al. |
| 2017/0188910 | A1 | 7/2017 | Halac et al. |
| 2017/0188912 | A1 | 7/2017 | Halac et al. |
| 2017/0216536 | A1 | 8/2017 | Scott |
| 2017/0265791 | A1 | 9/2017 | Pace et al. |
| 2017/0290533 | A1 | 10/2017 | Antonio et al. |
| 2017/0290534 | A1 | 10/2017 | Antonio et al. |
| 2017/0290535 | A1 | 10/2017 | Rao et al. |
| 2017/0290546 | A1 | 10/2017 | Antonio et al. |
| 2017/0319137 | A1 | 11/2017 | Tsubouchi et al. |
| 2017/0367630 | A1 | 12/2017 | Arita et al. |
| 2017/0368268 | A1 | 12/2017 | Chopra |
| 2018/0116572 | A1 | 5/2018 | Simpson et al. |
| 2018/0125464 | A1 | 5/2018 | Kolb et al. |
| 2018/0235520 | A1 | 8/2018 | Rao et al. |
| 2018/0360493 | A1 | 12/2018 | Baker et al. |
| 2018/0368771 | A1 | 12/2018 | Gray et al. |
| 2019/0076073 | A1 | 3/2019 | Donnay et al. |
| 2019/0133501 | A1 | 5/2019 | Rao et al. |
| 2019/0133638 | A1 | 5/2019 | Ii et al. |
| 2019/0298240 | A1 | 10/2019 | Lee et al. |
| 2020/0077928 | A1 | 3/2020 | Brister et al. |
| 2020/0100712 | A1 | 4/2020 | Stafford |
| 2020/0113494 | A1 | 4/2020 | Akiyama |
| 2020/0178899 | A1 | 6/2020 | Chae et al. |
| 2020/0196919 | A1 | 6/2020 | Rao et al. |
| 2020/0397356 | A1 | 12/2020 | Yee et al. |
| 2021/0030969 | A1 | 2/2021 | Huang et al. |
| 2021/0113124 | A1 | 4/2021 | Yee et al. |
| 2021/0161437 | A1 | 6/2021 | Thomas et al. |
| 2021/0177315 | A1 | 6/2021 | Thomas et al. |
| 2021/0204841 | A1 | 7/2021 | Thomas et al. |
| 2021/0204843 | A1 | 7/2021 | Mazza et al. |
| 2021/0378592 | A1 | 12/2021 | Rodriguez et al. |
| 2022/0007973 | A1 | 1/2022 | Rao et al. |
| 2022/0079475 | A1 | 3/2022 | Cole et al. |
| 2022/0125480 | A1 | 4/2022 | Rao et al. |
| 2022/0273240 | A1* | 9/2022 | Hopcroft .............. A61B 5/6848 |
| 2023/0108476 | A1 | 4/2023 | Rao |
| 2024/0293615 | A1 | 9/2024 | Lanigan |

FOREIGN PATENT DOCUMENTS

| | | |
|---|---|---|
| CA | 2468577 | 6/2003 |
| CA | 2495648 | 2/2004 |
| CA | 2143172 | 7/2005 |
| CA | 2498682 | 9/2005 |
| CA | 2555749 | 9/2005 |
| CA | 2632709 | 6/2007 |
| CA | 2396613 | 3/2008 |
| CA | 2678336 | 5/2008 |
| CA | 2615575 | 6/2008 |
| CA | 2626349 | 9/2008 |
| CA | 2701374 | 4/2009 |
| CA | 2413148 | 8/2010 |
| CA | 2728831 | 7/2011 |
| CA | 2766693 | 9/2011 |
| CA | 2617965 | 10/2011 |
| CA | 2766685 | 12/2011 |
| CA | 3050721 | 7/2018 |
| CN | 1202872 | 5/2005 |
| CN | 101163440 | 4/2008 |
| CN | 101268932 | 9/2008 |
| CN | 101296650 | 10/2008 |
| CN | 201370857 | 12/2009 |
| DE | 44 01 400 | 7/1995 |
| DE | 201 10 059 | 8/2002 |
| DE | 101 17 285 | 11/2002 |
| DE | 10 2008 053 216 | 5/2010 |
| EP | 0 010 375 | 4/1980 |
| EP | 0 026 995 | 4/1981 |
| EP | 0 048 090 | 3/1982 |
| EP | 0 078 636 | 5/1983 |
| EP | 0 096 288 | 12/1983 |
| EP | 0 098 592 | 1/1984 |
| EP | 0 125 139 | 11/1984 |
| EP | 0 127 958 | 12/1984 |
| EP | 0 136 362 | 4/1985 |

(56) References Cited

FOREIGN PATENT DOCUMENTS

| | | |
|---|---|---|
| EP | 0 170 375 | 2/1986 |
| EP | 0 177 743 | 4/1986 |
| EP | 0 080 304 | 5/1986 |
| EP | 0 184 909 | 6/1986 |
| EP | 0 206 218 | 12/1986 |
| EP | 0 230 472 | 8/1987 |
| EP | 0 241 309 | 10/1987 |
| EP | 0 245 073 | 11/1987 |
| EP | 0 255 291 | 2/1988 |
| EP | 0 278 647 | 8/1988 |
| EP | 0 319 277 | 6/1989 |
| EP | 0 320 109 | 6/1989 |
| EP | 0 353 328 | 2/1990 |
| EP | 0 359 831 | 3/1990 |
| EP | 0 368 209 | 5/1990 |
| EP | 0 390 390 | 10/1990 |
| EP | 0 396 788 | 11/1990 |
| EP | 0 400 918 | 12/1990 |
| EP | 0 453 283 | 10/1991 |
| EP | 0 470 290 | 2/1992 |
| EP | 0 567 725 | 11/1993 |
| EP | 0 286 118 | 1/1995 |
| EP | 0 680 727 | 11/1995 |
| EP | 0 724 859 | 8/1996 |
| EP | 0 805 574 | 11/1997 |
| EP | 1 897 488 | 12/1999 |
| EP | 0 973 289 | 1/2000 |
| EP | 0 678 308 | 5/2000 |
| EP | 1 048 264 | 11/2000 |
| EP | 1 177 802 | 2/2002 |
| EP | 0 729 366 | 7/2002 |
| EP | 1 292 218 | 3/2003 |
| EP | 1 077 634 | 7/2003 |
| EP | 1 092 390 | 7/2004 |
| EP | 1 568 309 | 8/2005 |
| EP | 1 630 898 | 3/2006 |
| EP | 1 666 091 | 6/2006 |
| EP | 1 669 020 | 6/2006 |
| EP | 1 703 697 | 9/2006 |
| EP | 1 704 889 | 9/2006 |
| EP | 1 704 893 | 9/2006 |
| EP | 1 729 128 | 12/2006 |
| EP | 0 987 982 | 1/2007 |
| EP | 1 956 371 | 8/2008 |
| EP | 1 972 270 | 9/2008 |
| EP | 2 031 534 | 3/2009 |
| EP | 2 060 284 | 5/2009 |
| EP | 1 897 487 | 11/2009 |
| EP | 1 897 492 | 11/2009 |
| EP | 2 113 864 | 11/2009 |
| EP | 1 681 992 | 4/2010 |
| EP | 2 201 969 | 6/2010 |
| EP | 1 448 489 | 8/2010 |
| EP | 1 971 396 | 8/2010 |
| EP | 1 725 163 | 12/2010 |
| EP | 2 260 757 | 12/2010 |
| EP | 1 413 245 | 6/2011 |
| EP | 2 327 362 | 6/2011 |
| EP | 2 327 984 | 6/2011 |
| EP | 2 335 587 | 6/2011 |
| EP | 2 153 382 | 2/2012 |
| EP | 2 284 773 | 2/2012 |
| EP | 1 789 116 | 5/2013 |
| EP | 3 251 597 | 11/2019 |
| EP | 3 632 314 | 4/2020 |
| EP | 3 632 315 | 4/2020 |
| EP | 3 851 045 | 7/2021 |
| EP | 3 730 044 | 12/2021 |
| EP | 3 730 045 | 3/2022 |
| EP | 3 766 408 | 4/2022 |
| EP | 3 928 688 | 6/2022 |
| EP | 4 111 949 | 7/2023 |
| EP | 4 344 633 | 4/2024 |
| EP | 4 203 819 | 7/2024 |
| GB | 1 394 171 | 5/1975 |
| GB | 1 599 241 | 9/1981 |
| GB | 2 073 891 | 10/1981 |
| GB | 2 067 764 | 1/1984 |
| GB | 2 154 003 | 8/1985 |
| GB | 2 204 408 | 11/1988 |
| GB | 2 254 436 | 10/1992 |
| GB | 2 409 951 | 7/2005 |
| JP | 54-041191 | 4/1979 |
| JP | 55-010581 | 1/1980 |
| JP | 55-010583 | 1/1980 |
| JP | 55-010584 | 1/1980 |
| JP | 55-012406 | 1/1980 |
| JP | 56-163447 | 12/1981 |
| JP | 57-070448 | 4/1982 |
| JP | 60-173457 | 9/1985 |
| JP | 60-173458 | 9/1985 |
| JP | 60-173459 | 9/1985 |
| JP | 62-085855 | 4/1987 |
| JP | 62-114747 | 5/1987 |
| JP | 63-058149 | 3/1988 |
| JP | 63-128252 | 5/1988 |
| JP | 63-139246 | 6/1988 |
| JP | 63-294799 | 12/1988 |
| JP | 63-317757 | 12/1988 |
| JP | 63-317758 | 12/1988 |
| JP | 01-114746 | 5/1989 |
| JP | 01-114747 | 5/1989 |
| JP | 01-124060 | 5/1989 |
| JP | 01-134244 | 5/1989 |
| JP | 01-156658 | 6/1989 |
| JP | 02-062958 | 3/1990 |
| JP | 02-120655 | 5/1990 |
| JP | 02-287145 | 11/1990 |
| JP | 02-310457 | 12/1990 |
| JP | 03-020752 | 1/1991 |
| JP | 03-026956 | 2/1991 |
| JP | 03-028752 | 2/1991 |
| JP | 03-500940 | 2/1991 |
| JP | 03-194458 | 8/1991 |
| JP | 03-202764 | 9/1991 |
| JP | 05-072171 | 3/1993 |
| JP | 05-196595 | 8/1993 |
| JP | 06-190050 | 7/1994 |
| JP | 07-055757 | 3/1995 |
| JP | 07-072585 | 3/1995 |
| JP | 07-182462 | 7/1995 |
| JP | 07-311196 | 11/1995 |
| JP | 08-285814 | 11/1996 |
| JP | 08-285815 | 11/1996 |
| JP | 09-021778 | 1/1997 |
| JP | 09-101280 | 4/1997 |
| JP | 09-285459 | 4/1997 |
| JP | 10-170471 | 6/1998 |
| JP | 10-305016 | 11/1998 |
| JP | 11-506629 | 6/1999 |
| JP | 11-225359 | 8/1999 |
| JP | 2003-144417 | 5/2003 |
| JP | 2004-033438 | 2/2004 |
| JP | 2004-214014 | 7/2004 |
| JP | 2004-520103 | 7/2004 |
| JP | 2004-520898 | 7/2004 |
| JP | 2004-358016 | 12/2004 |
| JP | 2006-021031 | 1/2006 |
| JP | 2006-280464 | 10/2006 |
| JP | 2006-527036 | 11/2006 |
| JP | 2007-510499 | 4/2007 |
| JP | 2007-152037 | 6/2007 |
| JP | 2008-506468 | 3/2008 |
| KR | 10-2017-0068964 | 6/2017 |
| SU | 1281988 | 1/1987 |
| WO | WO 89/05119 | 6/1989 |
| WO | WO 89/08713 | 9/1989 |
| WO | WO 90/05300 | 5/1990 |
| WO | WO 90/05910 | 5/1990 |
| WO | WO 91/01680 | 2/1991 |
| WO | WO 91/04704 | 4/1991 |
| WO | WO 91/15993 | 10/1991 |
| WO | WO 92/13271 | 8/1992 |
| WO | WO 94/02062 | 9/1994 |

(56) References Cited

FOREIGN PATENT DOCUMENTS

| | | |
|---|---|---|
| WO | WO 95/28878 | 2/1995 |
| WO | WO 96/25089 | 8/1996 |
| WO | WO 96/35370 | 11/1996 |
| WO | WO 96/39977 | 12/1996 |
| WO | WO 97/02847 | 1/1997 |
| WO | WO 97/19344 | 5/1997 |
| WO | WO 97/21457 | 6/1997 |
| WO | WO 97/33513 | 9/1997 |
| WO | WO 97/42882 | 11/1997 |
| WO | WO 97/42883 | 11/1997 |
| WO | WO 97/42886 | 11/1997 |
| WO | WO 97/42888 | 11/1997 |
| WO | WO 97/43962 | 11/1997 |
| WO | WO 98/04902 | 2/1998 |
| WO | WO 98/35053 | 8/1998 |
| WO | WO 98/56293 | 12/1998 |
| WO | WO 99/27849 | 6/1999 |
| WO | WO 99/28736 | 6/1999 |
| WO | WO 99/33504 | 7/1999 |
| WO | WO 99/56613 | 11/1999 |
| WO | WO 00/40159 | 7/2000 |
| WO | WO 00/49940 | 8/2000 |
| WO | WO 00/59370 | 10/2000 |
| WO | WO 00/60350 | 10/2000 |
| WO | WO 00/74753 | 12/2000 |
| WO | WO 00/78992 | 12/2000 |
| WO | WO 01/17875 | 3/2001 |
| WO | WO 01/52727 | 7/2001 |
| WO | WO 01/52935 | 7/2001 |
| WO | WO 01/54753 | 8/2001 |
| WO | WO 01/58348 | 8/2001 |
| WO | WO 02/15778 | 2/2002 |
| WO | WO 02/16905 | 2/2002 |
| WO | WO 02/50534 | 6/2002 |
| WO | WO 02/058537 | 8/2002 |
| WO | WO 02/100457 | 12/2002 |
| WO | WO 03/026728 | 4/2003 |
| WO | WO 03/028784 | 4/2003 |
| WO | WO 03/056319 | 7/2003 |
| WO | WO 03/057027 | 7/2003 |
| WO | WO 03/072164 | 9/2003 |
| WO | WO 03/073936 | 9/2003 |
| WO | WO 03/076893 | 9/2003 |
| WO | WO 03/082091 | 10/2003 |
| WO | WO 03/085372 | 10/2003 |
| WO | WO 2004/006982 | 1/2004 |
| WO | WO 2004/015539 | 2/2004 |
| WO | WO 2004/028337 | 4/2004 |
| WO | WO 2004/030726 | 4/2004 |
| WO | WO 2004/034024 | 4/2004 |
| WO | WO 2004/047445 | 6/2004 |
| WO | WO 2004/049237 | 6/2004 |
| WO | WO 2004/054445 | 7/2004 |
| WO | WO 2004/060436 | 7/2004 |
| WO | WO 2004/061420 | 7/2004 |
| WO | WO 2004/090503 | 10/2004 |
| WO | WO 2004/098405 | 11/2004 |
| WO | WO 2004/098682 | 11/2004 |
| WO | WO 2004/098683 | 11/2004 |
| WO | WO 2004/098684 | 11/2004 |
| WO | WO 2004/098685 | 11/2004 |
| WO | WO 2004/107971 | 12/2004 |
| WO | WO 2004/112602 | 12/2004 |
| WO | WO 2005/011779 | 2/2005 |
| WO | WO 2005/018450 | 3/2005 |
| WO | WO 2005/037184 | 4/2005 |
| WO | WO 2005/041766 | 5/2005 |
| WO | WO 2005/044116 | 5/2005 |
| WO | WO 2005/045744 | 5/2005 |
| WO | WO 2005/046780 | 5/2005 |
| WO | WO 2005/051170 | 6/2005 |
| WO | WO 2005/057175 | 6/2005 |
| WO | WO 2005/065538 | 7/2005 |
| WO | WO 2005/084534 | 9/2005 |
| WO | WO 2005/089103 | 9/2005 |
| WO | WO 2005/092177 | 10/2005 |
| WO | WO 2005/121785 | 12/2005 |
| WO | WO 2005/123186 | 12/2005 |
| WO | WO 2006/001024 | 1/2006 |
| WO | WO 2006/015922 | 2/2006 |
| WO | WO 2006/017358 | 2/2006 |
| WO | WO 2006/020212 | 2/2006 |
| WO | WO 2006/024671 | 3/2006 |
| WO | WO 2006/026741 | 3/2006 |
| WO | WO 2006/032653 | 3/2006 |
| WO | WO 2006/036145 | 4/2006 |
| WO | WO 2006/040083 | 4/2006 |
| WO | WO 2006/042811 | 4/2006 |
| WO | WO 2006/061354 | 6/2006 |
| WO | WO 2006/064397 | 6/2006 |
| WO | WO 2006/072035 | 7/2006 |
| WO | WO 2006/079114 | 7/2006 |
| WO | WO 2006/086423 | 8/2006 |
| WO | WO 2006/094513 | 9/2006 |
| WO | WO 2006/108809 | 10/2006 |
| WO | WO 2006/110742 | 10/2006 |
| WO | WO 2006/114297 | 11/2006 |
| WO | WO 2006/118947 | 11/2006 |
| WO | WO 2006/121921 | 11/2006 |
| WO | WO 2006/124099 | 11/2006 |
| WO | WO 2007/002189 | 1/2007 |
| WO | WO 2007/007459 | 1/2007 |
| WO | WO 2007/016399 | 2/2007 |
| WO | WO 2007/019289 | 2/2007 |
| WO | WO 2007/027788 | 3/2007 |
| WO | WO 2007/041069 | 4/2007 |
| WO | WO 2007/041070 | 4/2007 |
| WO | WO 2007/041248 | 4/2007 |
| WO | WO 2007/053832 | 5/2007 |
| WO | WO 2007/056638 | 5/2007 |
| WO | WO 2007/065285 | 6/2007 |
| WO | WO 2007/089738 | 8/2007 |
| WO | WO 2007/092618 | 8/2007 |
| WO | WO 2007/097754 | 8/2007 |
| WO | WO 2007/101223 | 9/2007 |
| WO | WO 2007/120363 | 10/2007 |
| WO | WO 2007/126444 | 11/2007 |
| WO | WO 2007/140783 | 12/2007 |
| WO | WO 2007/143225 | 12/2007 |
| WO | WO 2007/149319 | 12/2007 |
| WO | WO 2008/001366 | 1/2008 |
| WO | WO 2008/014792 | 2/2008 |
| WO | WO 2008/021913 | 2/2008 |
| WO | WO 2008/031106 | 3/2008 |
| WO | WO 2008/031110 | 3/2008 |
| WO | WO 2008/039944 | 4/2008 |
| WO | WO 2008/042760 | 4/2008 |
| WO | WO 2008/048452 | 4/2008 |
| WO | WO 2008/051920 | 5/2008 |
| WO | WO 2008/051924 | 5/2008 |
| WO | WO 2008/052374 | 5/2008 |
| WO | WO 2008/061552 | 5/2008 |
| WO | WO 2008/062099 | 5/2008 |
| WO | WO 2008/065646 | 6/2008 |
| WO | WO 2008/073813 | 6/2008 |
| WO | WO 2008/086541 | 7/2008 |
| WO | WO 2008/103620 | 8/2008 |
| WO | WO 2008/114223 | 9/2008 |
| WO | WO 2008/115409 | 9/2008 |
| WO | WO 2008/128210 | 10/2008 |
| WO | WO 2008/129532 | 10/2008 |
| WO | WO 2008/130896 | 10/2008 |
| WO | WO 2008/130897 | 10/2008 |
| WO | WO 2008/130898 | 10/2008 |
| WO | WO 2008/133702 | 11/2008 |
| WO | WO 2008/138006 | 11/2008 |
| WO | WO 2008/143943 | 11/2008 |
| WO | WO 2008/144445 | 11/2008 |
| WO | WO 2008/147921 | 12/2008 |
| WO | WO 2008/150917 | 12/2008 |
| WO | WO 2008/153693 | 12/2008 |
| WO | WO 2008/155377 | 12/2008 |
| WO | WO 2008/157821 | 12/2008 |
| WO | WO 2009/007287 | 1/2009 |

(56) References Cited

FOREIGN PATENT DOCUMENTS

| | | |
|---|---|---|
| WO | WO 2009/010396 | 1/2009 |
| WO | WO 2009/016635 | 2/2009 |
| WO | WO 2009/016638 | 2/2009 |
| WO | WO 2009/018058 | 2/2009 |
| WO | WO 2009/035773 | 3/2009 |
| WO | WO 2009/039013 | 3/2009 |
| WO | WO 2009/062674 | 5/2009 |
| WO | WO 2009/062675 | 5/2009 |
| WO | WO 2009/066288 | 5/2009 |
| WO | WO 2009/068661 | 6/2009 |
| WO | WO 2009/086216 | 7/2009 |
| WO | WO 2009/096992 | 8/2009 |
| WO | WO 2009/097594 | 8/2009 |
| WO | WO 2010/062898 | 6/2010 |
| WO | WO 2010/077329 | 7/2010 |
| WO | WO 2010/091005 | 8/2010 |
| WO | WO 2010/099507 | 9/2010 |
| WO | WO 2010/112521 | 10/2010 |
| WO | WO 2010/141922 | 12/2010 |
| WO | WO 2011/000528 | 1/2011 |
| WO | WO 2011/002815 | 1/2011 |
| WO | WO 2011/015659 | 2/2011 |
| WO | WO 2011/022418 | 2/2011 |
| WO | WO 2011/025549 | 3/2011 |
| WO | WO 2011/104616 | 9/2011 |
| WO | WO 2011/119896 | 9/2011 |
| WO | WO 2011/119898 | 9/2011 |
| WO | WO 2012/103429 | 8/2012 |
| WO | WO 2013/090215 | 6/2013 |
| WO | WO 2016/183493 | 11/2016 |
| WO | WO 2017/027749 | 2/2017 |
| WO | WO 2017/116915 | 7/2017 |
| WO | WO 2017/134227 | 8/2017 |
| WO | WO 2018/136898 | 7/2018 |
| WO | WO 2018/166963 | 9/2018 |
| WO | WO 2019/005627 | 1/2019 |
| WO | 2019/236850 | 12/2019 |
| WO | 2019/236859 | 12/2019 |
| WO | 2019/236876 | 12/2019 |
| WO | WO 2022/046416 | 3/2022 |
| WO | WO 2022/060677 | 3/2022 |

OTHER PUBLICATIONS

AU, 2007309066 Examiner's Report, Aug. 16, 2013.
AU, 2008265541 Examiner's Report, Oct. 15, 2012.
AU, 2008265541 Examiner's Report, Nov. 29, 2013.
AU, 2010286917 Examiner's Report, Sep. 8, 2014.
AU, 2011230596 Examiner's Report, Feb. 28, 2014.
AU, 2011269796 Examiner's Report, Apr. 3, 2014.
AU, 2016201703 Examiner's Report, Mar. 22, 2017.
AU, 2017254903 Examiner's Report, Dec. 11, 2018.
AU, 2018200899 Examiner's Report, Dec. 6, 2018.
CA, 2,765,712 Examiner's Report, Apr. 10, 2017.
CA, 2,765,712 Examiner's Report, Mar. 27, 2018.
CA, 2,872,576 Examiner's Report, Feb. 17, 2015.
CA, 2,872,576 Examiner's Report, Feb. 19, 2016.
CA, 3,120,335 Examiner's Report, Mar. 31, 2023.
CA, 3,182,961 Examiner's Report, Mar. 29, 2023.
CN, 200780045373.9 Notice of Allowance, May 18, 2011.
CN, 200780045373.9 Office Action, Apr. 14, 2010.
CN, 201080027344.1 Office Action, Jun. 5, 2014.
CN, 201080027344.1 Office Action, Feb. 6, 2015.
CN, 201080006480.2 Office Action, May 6, 2013.
CN, 201080006480.2 Office Action, Dec. 11, 2013.
CN, 201080006481.7 Office Action, Dec. 2, 2014.
CN, 201180002616.7 Office Action, Apr. 24, 2014.
CN, 201180002617.1 Office Action, Jul. 3, 2014.
CN, 20160144860.1 Office Action, Mar. 23, 2018.
CN, 20160144860.1 Office Action, Dec. 10, 2018.
CN, 20160144860.1 Office Action, May 23, 2019.
CN, 201980082748.1 First Office Action, Jan. 10, 2023.
CN, 201980082748.1 Second Office Action, Jul. 10, 2023.
EP, 06804122.7 Decision to Refuse the Application, Feb. 25, 2013.
EP, 06804122.7 Examination Report, Nov. 30, 2011.
EP, 06804122.7 Examination Report, Jan. 25, 2011.
EP, 06815715.5 Extended Search Report, Oct. 30, 2009.
EP, 06851063.5 Extended Search Report, Sep. 21, 2009.
EP, 07842173.2 Examination Report, Mar. 21, 2013.
EP, 07842173.2 Extended Search Report, Dec. 29, 2010.
EP, 07842180.7 Examination Report, Oct. 23, 2012.
EP, 07842180.7 Examination Report, Dec. 14, 2011.
EP, 07842180.7 Examination Report, Feb. 23, 2011.
EP, 07842180.7 Extended Search Report, Sep. 28, 2009.
EP, 07843396.8 Extended Search Report, Dec. 22, 2010.
EP, 10739015.5 Extended Search Report, May 10, 2013.
EP, 10739031.2 Extended Search Report, May 7, 2013.
EP, 10739031.2 Examination Report, Oct. 28, 2016.
EP, 10739031.2 Notice of Opposition, Dec. 20, 2018.
EP, 10739031.2 Reply to Notice of Opposition, May 21, 2019.
EP, 10739031.2 Reply to Notice of Opposition Reply, Aug. 8, 2019.
EP, 10739031.2 Summons to Attend Oral Proceedings, Sep. 17, 2019.
EP, 10739031.2 Written Submissions, Dec. 3, 2019.
EP, 10739031.2 Response to Written Submissions, Jan. 24, 2020.
EP, 10739031.2 Summons to Attend Oral Proceedings, May 20, 2020.
EP, 10739031.2 Written Submissions, Nov. 20, 2020.
EP, 10739031.2 Response to Written Submissions, Jan. 7, 2021.
EP, 10739031.2 Decision and Grounds for Revoking Patent, Jun. 9, 2021.
EP, 10739031.2 Grounds of Appeal, Oct. 19, 2021.
EP, 10739031.2 Response to Grounds of Appeal, Mar. 1, 2022.
EP, 10739031.2 Response to Response to Grounds of Appeal, Jul. 29, 2022.
EP, 10739031.2 Response to Response to Response to Grounds of Appeal, Jan. 18, 2023.
EP, 10812438.9 Extended Search Report, Dec. 10, 2013.
EP, 11760268.0 Decision of the Oral Proceedings, Sep. 27, 2022.
EP, 11760268.0 Minutes of Oral Proceedings, Aug. 11, 2022.
EP, 11760268.0 Communication from Board of Appeals, Mar. 31, 2022.
EP, 11760268.0 Response to Written Submissions, Jan. 14, 2020.
EP, 11760268.0 Response to Notice of Appeal, Sep. 5, 2019.
EP, 11760268.0 Statement of Grounds of Appeal , Apr. 23, 2019.
EP, 11760268.0 Grounds of Appeal, Apr. 18, 2019.
EP, 11760268.0 Notice of Appeal Abbott Diabetes Care Inc., Feb. 25, 2019.
EP, 11760268.0 Notice of Appeal Dexcom, Feb. 22, 2019.
EP, 11760268.0 Interlocutory Decision, Dec. 13, 2018.
EP, 11760268.0 Response to Summons to Attend Oral Proceedings, Sep. 13, 2018.
EP, 11760268.0 Letter Regarding the Opposition Procedure, Sep. 12, 2018.
EP, 11760268.0 Summons to Attend Oral Proceedings, Mar. 22, 2018.
EP, 11760268.0 Comments on Reply to Notice of Opposition, Dec. 27, 2017.
EP, 11760268.0 Reply to Notice of Opposition, Sep. 4, 2017.
EP, 11760268.0 Notice of Opposition, Mar. 29, 2017.
EP, 11760268.0 Extended Search Report, Apr. 14, 2014.
EP, 13000104.3 Extended Search Report, Mar. 12, 2013.
EP, 13000105.0 Examination Report, Oct. 18, 2016.
EP, 13000105.0 Minutes of the Oral Proceedings, Oct. 18, 2016.
EP, 13000105.0 Notice of Opposition, Jan. 4, 2019.
EP, 14179905.6 Summons to Attend Oral Proceedings, Apr. 10, 2017.
EP, 14179905.6 Notice of Opposition, May 19, 2016.
EP, 14179905.6 Extended Search Report, Dec. 23, 2014.
EP, 15002441.2 Extended Search Report, Dec. 18, 2015.
EP, 15184320.8 Examination Report, Apr. 18, 2017.
EP, 16176370.1 Extended Search Report, Dec. 7, 2016.
EP, 16793637.6 Extended Search Report, Oct. 9, 2018.
EP, 17182379.2 Extended Search Report, Feb. 21, 2018.
EP, 17201183.5 Extended Search Report, May 7, 2018.

(56) References Cited

OTHER PUBLICATIONS

EP, 17201183.5 Examination Report, May 7, 2019.
EP, 18192278.2 Extended Search Report, Mar. 13, 2019.
EP, 18208224.8 Extended Search Report, Oct. 11, 2019.
EP, 18741791.0 Extended Search Report, Sep. 23, 2020.
EP, 19151577.4 Extended Search Report, Aug. 16, 2019.
EP, 19151577.4 Examination Report, May 27, 2022.
EP, 19184881.1 Extended Search Report, Dec. 4, 2019.
EP, 19900891.3 Extended Search Report, Sep. 26, 2022.
EP, 20177703.4 Reply to Reply to Notice of Opposition, Jun. 29, 2023.
EP, 20177703.4 Notice of Intervention, Jun. 23, 2023.
EP, 20177703.4 Reply to Notice of Opposition, Feb. 22, 2023.
EP, 20177703.4 Grounds of Opposition, Sep. 28, 2022.
EP, 20177703.4 Notice of Opposition, Sep. 28, 2022.
EP, 20177703.4 Examination Report, Jun. 25, 2021.
EP, 20177703.4 Extended Search Report, Sep. 25, 2020.
EP, 20177712.5 Notice of Intervention, Jun. 23, 2023.
EP, 20177712.5 Reply to Notice of Opposition, May 23, 2023.
EP, 20177712.5 Grounds of Opposition Gulde & Partner Patent, Dec. 22, 2022.
EP, 20177712.5 Grounds of Opposition Dexcom, Dec. 22, 2022.
EP, 20177712.5 Notice of Opposition Gulde & Partner Patent, Dec. 22, 2022.
EP, 20177712.5 Notice of Opposition Dexcom, Dec. 22, 2022.
EP, 20177712.5 Extended Search Report, Sep. 30, 2020.
EP, 20195922.8 Reply to Notice of Opposition, Jun. 20, 2023.
EP, 20195922.8 Notice of Intervention, Jun. 13, 2023.
EP, 20195922.8 Grounds of Opposition Dexcom, Jan. 26, 2023.
EP, 20195922.8 Notice of Opposition Dexcom, Jan. 26, 2023.
EP, 20195922.8 Extended Search Report, Dec. 16, 2020.
EP, 21152231.3 Extended Search Report, May 11, 2021.
EP, 21192910.4 Extended Search Report, Jan. 31, 2022.
EP, 21211041.5 Extended Search Report, Mar. 3, 2022.
EP, 22168031.7 Extended Search Report, Aug. 17, 2022.
EP, 22169853.3 Extended Search Report, Sep. 2, 2022.
IL, 198329 Office Action, Mar. 5, 2012.
JP, 2009-534798 Office Action, Sep. 25, 2012.
JP, 2012-526736 Office Action, Apr. 15, 2014.
JP, 2012-526736 Office Action, Dec. 16, 2014.
JP, 2013-501503 Office Action, Mar. 3, 2015.
JP, 2015-159805 Office Action, Aug. 9, 2016.
JP, 2016-44196 Office Action, Apr. 11, 2017.
JP, 2021-531135 Office Action, Feb. 22, 2023.
MX, MX/a/2009/004398 Office Action, Sep. 24, 2012.
MY, PI2021004760 Examination Report, Mar. 30, 2022.
MY, PI2021005830 Examination Report, Sep. 30, 2022.
MY, PI2021005830 Examination Report, Aug. 29, 2022.
MY, PI2022007295 Examination Report, Jul. 11, 2023.
NL, 2009963 Search Report, Aug. 12, 2013.
US, Final Written Decision, IPR No. 2022-00605, Jul. 10, 2023.
US, Institution Decision, IPR No. 2022-00605, Jul. 27, 2022.
US, Patent Owner's Preliminary Sur-Reply, IPR No. 2022-00605, Jun. 28, 2022.
US, Petitioner's Preliminary Reply to Patent Owner's Preliminary Response, IPR No. 2022-00605, Jun. 21, 2022.
US, Patent Owner's Preliminary Response, IPR No. 2022-00605, May 24, 2022.
US, Petition For Inter Partes Review Of U.S. Pat. No. 10,945,649, IPR No. 2022-00605, Feb. 15, 2022.
US, Institution Decision, IPR No. 2022-00637, Jul. 27, 2022.
US, Patent Owner's Preliminary Sur-Reply, IPR No. 2022-00637, Jun. 28, 2022.
US, Petitioner's Preliminary Reply to Patent Owner's Preliminary Response, IPR No. 2022-00637, Jun. 21, 2022.
US, Patent Owner's Preliminary Response, IPR No. 2022-00637, Jun. 9, 2022.
US, Petition For Inter Partes Review Of U.S. Pat. No. 11,013,440, IPR No. 2022-00637, Feb. 8, 2022.
US, Reexamination Serial No. 95/002,162 Request to Review Order Denying Request for Reexamination, Dec. 13, 2012.
US, Reexamination Serial No. 95/002,162 Order Denying Request for Reexamination, Nov. 13, 2012.
US, Request for Reexamination Serial No. 95/002,162 of U.S. Pat. No. 8,175,673, Sep. 7, 2012.
US, Reexamination Serial No. 95/002,113 Request to Review Order Denying Request for Reexamination, Dec. 13, 2012.
US, Reexamination Serial No. 95/002,113 Order Denying Request for Reexamination, Nov. 13, 2012.
US, Request for Reexamination Serial No. 95/002,113 of U.S. Pat. No. 6,990,366, Aug. 30, 2012.
US, Reexamination Serial No. 90/011,730 Notice of Intent to Issue Ex Parte Reexamination Certificate, Apr. 5, 2012.
US, Reexamination Serial No. 90/011,730 Office Action, Jan. 11, 2012.
US, Reexamination Serial No. 90/011,730 Order Granting Request for Reexamination, Aug. 24, 2011.
US, Request for Reexamination Serial No. 90/011,730 of U.S. Pat. No. 6,990,366, Jun. 3, 2011.
US, Reexamination Serial No. 90/010,791 Ex Parte Reexamination Certificate, May 17, 2011.
US, Reexamination Serial No. 90/010,791 Office Action, Dec. 17, 2010.
US, Reexamination Serial No. 90/010,791 Office Action, May 28, 2010.
US, Reexamination Serial No. 90/010,791 Order Granting Request for Reexamination, Feb. 22, 2010.
US, Request for Reexamination Serial No. 90/010,791 of U.S. Pat. No. 6,990,366, Dec. 22, 2009.
US, Reexamination Serial No. 90/009,328 Notice of Intent to Issue Ex Parte Reexamination Certificate, Nov. 20, 2009.
US, Reexamination Serial No. 90/009,328 Office Action, Sep. 30, 2009.
US, Reexamination Serial No. 90/009,328 Office Action, Aug. 4, 2009.
US, Reexamination Serial No. 90/009,328 Order Granting Request for Reexamination, Dec. 9, 2008.
US, Request for Reexamination Serial No. 90/009,328 of U.S. Pat. No. 6,990,366, Nov. 10, 2008.
US, Reexamination Serial No. 90/009,104 Notice of Intent to Issue Ex Parte Reexamination Certificate, Nov. 20, 2009.
US, Reexamination Serial No. 90/009,104 Office Action, Sep. 30, 2009.
US, Reexamination Serial No. 90/009,104 Office Action, Aug. 4, 2009.
US, Reexamination Serial No. 90/009,104 Office Action, Oct. 16, 2008.
US, Reexamination Serial No. 90/009,104 Order Granting Request for Reexamination, Jun. 5, 2008.
US, Request for Reexamination Serial No. 90/009,104 of U.S. Pat. No. 6,990,366, Apr. 8, 2008.
US, Reexamination Serial No. 90/008,457 Notice of Intent to Issue Ex Parte Reexamination Certificate, Mar. 13, 2008.
US, Reexamination Serial No. 90/008,457 Order Granting Request for Reexamination, Feb. 23, 2007.
US, Request for Reexamination Serial No. 90/008,457 of U.S. Pat. No. 6,990,366, Jan. 23, 2007.
US, Request for Reexamination Serial No. 90/008,172 of U.S. Pat. No. 6,990,366, Aug. 16, 2006.
US, Reexamination Serial No. 90/007,910 Patent Board Decision, May 17, 2013.
US, Reexamination Serial No. 90/007,910 Decision on Appeal, Jan. 18, 2011.
US, Reexamination Serial No. 90/007,910 Advisory Action, Jul. 30, 2009.
US, Reexamination Serial No. 90/007,910 Advisory Action, Feb. 6, 2009.
US, Reexamination Serial No. 90/007,910 Examiner's Answer to Appeal Brief, Nov. 19, 2009.
US, Reexamination Serial No. 90/007,910 Office Action, Oct. 2, 2008.

(56) References Cited

OTHER PUBLICATIONS

US, Reexamination Serial No. 90/007,910 Office Action, Feb. 13, 2008.
US, Reexamination Serial No. 90/007,910 Order Granting Request for Reexamination, Mar. 27, 2006.
US, Request for Reexamination Serial No. 90/007,910 of U.S. Pat. No. 6,175,752, Feb. 1, 2006.
US, Reexamination Serial No. 90/009,270 Order Denying Request for Reexamination, Dec. 1, 2008.
US, Request for Reexamination Serial No. 90/009,270 of U.S. Pat. No. 6,175,752, Sep. 8, 2008.
US, Reexamination Serial No. 90/009,497 Notice of Intent to Issue Reexamination Certificate, Aug. 23, 2010.
US, Reexamination Serial No. 90/009,497 Order Granting Request, Jul. 30, 2009.
US, Request for Reexamination Serial No. 90/009,497 of U.S. Pat. No. 6,175,752, Jun. 17, 2009.
WO, PCT/US2006/037312 ISR and Written Opinion, Apr. 17, 2007.
WO, PCT/US2006/037928 ISR and Written Opinion, Jul. 11, 2008.
WO, PCT/US2006/062690 ISR and Written Opinion, Jan. 2, 2008.
WO, PCT/US2007/078065 ISR and Written Opinion, Apr. 11, 2008.
WO, PCT/US2007/078073 ISR and Written Opinion, Apr. 11, 2008.
WO, PCT/US2007/079774 ISR and Written Opinion, Apr. 1, 2008.
WO, PCT/US2007/082114 ISR and Written Opinion, May 9, 2008.
WO, PCT/US2010/002401 ISR and Written Opinion, Nov. 12, 2010.
WO, PCT/US2010/022860 ISR and Written Opinion, Mar. 23, 2010.
WO, PCT/US2010/022928 ISR and Written Opinion, Mar. 21, 2010.
WO, PCT/US2010/047381 ISR and Written Opinion, Oct. 15, 2010.
WO, PCT/US2010/050772 ISR and Written Opinion, Dec. 3, 2010.
WO, PCT/US2010/050888 ISR and Written Opinion, Nov. 29, 2010.
WO, PCT/US2010/051861 ISR and Written Opinion, Nov. 30, 2010.
WO, PCT/US2011/029881 ISR and Written Opinion, May 20, 2011.
WO, PCT/US2011/029883 ISR and Written Opinion, Jun. 2, 2011.
WO, PCT/US2011/029884 ISR and Written Opinion, Jun. 1, 2011.
WO, PCT/US2012/062551 ISR and Written Opinion, Jan. 2, 2013.
WO, PCT/US2012/068839 ISR and Written Opinion, Feb. 22, 2013.
WO, PCT/US2013/052397 ISR and Written Opinion, Dec. 2, 2013.
WO, PCT/US2016/032485 ISR and Written Opinion, Sep. 12, 2016.
WO, PCT/US2018/014745 ISR and Written Opinion, Jun. 4, 2018.
WO, PCT/US2019/035843 ISR and Written Opinion, Sep. 18, 2019.
WO, PCT/US2021/040541 ISR and Written Opinion, Dec. 20, 2021.
WO, PCT/US2021/045576 ISR and Written Opinion, Jan. 27, 2022.
WO, PCT/US2021/048086 ISR and Written Opinion, Feb. 28, 2022.
WO, PCT/US2021/050672 ISR and Written Opinion, Jan. 5, 2022.
WO, PCT/US2022/037291 ISR and Written Opinion, Nov. 22, 2022.
WO, PCT/US2022/037291 Invitation to Pay Additional Fees, Sep. 9, 2022.
WO, PCT/US2023/010054 ISR and Written Opinion, May 15, 2023.
WO, PCT/US2023/010054 Invitation to Pay Additional Fees, Mar. 24, 2023.
Abruna, H. D., et al., "Rectifying Interfaces Using Two-Layer Films of Electrochemically Polymerized Vinylpyridine and Vinylbipyridine Complexes of Ruthenium and Iron on Electrodes", Journal of the American Chemical Society, 1981, vol. 103, No. 1, pp. 1-5.
ACCU-CHEK Compact Plus Owner's Booklet, 2008, pp. 1-100.
ACCU-CHEK Softclix Plus Lancet Device retrieved from https://web.archive.org/web/20061018055737/http://www.accu-check.com/us/rewrite/content/en_US/2.1.7.1:10/article/ACCM_general_article_3303.htm, 2006, pp. 1-2.
Affidavit of Richard Paragas signed on May 18, 2016, pp. 1-4.
Affidavit of Paul Neale signed on May 18, 2016, pp. 1-2.
Ahson, S., et al., "RFID Handbook: Applications, Technology, Security, and Privacy", 2008, Chapter 4, Far-Field Tag Antenna Design Methodology, and Chapter 13, RFID Tags for Metallic Object Identification, pp. 71 and 253-254.
Albery, W.J., et al., "Amperometric Enzyme Electrodes Part II: Conducting Salts as Electrode Materials for the Oxidation of Glucose Oxidase", Journal of ElectroAnalytical Chemistry, 1985, vol. 194, pp. 223-235.
Albery, W.J., et al., "Amperometric Enzyme Electrodes", Philosophical Transactions of the Royal Society of London, 1987, vol. 316, pp. 107-119.
Alcock, S J, et al., "Continuous analyte monitoring to aid clinical practice," IEEE Engineering in Medicine & BioloXY Magazine, 1994, vol. 13. pp. 319-25.
Ambade, V. N., et al., "Methods for Estimation of Blood Glucose: A Comparative Evaluation", Medical Journal Armed Forces India, 1998, vol. 54, No. 2, pp. 131-133.
Anderson, A. J., "Foundations of Computer Technology", 1994, pp. 55-57.
Anderson, L. B., et al., "Thin-Layer Electrochemistry: Steady-State Methods of Studying Rate Processes", Journal of ElectroAnalytical Chemistry, 1965, vol. 10, pp. 295-305.
Application Note AN048, Antenna Part No. FR05-S1-N-0-102, Compact Reach Xtend™, Bluetooth®, 802.11b/g WLAN Chip Antenna, 2008, pp. 1-13.
Application Note AVR2023—AT86RF231 PCB reference design for antenna diversity, Atmel Corporation, 2008, pp. 1-15.
Application Note nRF9E5 RF and antenna layout, Nordic Semiconductor, 2006, pp. 1-13.
Armour, J. C., et al., "Application of Chronic Intravascular Blood Glucose Sensor in Dogs," Diabetes, 1990, vol. 39, pp. 1519-1526.
ASTM International, Designation D2240-05, 2010, pp. 1-13.
Aussedat, B., et al., "A User-Friendly Method for Calibrating a Subcutaneous Glucose Sensor-Based Hypoglycemic Alarm", Biosensors & Bioelectronics, 1997, vol. 12, No. 11, pp. 1061-1071.
Bartlett, P. N., et al., "Covalent Binding of Electron Relays to Glucose Oxidase", Journal of the Chemical Society, Chemical Communications, 1987, pp. 1603-1604.
Bartlett, P. N., et al., "Modification of Glucose Oxidase by Tetrathiafulvalene", Journal of the Chemical Society, Chemical Communications, 1990, pp. 1135-1136.
Benki, K., et al., "Using RSSI value for distance estimation in Wireless sensor networks based on ZigBee", 15th International Conference on Systems, Signals and Image Processing, Bratislava, Slovakia, 2008, pp. 1-4.
Bennion, N., et al., "Alternate Site Glucose Testing: A Crossover Design", Diabetes Technology & Therapeutics, 2002, vol. 4, No. 1, pp. 25-33.
Bindra, D.S., et al., "Pulsed Amperometric Detection of Glucose in Biological Fluids at a Surface-Modified Gold Electrode", American Chemical Society, 1989, vol. 61, No. 22, pp. 2566-2570.
Bindra, D.S., et al., "Design and in Vitro Studies of a Needle-Type Glucose Sensor for Subcutaneous Monitoring," Anal. Chem., 1991, vol. 63, No. 17, pp. 1692-1696.
Biosensors: Fundamentals and Applications, Turner et al., Eds., 1987, pp. 1-786.
Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, 2002, vol. 4624, pp. 1-10.
"Bluetooth Antenna Design", National Semiconductor Application Note, 2005, pp. 1-16.
Bluetooth Core Specification 4.0, Jun. 30, 2010, Master Table of Contents & Compliance Requirements, pp. 1-89.
Bobbioni-Harsch, E. et al., "Lifespan of subcutaneous glucose sensors and their performances during dynamic glycaemia changes in rats," J. Biomed. Eng., 1993, vol. 15, pp. 457-463.
Bonnett, A. H., et al., "Squirrel-Cage Rotor Options for AC Induction Motors", IEEE Transactions on Industry Applications, 2001, vol. 37, No. 4, pp. 1197-1209.
Brandt, J., et al., "Covalent Attachment of Proteins to Polysaccharide Carriers by Means of Benzoquinone", Biochimica et Biophysica Acta, 1975, vol. 386, pp. 196-202.

(56) References Cited

OTHER PUBLICATIONS

Brooks, S. L., et al., "Development of an On-Line Glucose Sensor for Fermentation Monitoring", Biosensors, 1987/88, vol. 3, pp. 45-56.
Brownlee, M., et al., "A Glucose-Controlled Insulin-Delivery System: Semisynthetic Insulin Bound to Lectin", Science, 1979, vol. 206, pp. 1190-1191.
Bühling, K. J., et al., "Optimal timing for postprandial glucose measurement in pregnant women with diabetes and a non-diabetic pregnant population evaluated by the Continuous Glucose Monitoring System (CGMS®)", Journal of Perinatal Medicine, 2005, vol. 33, No. 2, pp. 125-131.
Callaway, Jr., E. H., "Wireless Sensor Networks: Architectures and Protocols", 2004, Chapter 8, Antennas and the Definition of RF Performance, pp. 201-202.
Cass, A.E.G. et al., "Ferrocene-Mediated Enzyme Electrode for Amperometric Determination of Glucose," Anal. Chem., 1984, vol. 56, No. 4, pp. 667-671.
Cass, A.E.G. et al., "Ferricinium Ion as an Electron Acceptor for Oxido-Reductases", Journal of ElectroAnalytical Chemistry, 1985, vol. 190, pp. 117-127.
Castner, J. F., et al., "Mass Transport and Reaction Kinetic Parameters Determined Electrochemically for Immobilized Glucose Oxidase", Biochemistry, 1984, vol. 23, No. 10, pp. 2203-2210.
U.S. Appl. No. 60/424,099, filed Nov. 5, 2002.
Cheyne, E.H., et al., "Performance of a Continuous Glucose Monitoring System During Controlled Hypoglycaemia in Healthy Volunteers", Diabetes Technology & Therapeutics, 2002, vol. 4, No. 5, pp. 607-613.
Choleau, C., et al., "Calibration of a Subcutaneous Amperometric Glucose Sensor Implanted for 7 Days in Diabetic Patients Part 2. Superiority of the One-Point Calibration Method", Biosensor & Bioelectronics, 2002, vol. 17, No. 8, pp. 647-654.
Choleau, C., et al., "Calibration of a Subcutaneous Amperometric Glucose Sensor Part 1. Effect of Measurement Uncertainties on the Determination of Sensor Sensitivity and Background Current", Biosensor & Bioelectronics, 2002, vol. 17, No. 8, pp. 641-646.
Claremont, D. J., et al., "Biosensors for Continuous In Vivo Glucose Monitoring", Proceedings of the Annual International Conference of the IEEE Engineering in Medicine and Biology Society, 1988, vol. 10, pp. 1-2.
Clark Jr., L. C., et al., "Electrode Systems for Continuous Monitoring in Cardiovascular Surgery", Annals New York Academy of Sciences, 1962, pp. 29-45.
Clark Jr., L. C., et al., "Differential Anodic Enzyme Polarography for the Measurement of Glucose", Oxygen Transport to Tissue: Instrumentation, Methods, and Physiology, 1973, pp. 127-133.
Clark Jr., L. C., et al., "Long-term Stability of Electroenzymatic Glucose Sensors Implanted in Mice", American Society of Artificial Internal Organs Transactions, 1988, vol. XXXIV, pp. 259-265.
Clarke, W. L., et al., "Evaluating Clinical Accuracy of Systems for Self-Monitoring of Blood Glucose", Diabetes Care, 1987, vol. 10, No. 5, pp. 622-628.
Clarke, W., et al., "Statistical Tools to Analyze Continuous Glucose Monitor Data", Diabetes Technology & Therapeutics, 2009, vol. 11, Suppl. 1, pp. S-45-S-54.
Cleo™ 90 Infusion Set, 510(k) Summary of Safety and Effectiveness, Aug. 10, 2004, pp. 1-618.
Cleo® 90 Infusion Set Training Guide, 2011, 1 page.
Compact Plus Blood Glucose Meter retrieved from https://web.archive.org/web/20090316065810/http://www.accu-check.com/us/rewrite/content/en_US/2.1.9:0/article/ACCM_general_article_5136.htm, 2009, pp. 1-3.
Complaint *Abbott Diabetes Care Inc.* v. *Dexcom, Inc.* U.S. District Court Delaware C.A. No. 05-590 filed Aug. 11, 2005.
Complaint, Amended, *Abbott Diabetes Care Inc.* v. *Dexcom, Inc.* U.S. District Court Delaware C.A. No. 05-590 filed Jun. 27, 2006.
Complaint *Abbott Diabetes Care Inc.* v. *Dexcom, Inc.* U.S. District Court Delaware C.A. No. 06-514 filed Aug. 17, 2006.
Cox, M., "An Overview of Continuous Glucose Monitoring Systems", Journal of Pediatric Health Care, 2009, vol. 23, No. 5, pp. 344-347.
Csoregi, E., et al., "Design and Optimization of a Selective Subcutaneously Implantable Glucose Electrode Based on 'Wired' Glucose Oxidase", Analytical Chemistry, 1995, vol. 67, No. 7, pp. 1240-1244.
Csoregi, E., et al., "Design, Characterization, and One-Point in Vivo Calibration of a Subcutaneously Implanted Glucose Electrode", Analytical Chemistry, 1994, vol. 66 No. 19, pp. 3131-3138.
Csoregi, E., et al., "On-Line Glucose Monitoring by Using Microdialysis Sampling and Amperometric Detection Based on 'Wired' Glucose Oxidase in Carbon Paste", Mikrochimica Acta, 1995, vol. 121, pp. 31-40.
Cullen, M.T., et al., "The Changing Presentations of Diabetic Ketoacidosis During Pregnancy", Amer. J. Perinatol, 1996, vol. 13, No. 7, pp. 449-451 (abstract only).
In Vivo Glucose Sensing, Cunningham et al., Eds., 2010, Chemical Analysis, vol. 174, pp. 1-466.
Darley, J., "Is your user experience as good as your technology?", 2019, retrieved from https://www.massdevice.com/is-your-user-experience-as-good-as-your-technology/, pp. 1-16.
Davis, G., "Electromechanical Techniques for the Development of Amperometric Biosensors", Biosensors, 1985, vol. 1, pp. 161-178.
De Block, C., et al., "Minimally-Invasive and Non-Invasive Continuous Glucose Monitoring Systems: Indications, Advantages, Limitations and Clinical Aspects", Current Diabetes Reviews, 2008, vol. 4, No. 3, pp. 159-168.
IPR2022-00605 (Ex. 2001) Declaration of Michael Cima, Ph.D dated May 24, 2022, pp. 1-70.
IPR2022-00637 (Ex. 2001) Declaration of Michael Cima, Ph.D dated Jun. 9, 2022, pp. 1-79.
IPR2022-00605 (Ex. 1003) Declaration of Gary D. Fletcher, Ph.D dated Feb. 15, 2022, pp. 1-122.
IPR2022-00605 (Ex. 1003) Corrected Declaration of Gary D. Fletcher, Ph.D dated Feb. 18, 2022, pp. 1-124.
IPR2022-00637 (Ex. 1035) Second Declaration of Gary D. Fletcher, Ph.D dated Feb. 28, 2022, pp. 1-136.
Decuir, J., "Bluetooth 4.0: Low Energy", IEEE SCV Consultants' Network of Silicon Valley, 2012, pp. 1-68.
Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", The Journal of Physical Chemistry, 1987, vol. 91, No. 6, pp. 1285-1289.
Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", Journal of the American Chemical Society, 1988, vol. 110, No. 8, pp. 2615-2620.
Degani, Y., et al., "Electrical Communication Between Redox Centers of Glucose Oxidase and Electrodes via Electrostatically and Covalently Bound Redox Polymers", Journal of the American Chemical Society, 1989, vol. 111, pp. 2357-2358.
Dehez, B., et al., "Development of a Spherical Induction Motor With Two Degrees of Freedom", IEEE Transactions on Magnetics, 2006, vol. 42, No. 8, pp. 2077-2089.
Delve Talks: Jake Leach, Dexcom, retrieved from https://www.delve.com/podcasts/delve-talks-jake-leach-dexcom, 2019, pp. 1-9.
Dementyev, A., et al., "Power Consumption Analysis of Bluetooth Low Energy, ZigBee and ANT Sensor Nodes in a Cyclic Sleep Scenario", IEEE International Wireless Symposium (IWS), 2013, Beijing, China, pp. 1-4.
Denisevich, P., et al., "Unidirectional Current Flow and Charge State Trapping at Redox Polymer Interfaces on Bilayer Electrodes: Principles, Experimental Demonstration, and Theory", Journal of the American Chemical Society, 1981, vol. 103, pp. 4727-4737.
"Dexcom CEO tells investors not to fear new competition from Abbott's Freestyle Libre", 2017, retrieved from https://www.mobihealthnews.com/content/dexcom-ceo-tells-investors-not-fear-new-competition-abbotts-freestyle-libre, pp. 1-3.
Dexcom G5 Mobile System User Guide, 2020, pp. 1-410.

(56) References Cited

OTHER PUBLICATIONS

Dexcom G6, Winner Health & Wellness Award, Core77 Design Awards, 2019, retrieved from https://designawards.core77.com/health-wellness/85111/Dexcom-G6, pp. 1-8.
DexCom™ STS™ Continuous Glucose Monitoring System User's Guide, 2006, pp. 1-57.
Dexcom STS®—7 Continuous Glucose Monitoring System User's Guide, 2007, pp. 1-74.
Dicks, J.M., et al., "Ferrocene Modified Polypyrrole with Immobilised Glucose Oxidase and its Application in Amperometric Glucose Microbiosensors", Annales de Biologie Clinique, 1989, vol. 47, pp. 607-619.
Diem, P., et al., "Clinical Performance of a Continuous Viscometric Affinity Sensor for Glucose", Diabetes Technology & Therapeutics, 2004, vol. 6, pp. 790-799.
ECMA International Standard ECMA-340, Near Field Communication Interface and Protocol (NFCIP-1), 2nd Edition, 2004, pp. 1-65.
El-Khatib, F. H, et al., "Adaptive Closed-Loop Control Provides Blood-Glucose Regulation Using Subcutaneous Insulin and Glucagon Infusion in Diabetic Swine", Journal of Diabetes Science and Technology, 2007, vol. 1, No. 2, pp. 181-192.
Ellis, C. D., et al., "Selectivity and Directed Charge Transfer through an Electroactive Metallopolymer Film", Journal of the American Chemical Society, 1981, vol. 103, No. 25, pp. 7480-7483.
Engstrom, R. C., "Electrochemical Pretreatment of Glassy Carbon Electrodes", Analytical Chemistry, 1982, vol. 54, No. 13, pp. 2310-2314.
Engstrom, R. C., et al., "Characterization of Electrochemically Pretreated Glassy Carbon Electrodes", Analytical Chemistry, 1984, vol. 56, No. 2, pp. 136-141.
Facchinetti, A., et al., "A New Index to Optimally Design and Compare Continuous Glucose Monitoring Glucose Prediction Algorithms", Diabetes Technology & Therapeutics, 2011, vol. 13, No. 2, pp. 111-119.
Feldman, B., et al., "Electron Transfer Kinetics at Redox Polymer/Solution Interfaces Using Microelectrodes and Twin Electrode Thin Layer Cells", Journal of ElectroAnalytical Chemistry, 1985, vol. 194, pp. 63-81.
Feldman, B., et al., "A Continuous Glucose Sensor Based on Wired Enzyme™ Technology—Results from a 3-Day Trial in Patients with Type 1 Diabetes", Diabetes Technology & Therapeutics, 2003, vol. 5, No. 5, pp. 769-779.
Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.
U.S. Appl. No. 60/587,787.
U.S. Appl. No. 10/633,367.
U.S. Appl. No. 12/250,760.
Fischer, H., et al., "Intramolecular Electron Transfer Medicated by 4,4'-Bypyridine and Related Bridging Groups", Journal of the American Chemical Society, 1976, vol. 98, No. 18, pp. 5512-5517.
Foulds, N. C., et al., "Enzyme Entrapment in Electrically Conducting Polymers: Immobilisation of Glucose Oxidase in Polypyrrole and its Application in Amperometric Glucose Sensors", Journal of the Chemical Society, Faraday Transactions 1, 1986, vol. 82, pp. 1259-1264.
Foulds, N. C., et al., "Immobilization of Glucose Oxidase in Ferrocene-Modified Pyrrole Polymers", Analytical Chemistry, 1988, vol. 60, No. 22, pp. 2473-2478.
Freedman, D., et al., Statistics: Second Edition, 1991, Chapter 5, p. 74.
Freestyle Navigator Continuous Glucose Monitor FDA Premarket Approval (PMA), May 2022, pp. 1-6.
Freestyle Navigator Summary of Safety and Effectiveness Data, 2008, pp. 1-27.
Freestyle Navigator User's Guide, 2008, pp. 1-195.
Frenzel, L. E., "Printed-Circuit-Board Antennas, retrieved from https://www.electronicdesign.com/technologies/boards/article/21751417/printedcircuitboard-antennasprint/3266", Electronic Design, 2005, pp. 1-4.
Frew, J. E., et al., "Electron-Transfer Biosensors", Philosophical Transactions of the Royal Society of London, 1987, vol. 316, pp. 95-106.
Fujipoly Silver ZEBRA® Connector Data Sheet FSDS 01-34, Version 5, 2006, pp. 1-7.
Garg, S., et al., "Improvement in Glycemic Excursions with a Transcutaneous, Real-Time Continuous Glucose Sensor", Diabetes Care, 2006, vol. 29, No. 1, pp. 44-50.
Garibotto, J., et al., "An Innovative Application of Shape Memory Alloy Technology Yields a Novel Therapeutic Approach to Diabetes Management", Insulet Corporation, 2006, p. A41.
Gilligan, B. J., et al., "Evaluation of a Subcutaneous Glucose Sensor out to 3 Months in a Dog Model", Diabetes Care, 1994, vol. 17, No. 8, pp. 882-887.
Gonzales, W. V., et al., "The Progress of Glucose Monitoring—A Review of Invasive to Minimally and Non-Invasive Techniques, Devices and Sensors", Sensors, 2019, vol. 19, No. 800, pp. 1-45.
Gonzalez, O. L., et al., "Low-Cost Wireless Sensors—Designer Reference Manual", Freescale Semiconductor, 2007, pp. 1-146.
Gorton, L., et al., "Selective Detection in Flow Analysis Based on the Combination of Immobilized Enzymes and Chemically Modified Electrodes", Analytica Chimica Acta, 1991, vol. 250, pp. 203-248.
Gregg, B. A., et al., "Cross-Linked Redox Gels Containing Glucose Oxidase for Amperometric Biosensor Applications," Analytical Chemistry, 1990, vol. 62, No. 3, pp. 258-263.
Gregg, B. A., et al., "Redox Polymer Films Containing Enzymes. 1. A Redox-Conducting Epoxy Cement: Synthesis, Characterization, and Electrocatalytic Oxidation of Hydroquinone", Journal of Physical Chemistry, 1991, vol. 95, No. 15, pp. 5970-5975.
Gregg, T. H., "How Continuous Glucose Monitoring is Transforming Diabetes Treatment", Qualcomm Life Connect, 2013, pp. 1-33.
Guardian® RT Continuous Glucose Monitoring System REF MMT-7900 User Guide, 2005, pp. 1-128.
Guerci, B., et al., "Clinical Performance of CGMS in Type 1 Diabetic Patients Treated by Continuous Subcutaneous Insulin Infusion Using Insulin Analogs", Diabetes Care, 2003, vol. 26, No. 3, pp. 582-589.
Guerra, S., et al., "A Dynamic Risk Measure from Continuous Glucose Monitoring Data", Diabetes Technology & Therapeutics, 2011, vol. 13, No. 8, pp. 843-852.
Güler, N. F., et al., "Theory and Applications of Biotelemetry", Journal of Medical Systems, 2002, vol. 26, No. 2, pp. 159-178.
Gunasingham, et al., "Electrochemically Modulated Optrode for Glucose", Biosensors & Bioelectronics, 1992, vol. 7, pp. 353-359.
Hale, P. D., et al., "A New Class of Amperometric Biosensor Incorporating a Polymeric Electron-Transfer Mediator", Journal of the American Chemical Society, 1989, vol. 111, No. 9, pp. 3482-3484.
Hao, Y., "Wireless body sensor networks for health-monitoring applications", Physiol. Meas., 2008, vol. 29, R27-R56.
Harrison, D. J. et al., "Characterization of Perfluorosulfonic Acid Polymer Coated Enzyme Electrodes and a Miniaturized Integrated Potentiostat for Glucose Analysis in Whole Blood," Anal. Chem., 1988, vol. 60, No. 19, pp. 2002-2007.
Hawkridge, F. M., et al., "Indirect Coulometric Titration of Biological Electron Transport Components", Analytical Chemistry, 1973, vol. 45, No. 7, pp. 1021-1027.
Heftman, G., "Chip Antenna Reduces Cell-Phone Dimensions", Microwaves & RF, 1999, p. 182.
Heise, T., et al., "Hypoglycemia Warning Signal and Glucose Sensors: Requirements and Concepts", Diabetes Technology & Therapeutics, 2003, vol. 5, No. 4, pp. 563-571.
Heller, A., "Electrical Connection of Enzyme Redox Centers to Electrodes," J. Phys. Chem., 1992, vol. 96, No. 9, pp. 3579-3587.
Heller, A., "Electrical Wiring of Redox Enzymes," Acc. Chem. Res., 1990, vol. 23, No. 5, pp. 129-134.

(56) References Cited

OTHER PUBLICATIONS

Heller, A., et al., "Amperometric Biosensors Based on Three-Dimensional Hydrogel-Forming Epoxy Networks", Sensors and Actuators B, 1993, vol. 13-14, pp. 180-183.
Heller, A., "Implanted Electrochemical Glucose Sensors for the Management of Diabetes", Annnu. Rev. Biomed. Eng., 1999, vol. 1, pp. 153-175.
Hirsch, I. B., "Introduction: History of Glucose Monitoring", Clinical Compendia, 2018, vol. 2018, No. 1, 1 page.
Hoel, P. G., Elementary Statistics: Fourth Edition, 1976, Chapter 5, pp. 113-114.
Howe, D., "Comparing the Dexcom G6 to the G5", 2018, retrieved from https://beyondtype1.org/comparing-the-dexcom-g6-to-the-g5/, pp. 1-10.
Huang, Y., et al., "Antennas from Theory to Practice", 2008, Chapter 8, Antenna Diversity, pp. 322-325.
Ianniello, R. M., et al., "Immobilized Enzyme Chemically Modified Electrode as an Amperometric Sensor", Analytical Chemistry, 1981, vol. 53, No. 13, pp. 2090-2095.
Ianniello, R. M., et al., "Differential Pulse Voltammetric Study of Direct Electron Transfer in Glucose Oxidase Chemically Modified Graphite Electrodes", Analytical Chemistry, 1982, vol. 54, No. 7, pp. 1098-1101.
Ikeda, T., et al., "Kinetics of Outer-Sphere Electron Transfers Between Metal Complexes in Solutions and Polymeric Films on Modified Electrodes", Journal of the American Chemical Society, 1981, vol. 103, No. 25, pp. 7422-7425.
Ikeda, T., et al., "Glucose Oxidase-Immobilized Benzoquinone-Carbon Paste Electrode as a Glucose Sensor", Agricultural and Biological Chemistry, 1985, vol. 49, No. 2, pp. 541-543.
Ikeda, T., et al., "Artificial Pancreas—Investigation of the Stability of Glucose Sensors Using a Telemetry System" (English language translation of abstract), Jpn. J. Artif. Organs, 1990, vol. 19, No. 2, pp. 889-892.
"In Vitro Diagnostic Products for Human Use", Federal Register, 1974, vol. 39, No. 126, pp. 24136-24147.
Isermann, R., "Supervision, Fault-Detection and Fault-Diagnosis Methods—An Introduction", Control Engineering Practice, 1997, vol. 5, No. 5, pp. 639-652.
Isermann, R., et al., "Trends in the Application of Model-Based Fault Detection and Diagnosis of Technical Processes", Control Engineering Practice, 1997, vol. 5, No. 5, pp. 709-719.
Jain, A.K., et al., "Wound Rotor Induction Generator With Sensorless Control and Integrated Active Filter for Feeding Nonlinear Loads in a Stand-Alone Grid", IEEE Transactions on Industrial Electronics, 2008, vol. 55, No. 1, pp. 218-228.
James, Jr., et al., "Handbook of Microstrip Antennas", 1969, pp. 1038-1047.
Johnson, J. M., et al., "Potential-Dependent Enzymatic Activity in an Enzyme Thin-Layer Cell", Analytical Chemistry, 1982, vol. 54, No. 8, pp. 1377-1383.
Johnson, K. W., "Reproducible Electrodeposition of Biomolecules for the Fabrication of Miniature Electroenzymatic Biosensors", Sensors and Actuators B, 1991, vol. 5, pp. 85-89.
Johnson, K. W., et al., "In vivo evaluation of an electroenzymatic glucose sensor implanted in subcutaneous tissue," Biosensors and Bioelectronics, 1992, vol. 7, pp. 709-714.
Johnson, P. C., "Peripheral Circulation", John Wiley & Sons, 1978, p. 198.
Jönsson, G., et al., "An Amperometric Glucose Sensor Made by Modification of a Graphite Electrode Surface With Immobilized Glucose Oxidase and Adsorbed Mediator", Biosensors, 1985, vol. 1, pp. 355-368.
Josowicz, M., et al., "Electrochemical Pretreatment of Thin Film Platinum Electrodes", Journal of the Electrochemical Society, 1988, vol. 135, No. 1, pp. 112-115.
Jovanovic, L., "The Role of Continuous Glucose Monitoring in Gestational Diabetes Mellitus", Diabetes Technology & Therapeutics, 2000, vol. 2, Supplement 1, pp. S-67-S-71.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", Diabetes Care, 2001, vol. 24, No. 7, pp. 1303-1304.
Kaplan, S. M., "Wiley Electrical and Electronics Engineering Dictionary", IEEE Press, 2004, pp. 141, 142, 548, 549.
Katakis, I., et al., "L-α-Glycerophosphate and L-Lactate Electrodes Based on the Electrochemical 'Wiring' of Oxidases", Analytical Chemistry, 1992, vol. 64, No. 9, pp. 1008-1013.
Katakis, I., et al., "Electrostatic Control of the Electron Transfer Enabling Binding of Recombinant Glucose Oxidase and Redox Polyelectrolytes", Journal of the American Chemical Society, 1994, vol. 116, No. 8, pp. 3617-3618.
Kenausis, G., et al., "'Wiring' of Glucose Oxidase and Lactate Oxidase Within a Hydrogel Made with Poly(vinyl pyridine) complexed with [Os(4,4'-dimethoxy-2,2'-bipyridine) $_2$Cl]$^{+/2+}$" , Journal of the Chemical Society, Faraday Transactions, 1996, vol. 92, No. 20, pp. 4131-4136.
Klonoff, D. C., "A Review of Continuous Glucose Monitoring Technology", Diabetes Technology & Therapeutics, 2005, vol. 7, No. 5, pp. 770-775.
Kondepati, V., et al., "Recent Progress in Analytical Instrumentation for Glycemic Control in Diabetic and Critically Ill Patients", Analytical Bioanalytical Chemistry, 2007, vol. 388, pp. 545-563.
Koudelka, M., et al., "In-Vivo Behaviour of Hypodermically Implanted Microfabricated Glucose Sensors", Biosensors & Bioelectronics, 1991, vol. 6, pp. 31-36.
Kulys, J., et al., "Mediatorless Peroxidase Electrode and Preparation of Bienzyme Sensors", Bioelectrochemistry and Bioenergetics, 1990, vol. 24, pp. 305-311.
Lager, W., et al., "Implantable Electrocatalytic Glucose Sensor", Hormone Metabolic Research, 1994, vol. 26, pp. 526-530.
León, L. P., et al., "Continuous-Flow Analysis for Glucose in Serum, with Use of Hexokinase and Glucose-6-Phosphate Dehydrogenase Co-Immobilized in Tubular Form", Clinical Chemistry, 1980, vol. 26, No. 1, pp. 123-129.
Lindner, E., et al., "Flexible (Kapton-Based) Microsensor Arrays of High Stability for Cardiovascular Applications", Journal of the Chemical Society, Faraday Transactions, 1993, vol. 89, No. 2, pp. 361-367.
Lo, B., et al., "Key Technical Challenges and Current Implementations of Body Sensor Networks", Body Sensor Networks, 2005, pp. 1-5.
Lodwig, V., et al., "Continuous Glucose Monitoring with Glucose Sensors: Calibration and Assessment Criteria", Diabetes Technology & Therapeutics, 2003, vol. 5, No. 4, pp. 573-587.
Lortz, J., et al., "What is Bluetooth? We Explain The Newest Short-Range Connectivity Technology", Smart Computing Learning Series, Wireless Computing, 2002, vol. 8, Issue 5, pp. 72-74.
Loy, M., et al., "ISM-Band and Short Range Device Antennas", Texas Instruments Application Report, 2005, pp. 1-38.
Maidan, R. et al., "Elimination of Electroaxidizable Interferant-Produced Currents in Amperometric Biosensors," Analytical Chemistry, 1992, vol. 64, No. 23, pp. 2889-2896.
Malin, S. F., et al., "Noninvasive Prediction of Glucose by Near-Infrared Diffuse Reflectance Spectoscopy", Clinical Chemistry, 1999, vol. 45, No. 9, pp. 1651-1658.
Mastrototaro, J.J., et al., "An Electroenzymatic Glucose Sensor Fabricated on a Flexible Substrate," Sensors and Biosensors B Chemical, 1991, B5, pp. 139-144.
Mauras, N., et al., "Lack of Accuracy of Continuous Sensors in Healthy, Nondiabetic Children: Results of the Diabetes Research in Children Network (DirecNet) Accuracy Study", Journal of Pediatrics, 2004, pp. 770-775.
Mcgarraugh, G., et al., "Glucose Measurements Using Blood Extracted from the Forearm and the Finger", TheraSense, Inc., 2001, 16 Pages.
Mcgarraugh, G., et al., "Physiological Influences on Off-Finger Glucose Testing", Diabetes Technology & Therapeutics, 2001, vol. 3, No. 3, pp. 367-376.

(56) References Cited

OTHER PUBLICATIONS

Mckean, B., et al., "A Telemetry-Instrumentation System for Chronically Implanted Glucose and Oxygen Sensors," IEEE Transactions on Biomedical Engineering, 1988, vol. 35, No. 7, pp. 526-532.
Mcneil, C. J., et al., "Thermostable Reduced Nicotinamide Adenine Dinucleotide Oxidase: Application to Amperometric Enzyme Assay", Analytical Chemistry, 1989, vol. 61, No. 1, pp. 25-29.
Medtronic Guardian® REAL-Time Continuous Glucose Monitoring System User Guide, 2006, pp. 1-181.
Medtronic Guardian® REAL-Time Continuous Glucose Monitoring System User Guide, 2006, pp. 1-184.
Medtronic MiniMed Sen-Serter® User Guide, 2006, pp. 1-96.
IPR2022-00605 (Ex. 1027) The Merriam-Webster Dictionary, Merriam Webster, Incorporated (2005), pp. 66, 403, and 415.
Microchip Technology Inc., MRF24J40MA Data Sheet, 2008, pp. 1-30.
IPR2022-00605 (Ex. 2008) MiniMed® Glucose Sensor, REF MMT-7002, Instructions for Use, May 1999, pp. 1-4.
Minimed Technologies, "Tape Tips and Other Infusion Site Information", 1995.
MINIMED Quick-set™ retrieved from https://web.archive.org/web/20010412224824/http://www.minimed.com/patientfam/pf_ipt_pumpinfusion_quickset.shtml, Apr. 12, 2001, pp. 1-2.
MINIMED Sof-set Micro QR® Sof-set Ultimate QR® retrieved from https://web.archive.org/web/20010412225617/http://www.minimed.com/patientfam/pf_ipt_pumpinfusion_sofset.shtml, Apr. 12, 2001, pp. 1-2.
Miyawaki, O., et al., "Electrochemical and Glucose Oxidase Coenzyme Activity of Flavin Adenine Dinucleotide Covalently Attached to Glassy Carbon at the Adenine Amino Group", Biochimica et Biophysica Acta, 1985, vol. 838, pp. 60-68.
Moatti-Sirat, D., et al., "Evaluating In Vitro and In Vivo the Interference of Ascorbate and Acetaminophen on Glucose Detection by a Needle-Type Glucose Sensor", Biosensors & Bioelectronics, 1992, vol. 7, pp. 345-352.
Moatti-Sirat, D., et al., "Reduction of Acetaminophen Interference in Glucose Sensors by a Composite Nafion Membrane: Demonstration in Rats and Man", Diabetologia, 1994, vol. 37, pp. 610-616.
Moatti-Sirat, D., et al., "Towards Continuous Glucose Monitoring: In Vivo Evaluation Of A Miniaturized Glucose Sensor Implanted For Several Days In Rat Subcutaneous Tissue," Diabetolocia, 1992, vol. 35, No. 3 (1 page—Abstract only).
IPR2022-00605 (Ex. 2003) "Monitoring Your Blood Sugar", retrieved from https://www.cdc.gov/diabetes/managing/managing-blood-sugar/bloodglucosemonitoring.html, 2021, pp. 1-3.
Moore, B., "The Potential Use of Radio Frequency Identification Devices for Active Monitoring of Blood Glucose Levels", Journal of Diabetes Science and Technology, 2009, vol. 3, No. 1, pp. 180-183.
Morak, J., et al., "Design and Evaluation of a Telemonitoring Concept Based on NFC-Enabled Mobile Phones and Sensor Devices", IEEE Transactions on Information Technology in Biomedicine, 2012, vol. 16, No. 1, pp. 17-23.
Morbiducci, U., et al., "Improved Usability of the Minimal Model of Insulin Sensitivity Based on an Automated Approach and Genetic algorithms for Parameter Estimation", Clinical Science, vol. 112, 2007, pp. 257-263.
Mougiakakou, S. G., et al., "A Real Time Simulation Model of Glucose-Insulin Metabolism for Type 1 Diabetes Patients", Proceedings of the 2005 IEEE, 2005, pp. 298-301.
Movassaghi, S., et al., "Wireless Technologies for Body Area Networks: Characteristics and Challenges", 2012 International Symposium on Communications and Information Technologies (ISCIT), 2012, Gold Coast, QLD, Australia, pp. 42-47.
"Murata Puts Antenna on a Chip", Passives, 1999, vol. 44, 1 page.
Nagy, G., et al., "A New Type of Enzyme Electrode: The Ascorbic Acid Eliminator Electrode", Life Sciences, 1982, vol. 31, No. 23, pp. 2611-2616.
Nakamura, S., et al., "Effect of Periodate Oxidation on the Structure and Properties of Glucose Oxidase", Biochimica et Biophysica Acta., 1976, vol. 445, pp. 294-308.
Narasimham, K., et al., "p-Benzoquinone Activation of Metal Oxide Electrodes for Attachment of Enzymes", Enzyme and Microbial Technology, 1985, vol. 7, pp. 283-286.
Ohara, T. J., et al., "Glucose Electrodes Based on Cross-Linked $[Os(bpy)_2Cl]^{+/2+}$ Complexed Poly(1-vinylimadazole) Films," Analytical Chemistry, 1993, vol. 65, No. 23, pp. 3512-3516.
Ohara, T. J., et al., "'Wired' Enzyme Electrodes for Amperometric Determination of Glucose or Lactate in the Presence of Interfering Substances", Analytical Chemistry, 1994, vol. 66, No. 15, pp. 2451-2457.
Ohara, T. J., "Osmium Bipyridyl Redox Polymers Used in Enzyme Electrodes", Platinum Metals Review, 1995, vol. 39, No. 2, pp. 54-62.
Olievier, C. N., et al., "In Vivo Measurement of Carbon Dioxide Tension with a Miniature Electrodes", Pflugers Archiv: European Journal of Physiology, 1978, vol. 373, pp. 269-272.
OmniPod Insulet UST400 User Manual, 2011, pp. 1-190.
Opinion of the Court, Supreme Court of the United States, No. 04-1350, *KSR International co.*, Petitioner v. *Teleflex Inc. et al.*, Apr. 30, 2007.
Osmonics, Poretics® Polycarbonate Membrane; Product Leaflet; Engineering Purity, 2002, pp. 1-2.
Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", Journal of ElectroAnalytical Chemistry, 1989, vol. 260, pp. 487-494.
Palleschi, G., et al., "A Study of Interferences in Glucose Measurements in Blood by Hydrogen Peroxide Based Glucose Probes", Analytical Biochemistry, 1986, vol. 159, pp. 114-121.
Pankratov, I., et al., "Sol-Gel Derived Renewable-Surface Biosensors", Journal of ElectroAnalytical Chemistry, 1995, vol. 393, pp. 35-41.
Parker, R., et al., "Robust $H_\infty$ Glucose Control in Diabetes Using a Physiological Model", AIChE Journal, 2000, vol. 46, No. 12, 2000, pp. 2537-2549.
Passey, R. B., et al., "Evaluation and Comparison of 10 Glucose Methods and the Reference Method Recommendation in the Proposed Product Class Standard (1974)", Clinical Chemistry, 1977, vol. 23, No. 1, pp. 131-139.
Pathak, C., et al., "Rapid Photopolymerization of Immunoprotective Gels in Contact with Cells and Tissue", Journal of the American Chemical Society, 1992, vol. 114, No. 21, pp. 8311-8312.
Patton, S. R., et al., "Continuous Glucose Monitoring Versus Self-monitoring of Blood Glucose in Children with Type 1 Diabetes—Are there Pros and Cons for Both?", US Endocrinol., 2012, vol. 8, No. 1, pp. 27-29.
Pickup, J., "Developing Glucose Sensors for In Vivo Use", Tibtech, 1993, vol. 11, pp. 285-291.
Pickup, J., et al., "Implantable Glucose Sensors: Choosing the Appropriate Sensing Strategy", Biosensors, 1987/88, vol. 3, pp. 335-346.
Pickup, J. C., et al., "In Vivo Molecular Sensing In Diabetes Mellitus: An Implantable Glucose Sensor With Direct Electron Transfer," Diabetologia, 1989, vol. 32, No. 3, pp. 213-217.
Pickup, J., et al., "Potentially-Implantable, Amperometric Glucose Sensors with Mediated Electron Transfer: Improving the Operating Stability", Biosensors, 1989, vol. 4, pp. 109-119.
Pishko, M. V., et al., "Amperometric Glucose Microelectrodes Prepared Through Immobilization of Glucose Oxidase in Redox Hydrogels," Anal. Chem., 1991, vol. 63, No. 20, pp. 2268-2272.
Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", Diabetologia, 1993, vol. 36, pp. 658-663.
Poitout, V., et al., "Calibration in Dogs of a Subcutaneous Miniaturized Glucose Sensor Using a Glucose Meter for Blood Glucose Determination", Biosensors & Bioelectronics, 1992, vol. 7, pp. 587-592.

(56) References Cited

OTHER PUBLICATIONS

Poitout, V., et al., "In Vitro and in Vivo Evaluation in Dogs of a Miniaturized Glucose Sensor," ASAIO Transactions, 1991, vol. 37, No. 3 (1 page—Abstract only).
Pollak, A., et al., "Enzyme Immobilization by Condensation Copolymerization into Cross-Linked Polyacrylamide Gels", Journal of the American Chemical Society, 1980, vol. 102, No. 20, pp. 6324-6336.
Quinn, C. P., et al., "Kinetics of Glucose Delivery to Subcutaneous Tissue in Rats Measured with 0.3-mm Amperometric Microsensors", The American Physiological Society, 1995, E155-E161.
Ratner, B. D., "Reducing Capsular Thickness and Enhancing Angeiogenesis Around Implant Drug Release Systems", Journal of Controlled Release, 2002, vol. 78, pp. 211-218.
Reach, G., et al., "Can Continuous Glucose Monitoring Be Used for the Treatment of Diabetes?", Analytical Chemistry, 1992, vol. 64, No. 6, pp. 381-386.
Rebrin, K., et al., "Automated Feedback Control of Subcutaneous Glucose Concentration in Diabetic Dogs," Diabetologia, 1989, vol. 32, No. 8, pp. 573-576.
Repas, R., "Sensor Sense: RFID for smart position sensing", retrieved from https://www/machinedesign/com/automation-iiot/article/21818777/sensor-sense-rfid-for- smart-position-sensing, 2010, pp. 1-2.
Rodriguez, N., et al., "Flexible Communication and Control Protocol for Injectable Neuromuscular Interfaces", IEEE Transactions on Biomedical Circuits and Systems, 2007, vol. 1, No. 1, pp. 19-27.
Roe, J. N., et al., "Bloodless Glucose Measurements", Critical Review in Therapeutic Drug Carrier Systems, vol. 15, Issue 3, 1998, pp. 199-241.
IPR2022-00605 (Ex. 1024) "Rotor," Dictionary of Mechanical Engineering, Fourth Ed., G.H.F. Nayler, Society of Automotive Engineers, Inc., 1996, p. 328.
IPR2022-00605 (Ex. 1025) "Rotor," Random House Kernerman Webster's College Dictionary, K Dictionaries Ltd. (2010), available at https://www.thefreedictionary.com/rotor.
IPR2022-00605 (Ex. 1026) "Rotate," Random House Kernerman Webster's College Dictionary, K Dictionaries Ltd. (2010), available at https://www.thefreedictionary.com/rotate.
Sakakida, M., et al., "Ferrocene-mediated needle-type glucose sensor covered with newly designed biocompatible membrane," Sensors and Actuators B, 1993, vols. 13-14, pp. 319-322.
Sakakida, M., et al., "Development of ferrocene-mediated needle-type glucose sensor as a measure of true subcutaneous tissue glucose concentrations", Artif Organs Today, 1992, vol. 2, No. 2, pp. 145-458.
Salditt, P., "Trends in Medical Device Design and Manufacturing", SMTA News and Journal of Surface Mount Technology, 2004, vol. 17, pp. 19-24.
Salehi, C., et al., "A Telemetry-Instrumentation System for Long-Term Implantable Glucose and Oxygen Sensors", Analytical Letters, 1996, vol. 29, No. 13, pp. 2289-2308.
Samuels, G. J., et al., "An Electrode-Supported Oxidation Catalyst Based on Ruthenium (IV). pH "Encapsulation" in a Polymer Film", Journal of the American Chemical Society, 1981, vol. 103, No. 2, pp. 307-312.
Sandham, W., et al., "Blood Glucose Prediction for Diabetes Therapy Using a Recurrent Artificial Neural Network", $9^{th}$ European Signal Processing Conference, 1998, Rhodes, Greece, pp. 1-4.
Sasso, S. V., et al., "Electropolymerized 1,2-Diaminobenzene as a Means to Prevent Interferences and Fouling and to Stabilize Immobilized Enzyme in Electrochemical Biosensors", Analytical Chemistry, 1990, vol. 62, No. 11, pp. 1111-1117.
IPR2022-00605 (Ex. 1013) Scheduling Order in *Abbott Diabetes Care Inc., et al.* v. *Dexcom, Inc.*, 1:21-cv-00977 (D. Del.), dated Dec. 2, 2021.
Scheller, F., et al., "Enzyme Electrodes and Their Application", Philosophical Transactions of The Royal Society of London B, 1987, vol. 316, pp. 85-94.
Schmehl, R. H., et al., "The Effect of Redox Site Concentration on the Rate of Mediated Oxidation of Solution Substrates by a Redox Copolymer Film", Journal of ElectroAnalytical Chemistry, 1983, vol. 152, pp. 97-109.
Schmidt, F. J., et al., "Calibration of a Wearable Glucose Sensor", The International Journal of Artificial Organs, 1992, vol. 15, No. 1, pp. 55-61.
Schmidtke, D. W., et al., "Accuracy of the One-Point In Vivo Calibration of "Wired" Glucose Oxidase Electrodes Implanted in Jugular Veins of Rats in Periods of Rapid Rise and Decline of the Glucose Concentration", Analytical Chemistry, 1998, vol. 70, No. 10, pp. 2149-2155.
Schmidtke, D. W., et al., "Measurement and Modeling of the Transient Difference Between Blood and Subcutaneous Glucose Concentrations in the Rat After Injection of Insulin", Proceedings of the National Academy of Sciences, 1998, vol. 95, pp. 294-299.
Schoepke, E., "Chip Antenna Layout Considerations for 802.11 Applications", Johanson Technology, 2006, retrieved from https://www.johansontechnology.com/chip-antenna-layout-considerations-for-802-11-applications, pp. 1-7.
Sharawi, M. S., "Use of low-cost patch antennas in modern wireless technology", IEEE Potentials, 2006, pp. 35-38 and 47.
Shaw, G. W., et al., "In Vitro Testing of a Simply Constructed, Highly Stable Glucose Sensor Suitable for Implantation in Diabetic Patients", Biosensors & Bioelectronics, 1991, vol. 6, pp. 401-406.
Shichiri, M., et al., "Glycaemic Control in Pancreatectomized Dogs with a Wearable Artificial Endocrine Pancreas," Diabetologia, 1983, vol. 24, No. 3, pp. 179-18.
Shichiri, M., et al., "Membrane Design for Extending the Long-Life of an Implantable Glucose Sensor", Diabetes Nutrition and Metabolism, 1989, vol. 2, pp. 309-313.
Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.
Shichiri, M., et al., "Telemetry Glucose Monitoring Device with Needle-type Glucose Sensor: A Useful Tool for Blood Glucose Monitoring in Diabetic Individuals," Diabetes Care, 1986, vol. 9, No. 3, pp. 298-301.
Shichiri, M., et al., "In Vivo Characteristics Of Needle-Type Glucose Sensor—Measurement Of Subcutaneous Glucose Concentrations In Human Volunteers," Horm Metab Res Suppl. 1988, vol. 20, pp. 17-20.
Shichiri, M., et al., "Wearable Artificial Endocrine Pancreas With Needle-Type Glucose Sensor," The Lancet, 1982, vol. 2, No. 8308, pp. 1129-1131.
Shults, M., "A Telemetry-Instrumentation System for Monitoring Multiple Subcutaneously Implanted Glucose Sensors," IEEE Transactions on Biomedical Engineering, 1994, vol. 41, No. 10, pp. 937-942.
Sittampalam, G., et al., "Surface-Modified Electrochemical Detector for Liquid Chromatography", Analytical Chemistry, 1983, vol. 55, No. 9, pp. 1608-1610.
Soegijoko, S., et al., "External Artificial Pancreas: A New Control Unit Using Microprocessor", Hormone and Metabolic Research Supplement Series, 1982, vol. 12, pp. 165-169.
Sparacino, G., et al., "Glucose Concentration Can Be Predicted Ahead in Time from Continuous Glucose Monitoring Sensor Time-Series", IEEE Transactions on Biomedical Engineering, 2007, vol. 54, No. 5, pp. 931-937.
Sprules, S. D., et al., "Evaluation of a New Disposable Screen-Printed Sensor Strip for the Measurement of NADH and Its Modification to Produce a Lactate Biosensor Employing Microliter Volumes", Electroanalysis, 1996, vol. 8, No. 6, pp. 539-543.
Sternberg, F., et al., "Calibration Problems of Subcutaneous Glucosensors when Applied "In-Situ" in Man", Hormone and Metabolic Research, 1994, vol. 26, pp. 523-526.
Sternberg, R., et al., "Covalent Enzyme Coupling on Cellulose Acetate Membranes for Glucose Sensor Development", Analytical Chemistry, 1988, vol. 60, No. 24, pp. 2781-2786.
Sternberg, R., et al., "Study and Development of Multilayer Needle-type Enzyme-based Glucose Microsensors," Biosensors, 1988, vol. 4, pp. 27-40.

(56) References Cited

OTHER PUBLICATIONS

Suekane, M., et al., "Immobilization of Glucose Isomerase", Zettschrift fur Allgemeine Mikrobiologie, 1982, vol. 22, No. 8, pp. 565-576.
Tajima, S., et al., "Simultaneous Determination of Glucose and 1,5-Anydroglucitol", Chemical Abstracts, 1989, vol. 111, No. 25, p. 394.
Tarasevich, M. R., "Bioelectrocatalysis", Comprehensive Treatise of Electrochemistry, 1985, vol. 10, pp. 231-295.
Tatsuma, T., et al., "Enzyme Monolayer- and Bilayer-Modified Tin Oxide Electrodes for the Determination of Hydrogen Peroxide and Glucose", Analytical Chemistry, 1989, vol. 61, No. 21, pp. 2352-2355.
Taylor, C., et al., ""Wiring" of Glucose Oxidase Within a Hydrogel Made with Polyvinyl Imidazole Complexed with [(Os-4,4'-dimethoxy-2,2'-bipyridine)Cl]$^{+/2+}$", Journal of ElectroAnalytical Chemistry, 1995, vol. 396, pp. 511-515.
Thompson, M., et al., "In Vivo Probes: Problems and Perspectives", Clinical Biochemistry, 1986, vol. 19, pp. 255-261.
Townsend, K., et al., "Getting Started with Bluetooth Low Energy—Chapter 1", 2014, pp. 1-26.
Trojanowicz, M., et al., "Enzyme Entrapped Polypyrrole Modified Electrode for Flow-Injection Determination of Glucose", Biosensors & Bioelectronics, 1990, vol. 5, pp. 149-156.
Tsalikian, E., et al., "Accuracy of the GlucoWatch G2® Biographer and the Continuous Glucose Monintoring System During Hypoglycemia: Experience of the Diabetes Research in Children Network", Diabetes Care, 2004, vol. 27, No. 3, pp. 722-726.
Tung, S., "Layers of Security for Active RFID Tags", RFID Handbook: Applications, Technology, Security, and Privacy, Edited by Ehson, et al., Chapter 33, 2008, pp. 1-28.
Turner, A.P.F., et al., "Diabetes Mellitus: Biosensors for Research and Management", Biosensors, 1985, vol. 1, pp. 85-115.
Turner, R.F.B., et al., "A Biocompatible Enzyme Electrode for Continuous in vivo Glucose Monitoring in Whole Blood", Sensors and Actuators B, 1990, vol. 1, pp. 561-564.
Tuzhi, P., et al., "Constant Potential Pretreatment of Carbon Fiber Electrodes for in Vivo Electrochemistry", Analytical Letters, 1991, vol. 24, No. 6, pp. 935-945.
Umana, M., "Protein-Modified Electrochemically Active Biomaterial Surface", U.S. Army Research Office, Analytical and Chemical Sciences Research Triangle Institute, 1988, pp. 1-9.
United States Court of Appeals for the Federal Circuit, No. 06-1402, *Leapfrog Enterprises, Inc.* v. *Fisher-Price, Inc. and Mattel, Inc.*, May 9, 2007.
Updike, S. J., et al., "Principles of Long-term Fully Implanted Sensors with Emphasis on Radiotelemetric Monitoring of Blood Glucose from inside a Subcutaneous Foreign Body Capsule (FBC)", Biosensors in the Body: Continuous In vivo Monitoring, Chapter 4, 1997, pp. 117-137.
Updike, S. J., et al., "A Subcutaneous Glucose Sensor With Improved Longevity, Dynamic Range, and Stability of Calibration", Diabetes Care, 2000, vol. 23, pp. 208-214.
Urban, G., et al., "Miniaturized Thin-Film Biosensors Using Covalently Immobilized Glucose Oxidase", Biosensors & Bioelectronics, 1991, vol. 6, pp. 555-562.
Velho, G., et al., "In Vitro and In Vivo Stability of Electrode Potentials in Needle-Type Glucose Sensors", Diabetes, 1989, vol. 38, No. 2, pp. 164-171.
Velho, G. et al., "Strategies for Calibrating a Subcutaneous Glucose Sensor," Biomed. Biochim. Acta, 1989, 48 (11112), pp. 957-964.
Von Woedtke, T., et al., "In Situ Calibration of Implanted Electrochemical Glucose Sensors", Biomedica Biochimica Acta, 1989, vol. 48, pp. 943-952.
Vreeke, M. S., et al., "Hydrogen Peroxide Electrodes Based on Electrical Connection of Redox Centers of Various Peroxidases to Electrodes through a Three-Dimensional Electron-Relaying Polymer Network", Diagnostic Biosensors Polymers, Chapter 15, 1993, pp. 180-193.
Vreeke, M., et al., "Hydrogen Peroxide and B-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", Analytical Chemistry, 1992, vol. 64, No. 24, pp. 3084-3090.
Wang, D. L., et al., "Miniaturized Flexible Amperometric Lactate Probe", Analytical Chemistry, 1993, vol. 65, No. 8, pp. 1069-1073.
Wang, J., et al., "Activation of Glassy Carbon Electrodes by Alternating Current Electrochemical Treatment", Analytica Chimica Acta, 1985, vol. 167, pp. 325-334.
Wang, J., et al., "Amperometric Biosensing of Organic Peroxides with Peroxidase-Modified Electrodes", Analytica Chimica Acta, 1991, vol. 254, pp. 81-88.
Wang, J., et al., "Screen-Printable Sol-Gel Enzyme-Containing Carbon Inks", Analytical Chemistry, 1996, vol. 68, No. 15, pp. 2705-2708.
Wang, J., et al., "Sol-Gel-Derived Metal-Dispersed Carbon Composite Amperometric Biosensors", Electroanalysis, 1997, vol. 9, No. 1, pp. 52-55.
Wang, X.H., et al., "Bluetooth: Opening a blue sky for healthcare", Mobile Information Systems, 2006, vol. 2, pp. 151-167.
Ward, W. K., et al., "Rise in Background Current Over Time in a Subcutaneous Glucose Sensor in the Rabbit: Relevance to Calibration and Accuracy", Biosensors & Bioelectronics, 2000, vol. 15, pp. 53-61.
Waterhouse, R., "Printed Antennas for Wireless Communications," 2007, pp. 116-129 and 284-289.
Williams, D. L., et al., "Electrochemical-Enzymatic Analysis of Blood Glucose and Lactate", Analytical Chemistry, 1970, vol. 42, No. 1, pp. 118-121.
Wilson, G. S., et al., "Progress Toward the Development of an Implantable Sensor for Glucose," Clinical Chemistry, 1992, vol. 38, No. 9, pp. 1613-1617.
Wong, KL, "Planar Antennas for Wireless Communications," 2003, Chapter 1, Introduction and Overview, pp. 4-17, 38-45, and 218-221.
Yabuki, S., et al., "Electro-Conductive Enzyme Membrane", Journal of the Chemical Society, Chemical Communications, 1989, pp. 945-946.
Yang, L., et al., "Determination of Oxidase Enzyme Substrates Using Cross-Flow Thin-Layer Amperometry", Electroanalysis, 1996, vol. 8, No. 8-9, pp. 716-721.
Yao, S. J., et al., "The Interference of Ascorbate and Urea in Low-Potential Electrochemical Glucose Sensing", Proceedings of the Twelfth Annual International Conference of the IEEE Engineering in Medicine and Biology Society, 1990, vol. 12, Part 2, pp. 487-489.
Yao, T., "A Chemically-Modified Enzyme Membrane Electrode as an Amperometric Glucose Sensor", Analytica Chimica Acta, 1983, vol. 148, pp. 27-33.
Ye, L. et al., "High Current Density "Wired" Quinoprotein Glucose Dehydrogenase Electroade," Anal. Chem., 1993, vol. 65, No. 3, pp. 238-241.
Yildiz, A., et al., "Evaluation of an Improved Thin-Layer Electrode", Analytical Chemistry, 1968, vol. 40, No. 7, pp. 1018-1024.
Zamzow, K., et al., "New Wearable Continuous Blood Glucose Monitor (BGM) and Artificial Pancreas (AP)", Diabetes, 1990, vol. 39, p. 5A-20.
Z-Carbon Connector, retrieved from http://www.zaxisconnector.com/SS_zc.shtml, 2004, 2 pages.
Zhang, Y., et al., "Application of Cell Culture Toxicity Tests to the Development of Implantable Biosensors", Biosensors & Bioelectronics, 1991, vol. 6, pp. 653-661.
Zhang, Y., et al., "Elimination of the Acetaminophen Interference in an Implantable Glucose Sensor", Analytical Chemistry, 1994, vol. 66, No. 7, pp. 1183-1188.
Zhu, J., et al., "Fabrication and Characterization of Glucose Sensors Based on a Microarray $H_2O_2$ electrode", Biosensors & Bioelectronics, 1994, vol. 9, pp. 295-300.
Zisser, H. C., "The OmniPod Insulin Management System: the Latest Innovation in Insulin Pump Therapy", Diabetes Ther, 2010, vol. 1, No. 1, pp. 10-24.
Z-Silver Connector, retrieved from http://www.zaxisconnector.com/SS_zs.shtml, 2004, 2 pages.
AU, 2019404908 Examiner's Report, Feb. 17, 2025.

(56) References Cited

OTHER PUBLICATIONS

CA, 2,617,192 Examiner's Report, Oct. 22, 2012.
CA, 2,984,939 Examiner's Report, Aug. 7, 2024.
CA, 2,984,939 Examiner's Report, Nov. 15, 2023.
CA, 3,050,721 Examiner's Report, Nov. 8, 2024.
CA, 3,120,335 Examiner's Report, May 27, 2024.
CA, 3,182,961 Examiner's Report, Dec. 6, 2023.
CA, 3,228,738 Examiner's Report, May 8, 2025.
CA, 3,254,151 Examiner's Report, Dec. 24, 2025.
CN, 200780039416.2 Second Office Action, Apr. 25, 2012.
CN, 200780039416.2 First Office Action, Apr. 30, 2011.
CN, 200880005149.1 Notice of Allowance, Jun. 21, 2013.
CN, 200880005149.1 Fourth Office Action, Dec. 3, 2012.
CN, 200880005149.1 Third Office Action, Feb. 16, 2012.
CN, 200880005149.1 Second Office Action, Aug. 17, 2011.
CN, 200880005149.1 First Office Action, Jul. 29, 2010.
CN, 200880005388.7 Second Office Action, May 16, 2012.
CN, 200880005388.7 First Office Action, Jul. 25, 2011.
CN, 201980082748.1 Final Office Action, Nov. 27, 2023.
CN, 202180063087.5 First Office Action, Aug. 14, 2025.
CN, 202211091194.1 Notification of Filing Divisional Application, Mar. 27, 2025.
DE, Complaint in Litigation of EP 3300658, Mar. 20, 2024.
EP, 06788869.3 Examination Report, Sep. 25, 2012.
EP, 06788869.3 Extended Search Report, Mar. 18, 2010.
EP, 06813967.4 Extended Search Report, Mar. 4, 2010.
EP, 07854298.2 Extended Search Report, Mar. 29, 2010.
EP, 08730066.1 Extended Search Report, Oct. 5, 2012.
EP, 10739031.2 Summons to Attend Oral Proceedings, Oct. 26, 2023.
EP, 10739031.2 Communication from Board of Appeals, Feb. 21, 2024.
EP, 10739031.2 Minutes of Oral Proceedings, May 10, 2024.
EP, 10739031.2 Decision of Oral Proceedings, Jun. 11, 2024.
EP, 17182379.2 Decision Revoking the European Patent, Nov. 24, 2025.
EP, 17182379.2 Minutes of the Oral Proceedings, Nov. 24, 2025.
EP, 17182379.2 Written Submissions, Aug. 6, 2025.
EP, 17182379.2 Summons to Attend Oral Proceedings, Jul. 4, 2025.
EP, 17182379.2 Reply to Reply to Opposition, May 16, 2025.
EP, 17182379.2 Reply to Opposition, Feb. 27, 2025.
EP, 17182379.2 Grounds of Opposition, Jul. 12, 2024.
EP, 17182379.2 Notice of Opposition, Jul. 12, 2024.
EP, 17182379.2 Reply to Examination Report, Apr. 9, 2021.
EP, 17182379.2 Reply to Search Report, Oct. 3, 2018.
EP, 18741791.0 Examination Report, Sep. 12, 2025.
EP, 18741791.0 Examination Report, Dec. 15, 2023.
EP, 19151577.4 Examination Report, Oct. 7, 2024.
EP, 19151577.4 Examination Report, Sep. 3, 2025.
EP, 19900891.3 Examination Report, May 8, 2025.
EP, 20177703.4 Response to Withdrawals, Jan. 7, 2025.
EP, 20177703.4 Withdrawal of Intervention, Dec. 27, 2024.
EP, 20177703.4 Withdrawal of Opposition, Dec. 27, 2024.
EP, 20177703.4 Written Submissions Dexcom, Nov. 22, 2024.
EP, 20177703.4 Summons to Attend Oral Proceedings, Apr. 29, 2024.
EP, 20177703.4 Reply to Reply to Reply to Notice of Opposition ADC, Dec. 18, 2023.
EP, 20177703.4 Reply to Notice of Intervention, Nov. 17, 2023.
EP, 20177712.5 Notice of Appeal, Jan. 28, 2026.
EP, 20177712.5 Decision Revoking the European Patent, Nov. 28, 2025.
EP, 20177712.5 Minutes of the Oral Proceedings, Nov. 28, 2025.
EP, 20177712.5 Written Submissions Gulde, Aug. 21, 2025.
EP, 20177712.5 Response to Summons to Attend Oral Proceedings, Aug. 21, 2025.
EP, 20177712.5 Summons to Attend Oral Proceedings, Oct. 1, 2024.
EP, 20177712.5 Response to Summons to Attend Oral Proceedings, Aug. 30, 2024.
EP, 20177712.5 Summons to Attend Oral Proceedings, Jul. 2, 2024.
EP, 20177712.5 Response to Written Submissions Dexcom, Feb. 26, 2024.
EP, 20177712.5 Written Submissions ADC, Jan. 26, 2024.
EP, 20177712.5 Reply to Reply to Reply to Notice of Opposition ADC, Dec. 18, 2023.
EP, 20177712.5 Reply to Notice of Intervention, Nov. 17, 2023.
EP, 20177712.5 Reply to Reply to Notice of Opposition Dexcom, Sep. 27, 2023.
EP, 20177712.5 Reply to Reply to Notice of Opposition Gulde & Partner Patent, Aug. 30, 2023.
EP, 20195922.8 Withdrawal of Intervention, Dec. 27, 2024.
EP, 20195922.8 Withdrawal of Opposition, Dec. 27, 2024.
EP, 20195922.8 Grounds of Appeal, Sep. 6, 2024.
EP, 20195922.8 Notice of Appeal, Jul. 4, 2024.
EP, 20195922.8 Written Submissions Dexcom, May 9, 2024.
EP, 20195922.8 Decision Revoking the European Patent, May 8, 2024.
EP, 20195922.8 Minutes of the Oral Proceedings, May 8, 2024.
EP, 20195922.8 Written Submissions Dexcom, Mar. 15, 2024.
EP, 20195922.8 Response to Summons to Attend Oral Proceedings, Feb. 15, 2024.
EP, 20195922.8 Written Submissions Dexcom, Dec. 12, 2023.
EP, 20195922.8 Written Submissions ADC, Oct. 23, 2023.
EP, 20195922.8 Summons to Attend Oral Proceedings, Sep. 21, 2023.
EP, 20195922.8 Reply to Notice of Intervention, Aug. 29, 2023.
EP, 20195922.8 Reply to Reply to Notice of Opposition, Aug. 21, 2023.
EP, 21192910.4 Reply to Notices of Opposition, Jan. 22, 2026.
EP, 21192910.4 Notice of Intervention SenEaron, Nov. 14, 2025.
EP, 21192910.4 Notice of Opposition Stolmar, Sep. 10, 2025.
EP, 21192910.4 Notice of Opposition Strawman, Sep. 10, 2025.
EP, 21211041.5 Summons to Attend Oral Proceedings, Dec. 15, 2025.
EP, 21211041.5 Grounds of Appeal, Apr. 23, 2025.
EP, 21211041.5 Withdrawal of Opposition, Dec. 27, 2024.
EP, 21211041.5 Notice of Appeal, Dec. 17, 2024.
EP, 21211041.5 Minutes of Oral Proceedings, Dec. 13, 2024.
EP, 21211041.5 Response to Summons to Attend Oral Proceedings Dexcom, Nov. 12, 2024.
EP, 21211041.5 Response to Summons to Attend Oral Proceedings, Nov. 12, 2024.
EP, 21211041.5 Summons to Attend Oral Proceedings, Sep. 23, 2024.
EP, 21211041.5 Reply to Notice of Opposition, Jul. 17, 2024.
EP, 21211041.5 Grounds of Opposition Dexcom, Mar. 28, 2024.
EP, 21211041.5 Notice of Opposition Dexcom, Mar. 28, 2024.
EP, 21772864.1 Examination Report, Dec. 9, 2025.
EP, 22754227.1 Examination Report, Jan. 2, 2026.
EP, 23166498.8 Examination Report, Dec. 10, 2025.
EP, 23166498.8 Examination Report, Sep. 2, 2024.
EP, 23166498.8 Extended Search Report, Nov. 17, 2023.
EP, 23190032.5 Examination Report, Dec. 10, 2025.
EP, 23190032.5 Examination Report, May 19, 2025.
EP, 23190032.5 Extended Search Report, Nov. 17, 2023.
EP, 24152079.0 Examination Report, Dec. 2, 2024.
EP, 24152079.0 Extended Search Report, Sep. 4, 2024.
EP, 24152079.0 Partial Search Report, Jun. 14, 2024.
EP, 24183336.7 Extended Search Report, Oct. 11, 2024.
EP, 24187206.8 Examination Report, Jan. 2, 2026.
EP, 24187206.8 Extended Search Report, Oct. 9, 2024.
EP, 24194029.5 Extended Search Report, Nov. 18, 2024.
EP, 24201435.5 Extended Search Report, Jan. 27, 2025.
EP, 24218309.3 Extended Search Report, Jul. 9, 2025.
EP, 24194029.5 Examination Report, Aug. 26, 2025.
EP, 24201435.5 Examination Report, Oct. 28, 2025.
EP, 24220160.6 Extended Search Report, Jun. 17, 2025.
GB, Claim No. HP-2021-000025 Approved Judgement, Oct. 18, 2023.
JP, 2009-534799 Final Office Action, Feb. 19, 2013.
JP, 2009-534799 Office Action, Sep. 27, 2011.
JP, 2021-531135 Office Action, Aug. 9, 2023.
JP, 2023-514023 Final Office Action, Aug. 20, 2025.

(56) References Cited

OTHER PUBLICATIONS

JP, 2023-514023 Office Action, Apr. 16, 2025.
JP, 2023-514024 Office Action, Apr. 30, 2025.
JP, 2023-516522 Office Action, Mar. 5, 2025.
JP, 2023-532327 Office Action, Jul. 23, 2025.
JP, 2024-31538 Office Action, Oct. 16, 2024.
JP, 2025-026588 Office Action, Aug. 27, 2025.
JP, 2025-117332 Office Action, Nov. 19, 2025.
MX, MX/a/2009/004322 Office Action, Mar. 11, 2013.
MX, MX/a/2009/004322 Office Action, Sep. 19, 2012.
MX, MX/a/2021/007294 Third Office Action, Sep. 10, 2025.
MX, MX/a/2021/007294 Second Office Action, Feb. 19, 2025.
MX, MX/a/2021/007294 Office Action, Aug. 20, 2024.
MY, PI2021003022 Examination Report, Mar. 5, 2025.
MY, PI2022002786 Examination Report, Jan. 8, 2025
MY, PI2023005466 Examination Report, Dec. 28, 2023.
RU, 2009134334 Office Action, Feb. 7, 2012.
RU, 2009135048 Office Action, Dec. 20, 2011.
RU, 2009119430 Office Action, Jun. 5, 2011.
UP, Second Expert Opinion of Dr Michael Schoemaker in Litigation of EP 3977921, Nov. 8, 2024.
UP, First Expert Opinion of Dr Michael Schoemaker in Litigation of EP 3977921, Jun. 11, 2024.
US, Decision Denying Institution of Inter Partes Review, IPR No. 2024-00860, Nov. 20, 2024.
US, Patent Owner's Response To Petitioner's Explanation Of Parallel Petitions Challenging U.S. Pat. No. 11,510,325, IPR No. 2024-00860, Aug. 23, 2024.
US, Patent Owner Preliminary Response Pursuant to 37 C.F.R. § 42.107, IPR No. 2024-00860, Aug. 23, 2024.
US, Declaration of Julia Castellano, IPR No. 2024-00860, Aug. 21, 2024.
US, Declaration of Scott E. Davis, IPR No. 2024-00860, Jun. 5, 2024.
US, Notice of Filing Date Accorded to Petition and Time for Filing Patent Owner Preliminary Response, IPR No. 2024-00860, May 23, 2024.
US, Declaration of Dr. Cameron Riviere, Ph.D., IPR No. 2024-00860, May 9, 2024.
US, Petitioner's Explanation Of Parallel Petitions Challenging U.S. Pat. No. 11,510,325, IPR No. 2024-00860, May 9, 2024.
US, Petition For Inter Partes Review Of U.S. Pat. No. 11,510,625, IPR No. 2024-00860, May 9, 2024.
US, Decision Denying Institution of Inter Partes Review, IPR No. 2024-00520, Aug. 8, 2024.
US, Patent Owner's Authorized Sur-Reply to Petitioner's Reply to Patent Owner's Preliminary Response, IPR No. 2024-00520, Jun. 11, 2024.
US, Petitioner's Authorized Reply to Patent Owner's Preliminary Response, IPR No. 2024-00520, May 31, 2024.
US, Patent Owner's Preliminary Response, IPR No. 2024-00520, May 8, 2024.
US, Patent Owner's Exhibit List, IPR No. 2024-00520, Mar. 25, 2024.
US, Telephonic Hearing, IPR No. 2024-00520, Mar. 13, 2024.
US, Petitioner's Explanation of Material Differences Between the Petition in IPR2024-00520 and Previously Filed Petitions in IPR2023-01396 and IPR2023-01397, IPR No. 2024-00520, Jan. 31, 2024.
US, Third Declaration of Gary Fletcher, Ph.D., IPR No. 2024-00520, Jan. 31, 2024.
US, Petition For Inter Partes Review Of U.S. Pat. No. 11,266,335, IPR No. 2024-00520, Jan. 31, 2024.
US, Termination Due to Settlement After Institution of Trial, IPR No. 2023-01409, Jan. 7, 2025.
US, Joint Motion to Treat Settlement Agreement as Business Confidential Information. IPR No. 2023-01409, Jan. 3, 2025.
US, Joint Motion to Terminate Proceeding Under 35 U.S.C. § 317(a), IPR No. 2023-01409, Jan. 3, 2025.
US, Order Setting Oral Argument, IPR No. 2023-01409, Dec. 11, 2024.
US, Patent Owner's Sur-Reply, IPR No. 2023-01409, Dec. 10, 2024.
US, Deposition of Gary D. Fletcher, Ph.D., IPR No. 2023-01409, Dec. 4, 2024.
US, Patent Owner's Request For Oral Argument, IPR No. 2023-01409, Dec. 3, 2024.
US, Petitioner's Request For Oral Argument, IPR No. 2023-01409, Dec. 3, 2024.
US, Patent Owner's Objections to Petitioner's Exhibits Submitted With Its Reply, IPR No. 2023-01409, Nov. 1, 2024.
US, Petitioner's Updated Exhibit List, IPR No. 2023-01409, Oct. 25, 2024.
US, Second Declaration of Gary Fletcher, Ph.D., IPR No. 2023-01409, Oct. 25, 2024.
US, Petitioner's Reply to Patent Owner's Response, IPR No. 2023-01409, Oct. 25, 2024.
US, Deposition of Karl R. Leinsing, MSME, PE, IPR No. 2023-01409, Oct. 17, 2024.
US, Conference Call Before The Patent Trial And Appeal Board • Before Judge Cynthia Hardman, IPR No. 2023-01409, Oct. 17, 2024.
US, Notice of Joint Stipulation to Modify Schedule, IPR No. 2023-01409, Sep. 26, 2024.
US, Declaration of Karl R. Leinsing, MSME, PE, IPR No. 2023-01409, Jul. 19, 2024.
US, Patent Owner's Response, IPR No. 2023-01409, Jul. 19, 2024.
US, Deposition of Gary Fletcher, Ph.D., IPR No. 2023-01409, Jun. 26, 2024.
US, Order, IPR No. 2023-01409, May 30, 2024.
US, Notice of Stipulation, IPR No. 2023-01409, May 29, 2024.
US, Patent Owner's Objections to Petitioner's Exhibits to the Petition, IPR No. 2023-01409, Apr. 29, 2024.
US, Patent Owner's Request for Rehearing by the Director, IPR 2023-01409, Apr. 24, 2024.
US, Email of Peter McAndrews, IPR 2023-01409, Apr. 29, 2024.
US, Decision Granting Institution of Inter Partes Review, IPR No. 2023-01409, Apr. 15, 2024.
US, Scheduling Order, IPR 2023-01409, Apr. 15, 2024.
US, Order Conduct of the Proceeding 37 C.F.R. § 42.5, IPR No. 2023-01409, Feb. 6, 2024.
US, Petitioner's Updated Exhibit List, IPR No. 2023-01409, Feb. 5, 2024.
US, Telephonic Conference Call, IPR No. 2023-01409, Feb. 2, 2024.
US, Patent Owner's Updated Mandatory Notices, IPR No. 2023-01409, Feb. 2, 2024.
US, Email of Andrew M. Mason, IPR 2023-01409, Jan. 30, 2024.
US, Patent Owner's Preliminary Response, IPR No. 2023-01409, Jan. 28, 2024.
US, Notice of Filing Date Accorded to Petition and Time for Filing Patent Owner Preliminary Response, IPR No. 2023-01409, Oct. 18, 2023.
US, Petition For Inter Partes Review Of U.S. Pat. No. 11,202,591, IPR No. 2023-01409, Oct. 11, 2024.
US, Decision Denying Institution of Inter Partes Review, IPR No. 2023-01397, Apr. 16, 2024.
US, Patent Owner's Updated Exhibit List, IPR No. 2023-01397, Mar. 25, 2024.
US, Telephonic Hearing, IPR No. 2023-01397, Mar. 13, 2024.
US, Petitioner's Updated Mandatory Notices Pursuant to 37 C.F.R. § 42.8(a)(3), IPR No. 2023-01397, Feb. 19, 2024.
US, Patent Owner's Updated Mandatory Notices, IPR No. 2023-01397, Feb. 2, 2024.
US, Patent Owner's Preliminary Response, IPR No. 2023-01397, Jan. 18, 2024.
US, Patent Owner's Response to Petitioner's Explanation of Material Differences Between Petitions, IPR Nos. 2023-01396 and 2023-01397, Jan. 18, 2024.
US, Petitioner's Explanation of Material Differences Between Petitions, IPR No. 2023-01397, Oct. 6, 2023.
US, Declaration of Gary D. Fletcher, Ph.D, IPR No. 2023-01396 and IPR No. 2023-01397, Oct. 6, 2023.

(56) References Cited

OTHER PUBLICATIONS

US, Petition For Inter Partes Review Of U.S. Pat. No. 11,266,335, IPR No. 2023-01397, Oct. 6, 2023.
US, Decision Denying Patent Owner's Request on Rehearing of Decision Denying Institution, IPR No. 2023-01396, Aug. 9, 2024.
US, Petitioner's Request for Rehearing of Decision Denying Institution, IPR No. 2023-01396, May 16, 2024.
US, Decision Denying Institution of Inter Partes Review, IPR No. 2023-01396, Apr. 16, 2024.
US, Patent Owner's Updated Exhibit List, IPR No. 2023-01396, May 25, 2024.
US, Telephonic Hearing, IPR No. 2023-01396, Mar. 13, 2024.
US, Petitioner's Updated Mandatory Notices Pursuant to 37 C.F.R. § 42.8(a)(3), IPR No. 2023-01396, Feb. 19, 2024.
US, Patent Owner's Preliminary Response, IPR No. 2023-01396, Jan. 18, 2024.
US, Notice of Filing Date Accorded to Petition and Time for Filing Patent Owner Preliminary Response, IPR No. 2023-01396, Oct. 18, 2023.
US, Petitioner's Explanation of Material Differences Between Petitions, IPR No. 2023-01396, Oct. 6, 2023.
US, Petition For Inter Partes Review Of U.S. Pat. No. 11,266,335, IPR No. 2023-01396, Oct. 6, 2023.
US, Notice of Final Written Decision re Inter Partes Review of the '649 Patent, IPR No. 2022-00605, Jul. 13, 2023.
US, Record of Oral Hearing, IPR No. 2022-00605, Apr. 26, 2023.
US, Supplemental Declaration of Gary D. Fletcher, Ph.D, IPR No. 2022-00605, Jan. 11, 2023.
US, Petitioner's Reply to Patent Owner's Response to Petition, IPR No. 2022-00605, Jan. 11, 2023.
US, Second Declaration by Dr. Michael Cima in Support of Patent Owner's Response, IPR No. 2022-00605, Oct. 19, 2022.
US, Patent Owner's Response, IPR No. 2022-00605, Oct. 19, 2022.
US, Reexamination Serial No. 90/019,329 Decision on Petition Under 37 C.F.R. § 1.181, Mar. 18, 2025.
US, Ex Parte Reexamination Certificate of U.S. Pat. No. 11,013,440, Oct. 30, 2024.
US, Reexamination Serial No. 90/019,329 Notice of Intent to Issue Ex Parte Reexamination Certificate, Oct. 8, 2024.
US, Reexamination Serial No. 90/019,329 Decision on Petition Under 37 C.F.R. § 1.59, Sep. 16, 2024.
US, Reexamination Serial No. 90/019,329 Statutory disclaimer per Manual of Patent Examining Procedure (MPEP) 1490, Sep. 3, 2024.
US, Reexamination Serial No. 90/019,329 Petition Under 37 C.F.R. § 1.182 to Seal Document Versions Filed via IDS and Substitute Redacted Document Versions Therfor, Aug. 1, 2024.
US, Reexamination No. 90/019,329 Petition Under 37 CFR § 1.59 to Expunge Application Papers, Aug. 1, 2024.
US, Reexamination No. 90/019,329 Ex Parte Reexamination Interview Summary, Jul. 25, 2024.
US, Reexamination Serial No. 90/019,329 Decision on Petition Under 37 C.F.R. § 1.59, Jul. 22, 2024.
US, Reexamination No. 90/019,329 Decision Sua Sponte Vacating Notice of Intent to Issue Ex Parte Reexamination Certificate, Jul. 3, 2024.
US, Reexamination No. 90/019,329 Petition Under 37 CFR § 1.59 to Expunge Application Papers, Jun. 12, 2024.
US, Reexamination Serial No. 90/019,329 Notification of Concurrent Proceedings, May 15, 2024.
US, Petition Under 37 CFR § 1.181 and/or § 1.182 to Terminate Reexamination No. 90/019,329, Apr. 26, 2024.
US, Reexamination Serial No. 90/019,329 Order Granting Request for Reexamination of U.S. Pat. No. 11,013,440, Jan. 30, 2024.
US, Reexamination Serial No. 90/019,329 Declaration of Gary D. Fletcher, Ph.D., Dec. 11, 2023.
US, Request for Ex Parte Reexamination Under 35.U.S.C. §§ 302-307 and 37 C.F.R. § 1.510 of U.S. Pat. No. 11,013,440, Dec. 11, 2023.
US, Ex Parte Reexamination Certificate of U.S. Pat. No. 11,000,216, Nov. 14, 2024.
US, Reexamination Serial No. 90/019,331 Notice of Intent to Issue Ex Parte Reexamination Certificate, Oct. 15, 2024.
US, Reexamination Serial No. 90/019,331 Decision on Petition Under 37 C.F.R. § 1.59, Sep. 16, 2024.
US, Reexamination Serial No. 90/019,331 Decision Granting Petition, Aug. 26, 2024.
US, Reexamination Serial No. 90/019,331 Petition Under 37 C.F.R. § 1.182 to Seal Document Versions Filed via IDS and Substitute Redacted Document Versions Therfor, Aug. 1, 2024.
US, Reexamination No. 90/019,331 Petition Under 37 CFR § 1.59 to Expunge Application Papers, Aug. 1, 2024.
US, Reexamination Serial No. 90/019,331 Petition to Withdraw From Issue and Reopen the Proceeding, Jul. 26, 2024.
US, Reexamination Serial No. 90/019,331 Decision on Petition Under 37 C.F.R. § 1.59, Jul. 16, 2024.
US, Reexamination Serial No. 90/019,331 Notice of Intent to Issue Ex Parte Reexamination Certificate, Jul. 10, 2024.
US, Reexamination No. 90/019,331 Petition Under 37 CFR § 1.59 to Expunge Application Papers, Jun. 12, 2024.
US, Reexamination Serial No. 90/019,331 Notification of Concurrent Proceedings, May 15, 2024.
US, Reexamination Serial No. 90/019,331 Order Granting Request for Reexamination of U.S. Pat. No. 11,000,216, Jan. 23, 2024.
US, Request for Ex Parte Reexamination Under 35.U.S.C. §§ 302-307 and 37 C.F.R. § 1.510 of U.S. Pat. No. 11,000,216, Dec. 11, 2023.
US, Reexamination No. 90/019,307 Final Office Action, Jul. 8, 2025.
US, Reexamination No. 90/019,307 Office Action, Mar. 18, 2025.
US, Reexamination No. 90/019,307 Decision on Petition, Feb. 13, 2025.
US, Reexamination No. 90/019,307 Petition Under 37 CFR § 1.181 to Terminate, Aug. 15, 2024.
US, Reexamination No. 90/019,307 Decision on Petitions, Aug. 7, 2024.
US, Reexamination No. 90/019,307 Petition Under 37 CFR § 1.59 to Expunge Application Papers, Aug. 1, 2024.
US, Reexamination No. 90/019,307 Petition Under 37 CFR § 1.59 to Expunge Application Papers, Jun. 12, 2024.
US, Reexamination Serial No. 90/019,307 Notification of Concurrent Proceedings, May 15, 2024.
US, Reexamination No. 90/019,307 Petition Under 37 CFR §§ 1.182 and/or § 1.183 to Allow Filing and Consideration of Response to Patent Owner's Extraordinary Petition to Suspend, Mar. 19, 2024.
US, Reexamination No. 90/019,307 Petition Under 37 CFR § 1.181 and/or § 1.183 to Suspend, Mar. 1, 2024.
US, Reexamination Serial No. 90/019,307 Order Granting Request for Reexamination of U.S. Pat. No. 10,973,443, Dec. 22, 2023.
US, Request for Ex Parte Reexamination Under 35.U.S.C. §§ 302-307 and 37 C.F.R. § 1.510 of U.S. Pat. No. 10,973,443, Nov. 17, 2023.
US, Ex Parte Reexamination Certificate of U.S. Pat. No. 10,959,654, Nov. 5, 2024.
US, Reexamination Serial No. 90/019,330 Notice of Intent to Issue Ex Parte Reexamination Certificate, Oct. 7, 2024.
US, Reexamination Serial No. 90/019,330 Decision on Petition Under 37 C.F.R. § 1.59, Sep. 16, 2024.
US, Reexamination Serial No. 90/019,330 Decision Granting Petition and Vacating a Reexamination Certificate, Aug. 26, 2024.
US, Ex Parte Reexamination Certificate of U.S. Pat. No. 10,959,654, Aug. 5, 2024.
US, Reexamination Serial No. 90/019,330 Petition Under 37 C.F.R. § 1.182 to Seal Document Versions Filed via IDS and Substitute Redacted Document Versions Therfor, Aug. 1, 2024.
US, Reexamination No. 90/019,330 Petition Under 37 CFR § 1.59 to Expunge Application Papers, Aug. 1, 2024.
US, Reexamination Serial No. 90/019,330 Petition to Withdraw From Issue and Reopen the Proceeding, Jul. 26, 2024.
US, Reexamination Serial No. 90/019,330 Decision on Petition Under 37 C.F.R. § 1.59, Jul. 16, 2024.
US, Reexamination Serial No. 90/019,330 Notice of Intent to Issue Ex Parte Reexamination Certificate of U.S. Pat. No. 10,959,654, Jul. 1, 2024.

(56) References Cited

OTHER PUBLICATIONS

US, Reexamination No. 90/019,330 Petition Under 37 CFR § 1.59 to Expunge Application Papers, Jun. 12, 2024.
US, Reexamination Serial No. 90/019,330 Notification of Concurrent Proceedings, May 15, 2024.
US, Reexamination Serial No. 90/019,330 Order Granting Request for Reexamination of U.S. Pat. No. 10,959,654, Jan. 23, 2024.
US, Reexamination Serial No. 90/019,330 Declaration of John Mastrototaro, Ph.D., Dec. 11, 2023.
US, Request for Ex Parte Reexamination Under 35.U.S.C. §§ 302-307 and 37 C.F.R. § 1.510 of U.S. Pat. No. 10,959,654, Dec. 11, 2023.
WO, PCT/US2006/029541 ISR and Written Opinion, Apr. 24, 2007.
WO, PCT/US2006/033885 ISR and Written Opinion, Aug. 3, 2007.
WO, PCT/US2007/082121 ISR and Written Opinion, May 9, 2008.
WO, PCT/US2008/054165 ISR and Written Opinion, Jun. 5, 2008.
WO, PCT/US2008/054186 ISR and Written Opinion, Aug. 8, 2008.
WO, PCT/US2008/065154 ISR and Written Opinion, Sep. 3, 2008.
WO, PCT/US2008/067791 ISR and Written Opinion, Sep. 30, 2008.
WO, PCT/US2010/047065 ISR and Written Opinion, Dec. 21, 2010.
WO, PCT/US2010/047414 ISR and Written Opinion, Dec. 27, 2010.
WO, PCT/US2010/047415 ISR and Written Opinion, Oct. 25, 2010.
WO, PCT/US24/11756 ISR and Written Opinion, Jun. 28, 2024.
WO, PCT/US24/11756 Invitation to Pay Additional Fees, May 7, 2024.
WO, PCT/US24/16127 ISR and Written Opinion, Sep. 11, 2024.
WO, PCT/US24/16127 Invitation to Pay Additional Fees, Jun. 4, 2024.
WO, PCT/US24/18665 ISR and Written Opinion, Jun. 21, 2024.
WO, PCT/US25/13698 ISR and Written Opinion, Jun. 5, 2025.
WO, PCT/US25/13698 Invitation to Pay Additional Fees, Apr. 15, 2025.
WO, PCT/US25/27260 ISR and Written Opinion, Sep. 16, 2025.
WO, PCT/US25/27260 Invitation to Pay Additional Fees, Jul. 24, 2025.
"27 Winners Announced at the 19$^{th}$ Annual Medical Design Excellence Awards (MDEA) Award Ceremony", UBM Americas, 2017, 4 pages.
"55 Chosen as Winners in Annual BIG Innovation Awards", 2018, retrieved from https://www.bintelligence.com/posts/55-chosen-as-winners-in-annual-big-innovation-awards, 2 pages.
2017 Good Design Award, retrieved from https://www.g-mark.org/gallery/winners/9dda01a3-803d-11ed-af7e-0242ac130002, 9 pages.
"2019 Top 10 Innovations", The Scientist, retrieved from https://www.the-scientist.com/2019-top-10-innovations-66738, 7 pages.
Abbott 2023 Annual Report, retrieved from https://www.abbottinvestor.com/static-files/6cb09c09-2422-40e0-a24b-6545ffcf5267, pp. 1-82.
Abbott Clinical Trials Competitor and Ecosystem Players, 2020, 28 pages.
Abbott Patent Marking Diabetes, 2024, retrieved from https://www.abbott.com/patents/diabetes-patents.html, 6 pages.
"Abbott's Freestyle Libre® Is Named Best Medical Technology In Last 50 Years By The Galien Foundation", 2022, PRNewswire, 1 page.
"Abbott's Freestyle® Libre 2 ICGM Cleared in U.S. for Adults and Children With Diabetes, Achieving Highest Level of Accuracy and Performance Standards", retrieved from https://abbott.mediaroom.com/2020-06-15-Abbotts-FreeStyle-R-Libre-2-iCGM-Cleared-in-U-S-for-Adults-and-Children-with-Diabetes-Achieving-Highest-Level-of-Accuracy-and-Performance-tandards#:~:text=FDA%20clears%20Abbott's%20FreeStyle%20Libre,high%20or%20low%20without%20scanning, on Jul. 7, 2024, 3 pages.
"Abbott's Freestyle Libre® 3 Receives U.S. FDA Clearance—Features World's Smallest, Thinnest and Most Accurate 14-Day Glucose Sensor", 2022, PRNewswire, 3 pages.
"Abbott's Freestyle Libre Flash Glucose Monitoring System Wins the IMSTA Most Innovative Product Multi-National Award 2017", retrieved from https://www.ie.abbott/media-center/news/abbotts-freestyle-libre-flash-glucose-monitoring-system-wins-the-imsta-award-2017.html, 2 pages.
"Abbott's Freestyle® Libre 14 Day Flash Glucose Monitoring System Now Approved in U.S.", 2018, PRNewswire, 2 pages.
"Abbott Receives CE Mark for Freestyle® Libre, A Revolutionary Glucose Monitoring System for People With Diabetes", 2014, 7 pages.
About the Edison Awards retrieved from https://edisonawards.com/about/, 2024, 3 pages.
ACCU-CHEK® Softclix Lancet Device retrieved from file:///C:/Users/afredericks/Downloads/softclix-user-manual.pdf, 2007, 2 pages.
Using your ACCU-CHEK® Multiclix Lancet Device, 2005, retrieved from https://www.northcoastmed.com/wp-content/uploads/2023/03/multiclix_userguide.pdf, 2 pages.
"The Advantages of the Cleo® 90 Infusion Set Are Clear", 2019, retrieved from https://web.archive.org/web/20220816002119/https:/smiths-medical.com/-/media/M/Smiths-medical_com//Files/Import-Files/Product-Literature/IN193873GB-092019_LR.pdf, 2 pages.
Ahn, D., "Abbott's Euro approved wearable glucose monitor is different than anything on the market", 2014, retrieved from https://www.imedicalapps.com/2014/09/abbotts-wearable-glucose-monitor/, 6 pages.
"Alcove", Webster's New College Dictionary, 2001, p. 26.
American National Standard, ANSI/AAMI HE75:2009, Human factors engineering—Design of medical devices, 2010, 465 pages.
Automated Retractable VanishPoint Syringe 510(k) Safety and Effectiveness Summary, 1998, 5 pages.
"BinaxNOW, FreeStyle Libre 2 win BIG innovation honors", 2021, retrieved from https://www.abbott.com/corpnewsroom/strategy-and-strength/binaxnow-freestyle-libre-win-big-innovation-honors.html, 6 pages.
"Bluetooth rival unveiled by Nokia", 2006, retrieved from news.bbc.co.uk/1/hi/technology/5403564.stm, 2 pages.
Blum, A., "Freestyle Libre Glucose Monitoring System", Clinical Pharmacology Update, 2018, vol. 36, No. 2, pp. 203-204.
Boise, M., "Dexcom CEO Kevin Sayer Explains G6", 2018, retrieved from https://beyondtype1.org/dexcom-ceo-kevin-sayer-explains-g6/, 9 pages.
Breton, M. D., et al., "Optimum Subcutaneous Glucose Sampling and Fourier Analysis of Continuous Glucose Monitors", Journal of Diabetes Science and Technology, 2008, vol. 2, No. 3, pp. 495-500.
Breton, M., et al., "Fully Integrated Artificial Pancreas in Type 1 Diabetes: Modular Closed-Loop Glucose Control Maintains Near Normoglycemia", Diabetes, 2012, vol. 61, No. 9, pp. 2230-2237.
Burge, M. R., et al., "Continuous Glucose Monitoring: The Future of Diabetes Management", Diabetes Spectrum, 2008, vol. 21, No. 2, pp. 112-119.
Cather, D. E., "CGM Frustrations Survey", 2020, 36 pages.
Certified U.S. Appl. No. 61/149,639, filed Feb. 3, 2009.
Certified Preliminary Amendment filed on Apr. 20, 2018 for U.S. Pat. No. 10,827,954, 7 pages.
Certified Excerpts of the File History of U.S. Pat. No. 10,973,443, 22 pages.
CES 2022 Innovation Award Honorees, retrieved from https://www.ces.tech/innovation-awards/honorees/2022/best-of/f/freestyle-libre-3-system.aspx, 1 page.
CGMs Changing Diabetes Management: Kevin Sayer, DIC Interview Transcript, 2019, retrieved from https://www.diabetesincontrol.com/cgms-changing-diabetes-management-kevin-sayer-dic-interview-transcript/, 10 pages.
2019 Chicago Innovation Award Winner Abbott Laboratories, retrieved from https://chicagoinnovation.com/winners/abbott-laboratories/, 4 pages.
Clancy, N. T., et al., "A new device for assessing changes in skin viscoelasticity using indentation and optical measurement", Skin Research and Technology, 2010, vol. 16, pp. 210-228.
Cleo® 90 Infusion Set 510(k) Premarket Notification, 2004, 1 page.
Continuous Glucose Monitoring Systems Product Reference Guide, Diabetes Health, 2006-2007, pp. 50-51.
Das, S. D., et al., "Review—Electrochemistry and Other Emerging Technologies for Continuous Glucose Monitoring Devices", ECS Sensors Plus, 2022, 19 pages.

(56) References Cited

OTHER PUBLICATIONS

"Deciding When to Submit a 510(k) for a Change to an Existing Device, Guidance for Industry and Food and Drug Administration Staff", 2017, pp. 1-77.
"Deciding When to Submit a 510(k) for a Software Change to an Existing Device, Guidance for Industry and Food and Drug Administration Staff", 2017, pp. 1-31.
Design Concepts Project Status Update, Glucose Sensor Applicator Dexcom (project #2554), 2014, 5 pages.
Dexcom CEO—Prime Position in Our Market—Mad Money—CNBC.mp4, Transcript 2023 by Sonix, 2 pages.
DexCom (DXCM) 2017 Q4 Earnings Call Transcript, 2017, retrieved from https://docoh.com/transcript/1093557/2017Q4/DXCM, 11 pages.
DexCom (DXCM) Q1 2018 Results—Earnings Call Transcript, 2018, retrieved from https://seekingalpha.com/article/4168949-dexcom-dxcm-q1-2018-results-earnings-call-transcript, 4 pages.
DexCom, Inc. NasdaqGS:DXCM Company Conference Presentation, 2019, 10 pages.
DexCom, Inc. NasdaqGS:DXCM Company Conference Presentation, 2020, 9 pages.
DexCom, Inc. NasdaqGS:DXCM Company Conference Presentation, 2021, 16 pages.
Dexcom G5 Mobile System User Guide, 2015, pp. 1-260.
Dexcom G5 Quick Start Guide, 2020, pp. 1-31.
Dexcom G6 Continuous Glucose Monitoring System User Guide, 2022, 346 pages.
Dexcom G6 Start Here Set up Guide, 2019, pp. 1-8.
Dexcom G6 Start Here Set up Guide, 2022, pp. 18 pages.
Dexcom G6 Using Your G6 Guide, Mar. 2020, pp. 1-7.
Dexcom G6 Continuous Glucose Monitoring (CGM) System Section 510(k) Approval, 2022, 7 pages.
"The Dexcom G7. The most accurate CGM system.1" retrieved from https://www.dexcom.com/g7-cgm-system on Jun. 27, 2024, 20 pages.
Dexcom G7 Continuous Glucose Monitoring (CGM) System Section 510(k) Approval, 2022, 10 pages.
Dexcom G7 Inserting Sensor Instructions for Use, 2021, pp. 1-2.
Dexcom G7, Start Here, Operational Manual, 2022, pp. 1-9 (English Abstract).
Dexcom G7, User Guide, 2022, p. 1-179 (English Abstract).
Dexcom G7 User Guide, 2024, p. i-186.
Dexcom Seven® Plus Continuous Glucose Monitoring System User's Guide, 2011, pp. 1-144.
Dexcom STS Continuous Glucose Monitoring System FDA Premarket Approval (PMA), 2007, pp. 1-7.
Dexcom STS Continuous Monitors FDA Premarket Approval (PMA), 2006, 2 pages.
DexCom™ STS™ Continuous Glucose Monitoring System Summary of Safety and Effectiveness Data, 2006, 20 pages.
DexCom™ STS™ Sensor Instructions for Use, 2006, pp. 1-6.
Dexcom STS-7 Continuous Glucose Monitoring System FDA Premarket Approval (PMA), 2007, pp. 1-7.
Dexcom STS®—7 Continuous Glucose Monitoring System Summary of Safety and Effectiveness Data, 2007, 14 pages.
Diglas, J., et al., "Reduced pain perception with Pen Mate™, an automatic needle insertion device for use with an insulin pen", Practical Diabetes International, 1999, vol. 16, No. 2, pp. 39-41.
"Does Dexcom Really Have a Future If It Can't Match Abbott's Scale", 2019, retrieved from https://www.sprucepointcap.com/reports/dxcm_research_thesis_3-21-2019.pdf, p. 46.
Edison Awards Announces 2016 Gold, Silver, and Bronze Awards Winners, Edison Awards, 9 pages.
Edison Best New Product Awards™ 2021 Winners retrieved from https://edisonawards.com/2021-winners/, 19 pages.
Edison Best New Product Awards™ 2022 Winners retrieved from https://edisonawards.com/2022-winners/, 52 pages.
Email chain from Sophie Hood, oldest email dated Jan. 24, 2023, 5 pages.
Email from Christopher M Dougherty dated Dec. 17, 2019, 68 pages.
Email from John Shaw of Shaw & Keller dated May 16, 2023, 2 pages.
Englert, K., et al., "Skin and Adhesive Issues With Continuous Glucose Monitors: A Sticky Situation", Journal of Diabetes Science and Technology, 2014, vol. 8, No. 4, pp. 745-751.
European Standard, ISO 11607-1, Packaging for terminally sterilized medical devices—Part 1: Requirements for materials, sterile barrier systems and packaging systems, 2006, 32 pages.
European Standard, ISO 13485, Medical devices—Quality management systems—Requirement for regulatory purposes, 2003, 69 pages.
European Standard, ISO 15197, In vitro diagnostic test systems—Requirements for blood glucose monitoring systems for self-testing in managing diabetes mellitus, 2003, 43 pages.
Explore The Monroe Street Market Community, retrieved from https://www.monroestreetmarket.com/floor-plans/apartment/B-231 on May 10, 2023, 2 pages.
"FDA authorizes first fully interoperable continuous glucose monitoring system, streamlines review pathway for similar devices", FDA News Release, 2018, retrieved from https://www.fda.gov/news-events/press-announcements/fda-authorizes-first-fully-interoperable-continuous-glucose-monitoring-system-streamlines-review, 3 pages.
U.S. Appl. No. 61/317,243.
U.S. Appl. No. 61/345,562.
U.S. Appl. No. 61/361,374.
U.S. Appl. No. 61/411,262.
U.S. Appl. No. 61/569,287.
U.S. Appl. No. 62/524,247.
Food and Drug Administration, HHS, 2009, Code of Federal Regulation § 820.30, Subpart C-Design Controls, pp. 147-148.
Freckmann, G., et al., "Performance Evaluation of Three Continuous Glucose Monitoring Systems: Comparison of Six Sensors per Subject in Parallel", Journal of Diabetes Science and Technology, 2013, vol. 7, No. 4, pp. 842-853.
Freestyle Libre Brochure, 2016, 10 pages.
Freestyle Libre Fact Sheet, 2016, retrieved from www.FreeStyleLibre.de, 2 pages.
Freestyle Libre FAQ, 2024, retrieved from https://www.freestyle.abbott/uk-en/support/faq/question-answer.html?q=UKFaqquestion-55#, 2 pages.
"FreeStyle Libre Honored by Prix Galien", 2019, 4 pages.
FreeStyle Libre In-Service Guide, 2021, 28 pages.
FreeStyle Libre 2 Get Started Guide, 2023, pp. 1-28.
FreeStyle Libre 2 HCP Pulse Report, 2021, 13 pages.
"FreeStyle Libre 2—Zucker messen ohne stechen per Sensor und App", German Innovation Awards Gold Winner, 2020, retrieved from https://www.german-innovation-award.de/preistraeger/preis/gewinner/freestyle-libre-2-zucker-messen-ohne-stechen-per-sensor-und-app/#:~:text=Beschreibung%20Die%20kontinuierliche%20Glukosemessung%20mit,um%20die%20Glukosewerte%20kontinuierlich%20aufzuzeichnen, 1 page.
FreeStyle Libre 3 Get Started Guide, 2023, pp. 1-20.
FreeStyle Libre 3 User's Manual, 2022-2023, pp. iv-241.
Freestyle Libre Pro Flash Glucose Monitoring System Summary of Safety and Effectiveness Data, 2016, 31 pages.
FreeStyle Lite Blood Glucose Monitoring System Owner's Booklet, 2006, 15 pages.
Freestyle Navigator Answers to Frequently Asked Questions, 2007, retrieved from https://web.archive.org/web/20080917183534/http:/www.freestylenavigator.com/ab_nav/url/content/en_US/3 0.10.10:1 O/general_content/General_ContenL0000004.htm, 2 pages.
FreeStyle Navigator Continuous Glucose Monitoring System FDA Premarket Approval (PMA), 2008, pp. 1-7.
"The Future is Bright for Veteran-centric Rehabilitation Research Publications", Journal of Rehabilitation Research & Development (JRRD), 2013, retrieved from https://www.rehab.research.va.gov/jrrd/index.html, 2 pages.
The Galien Foundation is proud to announce the laureates of the best-of-the-best from the half century 1970-2020, The 2022 Galien Golden Jubilee Winners, retrieved from https://www.galienfoundation.org/galien-golden-jubilee, 3 pages.

(56) References Cited

OTHER PUBLICATIONS

Gough, D. A., et al., "Development of the Implantable Glucose Sensor: What Are the Prospects and Why Is It Taking So Long?", Diabetes, 1995, vol. 44, pp. 1005-1009.
Harris, J. M., et al., "Common Causes of Glucose Oxidase Instability in In Vivo Biosensing: A Brief Review", Journal of Diabetes Science and Technology. 2013, vol. 7, No. 4, pp. 1030-1038.
Hemmerich, K. J., et al., "Sterilization Methods Stand the Test of Time", 2004, retrieved from https://www.mddionline.com/sterilization/sterilization-methods-stand-test-time, pp. 1-8.
Hermanides, J., et al., "Current Application of Continuous Glucose Monitoring in the Treatment of Diabetes", Diabetes Care, 2011, vol. 34, Suppl. 2, pp. S197-S201.
Hirsch, I. B., "Realistic Expectations and Practical Use of Continuous Glucose Monitoring for the Endocrinologist", The Journal of Clinical Endocrinology & Metabolism, 2009, vol. 94, No. 7, pp. 2232-2238.
Hoss, U., et al., "Continuous glucose monitoring in the tissue: Do we really need to calibrate in-vivo?", Feb. 28, 2009, pp. 1-21.
Hoss, U., et al., "Continuous Glucose Monitoring in Subcutaneous Tissue Using Factory-Calibrated Sensors: A Pilot Study", Diabetes Technology & Therapeutics, 2010, vol. 12, No. 8, pp. 591-597.
Hoss, U., et al., "Feasibility of Factory Calibration for Subcutaneous Glucose Sensors in Subjects With Diabetes", Journal of Diabetes Science and Technology, 2014, vol. 8, No. 1, pp. 89-94.
"Housing", "recess", "release", and "retain", Merriam-Webster's Collegiate Dictionary, Tenth Edition, 1999, pp. 563, 975, 987, and 999.
"Housing" and "recess", The New Penguin English Dictionary, 2000, pp. 678 and 1167.
Hovorka, R., "Continuous glucose monitoring and closed-loop systems", Diabetic Medicine, 2005, vol. 23, pp. 1-12.
Hughes, M. D., "The Business of Self-Monitoring of Blood Glucose: A Market Profile", Journal of Diabetes Science and Technology, 2009, vol. 3, No. 5, pp. 1219-1223.
IEEE 100 The Authoritative Dictionary of IEEE Standards Terms, Seventh Edition, 2000, 3 pages.
Insert Molding, 1996, retrieved from https://www.mddionline.com/equipment/insert-molding, 4 pages.
International Diabetes Device 2022 Blue Book, Seagrove Partners, 142 pages.
International Standard, IEC 62366, Medical devices—Application of usability engineering to medical devices, 2007, 214 pages.
International Standard, ISO 14971, Medical devices—Application of risk management to medical devices, 2007, 90 pages.
"An Interview with Kevin Sayer, President and CEO of Dexcom, About The New G6", 2021, 5 pages.
Joseph, J. I., et al., "Glucose Sensing in the Subcutaneous Tissue: Attempting to Correlate the Immune Response with Continuous Glucose Monitoring Accuracy", Diabetes Technology & Therapeutics, 2018, vol. 20, No. 5, pp. 321-324.
Kal, S., "Basic Electronics—Devices, Circuits and IT Fundamentals", 2006, Chapter 13, Microcomputers and Microprocessors, p. 412.
Kaye, R., et al., "Medical Device Use-Safety: Incorporating Human Factors Engineering into Risk Management", 2000, retrieved from https://www.qualysinnova.com/download/files/MD-Use-Safety.pdf, pp. 1-33.
Klueh, U., et al., "Inflammation and Glucose Sensors: Use of Dexamethasone to Extend Glucose Sensor Function and Life Span in Vivo", Journal of Diabetes Science and Technology, 2007, vol. 1, No. 4, pp. 496-504.
Klueh, U., et al., "Blood-Induced Interference of Glucose Sensor Function in Vitro: Implications for in Vivo Sensor Function", Journal of Diabetes Science and Technology, 2007, vol. 1, No. 6, pp. 842-849.
Kovatchev, B. P., et al., "Evaluating the Accuracy of Continuous Glucose-Monitoring Sensors", Diabetes Care, 2004, vol. 27, No. 8, pp. 1922-1928.
Lomas, P., "Dexcom G7 Release: The Most Exciting New Features", 2024, retrieved from https://notjustapatch.com/dexcom-g7-features/, 13 pages.
Lovett, L., "What's next for Dexcom? CEO, CTO talk G6 for inpatient use, expanding CGMs for patients without diabetes", 2020, retrieved from https://www.mobihealthnews.com/news/whats-next-dexcom-ceo-cto-talk-g6-inpatient-use-expanding-cgms-patients-without-diabetes, 6 pages.
Mazze, R. S., et al., "Evaluating the Accuracy, Reliability, and Clinical Applicability of Continuous Glucose Monitoring (CGM): Is CGM Ready for Real Time?", Diabetes Technology & Therapeutics, 2009, vol. 11, No. 1., pp. 11-18.
Medtronic MiniMed Enlite Serter User Guide, 2014, 26 pages.
Medtronic MiniMed Guardian RT FDA Premarket Approval (PMA), 2005, pp. 1-6.
Medtronic MiniMed Guardian RT Summary of Safety and Effectiveness Data, 2005, 13 pages.
Medtronic MiniMed Guardian® REAL-Time Components, 2007, retrieved from https://web.archive.org/20071013095335/http:/www.medtronicdiabetes.com/products/guardian/components.html, 2 pages.
Medtronic MiniMed Guardian® REAL-Time Features, 2007, retrieved from https://web.archive.org/20071025084715//http:/www.medtronicdiabetes.com/products/guardian/features.html, 2 pages.
Medtronic MiniMed iPro2 User Guide, 2010, pp. 1-99.
Medtronic MiniMed One-press Serter User Guide, 2015, 26 pages.
Medtronic MiniMed Paradigm® 512 and 712 Insulin Pumps User Guide, 2005, pp. 1-136.
Medtronic MiniMed Paradigm® REAL-TIME 522 and 722 Insulin Pumps User Guide, 2008, pp. 1-262.
Meltsner, M A, et al., "Observations on rotating needle insertions using a brachytherapy robot", Phys. Med. Biol., 2007, vol. 52, pp. 6027-6037.
Microlet® 2 Lancing Device, 2008, retrieved from https://image.tigermedical.com/Manuals/BAY6606-20141216010820833.pdf, 1 page.
Nichols, S. P., et al., "Biocompatible Materials for Continuous Glucose Monitoring Devices", Chem Rev., 2013, vol. 113, No. 4, pp. 2528-2549.
Occupational Safety and Health Admin., Labor, 2003, 29 CFR § 1910.1030 Bloodborne pathogens, pp. 260-273.
Ólafsdóttir, A. F., et al., "A Clinical Trial of the Accuracy and Treatment Experience of the Flash Glucose Monitor FreeStyle Libre in Adults with Type 1 Diabetes", Diabetes Technology & Therapeutics, 2017, vol. 19, No. 3, pp. 164-172.
Omnipod image, Exhibit 182 of ADC Reply Brief SJ, Daubert, Sep. 22, 2022, 2 pages.
OneTouch® Ultra™ Blood Glucose Monitoring System Owner's Booklet, 2000, 23 pages.
OneTouch Ultra2 Blood Glucose Monitoring System Owner's Booklet, 2005, 34 pages.
Order, Federal Communications Commission, 2006, pp. 1-8.
Panteleon, A. E., et al., "The Role of the Independent Variable to Glucose Sensor Calibration", Diabetes Technology & Therapeutics, 2003, vol. 5, No. 3, pp. 401-410.
Parker, S. P., ed., McGraw-Hill Dictionary of Mechanical and Design Engineering, 1984 (excerpted), pp. 1-4.
"Periphery", Cambridge Dictionary of American English, 2000, p. 631.
Piper, H. G., et al., "Real-Time Continuous Glucose Monitoring in Pediatric Patients During and After Cardiac Surgery", Pediatrics, 2006, vol. 118, No. 3, pp. 1176-1184.
"Product Review: Abbott FreeStyle Libre Flash Glucose Monitor", DiabetesMine Team, 2021, retrieved from https://www.healthline.com/diabetesmine/abbott-freestyle-libre-review#bottom-line, 6 pages.
Program, $2^{nd}$ International Conference on Advanced Technologies & Treatments for Diabetes, Athens, Greece, 2009, 3 pages.
Rabiee, A., et al., "Numerical and Clinical Accuracy of a Continuous Glucose Monitoring System during Intravenous Insulin Therapy in the Surgical and Burn Intensive Care Units", Journal of Diabetes Science and Technology, 2009, vol. 3, No. 4, pp. 951-959.
"Real-World Data Show Abbott's Freestyle LibreR Systems And GLP-1 Medicines Work Better Together For People With Type 2 Diabetes", 2024, PRNewswire, 2 pages.

(56) References Cited

OTHER PUBLICATIONS

"Recess", Cambridge Dictionary of American English, 2000, pp. 710-711.
"Retract", The Chambers Dictionary, 1998, p. 1410.
"Retract", The New Oxford American Dictionary, 2001, p. 1455.
"Retract", Webster's Third New International Dictionary, 1993, pp. 1939-1940.
Rice, M. J., et al., "Continuous Measurement of Glucose: Facts and Challenges", Anesthesiology, 2012, vol. 116, No. 1, pp. 199-204.
Rigo, R. S., et al., "Cutaneous Reactions to Continuous Glucose Monitoring and Continuous Subcutaneous Insulin Infusion Devices in Type 1 Diabetes Mellitus", Journal of Diabetes Science and Technology, 2021, vol. 15, No. 4, pp. 786-791.
Rocchitta, G., et al., "Enzyme Biosensors for Biomedical Applications: Strategies for Safeguarding Analytical Performances in Biological Fields", Sensors, 2016. Vol. 16, No. 6, 21 pages.
Sacks, A. H., et al., "Skin blood flow changes and tissue deformations produced by cylindrical indentors", Journal of Rehabilitation Research and Development, 1985, vol. 22, No. 3, pp. 1-6.
Schneider, M., et al., "Evaluating the use of the Cleo® 90 infusion set for patients on a palliative care unit", International Journal of Palliative Nursing, 2009, vol. 15, No. 8, pp. 372-376.
Sclater, N., et al., eds., Mechanisms and Mechanical Devices Sourcebook, Fourth Edition, 2007, Chapter 12—Shaft Couplings and Connections, pp. 290-307.
Shenoi, B. A., ed., Introduction to Digital Signal Processing and Filter Design, 2006, "Introduction", Chapter 1, pp. 1-30.
Smith, S. S., ed., The Scientist and Engineer's Guide to Digital Signal Processing, Second Edition, 1997-1999, "Digital Signal Processors", Chapter 28, pp. 503-534.
"Submission and Review of Sterility Information in Premarket Notification (510(k)) Submissions for Devices Labeled as Sterile, Guidance for Industry and Food and Drug Administration Staff", 2016, pp. 1-11.
Tegnestedt, C., et al., "Levels and sources of sound in the intensive care unit—an observational study of three room types", Acta Anaesthiesiologica Scandinavica, 2013, pp. 1-10.
Tierney, M. J., et al., "Effect of Acetaminophen on the Accuracy of Glucose Measurements Obtained with the GlucoWatch Biographer", Diabetes Technology & Therapeutics, 2000, vol. 2, No. 2, pp. 199-207.
"Transcutaneous", Webster's Third New International Dictionary, 2002, pp. 2426.
Tsalikian, E., et al., "Accuracy of the GlucoWatch G2® Biographer and the Continuous Glucose Monitoring System During Hypoglycemia: Experience of the Diabetes Research in Children Network", Diabetes Care, 2004, vol. 27, No. 3, pp. 722-726.
Tsumura, R., et al., "Histological Evaluation of Tissue Damage Caused by Rotational Needle Insertion", Proceedings of the Annual International Conference of the IEEE Engineering in Medicine and Biology Society, 2016, pp. 5120-5123.
Van Den Boom, L., et al., "Changes in the utilization of blood glucose test strips among patients using intermittent-scanning continuous glucose monitoring in Germany", Diabetes, Obesity and Metabolism, 2020, vol. 22, pp. 922-928.
Watkin, J., "An Introduction to Flash Glucose Monitoring", 2013, 14 pages.
Xu, J., et al., "Anti-Biofouling Strategies for Long-Term Continuous Use of Implantable Sensors", Chemosensors, 2020, vol. 20 No. 3, 29 pages.

* cited by examiner

160 Sensor Electronics
172
Power Source
102
Sensor Control Device
ASIC
164
Power Mgmt. Circuitry
Processor
166
Memory
AFE
162
Communication Circuitry
168
163
161
Analyte Sensor
104
171

160 Sensor Electronics
172
Power Source
166
164
Power Mgmt. Circuitry
Processor
174
Chip
Memory
165
Communication Circuitry
168
163
162
AFE
Memory
171
ASIC 161
Analyte Sensor
104
102
Sensor Control Device

SYSTEMS, DEVICES, AND METHODS FOR ANALYTE MONITORING

CROSS-REFERENCE TO RELATED APPLICATIONS

This application claims priority to U.S. Provisional Application No. 63/296,262, filed Jan. 4, 2022, which is herein expressly incorporated by reference in its entirety for all purposes.

FIELD

The subject matter described herein relates generally to systems, devices, and methods for in vivo analyte monitoring.

BACKGROUND

The detection and/or monitoring of analyte levels, such as glucose, ketones, lactate, oxygen, hemoglobin AIC, or the like, can be vitally important to the overall health of a person, particularly for an individual having diabetes. Patients suffering from diabetes mellitus can experience complications including loss of consciousness, cardiovascular disease, retinopathy, neuropathy, and nephropathy. Persons with diabetes are generally required to monitor their glucose levels to ensure that they are being maintained within a clinically safe range, and may also use this information to determine if and/or when insulin is needed to reduce glucose levels in their bodies, or when additional glucose is needed to raise the level of glucose in their bodies.

Growing clinical data demonstrates a strong correlation between the frequency of glucose monitoring and glycemic control. Despite such correlation, however, many individuals diagnosed with a diabetic condition do not monitor their glucose levels as frequently as they should due to a combination of factors including convenience, testing discretion, pain associated with glucose testing, and cost.

Devices have been developed for the automatic monitoring of analyte(s), such as glucose, in bodily fluid such as in the blood stream or in interstitial fluid ("ISF"), or other biological fluid. Some of these analyte measuring devices are configured so that at least a portion of the devices are positioned below a skin surface of a user, e.g., in a blood vessel or in the subcutaneous tissue of a user, so that the monitoring is accomplished in vivo.

With the continued development of analyte monitoring devices and systems, there is a need for such analyte monitoring devices, systems, and methods, as well as for processes for manufacturing analyte monitoring devices and systems that are cost effective, convenient, and provide discreet monitoring to encourage frequent analyte monitoring to improve glycemic control. Additionally, there is a need for such analyte monitoring devices, systems, and methods that reduce pain and trauma associated with analyte monitoring and testing.

While current sensors can be convenient for users, they are also susceptible to malfunctions. These malfunctions can be caused by user error, lack of proper training, poor user coordination, overly complicated procedures, physiological responses to the inserted sensor, and other issues. This can be particularly true for analyte monitoring systems having sensors used to measure an analyte level in ISF, and which are inserted using sharps (also known as "introducers" or "needles"). In addition, some prior art systems may utilize sharps that can create trauma to surrounding tissue at the sensor insertion site, which can lead to inaccurate analyte level measurements. These challenges and others described herein can lead to a failure to properly monitor the patient's analyte level.

Thus, a need exists for more reliable sensor insertion devices, systems and methods, that are easy to use by the patient, less prone to error, and which reduce trauma to an insertion site.

SUMMARY

Provided herein are example embodiments of systems, devices and methods for the assembly and use of an applicator and a sensor control device of an in vivo analyte monitoring system. An applicator can be provided to the user in a sterile package with an electronics housing of the sensor control device contained therein. According to some embodiments, a structure separate from the applicator, such as a container, can also be provided to the user as a sterile package with a sensor module and a sharp module contained therein. The user can couple the sensor module to the electronics housing, and can couple the sharp to the applicator with an assembly process that involves the insertion of the applicator into the container in a specified manner. In other embodiments, the applicator, sensor control device, sensor module, and sharp module can be provided in a single package. In certain embodiments, the applicator comprises a sensor having a sharpened or V-shaped tip portion and/or a sharp having a V-shaped cross-sectional area. The V-shaped sensors and V-shaped sharps described herein are configured to minimize skin penetration and puncture wound size during sensor insertion. In some embodiments, the applicator is sharpless and, thus, does not comprise a sharp or sharp module. In the sharpless applicator embodiments described herein, the sensor may be configured to provide the necessary physical characteristics to increase insertion effectiveness.

The applicator can be used to position the sensor control device on a human body with a sensor in contact with the wearer's bodily fluid. The embodiments provided herein are improvements to prevent or reduce the likelihood that a sensor elicits an adverse physiological response. Other improvements and advantages are provided as well. The various configurations of these devices are described in detail by way of embodiments which are only examples.

Other systems, devices, methods, features and advantages of the subject matter described herein will be or will become apparent to one with skill in the art upon examination of the following figures and detailed description. It is intended that all such additional systems, devices, methods, features, and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 16J and 16J-1 are cross-sectional and call-out close-up views, respectively, depicting an example embodiment of a guide-sensor control device assembly.

DETAILED DESCRIPTION

Figure 1:
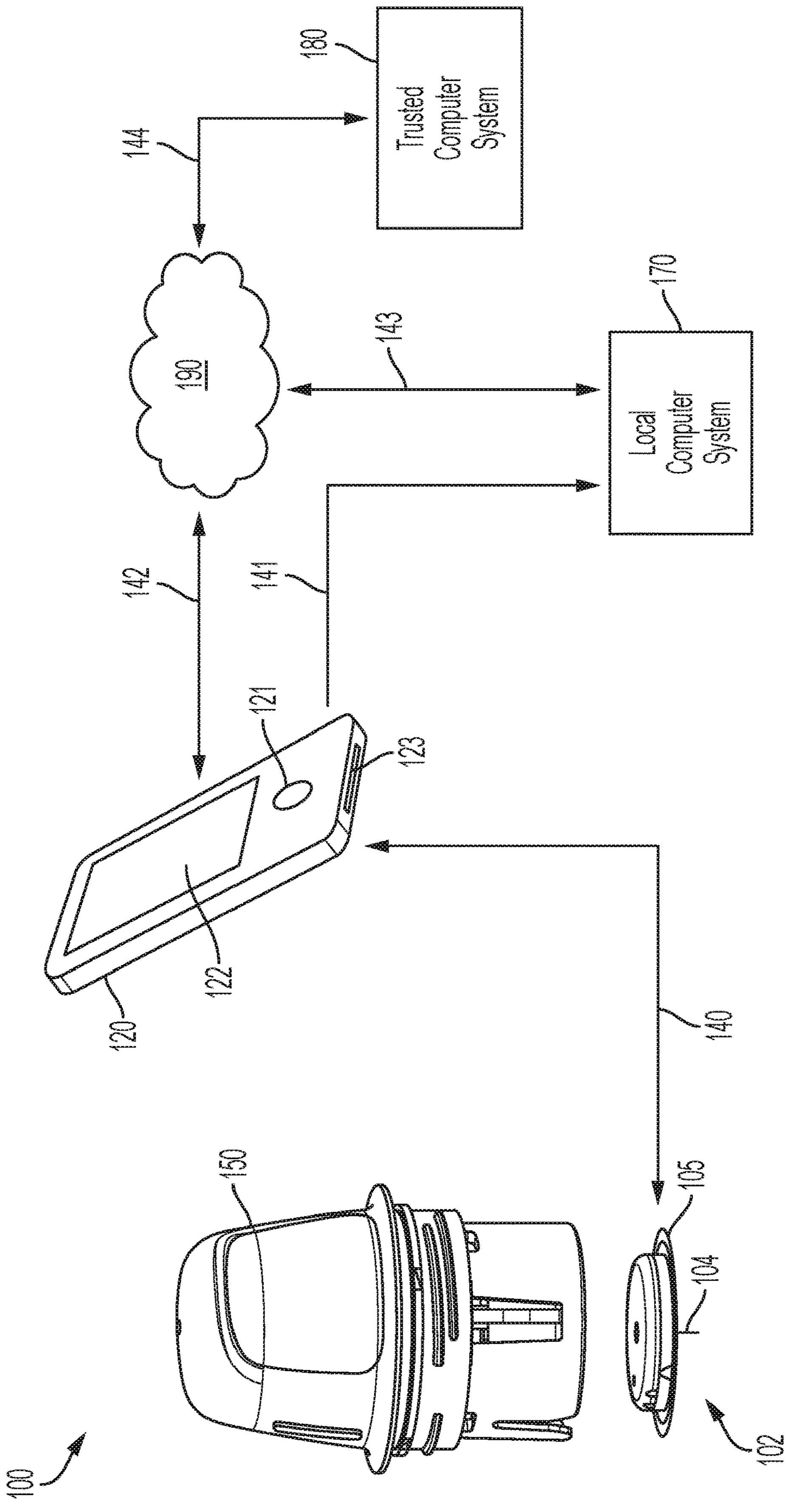
FIG. 1 is a system overview of a sensor applicator, reader device, monitoring system, network, and remote system.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

As used herein and in the appended claims, the singular forms "a," "an," and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

Generally, embodiments of the present disclosure include systems, devices, and methods for the use of analyte sensor insertion applicators for use with in vivo analyte monitoring systems. An applicator can be provided to the user in a sterile package with an electronics housing of the sensor control device contained therein. According to some embodiments, a structure separate from the applicator, such as a container, can also be provided to the user as a sterile package with a sensor module and a sharp module contained therein. The user can couple the sensor module to the electronics housing, and can couple the sharp to the applicator with an assembly process that involves the insertion of the applicator into the container in a specified manner. In other embodiments, the applicator, sensor control device, sensor module, and sharp module can be provided in a single package. The applicator can be used to position the sensor control device on a human body with a sensor in contact with the wearer's bodily fluid. The embodiments provided herein are improvements to reduce the likelihood that a sensor is improperly inserted or damaged, or elicits an adverse physiological response. Other improvements and advantages are provided as well. The various configurations of these devices are described in detail by way of the embodiments which are only examples.

Furthermore, many embodiments include in vivo analyte sensors structurally configured so that at least a portion of the sensor is, or can be, positioned in the body of a user to obtain information about at least one analyte of the body. It should be noted, however, that the embodiments disclosed herein can be used with in vivo analyte monitoring systems that incorporate in vitro capability, as well as purely in vitro or ex vivo analyte monitoring systems, including systems that are entirely non-invasive.

Furthermore, for each and every embodiment of a method disclosed herein, systems and devices capable of performing each of those embodiments are covered within the scope of the present disclosure. For example, embodiments of sensor control devices are disclosed and these devices can have one or more sensors, analyte monitoring circuits (e.g., an analog circuit), memories (e.g., for storing instructions), power sources, communication circuits, transmitters, receivers, processors and/or controllers (e.g., for executing instructions) that can perform any and all method steps or facilitate the execution of any and all method steps. These sensor control device embodiments can be used and can be capable of use to implement those steps performed by a sensor control device from any and all of the methods described herein.

As mentioned, a number of embodiments of systems, devices, and methods are described herein that provide for improved sensor insertion devices for use with in vivo analyte monitoring systems. Several embodiments of the present disclosure also provide for improved insertion sharp modules and sensors. Many embodiments of the present disclosure are designed to: improve the method of sensor insertion with respect to in vivo analyte monitoring systems, minimize trauma to an insertion site during a sensor insertion process, and reduce overall interference with sensor performance. Some embodiments, for example, include an applicator having a sharp with a V-shaped cross-sectional area comprising a vertex. This can allow for a smaller skin penetration and, thus, create a smaller wound with less trauma at the insertion site, which can reduce the chance of early signal attenuation ("ESA"). In other embodiments, the applicator includes a sensor with a V-shaped tip portion which can minimize trauma to an inserting site during a sensor insertion process and improve the likelihood of a successful sensor insertion. In still other embodiments, a sharpless applicator is configured to penetrate the skin utilizing a sensor having a sharpened or pointed V-shaped tip portion in order to reduce trauma to an insertion site. In some sharpless applicator embodiments, the design utilizes the deformation or "tenting" of the skin during insertion as a source of potential energy to provide for a more effective insertion. In sum, these embodiments can improve the likelihood of a successful sensor insertion and reduce the amount of trauma at the insertion site, to name a few advantages.

Before describing these aspects of the embodiments in detail, however, it is first desirable to describe examples of devices that can be present within, for example, an in vivo analyte monitoring system, as well as examples of their operation, all of which can be used with the embodiments described herein.

There are various types of in vivo analyte monitoring systems. "Continuous Analyte Monitoring" systems (or "Continuous Glucose Monitoring" systems), for example, can transmit data from a sensor control device to a reader device continuously without prompting, e.g., automatically according to a schedule. "Flash Analyte Monitoring" systems (or "Flash Glucose Monitoring" systems or simply "Flash" systems), as another example, can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

In vivo analyte monitoring systems can be differentiated from "in vitro" systems that contact a biological sample outside of the body (or "ex vivo") and that typically include a meter device that has a port for receiving an analyte test strip carrying bodily fluid of the user, which can be analyzed to determine the user's blood sugar level.

In vivo monitoring systems can include a sensor that, while positioned in vivo, makes contact with the bodily fluid of the user and senses the analyte levels contained therein. The sensor can be part of the sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few.

In vivo monitoring systems can also include a device that receives sensed analyte data from the sensor control device and processes and/or displays that sensed analyte data, in any number of forms, to the user. This device, and variations thereof, can be referred to as a "handheld reader device," "reader device" (or simply a "reader"), "handheld electronics" (or simply a "handheld"), a "portable data processing" device or unit, a "data receiver," a "receiver" device or unit (or simply a "receiver"), or a "remote" device or unit, to name a few. Other devices such as personal computers have also been utilized with or incorporated into in vivo and in vitro monitoring systems.

Exemplary In Vivo Analyte Monitoring System

FIG. 1 is a conceptual diagram depicting an example embodiment of an analyte monitoring system 100 that includes a sensor applicator 150, a sensor control device 102, and a reader device 120. Sensor applicator 150 can be used to deliver sensor control device 102 to a monitoring location on a user's skin where a sensor 104 is maintained in position for a period of time by an adhesive patch 105. Sensor control device 102 is further described in FIGS. 2B and 2C, and can communicate with reader device 120 via a communication path 140 using a wired or wireless technique. Example wireless protocols include Bluetooth, Bluetooth Low Energy (BLE, BTLE, Bluetooth SMART, etc.), Near Field Communication (NFC) and others. Users can monitor applications installed in memory on reader device 120 using screen 122 and input 121 and the device battery can be recharged using power port 123. More detail about reader device 120 is set forth with respect to FIG. 2A below. Reader device 120 can communicate with local computer system 170 via a communication path 141 using a wired or wireless technique. Local computer system 170 can include one or more of a laptop, desktop, tablet, phablet, smartphone, set-top box, video game console, or other computing device and wireless communication can include any of a number of applicable wireless networking protocols including Bluetooth, Bluetooth Low Energy, Wi-Fi or others. Local computer system 170 can communicate via communications path 143 with a network 190 similar to how reader device 120 can communicate via a communications path 142 with network 190, by wired or wireless technique as described previously. Network 190 can be any of a number of networks, such as private networks and public networks, local area or wide area networks, and so forth. A trusted computer system 180 can include a server and can provide authentication services and secured data storage and can communicate via communications path 144 with network 190 by wired or wireless technique.

Exemplary Reader Device

Figure 2A:
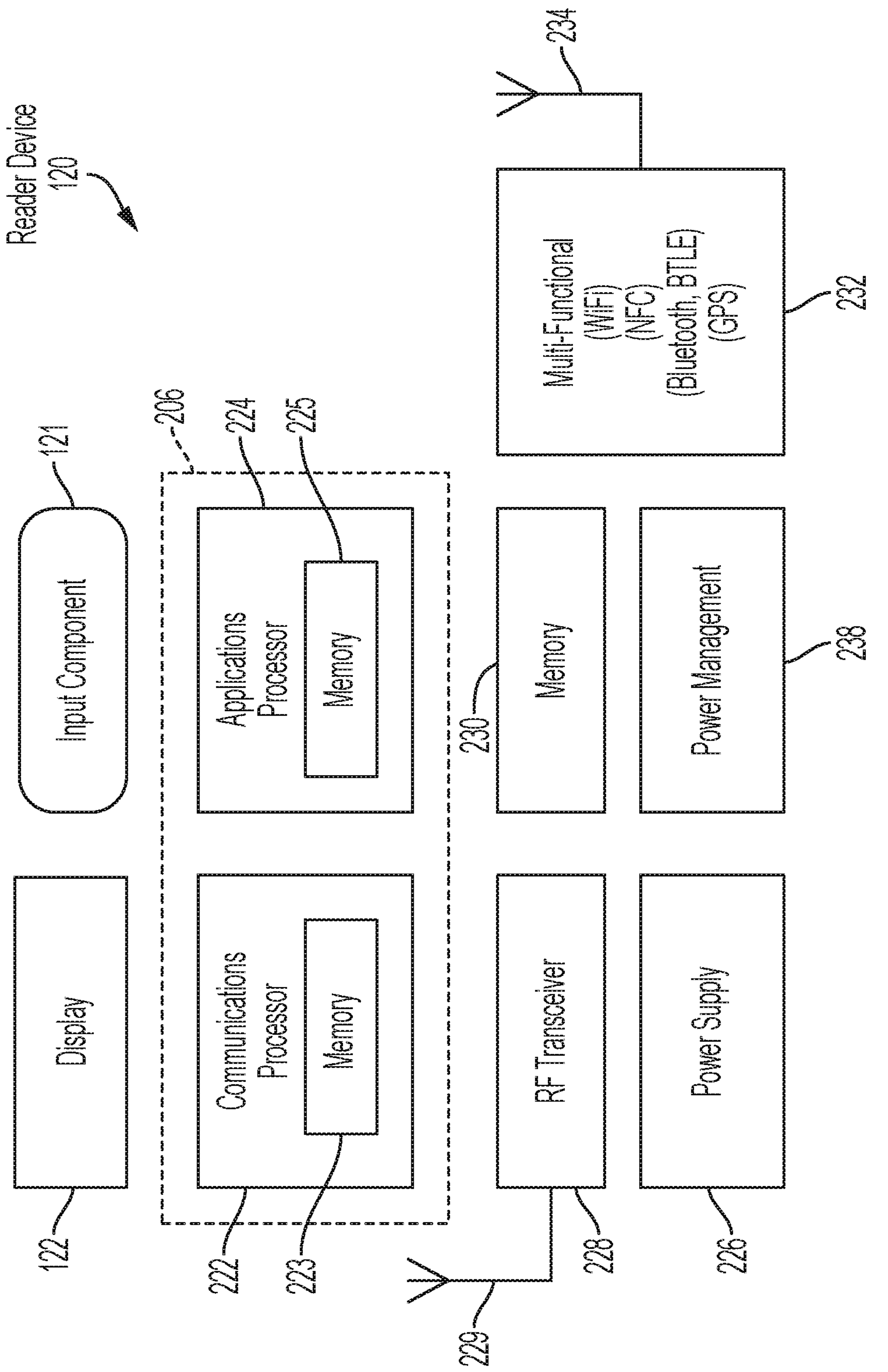
FIG. 2A is a block diagram depicting an example embodiment of a reader device.

FIG. 2A is a block diagram depicting an example embodiment of a reader device configured as a smartphone. Here, reader device 120 can include a display 122, input component 121, and a processing core 206 including a communications processor 222 coupled with memory 223 and an applications processor 224 coupled with memory 225. Also included can be separate memory 230, RF transceiver 228 with antenna 229, and power supply 226 with power management module 238. Further included can be a multifunctional transceiver 232 which can communicate over Wi-Fi, NFC, Bluetooth, BTLE, and GPS with an antenna 234. As understood by one of skill in the art, these components are electrically and communicatively coupled in a manner to make a functional device.

Exemplary Sensor Control Devices

Figure 2B:
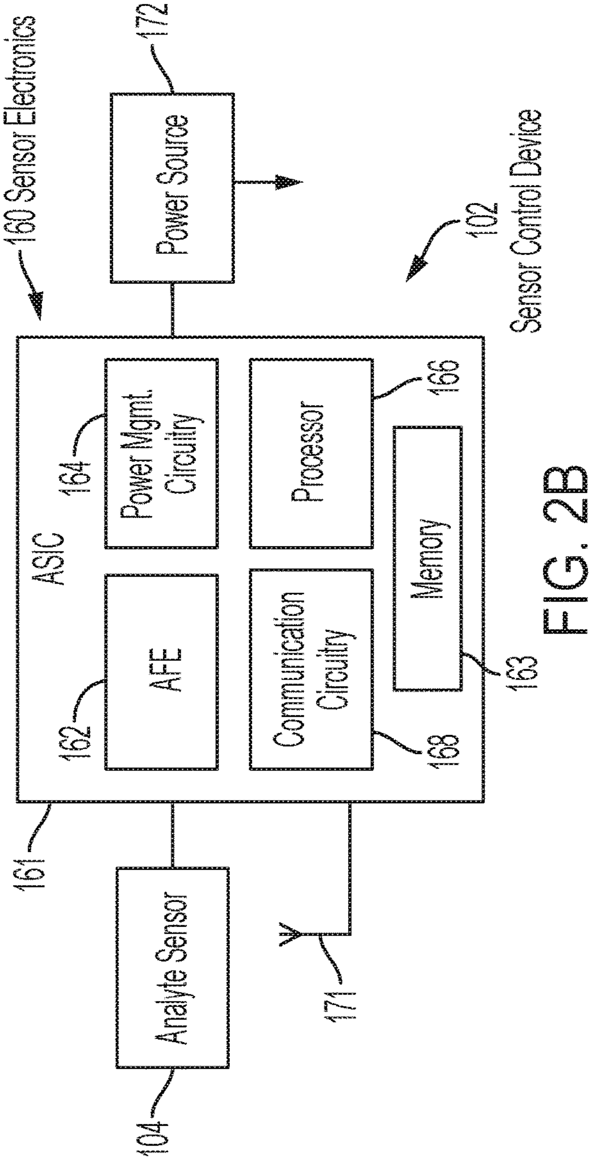
FIGS. 2B and 2C are block diagrams depicting example embodiments of sensor control devices.
Figure 2C:
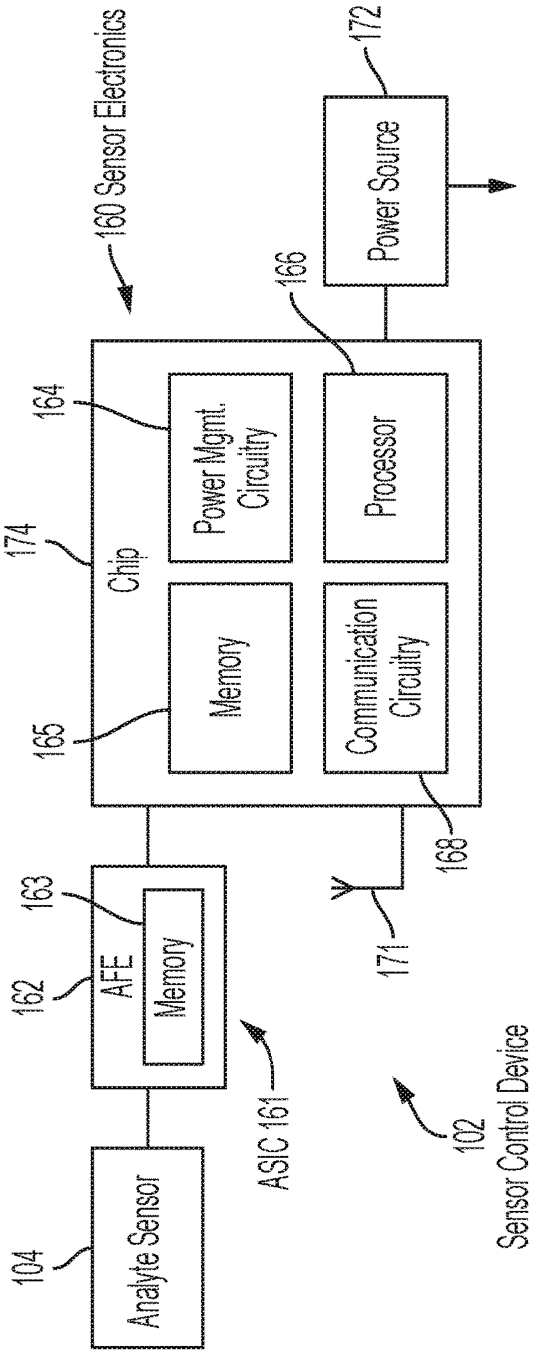

FIGS. 2B and 2C are block diagrams depicting example embodiments of sensor control device 102 having analyte sensor 104 and sensor electronics 160 (including analyte monitoring circuitry) that can have the majority of the processing capability for rendering end-result data suitable for display to the user. In FIG. 2B, a single semiconductor chip 161 is depicted that can be a custom application specific integrated circuit (ASIC). Shown within ASIC 161 are certain high-level functional units, including an analog front end (AFE) 162, power management (or control) circuitry 164, processor 166, and communication circuitry 168 (which can be implemented as a transmitter, receiver, transceiver, passive circuit, or otherwise according to the communication protocol). In this embodiment, both AFE 162 and processor 166 are used as analyte monitoring circuitry, but in other embodiments either circuit can perform the analyte monitoring function. Processor 166 can include one or more processors, microprocessors, controllers, and/or microcontrollers, each of which can be a discrete chip or distributed amongst (and a portion of) a number of different chips.

A memory 163 is also included within ASIC 161 and can be shared by the various functional units present within ASIC 161, or can be distributed amongst two or more of them. Memory 163 can also be a separate chip. Memory 163 can be volatile and/or non-volatile memory. In this embodiment, ASIC 161 is coupled with power source 172, which can be a coin cell battery, or the like. AFE 162 interfaces with in vivo analyte sensor 104 and receives measurement data therefrom and outputs the data to processor 166 in digital form, which in turn processes the data to arrive at the end-result glucose discrete and trend values, etc. This data can then be provided to communication circuitry 168 for sending, by way of antenna 171, to reader device 120 (not shown), for example, where minimal further processing is needed by the resident software application to display the data.

FIG. 2C is similar to FIG. 2B but instead includes two discrete semiconductor chips 162 and 174, which can be packaged together or separately. Here, AFE 162 is resident on ASIC 161. Processor 166 is integrated with power management circuitry 164 and communication circuitry 168 on chip 174. AFE 162 includes memory 163 and chip 174 includes memory 165, which can be isolated or distributed within. In one example embodiment, AFE 162 is combined with power management circuitry 164 and processor 166 on one chip, while communication circuitry 168 is on a separate chip. In another example embodiment, both AFE 162 and communication circuitry 168 are on one chip, and processor 166 and power management circuitry 164 are on another chip. It should be noted that other chip combinations are possible, including three or more chips, each bearing responsibility for the separate functions described, or sharing one or more functions for fail-safe redundancy.

Exemplary Assembly Processes for Sensor Control Devices

According to some embodiments, the components of sensor control device 102 can be acquired by a user in multiple packages requiring final assembly by the user before delivery to an appropriate user location. FIGS. 3A-3E depict an example embodiment of an assembly process for sensor control device 102 by a user, including preparation of separate components before coupling the components in order to ready the sensor for delivery. In other embodiments, components of the sensor control device 102 and applicator 150 can be acquired by a user in a single package. FIGS. 3F-3G depict an example embodiment of delivery of sensor control device 102 to an appropriate user location by selecting the appropriate delivery location and applying device 102 to the location.

Figure 3A:
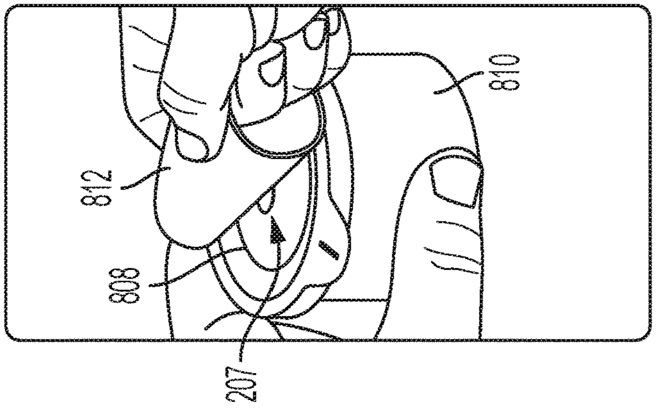
FIGS. 3A to 3G are progressive views of an example embodiment of the assembly and application of the system of FIG. 1 incorporating a two-piece architecture.

FIG. 3A depicts a sensor container or tray 810 that has a removable lid 812. The user prepares the sensor tray 810 by removing the lid 812, which acts as a sterile barrier to protect the internal contents of the sensor tray 810 and otherwise maintain a sterile internal environment. Removing the lid 812 exposes a platform 808 positioned within the sensor tray 810, and a plug assembly 207 (partially visible) is arranged within and otherwise strategically embedded within the platform 808. The plug assembly 207 includes a sensor module (not shown) and a sharp module (not shown). The sensor module carries the sensor 104 (FIG. 1), and the sharp module carries an associated sharp used to help deliver the sensor 104 transcutaneously under the user's skin during application of the sensor control device 102 (FIG. 1).

Figure 3B:
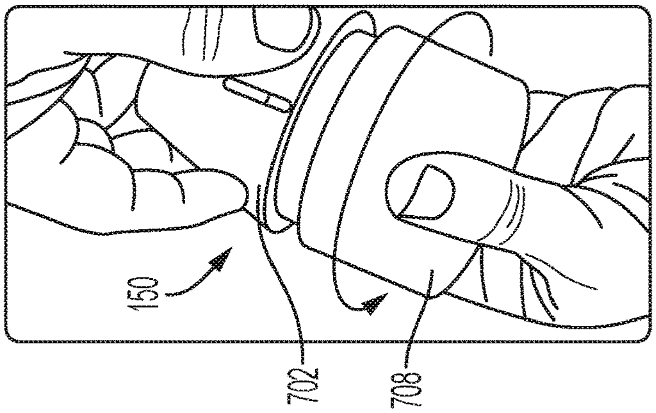

FIG. 3B depicts the sensor applicator 150 and the user preparing the sensor applicator 150 for final assembly. The sensor applicator 150 includes a housing 702 sealed at one end with an applicator cap 708. In some embodiments, for example, an O-ring or another type of sealing gasket may seal an interface between the housing 702 and the applicator cap 708. In at least one embodiment, the O-ring or sealing gasket may be molded onto one of the housing 702 and the applicator cap 708. The applicator cap 708 provides a barrier that protects the internal contents of the sensor applicator 150. In particular, the sensor applicator 150 contains an electronics housing (not shown) that retains the electrical components for the sensor control device 102 (FIG. 1), and the applicator cap 708 may or may not maintain a sterile environment for the electrical components. Preparation of the sensor applicator 150 includes uncoupling the housing 702 from the applicator cap 708, which can be accomplished by unscrewing the applicator cap 708 from the housing 702. The applicator cap 708 can then be discarded or otherwise placed aside.

Figure 3C:
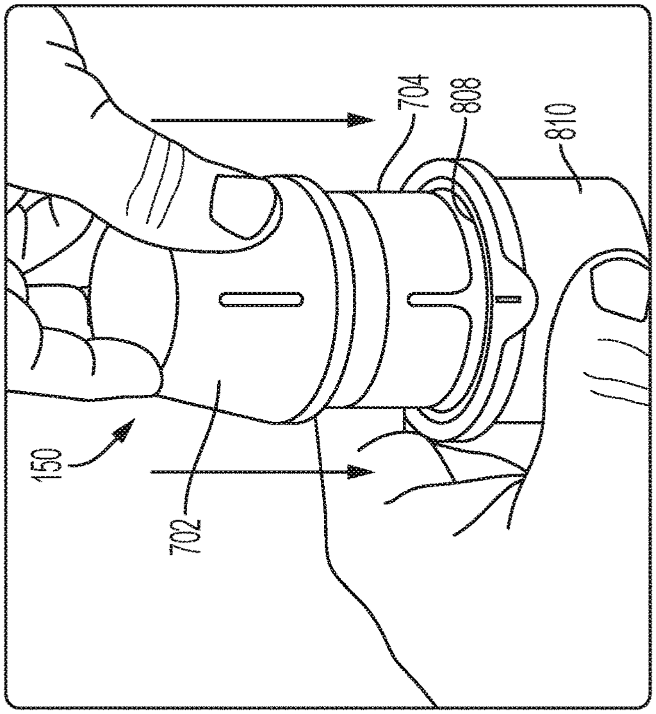
Figure 3E:
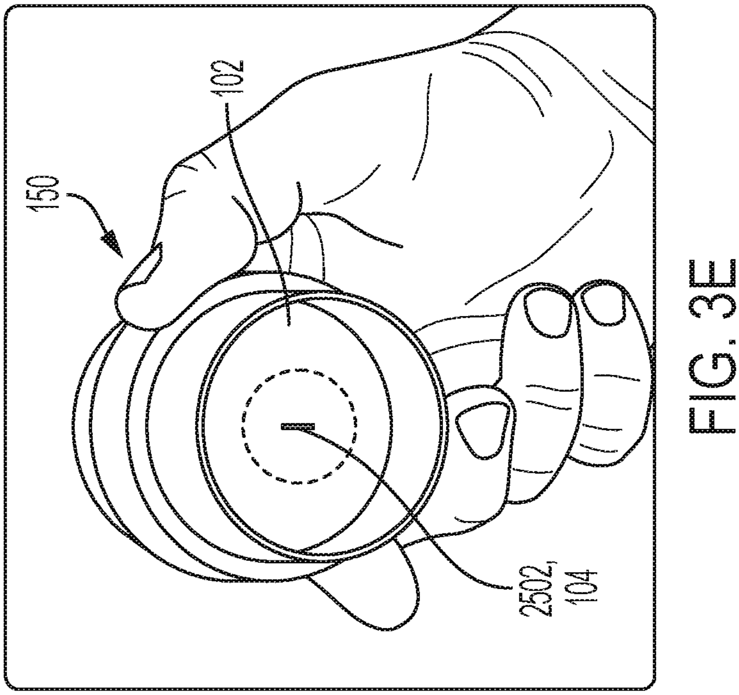

FIG. 3C depicts the user inserting the sensor applicator 150 into the sensor tray 810. The sensor applicator 150 includes a sheath 704 configured to be received by the platform 808 to temporarily unlock the sheath 704 relative to the housing 702, and also temporarily unlock the platform 808 relative to the sensor tray 810. Advancing the housing 702 into the sensor tray 810 results in the plug assembly 207 (FIG. 3A) arranged within the sensor tray 810, including the sensor and sharp modules, being coupled to the electronics housing arranged within the sensor applicator 150.

Figure 3D:
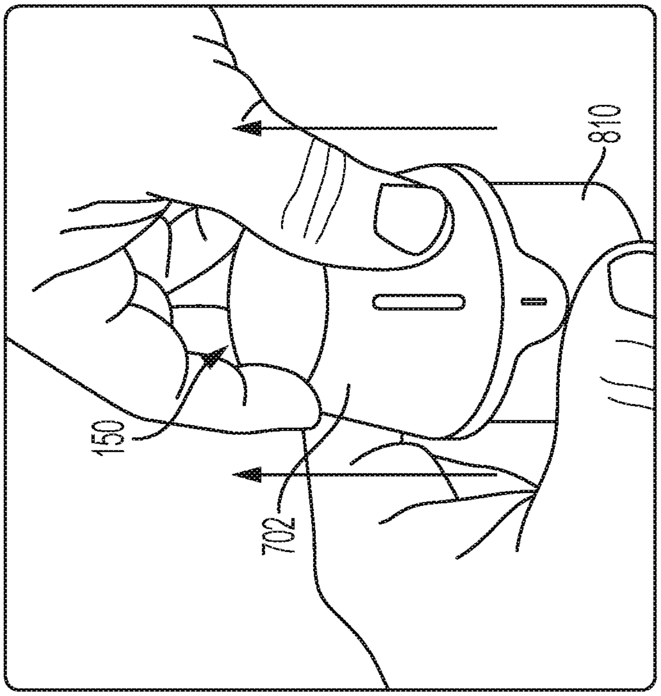
Figure 3G:
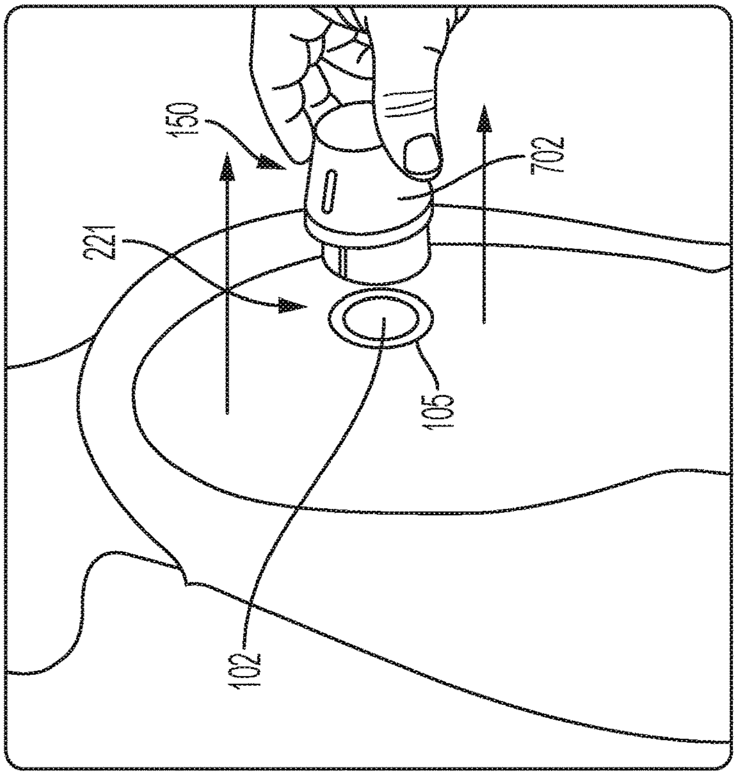
Figure 3F:
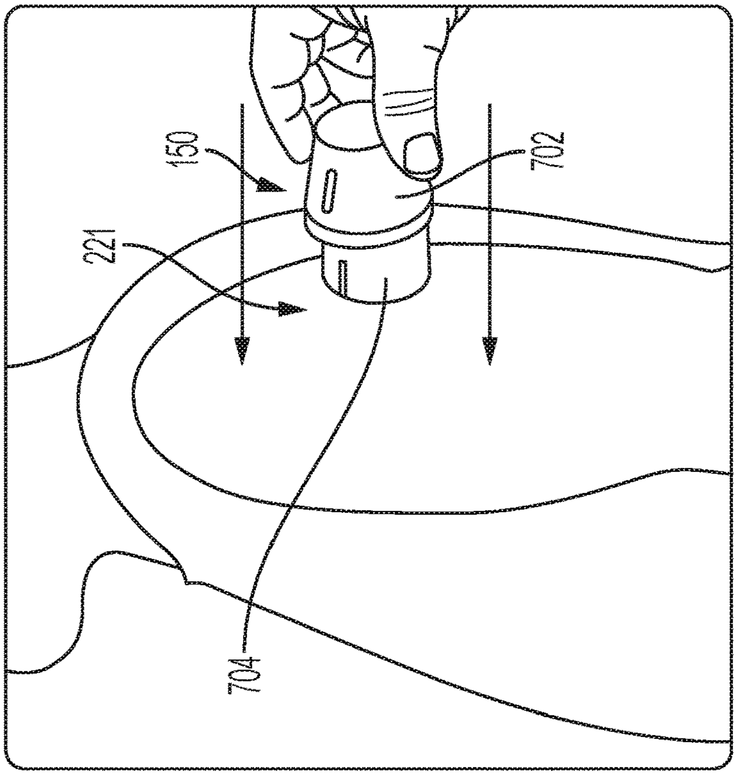

In FIG. 3D, the user removes the sensor applicator 150 from the sensor tray 810 by proximally retracting the housing 702 with respect to the sensor tray 810.

FIG. 3E depicts the bottom or interior of the sensor applicator 150 following removal from the sensor tray 810 (FIGS. 3A and 3C). The sensor applicator 150 is removed from the sensor tray 810 with the sensor control device 102 fully assembled therein and positioned for delivery to the target monitoring location. As illustrated, a sharp 2502 extends from the bottom of the sensor control device 102 and carries a portion of the sensor 104 within a hollow or recessed portion thereof. The sharp 2502 is configured to penetrate the skin of a user and thereby place the sensor 104 into contact with bodily fluid.

FIGS. 3F and 3G depict example delivery of the sensor control device 102 to a target monitoring location 221, such as the back of an arm of the user. FIG. 3F shows the user advancing the sensor applicator 150 toward the target monitoring location 221. Upon engaging the skin at the target monitoring location 221, the sheath 704 collapses into the housing 702, which allows the sensor control device 102 (FIGS. 3E and 3G) to advance into engagement with the skin. With the help of the sharp 2502 (FIG. 3E), the sensor 104 (FIG. 3E) is advanced transcutaneously into the patient's skin at the target monitoring location 221.

FIG. 3G shows the user retracting the sensor applicator 150 from the target monitoring location 221, with the sensor control device 102 successfully attached to the user's skin. The adhesive patch 105 (FIG. 1) applied to the bottom of sensor control device 102 adheres to the skin to secure the sensor control device 102 in place. The sharp 2502 (FIG. 3E) is automatically retracted when the housing 702 is fully advanced at the target monitoring location 221, while the sensor 104 (FIG. 3E) is left in position to measure analyte levels.

According to some embodiments, system 100, as described with respect to FIGS. 3A-3G and elsewhere herein, can provide a reduced or eliminated chance of accidental breakage, permanent deformation, or incorrect assembly of applicator components compared to prior art systems. Since applicator housing 702 directly engages platform 808 while sheath 704 unlocks, rather than indirect engagement via sheath 704, relative angularity between sheath 704 and housing 702 will not result in breakage or permanent deformation of the arms or other components. The potential for relatively high forces (such as in conventional devices) during assembly will be reduced, which in turn reduces the chance of unsuccessful user assembly. Further details regarding embodiments of applicators, their components, and variants thereof, are described in U.S. Patent Publication Nos. 2013/0150691, 2016/0331283, and 2018/0235520, all of which are incorporated by reference herein in their entireties and for all purposes.

Example Embodiment of Sensor Applicator Device

Figure 4C:
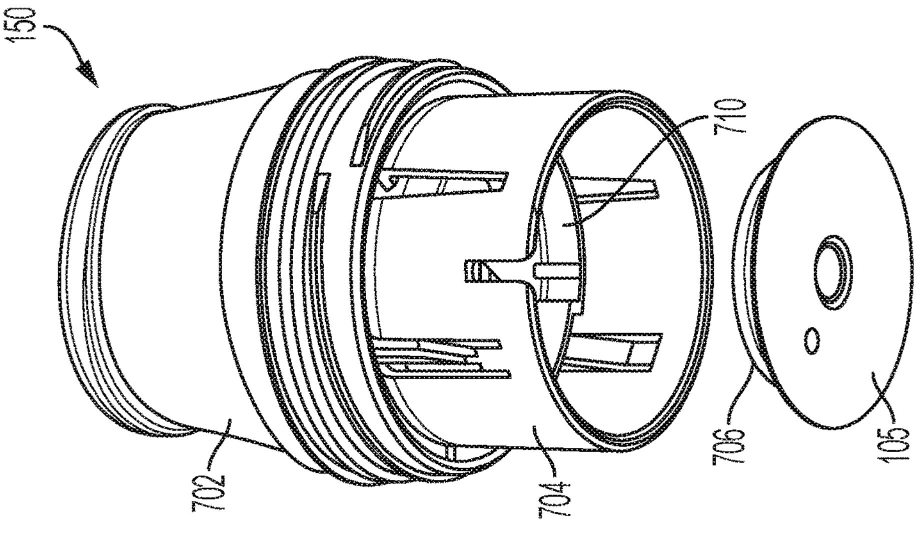
FIG. 4C is a perspective view depicting an example embodiment of a distal end of an applicator device and electronics housing.
Figure 4B:
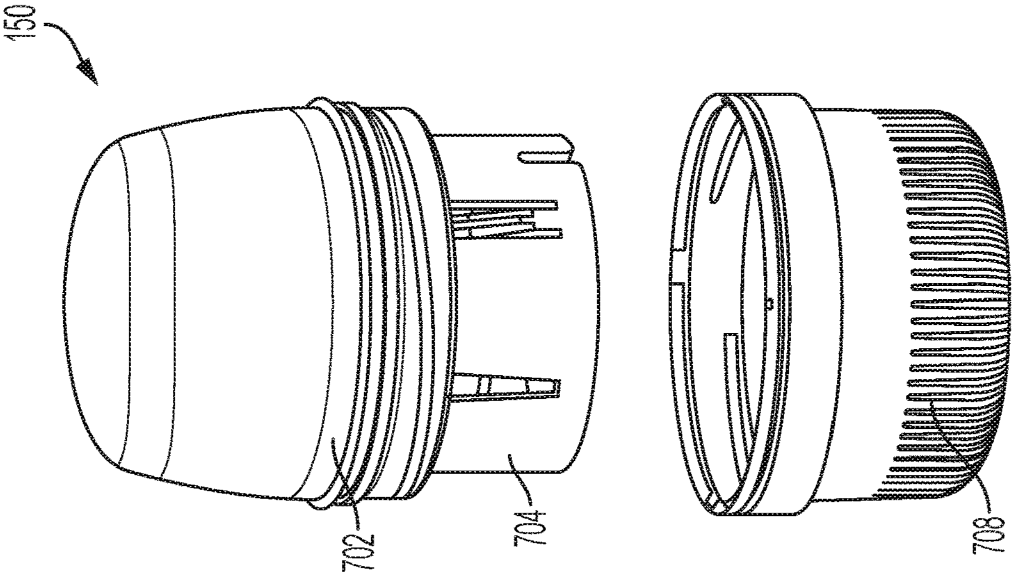
FIG. 4B is a side perspective view depicting an example embodiment of an applicator device and cap decoupled.
Figure 4A:
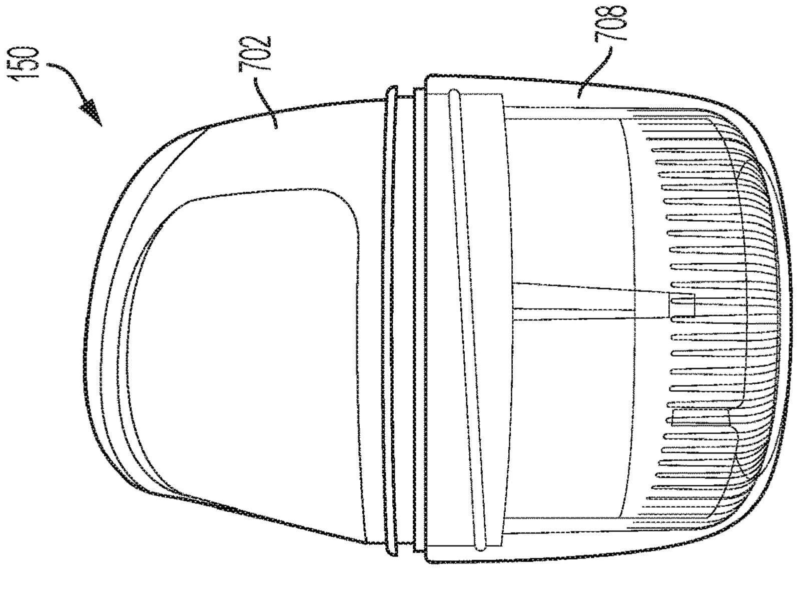
FIG. 4A is a side view depicting an example embodiment of an applicator device coupled with a cap.

FIG. 4A is a side view depicting an example embodiment of an applicator device 150 coupled with screw cap 708. This is one example of how applicator 150 is shipped to and received by a user, prior to assembly by the user with a sensor. In other embodiments, applicator 150 can be shipped to the user with the sensor and sharp contained therein. FIG. 4B is a side perspective view depicting applicator 150 and cap 708 after being decoupled. FIG. 4C is a perspective view depicting an example embodiment of a distal end of an applicator device 150 with electronics housing 706 and adhesive patch 105 removed from the position they would have retained within device carrier 710 of sheath 704, when cap 708 is in place.

Exemplary Tray and Sensor Module Assembly

Figure 5:
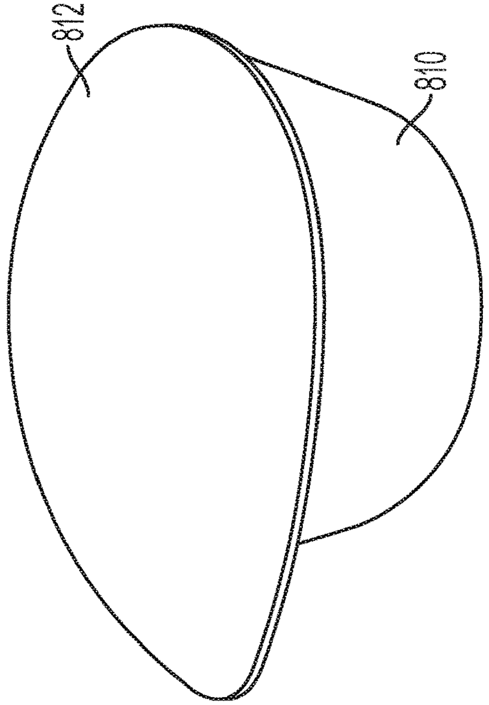
FIG. 5 is a proximal perspective view depicting an example embodiment of a tray with sterilization lid coupled.

FIG. 5 is a proximal perspective view depicting an example embodiment of a tray 810 with sterilization lid 812 removably coupled thereto, which may be representative of how the package is shipped to and received by a user prior to assembly.

Figure 6A:
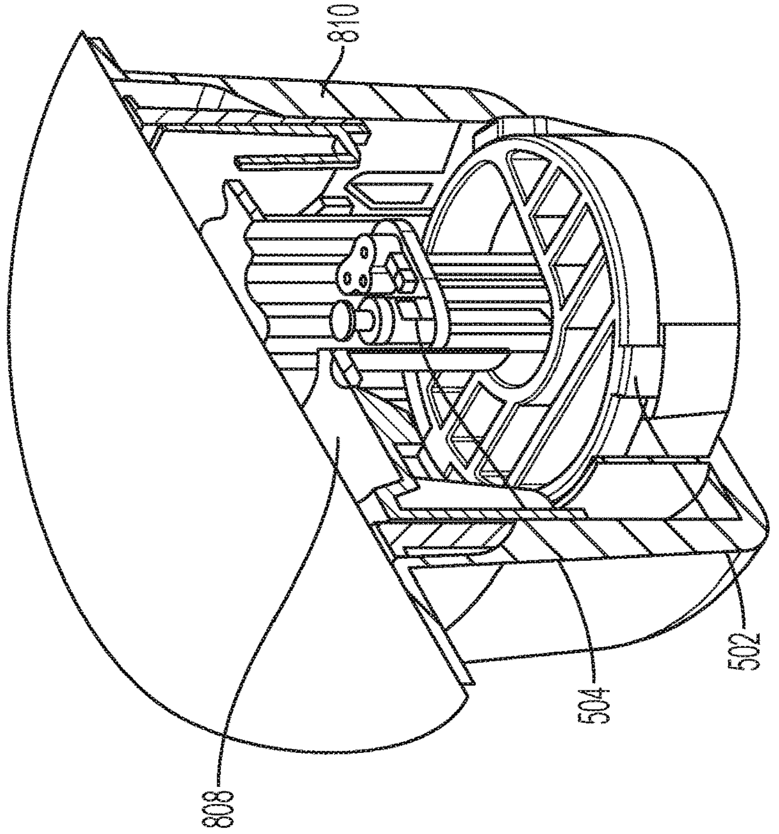
FIG. 6A is a proximal perspective cutaway view depicting an example embodiment of a tray with sensor delivery components.

FIG. 6A is a proximal perspective cutaway view depicting sensor delivery components within tray 810. Platform 808 is slidably coupled within tray 810. Desiccant 502 is stationary with respect to tray 810. Sensor module 504 is mounted within tray 810.

Figure 6B:
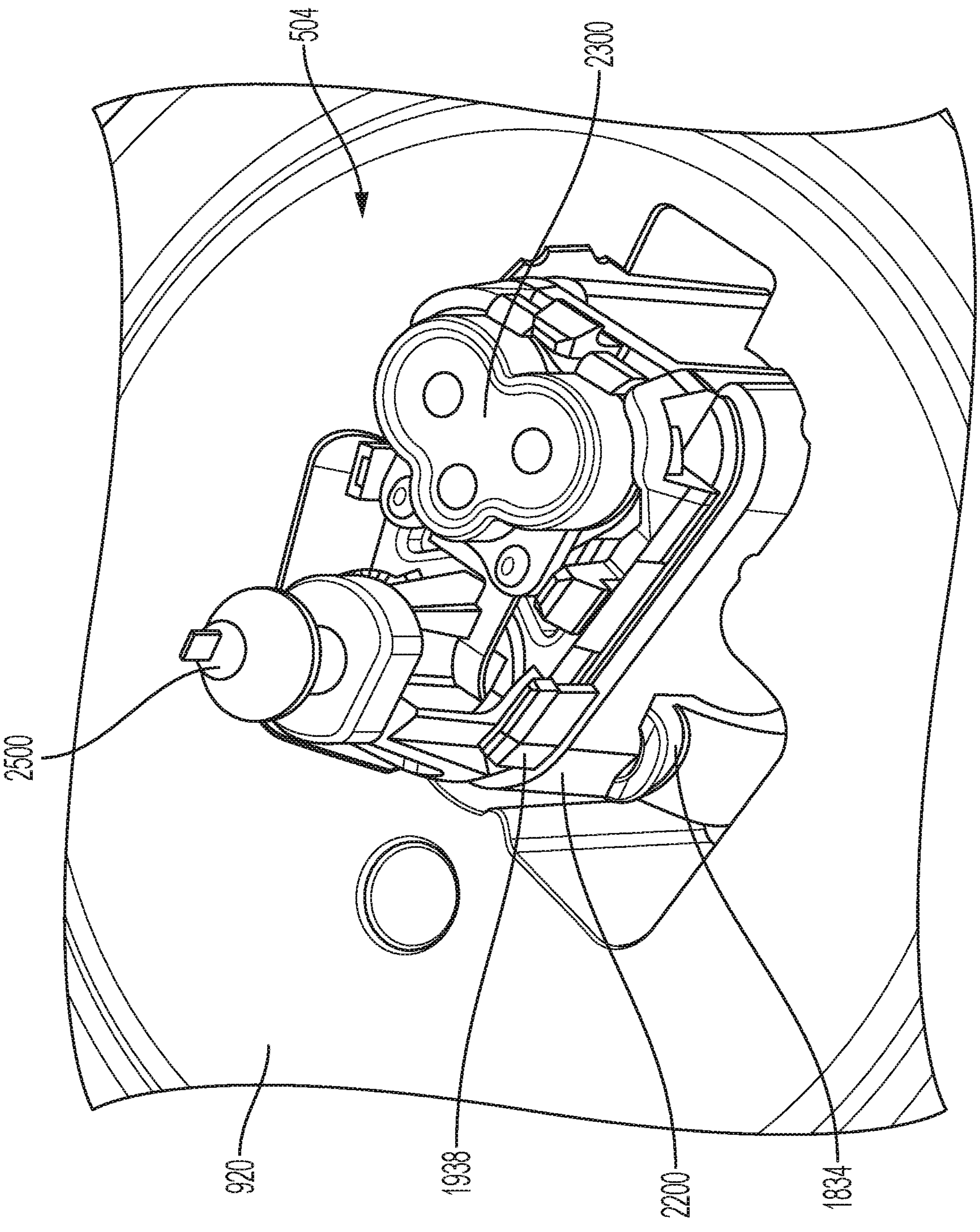
FIG. 6B is a proximal perspective view depicting sensor delivery components.

FIG. 6B is a proximal perspective view depicting sensor module 504 in greater detail. Here, retention arm extensions 1834 of platform 808 releasably secure sensor module 504 in position. Module 2200 is coupled with connector 2300, sharp module 2500 and sensor (not shown) such that during assembly they can be removed together as sensor module 504.

Example Embodiment of Applicator Housing

Figure 7A:
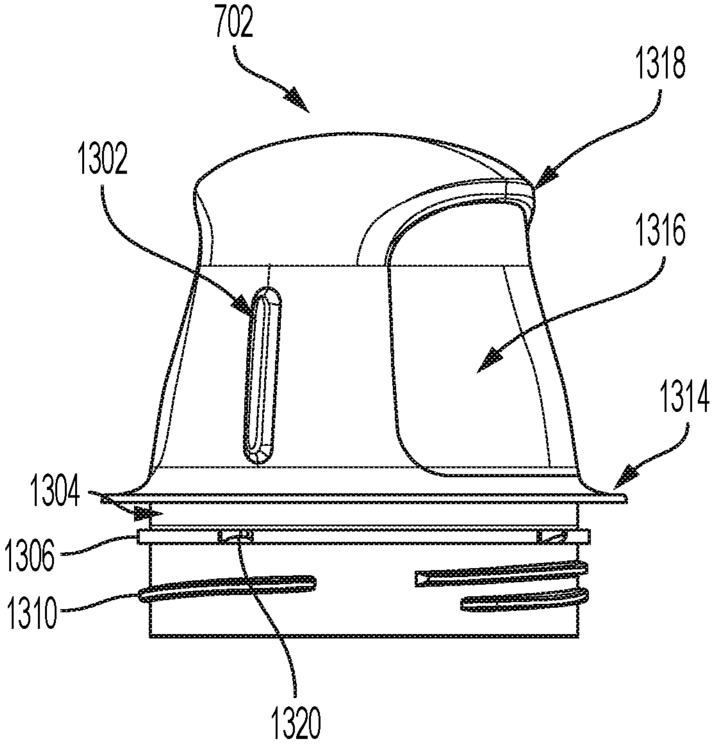
FIG. 7A is side view depicting an example embodiment of a housing.

FIG. 7A is side view depicting an example embodiment of the applicator housing 702 that can include an internal cavity with support structures for applicator function. A user can push housing 702 in a distal direction to activate the applicator assembly process and then also to cause delivery of sensor control device 102, after which the cavity of housing 702 can act as a receptacle for a sharp. In the example embodiment, various features are shown including housing orienting feature 1302 for orienting the device during assembly and use. Tamper ring groove 1304 can be a recess located around an outer circumference of housing 702, distal to a tamper ring protector 1314 and proximal to a tamper ring retainer 1306. Tamper ring groove 1304 can retain a tamper ring so users can identify whether the device has been tampered with or otherwise used. Housing threads 1310 can secure housing 702 to complimentary threads on cap 708 (FIGS. 4A and 4B) by aligning with complimentary cap threads and rotating in a clockwise or counterclockwise direction. A side grip zone 1316 of housing 702 can provide an exterior surface location where a user can grip housing 702 in order to use it. Grip overhang 1318 is a slightly raised ridge with respect to side grip zone 1316 which can aid in ease of removal of housing 702 from cap 708. A shark tooth 1320 can be a raised section with a flat side located on a clockwise edge to shear off a tamper ring (not shown), and hold tamper ring in place after a user has unscrewed cap 708 and housing 702. In the example embodiment four shark teeth 1320 are used, although more or less can be used as desired.

Figure 7B:
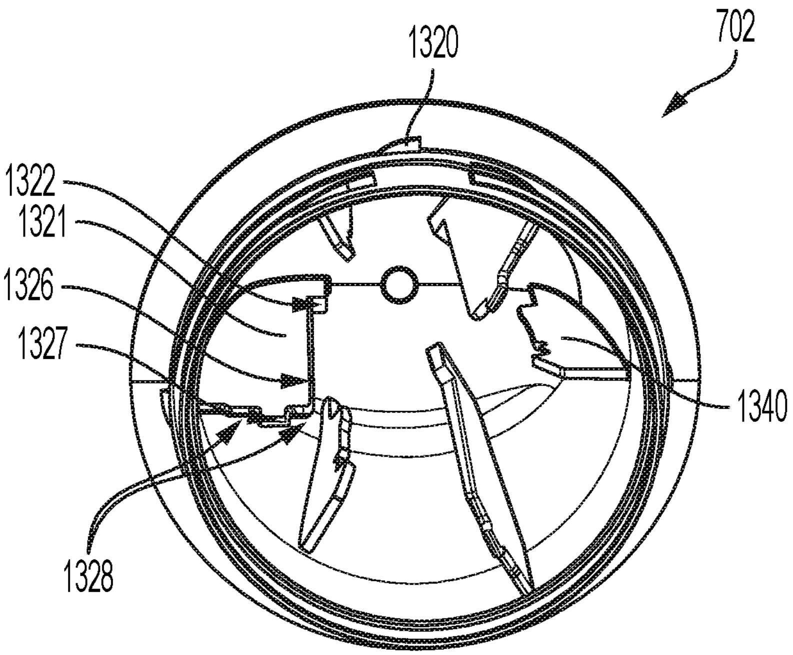
FIG. 7B is a perspective view depicting an example embodiment of a distal end of a housing.

FIG. 7B is a perspective view depicting a distal end of housing 702. Here, three housing guide structures (or "guide ribs") 1321 are located at 120 degree angles with respect to each other, and at 60 degree angles with respect to locking structures (or "locking ribs") 1340, of which there are also three at 120 degree angles with respect to each other. Other angular orientations, either symmetric or asymmetric, can be used, as well as any number of one or more structures 1321 and 1340. Here, each structure 1321 and 1340 is configured as a planar rib, although other shapes can be used. Each guide rib 1321 includes a guide edge (also called a "sheath guide rail") 1326 that can pass along a surface of sheath 704 (e.g., guide rail 1418 described with respect to FIG. 8A). An insertion hard stop 1322 can be a flat, distally facing surface of housing guide rib 1321 located near a proximal end of housing guide rib 1321. Insertion hard stop 1322 provides a surface for a sensor electronics carrier travel limiter face 1420 of a sheath 704 (FIG. 8B) to abut during use, preventing sensor electronics carrier travel limiter face 1420 from moving any further in a proximal direction. A carrier interface post 1327 passes through an aperture 1510 (FIG. 9A) of device carrier 710 during an assembly. A device carrier interface 1328 can be a rounded, distally facing surface of housing guide ribs 1321 which interfaces with device carrier 710.

Figure 7C:
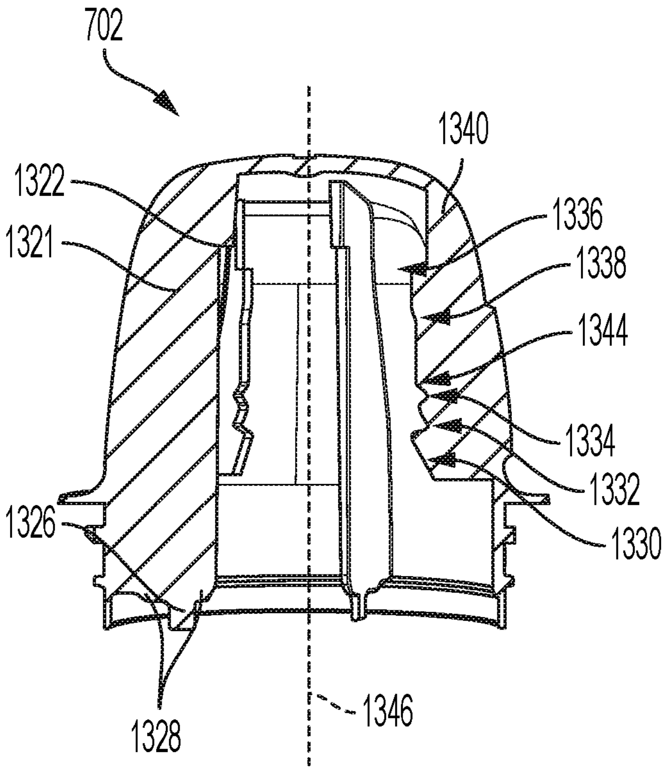
FIG. 7C is a side cross-sectional view depicting an example embodiment of a housing.

FIG. 7C is a side cross-section depicting an example embodiment of a housing. In the example embodiment, side cross-sectional profiles of housing guide rib 1321 and locking rib 1340 are shown. Locking rib 1340 includes sheath snap lead-in feature 1330 near a distal end of locking rib 1340 which flares outward from central axis 1346 of housing 702 distally. Each sheath snap lead-in feature 1330 causes detent snap round 1404 of detent snap 1402 of sheath 704 as shown in FIG. 8C to bend inward toward central axis 1346 as sheath 704 moves towards the proximal end of housing 702. Once past a distal point of sheath snap lead-in feature 1330, detent snap 1402 of sheath 704 is locked into place in locked groove 1332. As such, detent snap 1402 cannot be easily moved in a distal direction due to a surface with a near perpendicular plane to central axis 1346, shown as detent snap flat 1406 in FIG. 8C.

As housing 702 moves further in a proximal direction toward the skin surface, and as sheath 704 advances toward the distal end of housing 702, detent snaps 1402 shift into the unlocked grooves 1334, and applicator 150 is in an "armed" position, ready for use. When the user further applies force to the proximal end of housing 702, while sheath 704 is pressed against the skin, detent snap 1402 passes over firing detent 1344. This begins a firing sequence due to release of stored energy in the deflected detent snaps 1402, which travel in a proximal direction relative to the skin surface, toward sheath stopping ramp 1338 which is slightly flared outward with respect to central axis 1346 and slows sheath 704 movement during the firing sequence. The next groove encountered by detent snap 1402 after unlocked groove 1334 is final lockout groove 1336 which detent snap 1402 enters at the end of the stroke or pushing sequence performed by the user. Final lockout recess 1336 can be a proximally-facing surface that is perpendicular to central axis 1346 which, after detent snap 1402 passes, engages a detent snap flat 1406 and prevents reuse of the device by securely holding sheath 704 in place with respect to housing 702. Insertion hard stop 1322 of housing guide rib 1321 prevents sheath 704 from advancing proximally with respect to housing 702 by engaging sensor electronics carrier travel limiter face 1420.

Example Embodiment of Applicator Sheath

Figure 8A:
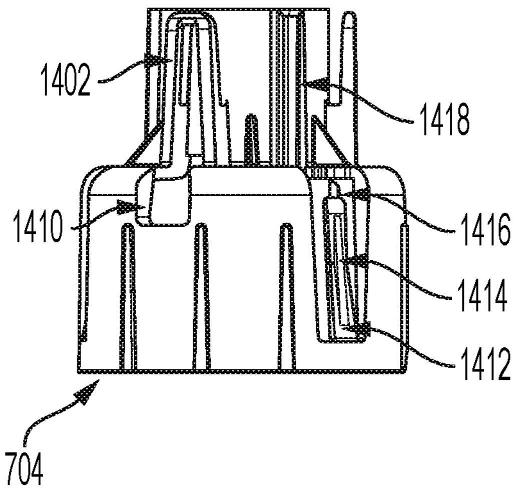
FIG. 8A is a side view depicting an example embodiment of a sheath.
Figure 8B:
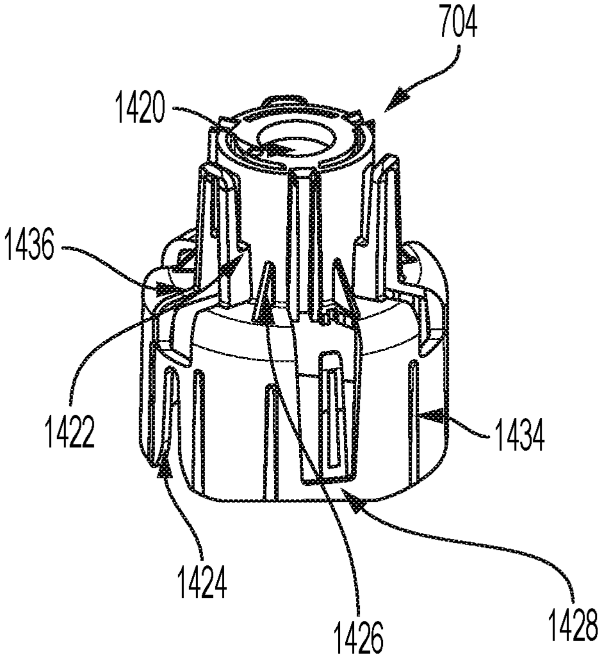
FIG. 8B is a perspective view depicting an example embodiment of a proximal end of a sheath.

FIGS. 8A and 8B are a side view and perspective view, respectively, depicting an example embodiment of sheath 704. In this example embodiment, sheath 704 can stage sensor control device 102 above a user's skin surface prior to application. Sheath 704 can also contain features that help retain a sharp in a position for proper application of a sensor, determine the force required for sensor application, and guide sheath 704 relative to housing 702 during application. Detent snaps 1402 are near a proximal end of sheath 704, described further with respect to FIG. 8C below. Sheath 704 can have a generally cylindrical cross section with a first radius in a proximal section (closer to top of figure) that is shorter than a second radius in a distal section (closer to bottom of figure). Also shown are a plurality of detent clearances 1410, three in the example embodiment. Sheath 704 can include one or more detent clearances 1410, each of which can be a cutout with room for sheath snap lead-in feature 1330 to pass distally into until a distal surface of locking rib 1340 contacts a proximal surface of detent clearance 1410.

Guide rails 1418 are disposed between sensor electronics carrier traveler limiter face 1420 at a proximal end of sheath 704 and a cutout around lock arms 1412. Each guide rail 1418 can be a channel between two ridges where the guide edge 1326 of housing guide rib 1321 can slide distally with respect to sheath 704.

Lock arms 1412 are disposed near a distal end of sheath 704 and can include an attached distal end and a free proximal end, which can include lock arm interface 1416. Lock arms 1412 can lock device carrier 710 to sheath 704 when lock arm interface 1416 of lock arms 1412 engage lock interface 1502 of device carrier 710. Lock arm strengthening ribs 1414 can be disposed near a central location of each lock arm 1412 and can act as a strengthening point for an otherwise weak point of each lock arm 1412 to prevent lock arm 1412 from bending excessively or breaking.

Detent snap stiffening features 1422 can be located along the distal section of detent snaps 1402 and can provide reinforcement to detent snaps 1402. Alignment notch 1424 can be a cutout near the distal end of sheath 704, which provides an opening for user alignment with sheath orientation feature of platform 808. Stiffening ribs 1426 can include buttresses, that are triangularly shaped here, which provide support for detent base 1436. Housing guide rail clearance 1428 can be a cutout for a distal surface of housing guide rib 1321 to slide during use.

FIG. 8C is a close-up perspective view depicting an example embodiment of detent snap 1402 of sheath 704. Detent snap 1402 can include a detent snap bridge 1408 located near or at its proximal end. Detent snap 1402 can also include a detent snap flat 1406 on a distal side of detent snap bridge 1408. An outer surface of detent snap bridge 1408 can include detent snap rounds 1404 which are rounded surfaces that allow for easier movement of detent snap bridge 1408 across interior surfaces of housing 702 such as, for example, locking rib 1340.

Figure 8D:
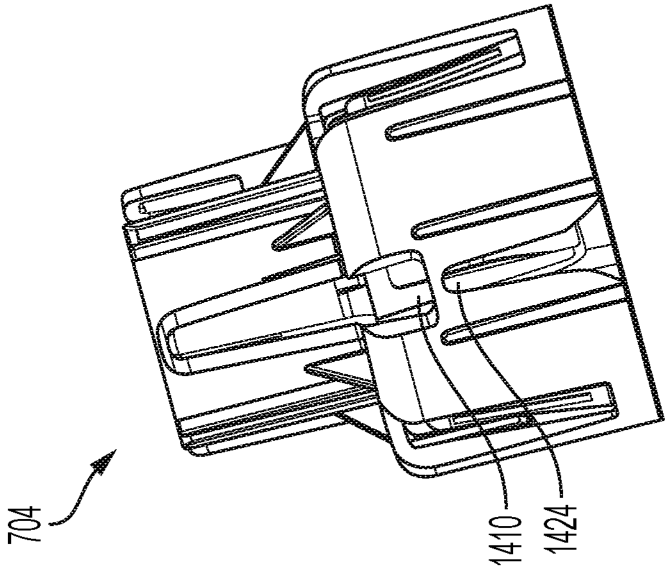
FIG. 8D is a side view depicting an example embodiment of features of a sheath.
Figure 8C:
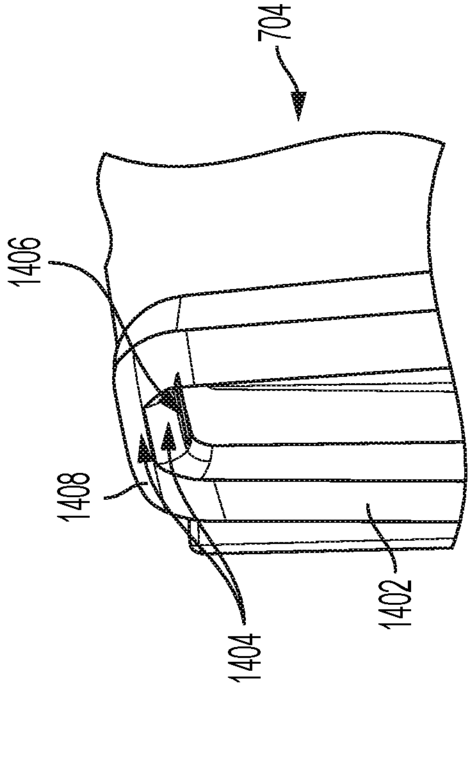
FIG. 8C is a close-up perspective view depicting an example embodiment of a distal side of a detent snap of a sheath.

FIG. 8D is a side view depicting an example embodiment of sheath 704. Here, alignment notch 1424 can be relatively close to detent clearance 1410. Detent clearance 1410 is in a relatively proximal location on distal portion of sheath 704.

Figure 8E:
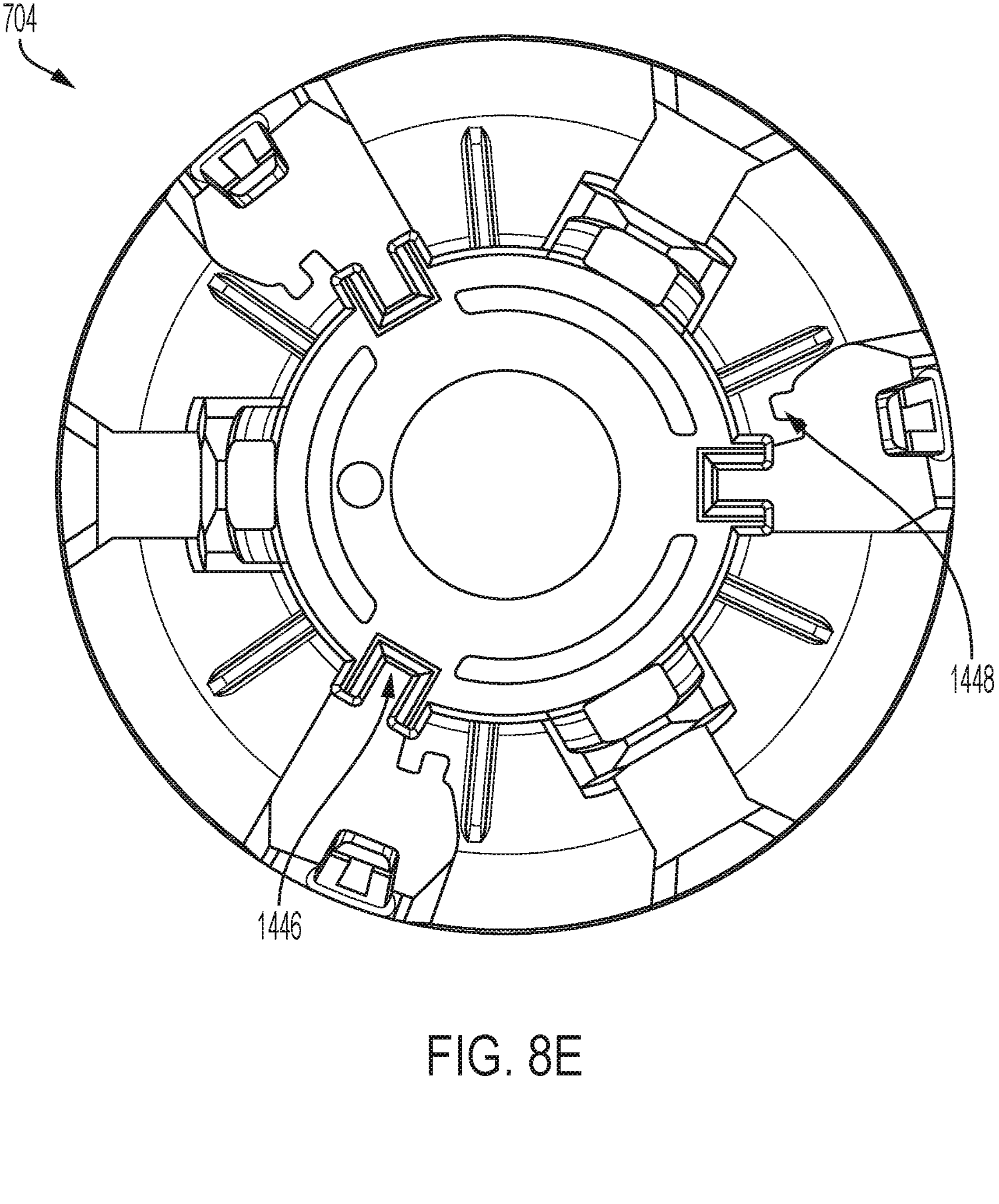
FIG. 8E is an end view of an example embodiment of a proximal end of a sheath.

FIG. 8E is an end view depicting an example embodiment of a proximal end of sheath 704. Here, a back wall for guide rails 1446 can provide a channel to slidably couple with housing guide rib 1321 of housing 702. Sheath rotation limiter 1448 can be notches which reduce or prevent rotation of the sheath 704. In a general sense, the embodiments described herein operate by flattening and stretching a skin surface at a predetermined site for sensor insertion. Moreover, the embodiments described herein may also be utilized for other medical applications, such as, e.g., transdermal drug delivery, needle injection, wound closure stitches, device implantation, the application of an adhesive surface to the skin, and other like applications.

By way of background, those of skill the art will appreciate that skin is a highly anisotropic tissue from a biomechanical standpoint and varies largely between individuals. This can affect the degree to which communication between the underlying tissue and the surrounding environment can be performed, e.g., with respect to drug diffusion rates, the ability to penetrate skin with a sharp, or sensor insertion into the body at a sharp-guided insertion site.

Example Embodiments of Device Carriers

Figure 9A:
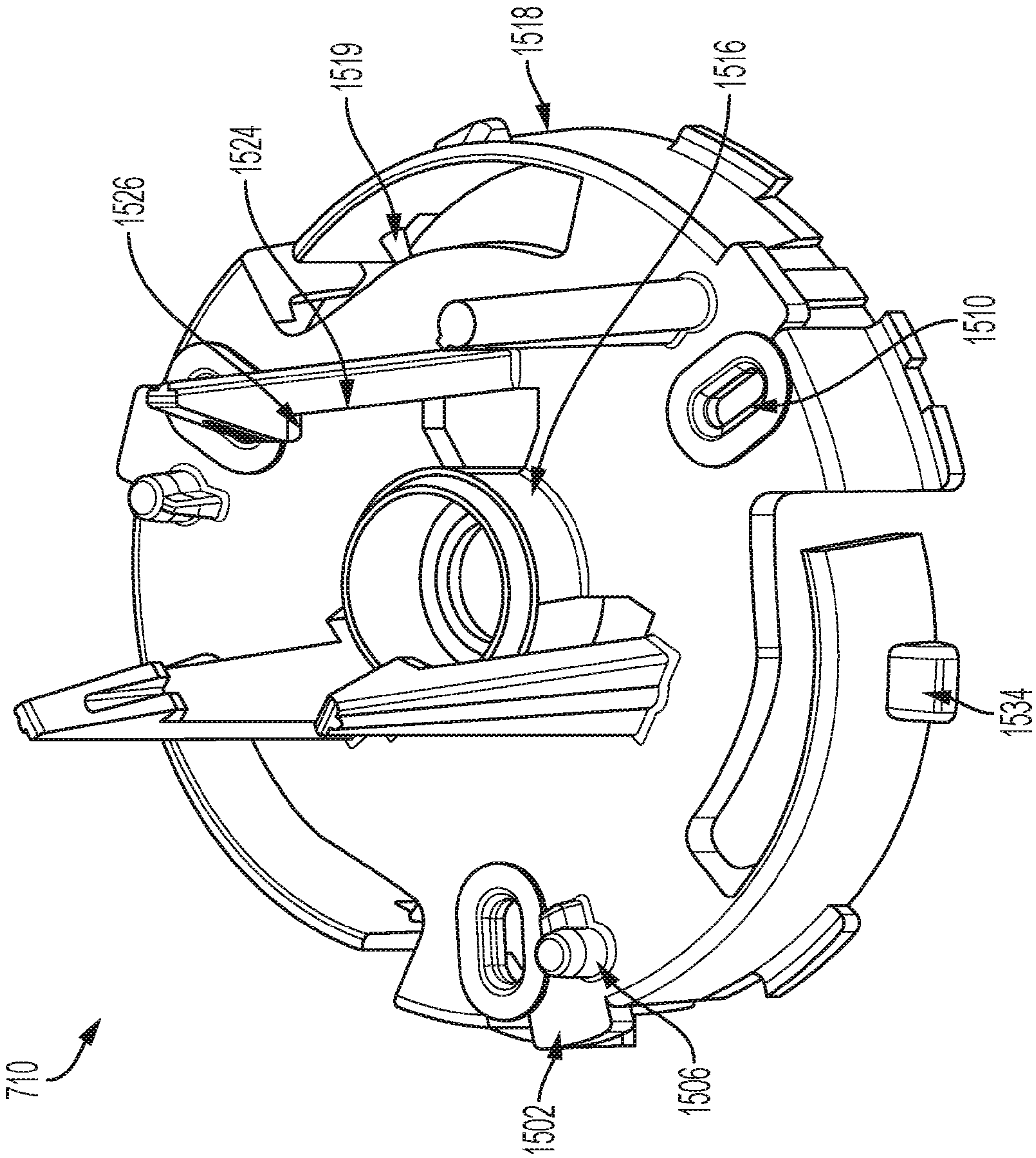
FIG. 9A is a proximal perspective view depicting an example embodiment of a device carrier.

FIG. 9A is a proximal perspective view depicting an example embodiment of device carrier 710 that can retain sensor electronics within applicator 150. It can also retain sharp carrier 1102 with sharp module 2500. In this example embodiment, carrier 710 generally has a hollow round flat cylindrical shape, and can include one or more deflectable sharp carrier lock arms 1524 (e.g., three) extending proximally from a proximal surface surrounding a centrally located spring alignment ridge 1516 for maintaining alignment of spring 1104. Each lock arm 1524 has a detent or retention feature 1526 located at or near its proximal end. Shock lock 1534 can be a tab located on an outer circumference of device carrier 710 extending outward and can lock device carrier 710 for added safety prior to firing. Rotation limiter 1506 can be a proximally extending relatively short protrusion on a proximal surface of device carrier 710 which limits rotation of carrier 710. Sharp carrier lock arms 1524 can interface with sharp carrier 1102 as described with reference to FIGS. 10 and 11 below.

Figure 9B:
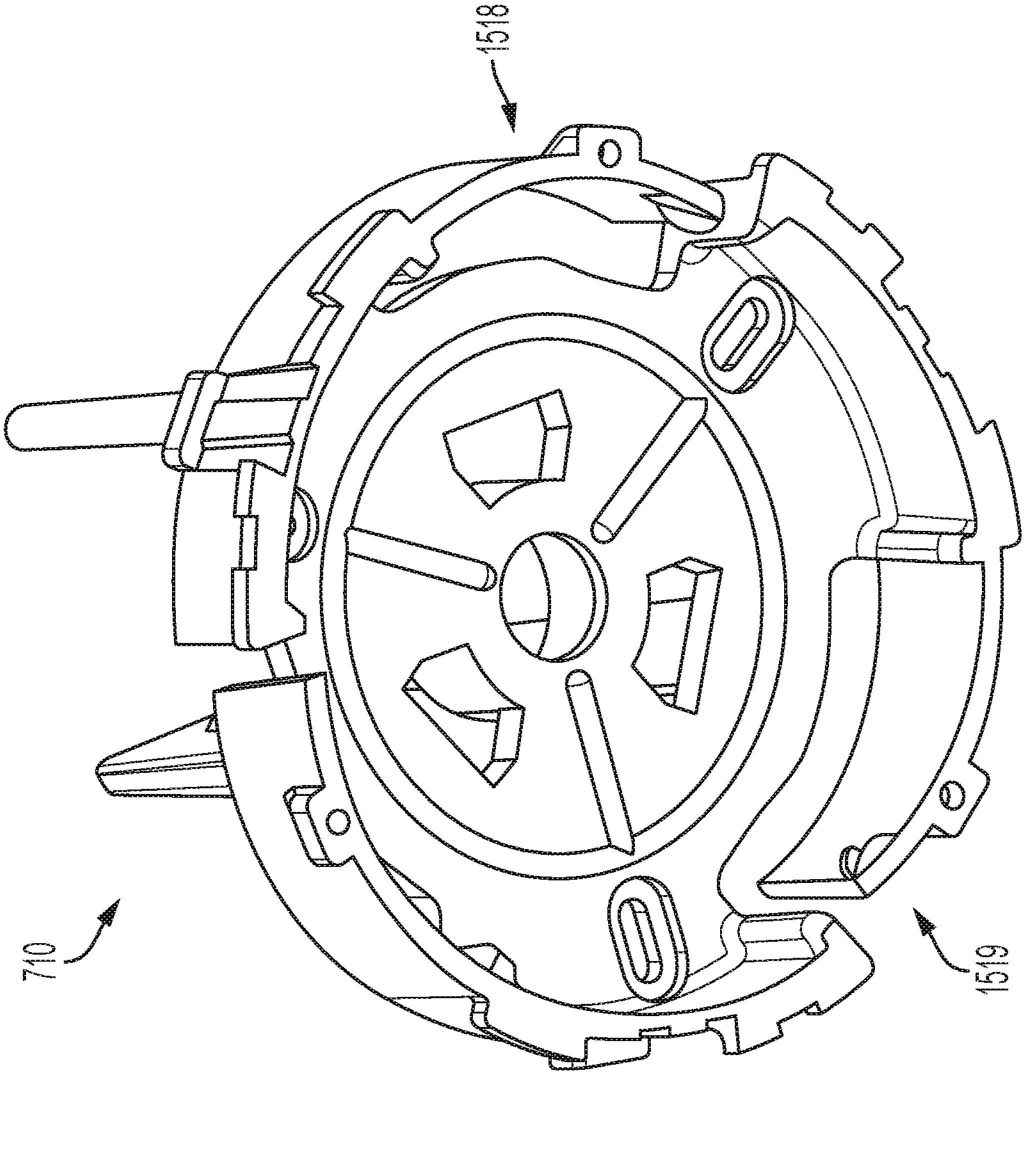
FIG. 9B is a distal perspective view depicting an example embodiment of a device carrier.

FIG. 9B is a distal perspective view of device carrier 710. Here, one or more sensor electronics retention spring arms 1518 (e.g., three) are normally biased towards the position shown and include a detent 1519 that can pass over the distal surface of electronics housing 706 of device 102 when housed within recess or cavity 1521. In certain embodiments, after sensor control device 102 has been adhered to the skin with applicator 150, the user pulls applicator 150 in a proximal direction, i.e., away from the skin. The adhesive force retains sensor control device 102 on the skin and overcomes the lateral force applied by spring arms 1518. As a result, spring arms 1518 deflect radially outwardly and disengage detents 1519 from sensor control device 102 thereby releasing sensor control device 102 from applicator 150.

Example Embodiments of Sharp Carriers

Figure 10:
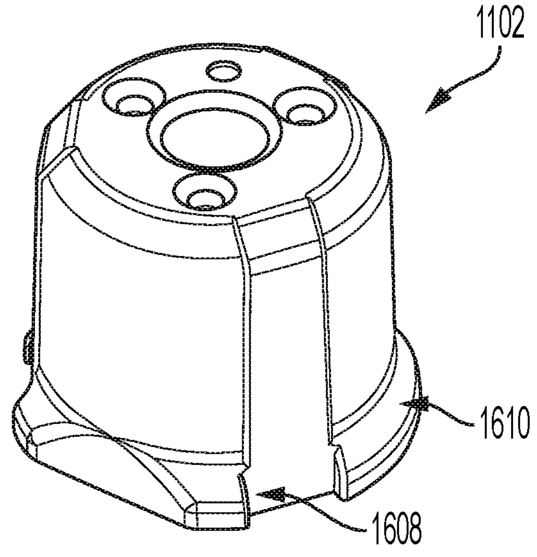
FIG. 10 is a proximal perspective view of an example embodiment of a sharp carrier.
Figure 11:
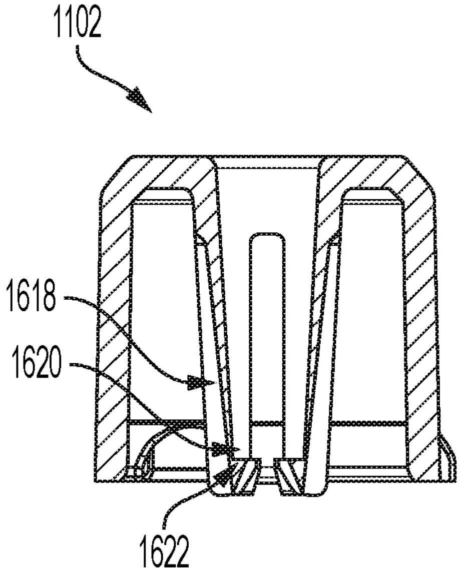
FIG. 11 is a side cross-section depicting an example embodiment of a sharp carrier.

FIGS. 10 and 11 are a proximal perspective view and a side cross-sectional view, respectively, depicting an example embodiment of sharp carrier 1102. Sharp carrier 1102 can grasp and retain sharp module 2500 within applicator 150. Near a distal end of sharp carrier 1102 can be anti-rotation slots 1608 which prevent sharp carrier 1102 from rotating when located within a central area of sharp carrier lock arms 1524 (as shown in FIG. 9A). Anti-rotation slots 1608 can be located between sections of sharp carrier base chamfer 1610, which can ensure full retraction of sharp carrier 1102 through sheath 704 upon retraction of sharp carrier 1102 at the end of the deployment procedure.

Figure 15A:
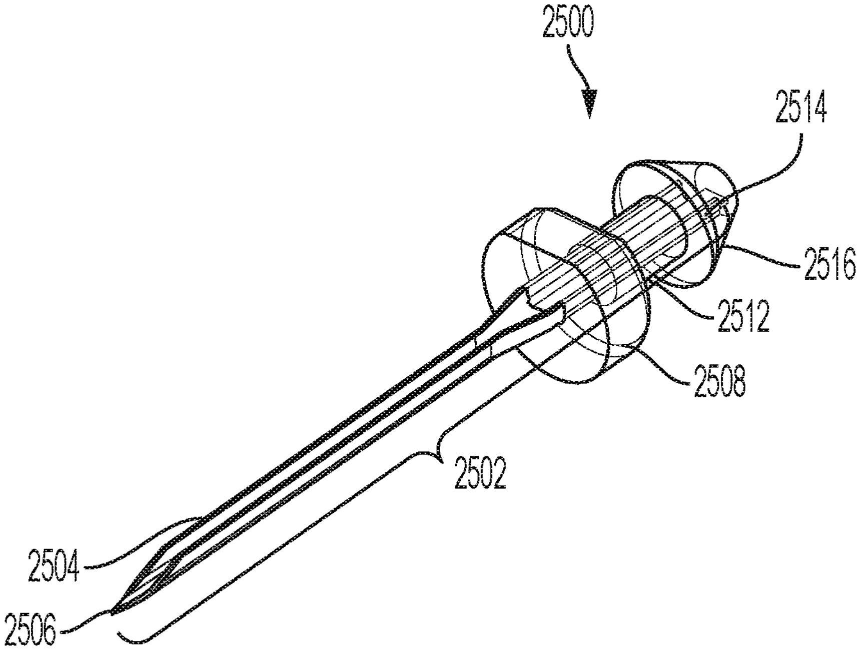
FIG. 15A is a perspective view depicting an example embodiment of a sharp module.

As shown in FIG. 11, sharp retention arms 1618 can be located in an interior of sharp carrier 1102 about a central axis and can include a sharp retention clip 1620 at a distal end of each arm 1618. Sharp retention clip 1620 can have a proximal surface which can be nearly perpendicular to the central axis and can abut a distally facing surface of sharp hub 2516 (FIG. 15A).

Exemplary Sensor Modules

Figure 12A:
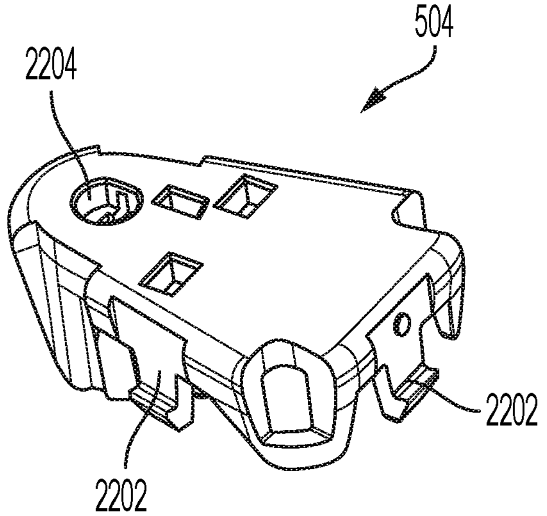
FIGS. 12A to 12B are top and bottom perspective views, respectively, depicting an example embodiment of a sensor module.
Figure 12B:
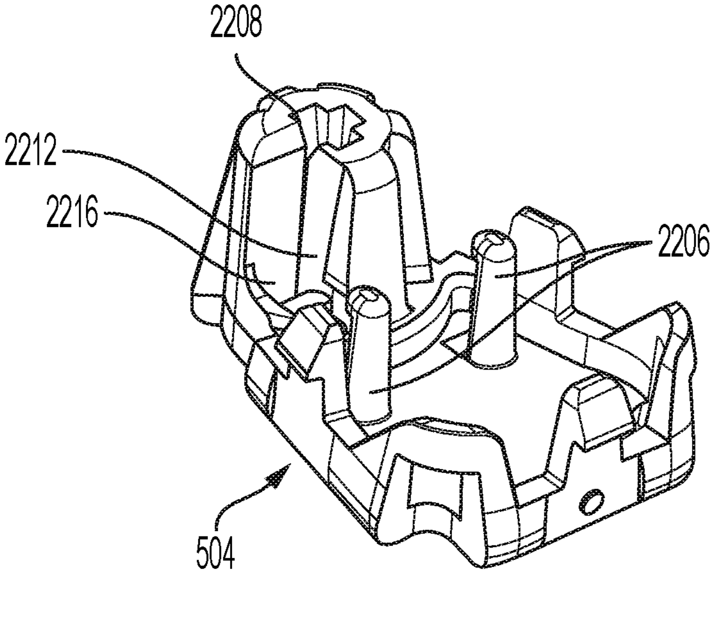

FIGS. 12A and 12B are a top perspective view and a bottom perspective view, respectively, depicting an example embodiment of sensor module 504. Module 504 can hold a connector 2300 (FIGS. 13A and 13B) and a sensor 104 (FIG. 14A). Module 504 is capable of being securely coupled with electronics housing 706. One or more deflectable arms or module snaps 2202 can snap into the corresponding features 2010 of housing 706. A sharp slot 2208 can provide a location for sharp tip 2502 to pass through and sharp shaft 2504 to temporarily reside. A sensor ledge 2212 can define a sensor position in a horizontal plane, prevent a sensor from lifting connector 2300 off of posts and maintain sensor 104 parallel to a plane of connector seals. It can also define sensor bend geometry and minimum bend radius. It can limit sensor travel in a vertical direction and prevent a tower from protruding above an electronics housing surface and define a sensor tail length below a patch surface. A sensor wall 2216 can constrain a sensor and define a sensor bend geometry and minimum bend radius.

Figure 13A:
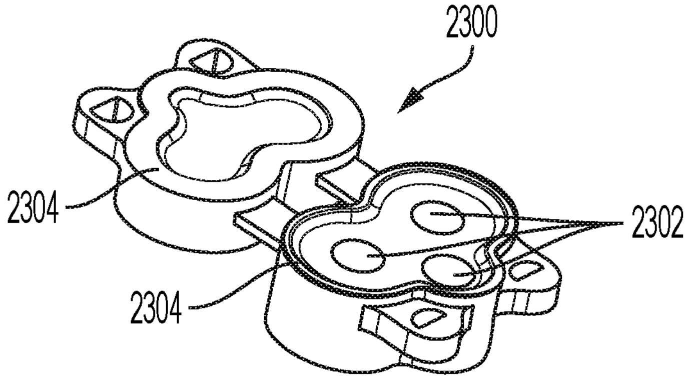
FIGS. 13A and 13B are perspective views depicting an example embodiment of a sensor connector.
Figure 13B:
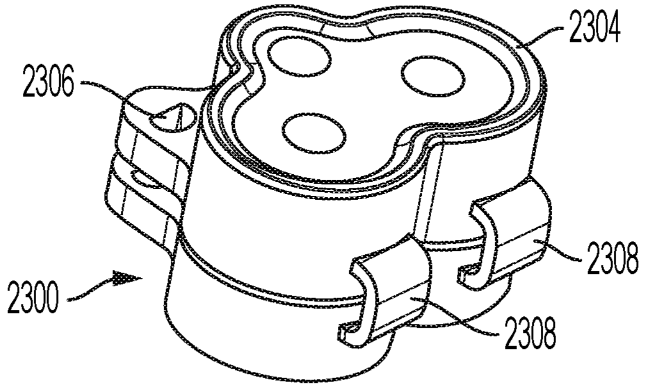
Figure 14A:
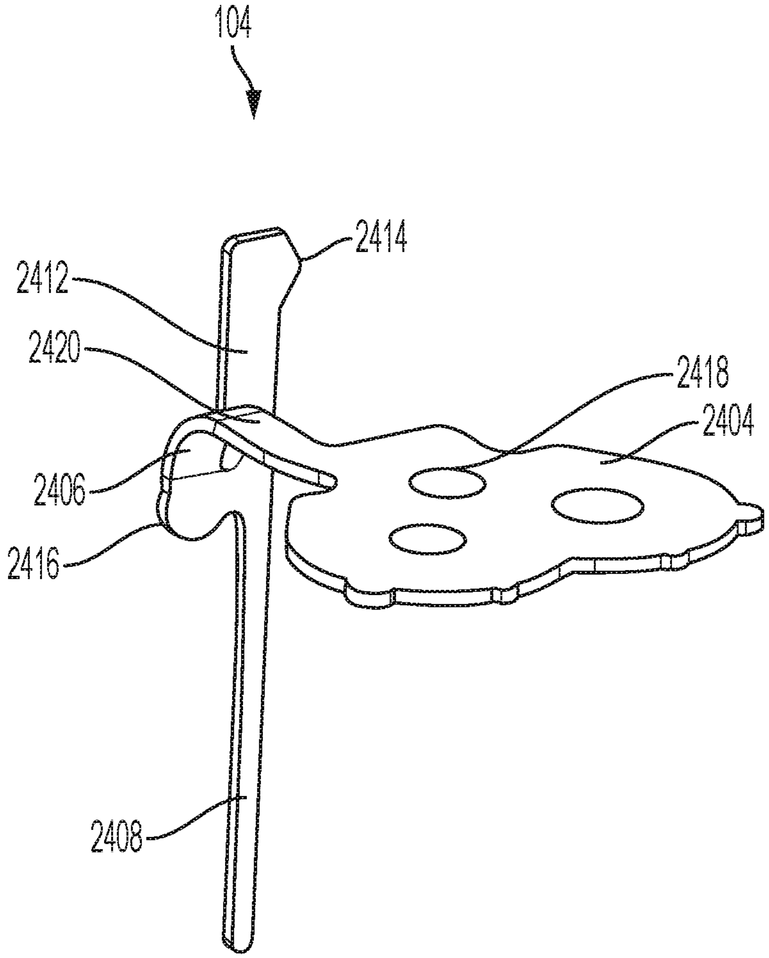
FIG. 14A is a perspective view depicting an example embodiment of a sensor.

FIGS. 13A and 13B are perspective views depicting an example embodiment of connector 2300 in an open state and a closed state, respectively. Connector 2300 can be made of silicone rubber that encapsulates compliant carbon impregnated polymer modules that serve as electrical conductive contacts 2302 between sensor 104 and electrical circuitry contacts for the electronics within housing 706. The connector can also serve as a moisture barrier for sensor 104 when assembled in a compressed state after transfer from a container to an applicator and after application to a user's skin. A plurality of seal surfaces 2304 can provide a watertight seal for electrical contacts and sensor contacts. One or more hinges 2308 can connect two distal and proximal portions of connector 2300.

FIG. 14A is a perspective view depicting an example embodiment of sensor 104. A neck 2406 can be a zone which allows folding of the sensor, for example ninety degrees. A membrane on tail 2408 can cover an active analyte sensing element of the sensor 104. Tail 2408 can be the portion of sensor 104 that resides under a user's skin after insertion. A flag 2404 can contain contacts and a sealing surface. A biasing tower 2412 can be a tab that biases the tail 2408 into sharp slot 2208. A bias fulcrum 2414 can be an offshoot of biasing tower 2412 that contacts an inner surface of a needle to bias a tail into a slot. A bias adjuster 2416 can reduce a localized bending of a tail connection and prevent sensor trace damage. Contacts 2418 can electrically couple the active portion of the sensor to connector 2300. A service loop 2420 can translate an electrical path from a vertical direction ninety degrees and engage with sensor ledge 2212 (FIG. 12B).

Figure 14B:
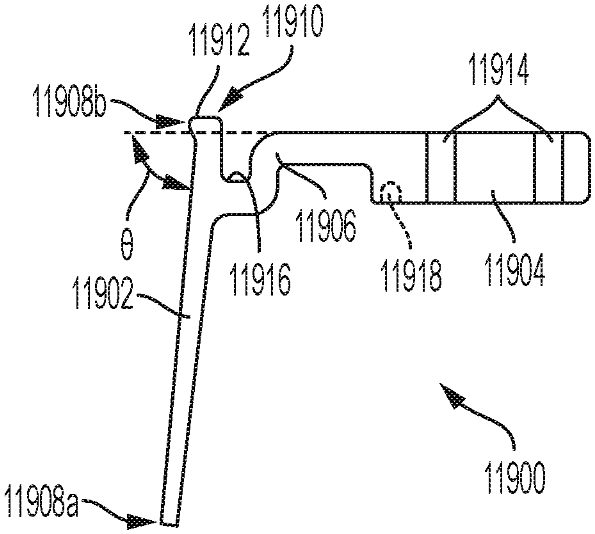
FIG. 14B is a side view of an exemplary sensor, in accordance with one embodiment of the disclosed subject matter.

FIG. 14B is a side view of an example sensor 11900, according to one or more embodiments of the disclosure.

The sensor 11900 may be similar in some respects to any of the sensors described herein and, therefore, may be used in an analyte monitoring system to detect specific analyte concentrations. As illustrated, the sensor 11900 includes a tail 11902, a flag 11904, and a neck 11906 that interconnects the tail 11902 and the flag 11904. The tail 11902 includes an enzyme or other chemistry or biologic and, in some embodiments, a membrane may cover the chemistry. In use, the tail 11902 is transcutaneously received beneath a user's skin, and the chemistry included thereon helps facilitate analyte monitoring in the presence of bodily fluids.

The tail 11902 may be received within a hollow or recessed portion of a sharp (not shown) to at least partially circumscribe the tail 11902 of the sensor 11900. As illustrated, the tail 11902 may extend at an angle Q offset from horizontal. In some embodiments, the angle Q may be about 85°. Accordingly, in contrast to other sensor tails, the tail 11902 may not extend perpendicularly from the flag 11904, but instead at an angle offset from perpendicular. This may prove advantageous in helping maintain the tail 11902 within the recessed portion of the sharp.

The tail 11902 includes a first or bottom end **11908*a* and a second or top end 11908*b* opposite the bottom end 11908*a*. A tower 11910 may be provided at or near the top end 11908*b* and may extend vertically upward from the location where the neck 11906 interconnects the tail 11902 to the flag 11904. During operation, if the sharp moves laterally, the tower 11910 will help pivot the tail 11902 toward the sharp and otherwise stay within the recessed portion of the sharp. Moreover, in some embodiments, the tower 11910 may provide or otherwise define a protrusion 11912 that extends laterally therefrom. When the sensor 11900 is mated with the sharp and the tail 11902 extends within the recessed portion of the sharp, the protrusion 11912 may engage the inner surface of the recessed portion. In operation, the protrusion 11912 may help keep the tail 11902** within the recessed portion.

The flag 11904 may comprise a generally planar surface having one or more sensor contacts 11914 arranged thereon. The sensor contact(s) 11914 may be configured to align with a corresponding number of compliant carbon impregnated polymer modules encapsulated within a connector.

In some embodiments, as illustrated, the neck 11906 may provide or otherwise define a dip or bend 11916 extending between the flag 11904 and the tail 11902. The bend 11916 may prove advantageous in adding flexibility to the sensor 11900 and helping prevent bending of the neck 11906.

In some embodiments, a notch 11918 (shown in dashed lines) may optionally be defined in the flag near the neck 11906. The notch 11918 may add flexibility and tolerance to the sensor 11900 as the sensor 11900 is mounted to the mount. More specifically, the notch 11918 may help take up interference forces that may occur as the sensor 11900 is mounted within the mount.

Figure 14C:
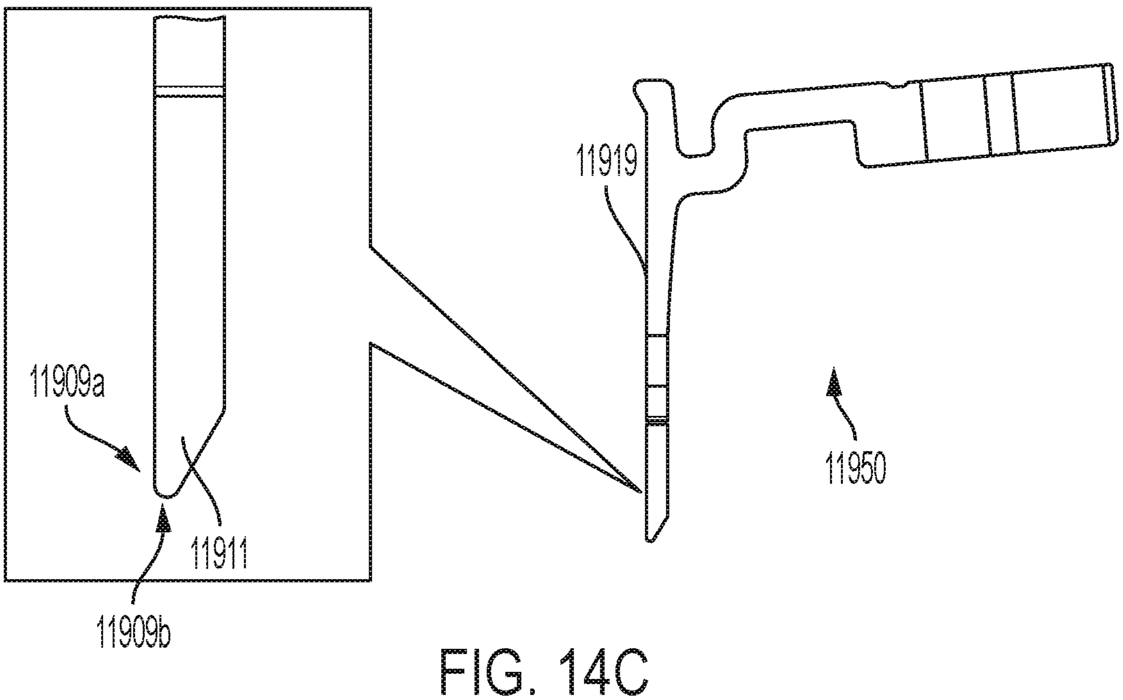
FIG. 14C is a side view of an exemplary sensor and a callout view of a tip portion of an exemplary sensor, in accordance with one embodiment of the disclosed subject matter.

FIG. 14C illustrates one embodiment of a sensor 11950 including a modified tail 11919. In some embodiments, the first or bottom end **11909*a* is chiseled or tapered so as to form a bottom end 11909*a* having one or more beveled edges. In some embodiments, the bottom end 11909*a* comprises a single beveled edge 11911. More specifically, the sensor tail 11919 comprises a bottom end 11909*a* which forms a tip portion 11909*b* having a sharpened, V-shaped vertex. This sensor design can be advantageous in that reduces the overall footprint of the sensor 11950, and minimizes the size of skin penetration and puncture wound as it dilates the tissue during sensor insertion. Consequently, the risk of ESA created by wound trauma can be mitigated by the sensor's 11950 bottom end 11909*a* having a V-shaped tip portion 11909*b*** with a sharpened vertex.

Generally, the sensor can be understood as including a tail, a flag, and a neck aligned along a planar surface having a vertical axis and a horizontal axis. The spring-like structure can be created by various orientations of turns in the bend of the neck of a sensor. Between the tail and the flag, the neck can include at least two turns in relation to the vertical axis providing a spring-like structure. The at least two turns can provide, in relation to an axis of the planar surface shared by the tail, the flag, and the neck, overlapping layers of the structure of the neck, where the neck itself remains unbroken. These overlapping turns make up the spring-like structure. In some embodiments, the overlapping layers of the neck are vertically-oriented. In some embodiments, the overlapping layers of the neck are horizontally-oriented.

The turns of the neck can be created by folding the neck of the sensor from a larger neck structure, laser cutting the sensor from a sheet of the material comprising the sensor, printing the sensor having the configuration with turns, stamping the sensor from a sheet of material of which the sensor is composed, or other suitable manufacturing processes for providing precision bends in the neck.

Example Embodiments of Sharp Modules

FIG. 15A is a perspective view depicting an example embodiment of sharp module 2500 prior to assembly within sensor module 504 (FIGS. 12A and 12B). Sharp 2502 can include a distal tip 2506 which can penetrate the skin while carrying sensor tail in a hollow or recess of sharp shaft 2504 to put the active surface of the sensor tail into contact with bodily fluid. A hub push cylinder 2508 can provide a surface for a sharp carrier to push during insertion. A hub small cylinder 2512 can provide a space for the extension of sharp hub contact faces 1622 (FIG. 11). A hub snap pawl locating cylinder 2514 can provide a distal-facing surface of hub snap pawl 2516 for sharp hub contact faces 1622 to abut. A hub snap pawl 2516 can include a conical surface that opens clip 1620 during installation of sharp module 2500. Further details regarding embodiments of sharp modules, sharps, their components, and variants thereof, are described in U.S. Patent Publication No. 2014/0171771, which is incorporated by reference herein in its entirety and for all purposes.

Figure 15B:
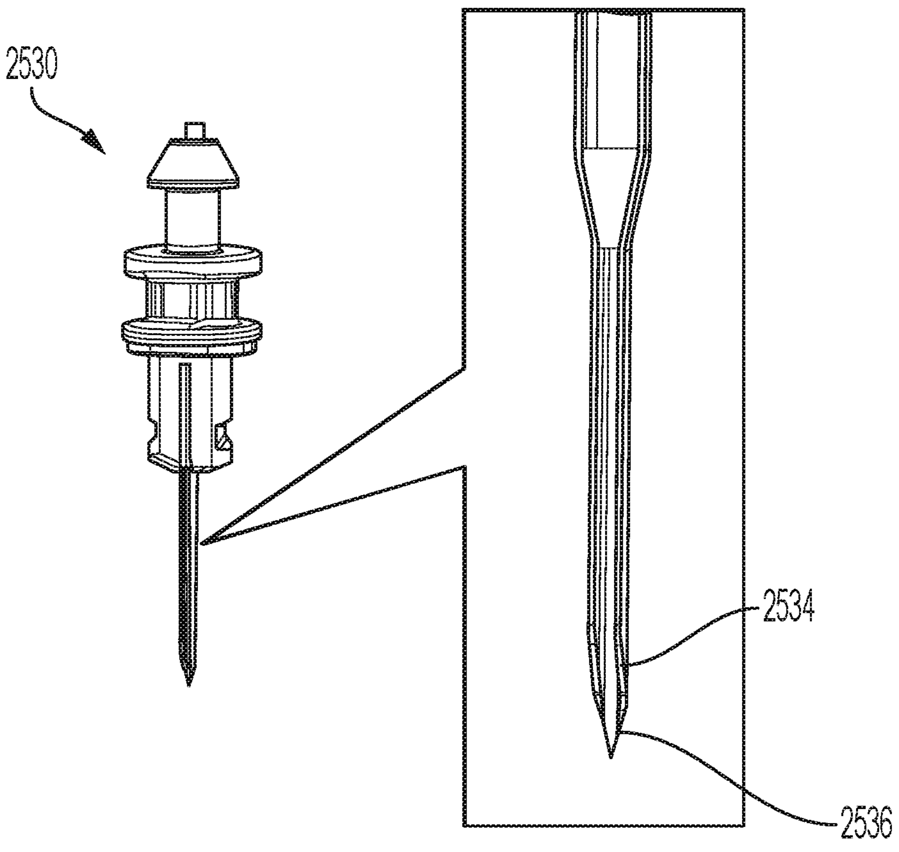
FIG. 15B is a perspective view depicting an example embodiment of a sharp module, and a callout view of the distal tip thereof.
Figure 15C:
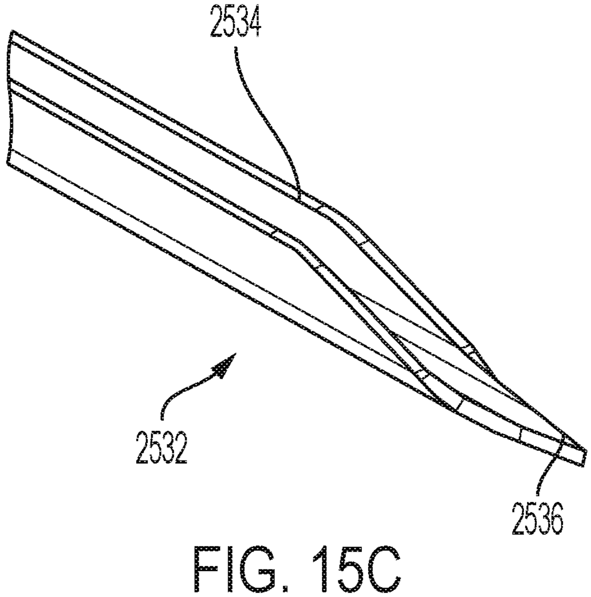
FIG. 15C is a close-up side perspective view depicting the distal tip of the sharp module illustrated in FIG. 15B.
Figure 15D:
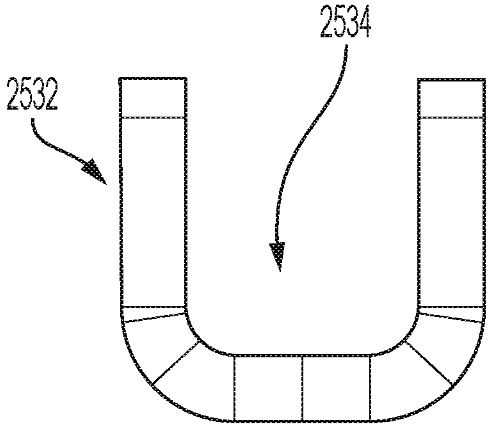
FIG. 15D is a cross-sectional view of a sharp embodiment for the sharp module illustrated in FIG. 15B.

FIG. 15B depicts another example embodiment of a sharp module 2530, and a callout view of the distal portion thereof, depicting the hollow or recess of sharp shaft 2534 and its distal tip 2536. FIG. 15C further illustrates a close-up side perspective view of distal tip 2536 which can penetrate the skin while carrying sensor tail (not shown) in a hollow or recess of sharp shaft 2534 to put the active surface of the sensor tail into contact with bodily fluid. The U-shaped implement of sharp 2532 is further illustrated in the cross-sectional view shown in FIG. 15D.

Figure 15F:
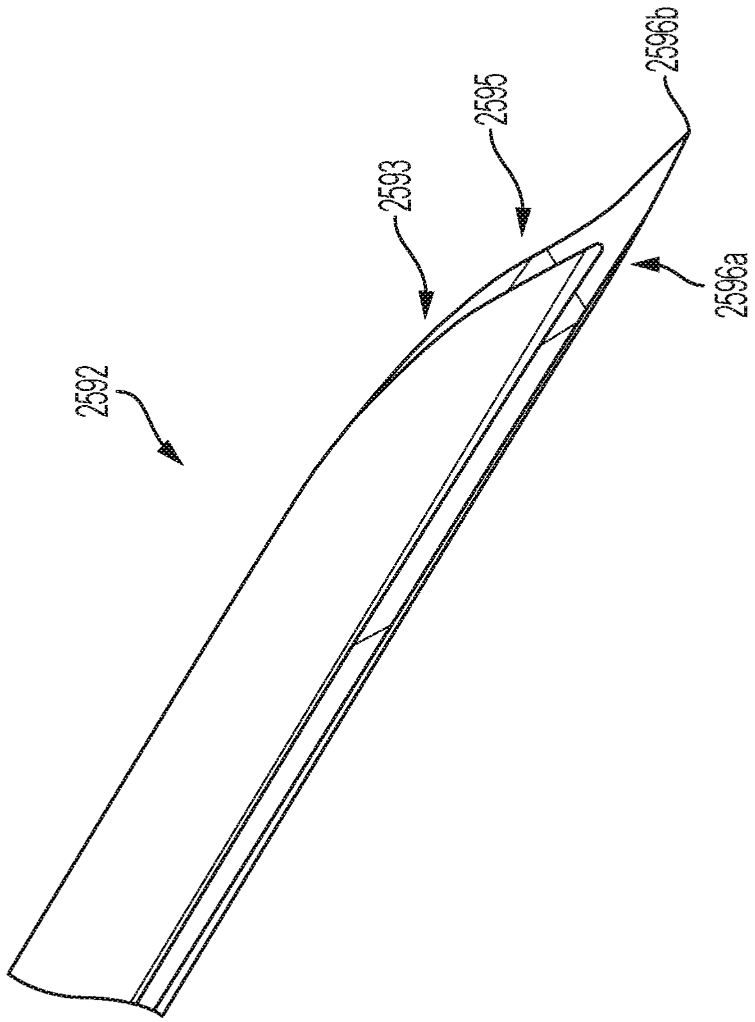
FIG. 15F is a close-up side view of a sharp in accordance with one embodiment of the disclosed subject matter.
Figure 15E:
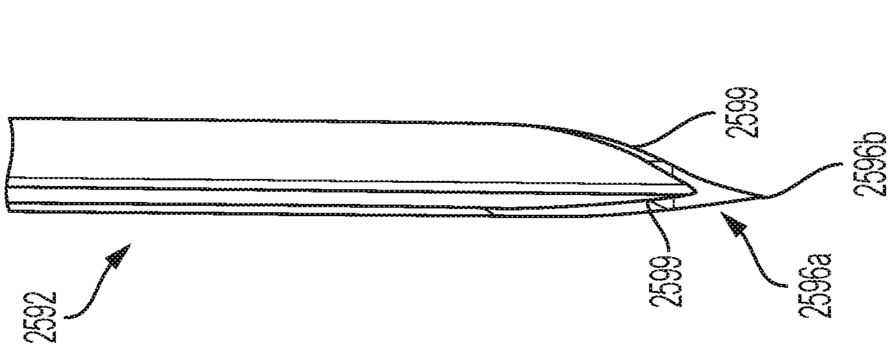
FIG. 15E is a close-up perspective view of a sharp in accordance with one embodiment of the disclosed subject matter.

Example embodiments of a sharp designed to reduce trauma during a sensor insertion and retraction process will now be described. FIG. 15E is a close-up perspective view of a sharp 2592. In FIG. 15E, the sharp distal tip **2596*a* includes double beveled edges or transitions 2599 that adjoin at a proximal portion of the distal tip 2596*a* to form a distal tip 2596*a* having a vertex 2596*b*. Specifically, the double beveled edges 2599 are concavely sloped so as to form the sharp distal tip 2596*a*. Referring to FIG. 15E once more, the distal portion is provided with a concavely angled distal tip 2596*a*. As shown in FIG. 15F, the angled distal tip 2596*a* may be provided with a first concavely angled tip portion 2593 and a second steep-angled tip portion 2595. More specifically, the first concavely angled tip portion 2593** slopes into the second steep-angled tip portion 2595. The exemplary configuration, which includes multiple edges and faces, provides a sharp point to reduce penetration force, trauma, and bleeding for the subject. The sharp 2592 has a substantially V-shaped profile in this embodiment.

Figure 15G:
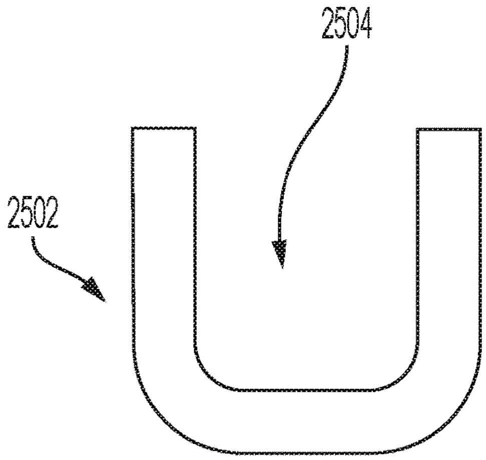
FIG. 15G is a cross-sectional view of a sharp in accordance with one embodiment of the disclosed subject matter.
Figure 15H:
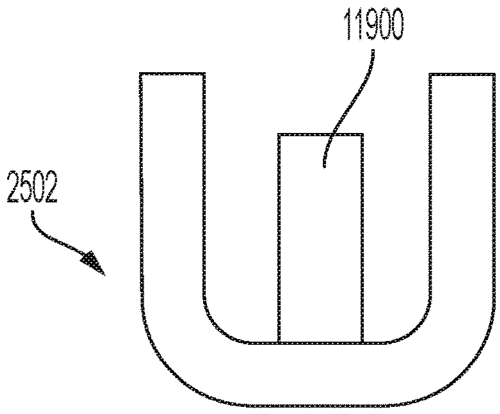
FIG. 15H is a cross-sectional view of the sharp depicted in FIG. 15G, further comprising a sensor in accordance with one embodiment of the disclosed subject matter.
Figure 15I:
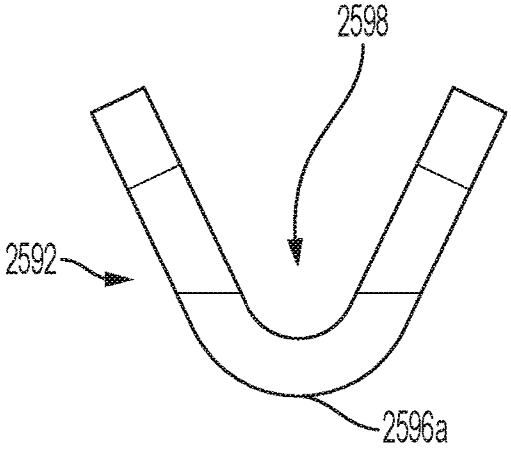
FIG. 15I is a cross-sectional view of a sharp in accordance with one embodiment of the disclosed subject matter.
Figure 15J:
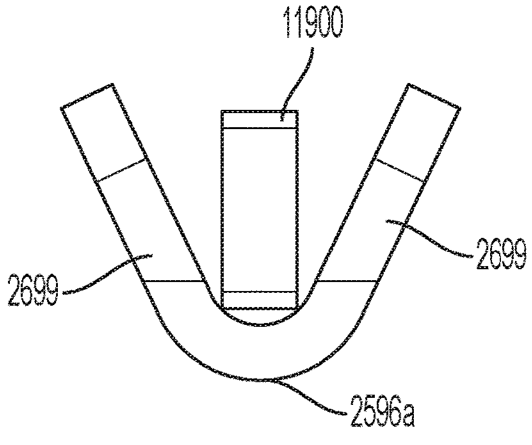
FIG. 15J is a cross-sectional view of the sharp depicted in FIG. 15I, further comprising a sensor in accordance with one embodiment of the disclosed subject matter.

FIGS. 15G and 15I are cross-sectional view of two embodiments of the sharps described herein. FIG. 15G is a cross-sectional view of a previous embodiment, illustrating a substantially U-shaped cross-sectional area of sharp 2502. FIG. 15I is a cross-sectional view of an embodiment depicting a V-shaped cross-sectional area of sharp 2592, having a vertex 2596*a*. In some embodiments, the vertex 2596*a* includes a bottom portion of the cross-sectional area with no sharp edges. Additionally, the bottom portion of the cross-sectional area, unlike some U-shaped embodiments, such as the sharp embodiment illustrated in FIG. 15G, is not flattened. FIGS. 15H and 15J are cross-sectional views of the embodiments depicted in FIGS. 15G and 15I, respectively, illustrating the sharp embodiments supporting a sensor, for example, sensor 11900 or sensor 11950, respectively.

15K is a perspective view depicting an example embodiment of a sharp module 2590 having one or more beveled edges and V-shaped geometry configured to create a smaller opening in the skin relative to other sharps (e.g., sharp 2502 depicted in FIG. 15A). Sharp module 2590 is shown here prior to assembly with sensor module 504 (FIGS. 12A and 12B), and can include components similar to those of the embodiment described with respect to FIG. 15A, including sharp 2592, sharp shaft 2594, sharp distal tip 2596*a*, hub push cylinder (not shown), hub small cylinder 2652, hub snap pawl 2656 and hub snap pawl locating cylinder (not shown). Similar to the previously described sharp module 2500, and as shown in the callout view also depicted in FIG. 15K, sharp module 2590 can include a sharp shaft 2594 coupled to a distal end of the hub portion 2692 at a proximal end, sensor channel 2598 configured to receive at least a portion of an analyte sensor, such as analyte sensor 11950, for example, and a distal tip 2596*a* configured to penetrate a skin surface during the sensor insertion process.

Figure 15K:
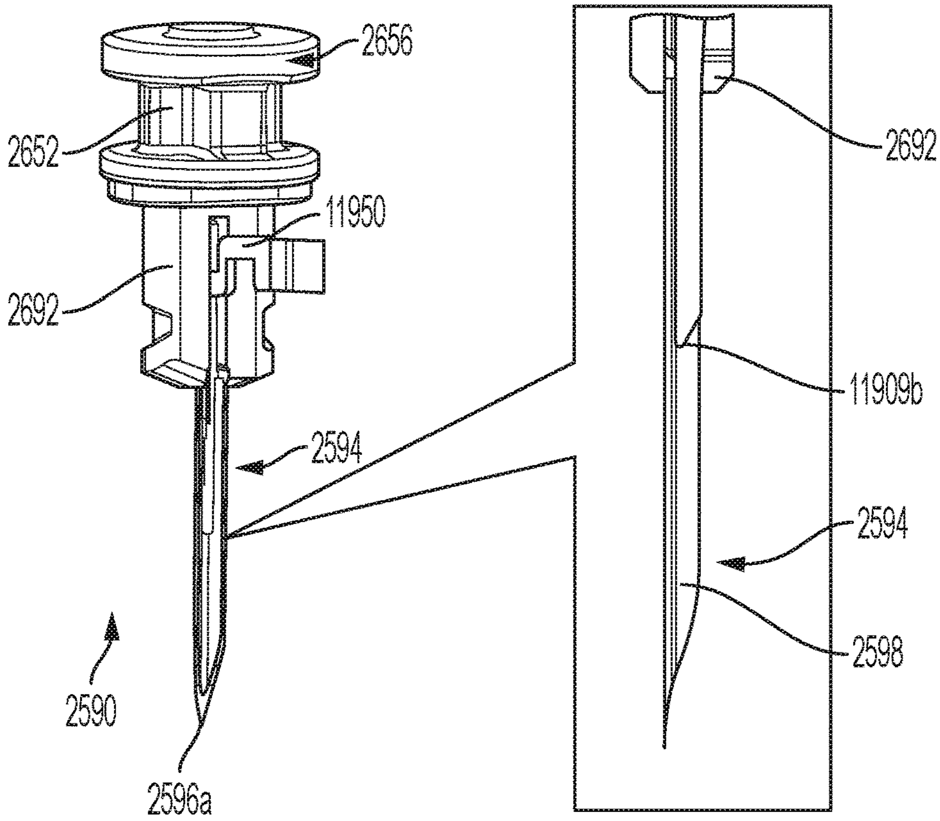
FIG. 15K is a partial perspective view of a sharp module in accordance with one embodiment of the disclosed subject matter, and a callout view of the distal tip thereof.
Figure 15L:
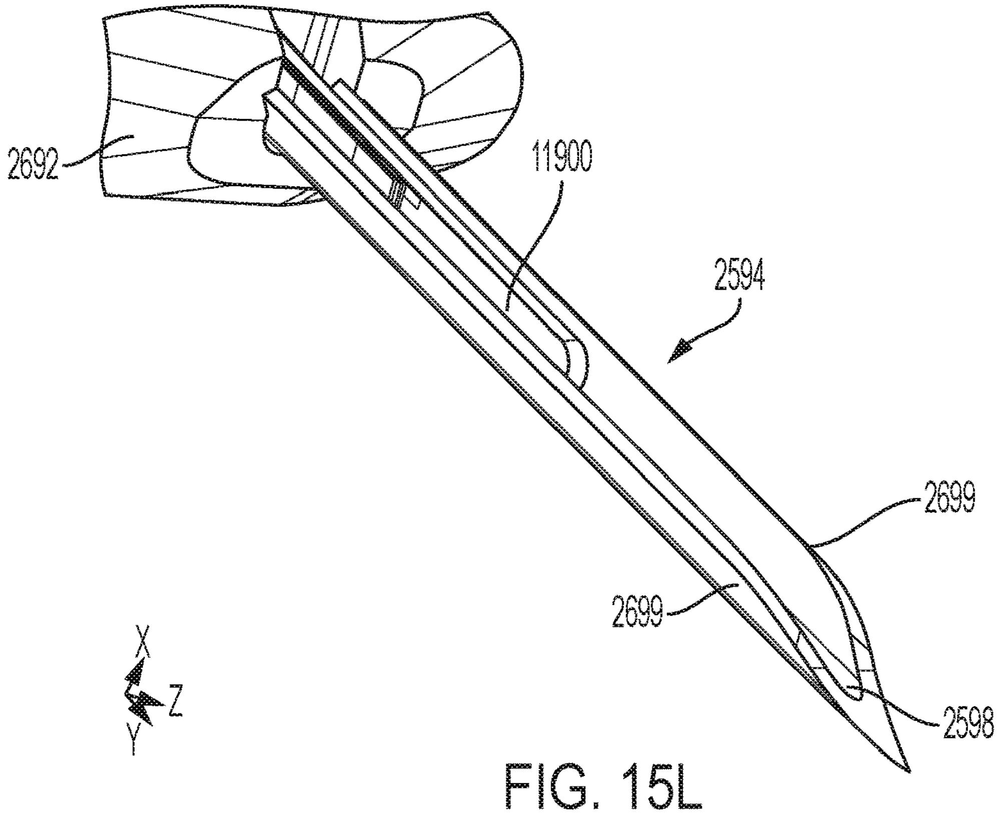
FIG. 15L is a close-up perspective view of the distal tip of a sharp module comprising a sensor, in accordance with one embodiment of the disclosed subject matter.

In FIG. 15L, a front perspective view of sharp shaft 2594 is depicted, and includes a sharp module 2590 comprising one or more sidewalls 2699 and a longitudinally-extending sensor channel 2598 that together form the sharp's V-shaped cross-sectional area comprising a vertex 2596*b*. Further, the sensor channel 2598 is configured to receive at least a portion of any analyte sensor which has been described herein, such as analyte sensor 1900 or 11950, for example. In some embodiments, such as the embodiment which is illustrated in FIG. 15L, sensor channel 2598 is configured to receive at least a portion of analyte sensor 11900. According to one aspect of the embodiments, one or all of the sharp portion 2592, the sharp shaft 2594, and/or the sharp distal tip 2596*a* of a sharp 2592 can comprise one or more concave beveled edges.

Referring to FIGS. 15K and 15L, according to one aspect of the embodiment, one or more sidewalls 2699 that form sensor channel 2598 are disposed along sharp shaft 2594 and are adjacent to the distal tip 2596*a*. Specifically, the one or more sidewalls 2699 are disposed along the sharp shaft 2594 such that the terminus of the one or more sidewalls 2699 is distal to the terminus of the sensor channel 2598. In some embodiments, for example, the terminus of the one or more sidewalls 2699 extend from the vertex 2596*b* (as depicted in FIG. 15E) of the sharp distal tip 2596*a*. The terminus of the one or more sidewalls 2699 adjoin at the proximal end of the distal tip 2596*a* so as to form the one or more beveled edges thereof. The one or more beveled edges are configured such that they concavely slope and define the vertex 2596*b* of the distal tip 2596*a*. In some embodiments, the vertex 2596*b* is centrally located at the sharp distal tip 2596*a*. According to one aspect of the embodiment, a sharp 2592 can be characterized as having a sharpened V-shaped distal tip 2596*a* with all other edges comprising double beveled edges.

The V-shaped tip portion 2596*a* of the sharp 2592 is designed such that it provides less surface area and includes a reduced cross-sectional footprint relative to, for example, distal tip 2506 of sharp module 2500. The cross-sectional area of the distal tip 2596*a* is the smallest cross-sectional area of the sharp module 2590. During insertion, as the sharp 2592 moves into the skin surface, the sharp point geometry and V-shaped cross-sectional area of the sharp 2592, as illustrated in FIGS. 15E-15L, penetrate the skin by making a smaller wound due to the smaller size of the tip portion. With respect to sensor insertion, puncture wounds can contribute to ESA in sensors. In this regard, the embodiments described herein provide for less trauma and, consequently, a reduced risk of ESA result during the sensor insertion process.

Furthermore, it will be understood by those of skill in the art that the sharp 2592 embodiment described herein can similarly be used with any of the sensors described herein, including in vivo analyte sensors that are configured to measure an analyte level in a bodily fluid of a subject. Moreover, the sharp embodiments described herein can similarly be used with in vivo analyte sensors comprising a V-shaped tip. For example, in some embodiments, as shown in FIG. 15K, sharp 2592 can include a sensor channel 2598 configured to receive at least a portion of an analyte sensor 11950 with a V-shaped tip 11909*b*. Further, the V-shaped tip portion 11909*b* of the sensor 11950 is adjacent to the sharp 2592 and permits the sharp 2592 to create an insertion path for the sensor 11950. In this embodiment, the sharp design itself, and the positioning of the needle with respect to the sensor can be implemented such that the assembly causes less trauma during the insertion process. The distal section of the sensor body has a width sized to fit within the sensor channel 2598. For example, the V-shaped tip portion 11909*b* of the sensor 11950 is designed to have a complementary shape to the V-shaped cross-sectional area of the sharp 2592. In this embodiment, the V-shaped tip portion 11909*b* of the sensor 11950 is configured such that its tip portion 11909*b* is co-axial to the vertex 2596*b* of the sharp 2592 so as to better follow the distal tip 2596*a* as it penetrates the subject's skin.

Example Embodiments of Sharpless Applicators

Figure 16A:
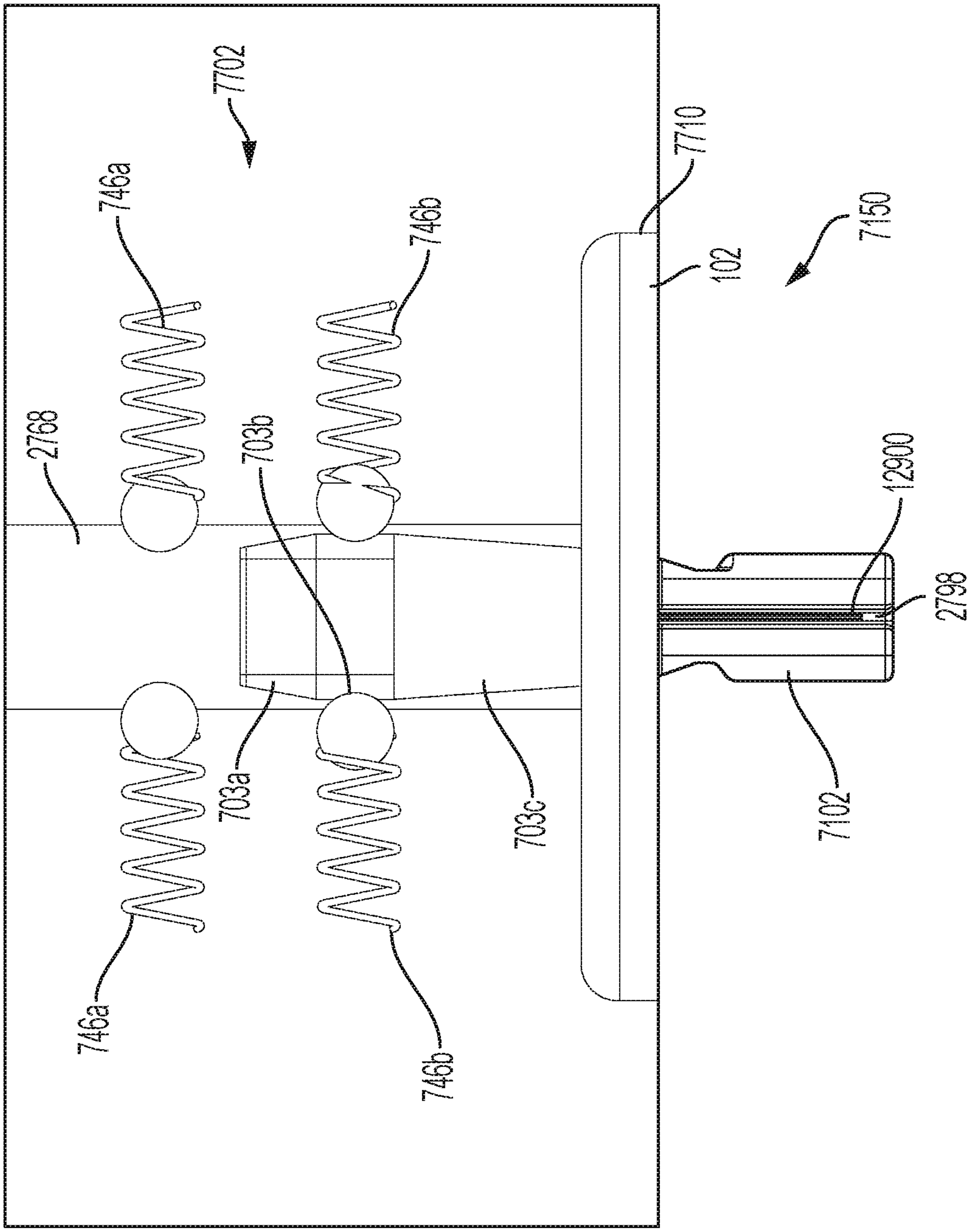
FIG. 16A is a cross-sectional view of a sharpless applicator, in accordance with one embodiment of the disclosed subject matter.

Example embodiments of various sharpless applicators will now be described. Referring first to FIG. 16A, a cross-sectional view of an example embodiment of a sharpless applicator 7150 (in an initial state) is depicted. According to one aspect of some embodiments, sharpless applicator assembly 7150 can include one or more of the following components: housing 7702, which can be movable between a proximal position and a distal position relative to a subject's skin; guide 7102; analyte sensor 12900; device carrier feature 7710 configured to releasably retain sensor control device 102; and a spring loaded system comprising a plurality of spring elements (e.g., spring elements 746*a*, 746*b*) which can be configured to engage with a proximal portion of guide 7102. Furthermore, in many embodiments, guide 7102 can be hollow and have a substantially cylindrical shape. In many embodiments, guide 7102 can also include a plurality of ramp surfaces 703*a*, 703*c* (e.g., two) with a groove or detent section 703*b* disposed in between the ramp surfaces.

According to another aspect of some embodiments, device carrier feature 7710 can have a concave or partially concave geometry that is complementary to the shape of sensor control device 102. For example, in some embodiments, device carrier feature 7710 can comprise a hollow round flat cylindrical shape configured to releasably contain sensor control device 102.

Referring still to FIG. 16A, in some embodiments, guide 7102 can comprise a sensor support channel 2798, wherein at least a portion of the sensor support channel 2798 can be disposed in a distal end of guide 7102. In some embodiments, the distal end of guide 7102 can be configured for placement on the skin of the subject. According to some embodiments, a first end of sensor support channel 2798 can terminate at the distal end of guide 7102. In some embodiments, the proximal end of guide 7102 can be hollow. In other embodiments, the proximal end of the guide 7102 can be solid.

According to another aspect of some embodiments, a width of at least a portion of the proximal end of the guide 7102 can be greater than a width of the distal end of guide 7102. Further, in some embodiments, a first ramp 703*a* can be located at the proximal end of guide 7102, whereas the second ramp 703*c* can be located distally relative to the first ramp 703*a* and groove section 703*b*. According to some embodiments, a width of the groove or detent section 703*b* of the guide 7102 can be less than the width of the first ramp 703*a* and the second ramp 703*c* (at least at the portion which connects the sections).

Referring still to FIG. 16A, according to another aspect of some embodiments, an analyte sensor 12900 can be at least partially disposed within sensor support channel 2798, and supported by guide 7102. Analyte sensor 12900 can include components similar to those of the embodiment described with respect to FIG. 14C. In many embodiments, analyte sensor 12900 comprises a tip portion 12909*b* (as depicted in FIG. 16D) with sufficient sharpness to initiate and complete insertion without the need for a separate sharp. Accordingly, analyte sensor 12900 can include a predetermined free length so as to provide the necessary sensor stiffness to facilitate effective insertion into the subject's skin. According to one aspect of the embodiments, stiffness of the sensor can be determined by free length of the sensor (e.g., an analyte sensor with a shorter free length will be stiffer). This can mitigate certain effects from "skin tenting," a phenomenon that occurs when a sharp tip contacts skin and, prior to penetration, the skin deforms inwardly into the body. As a result of "skin tenting," if the sharp or sensor is not sufficiently stiff, the sharp or sharpened sensor may fail to create a sufficiently large insertion point or misposition the sensor due to deflection.

Referring back to FIG. 16A, according to some embodiments, sharpless applicator 7150 can include an alignment shaft 2768 for maintaining the longitudinal alignment of the guide 7102 such that guide 7102 moves axially within the alignment shaft 2768 while it interfaces with a spring loaded system. In some embodiments, alignment shaft 2768 has a cylindrical geometry. According to one aspect of some embodiments, guide 7102 can be partially disposed within alignment shaft 2768 of the device support 7710 when the sharpless applicator 7150 is in the initial stage. According to another aspect of some embodiments, guide 7102 can be entirely disposed within alignment shaft 2768 after the sharpless applicator 7150 has completed the insertion and retraction steps.

According to another aspect of some embodiments, a plurality of spring elements can be disposed in or along an interior portion of alignment shaft 2768 to facilitate movement or positioning of guide 7102. In particular, the plurality of spring elements can be configured to control a position of guide 7102, increase or decrease the speed of guide 7102 during insertion and/or retraction, and also limit the free length of the sensor during various stages of operation. In this regard, the sensor stiffness can be maintained to aid in effective insertion. In some embodiments, a plurality of low friction rollers, ball-and-plunger sets, or an equivalent thereof, can be utilized to provide spring elements for the spring-loaded system. As shown in FIG. 16A, two pairs of ball-plunger sets 746*a*, 746*b* are utilized, an upper ball-plunger set 746*a* and a bottom ball-plunger set 746*b*, wherein each set can comprise a first ball-plunger that interacts with a left side of guide 7102, and a second ball-plunger that interacts a right side of guide 7102. Specifically, each ball-plunger set 746*a*, 746*b* can comprise a spring with one end anchored along the alignment shaft 2768 (or, alternatively, another stationary structure of sharpless applicator 7150, such as housing 7702), wherein a second end of the spring includes a ball structure configured to engage with a portion or side of guide 7102 as it travels along alignment shaft 2768. According to another aspect of the embodiments, each spring can be in a partially or fully compressed and/or expanded state during various stages of operation of the sharpless applicator 7150. According to yet another aspect of the embodiments, each of the spring elements can be configured to compress and/or expand at different times. For example, in some embodiments, at a certain stage of retraction, upper ball-plunger set 746*a* can be positioned further inward toward the center of alignment shaft 2768 relative to the bottom ball-plunger set 746*b*. In this regard, the sharpless applicator assembly retraction mechanism relies at least in part on an upward force of the subject's skin during insertion, combined with the ball-plunger interaction with the ramped surfaces 703*a*, 703*c* of the guides 7102 to allow for retraction of the guide 7102 into a container 711 within the housing 7702. Those of skill in the art will also appreciate that the embodiments of the present disclosure can allow for re-usability of sharpless applicator 7150.

FIGS. 16B-16H are various cross-sectional views depicting an example embodiment of a sharpless applicator assembly 7150 during various stages of operation.

Figure 16B:
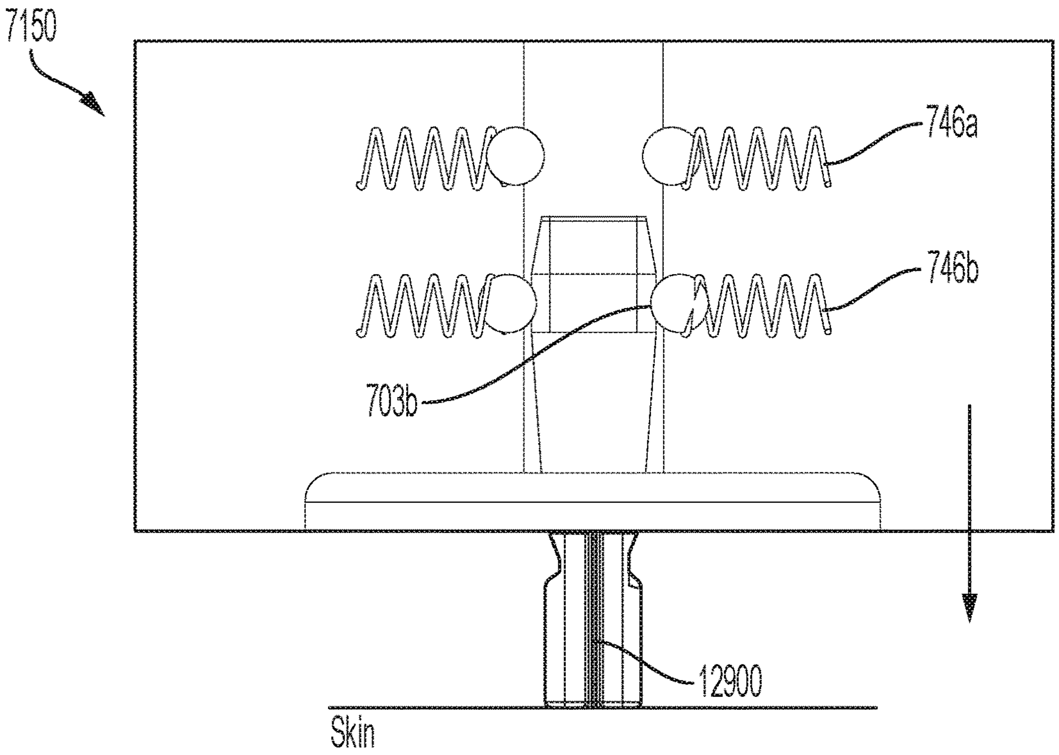
FIGS. 16B to 16H are cross-sectional views of the sharpless applicator depicted in FIG. 16A during various stages of operation.

FIG. 16B is a cross-sectional view of an example embodiment of a sharpless applicator assembly 7150 for insertion of an analyte sensor 12900 in a subject. In the initial state, the distal end of the guide 7102 is in contact with the subject's skin surface. In this initial state, as shown in FIG. 16B, the bottom ball-plunger set 746*b* is engaged with the groove or detent section 703*b* of guide 7102. According to one aspect of the embodiments, the ball portion of each ball-plunger set of the bottom spring elements 746*b* is in contact with the detent section 703*b*, and the corresponding spring of each ball-plunger set is in a partially compressed state. As shown in FIG. 16B, a force is applied to sharpless applicator 7150 causing it to move in a distal direction towards the subject's skin.

Figure 16C:
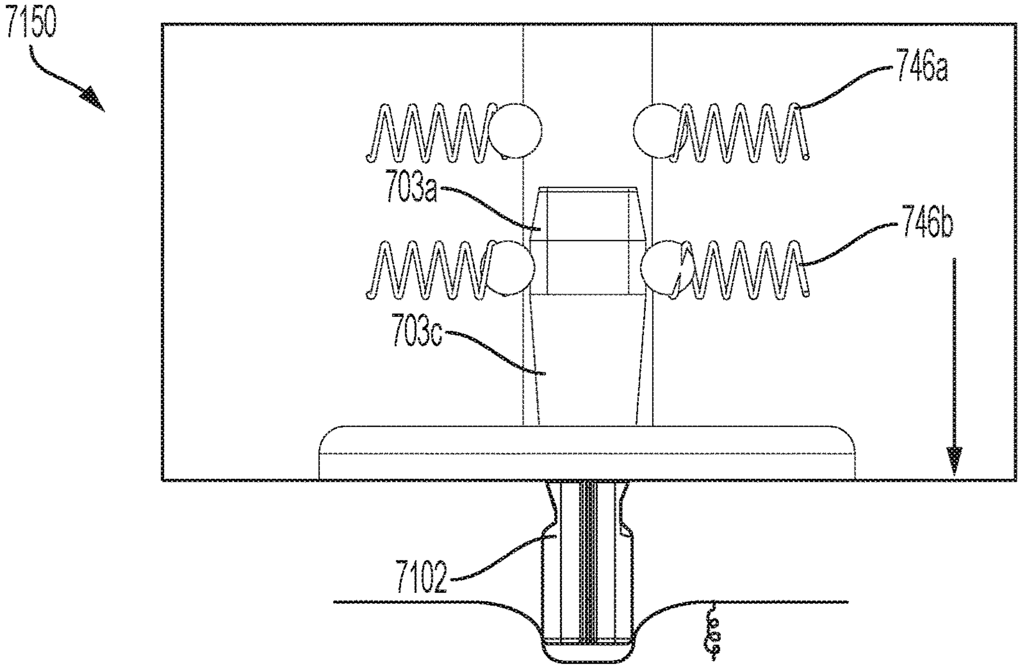
Figure 16D:
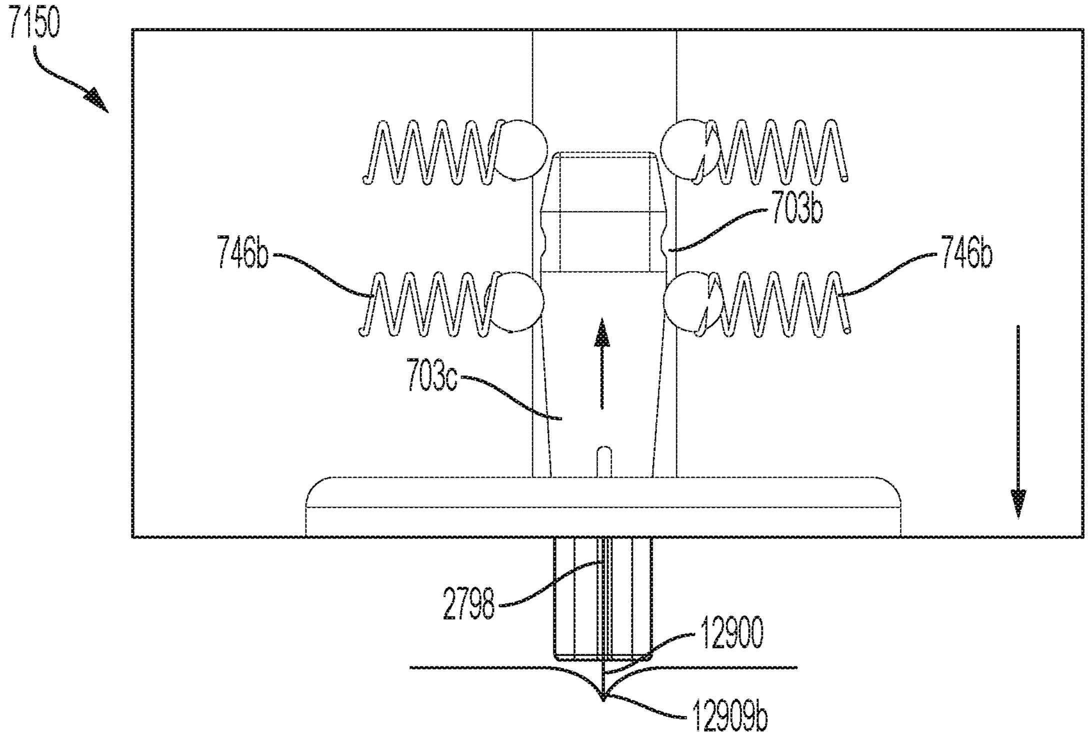

FIG. 16C is a cross-sectional view showing sharpless applicator assembly 7150 as applicator 7150 continues moving distally (e.g., in a downward direction) and creates a force in the distal direction against the skin. Meanwhile, according to one aspect of the embodiments, the bottom ball-plunger set 746*b* exerts a force on groove section 703*b* of guide 7102, and prevents guide 7102 from moving until a sufficient force in the proximal direction is received. As applicator 7150 continues to move distally, distal end of guide 7102 continues to push down on the subject's skin. As a result, as can be seen in FIG. 16C, the skin surface deforms from the force of guide 7102, and subsequently exerts a counterforce in the proximal direction against guide 7102. Consequently, the bottom ball-plunger set 746*b* begins to disengage from the groove section 703*b*.

Turning to FIG. 16D, as applicator assembly 7150 continues to move in a distal direction, the downward force from applicator 7150 further deforms the skin, which in turn increases the skin's counterforce exerted in the proximal direction against guide 7102. The upward force exerted by the skin exceeds the force imparted from the spring loaded system to hold guide 7102 in place. Consequently, bottom ball-plunger set 746*b* disengages from groove section 703*b* of guide 7102, as guide 7102 begins to travel in a proximal direction inside alignment shaft. According to another aspect of some embodiments, ramped surface of guide 7102 and the counterforce exerted by the deformed or stretched skin result in acceleration of guide 7102 in the proximal (e.g., upward) direction, and subsequently expose the sharp tip portion 12909*b* of analyte sensor 12900 disposed within the sensor support channel 2798. The acceleration of the guide 7102 increases the velocity of the skin relative to the sensor 12900, as the skin follows guide 7102. In this regard, the sharpless applicator assembly 7150 utilizes the skin deformation, or skin tenting, during insertion as a source of potential energy to further load the guide 7102 and increase relative velocity between skin and sensor. This increase in velocity can aid in insertion effectiveness. As the sharp sensor 12900 protrudes from the sensor support channel 2798, it begins to insert itself into the skin.

Figure 16E:
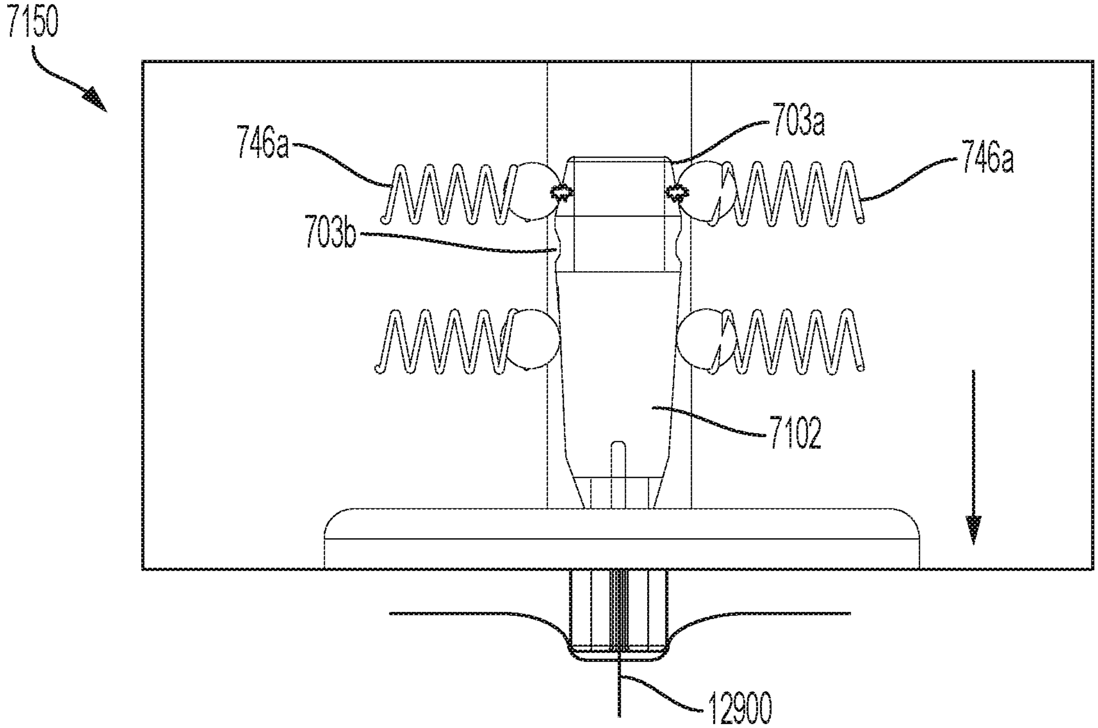

FIG. 16E shows the applicator assembly 7150 as it continues moving in a distal direction towards the skin. At the stage illustrated in FIG. 16E, guide 7102 continues to accelerate in the proximal direction until the first ramp 703*a* engages the upper ball-plunger set 746*a*, which impedes the motion of guide 7102. This ensures that sensor length during insertion is small enough to maintain the desired stiffness for effective insertion and avoid sensor bending. At this stage, the contact between the guide 7102 and the upper ball-plunger set 746*a* increases the force applied to skin, thereby causing further skin deformation. As this occurs, the counterforce created by the skin overcomes the force from the ball-plunger sets 746*a*, 746*b*, causing guide 7102 to accelerate in the proximal direction (e.g., away from the skin).

Figure 16F:
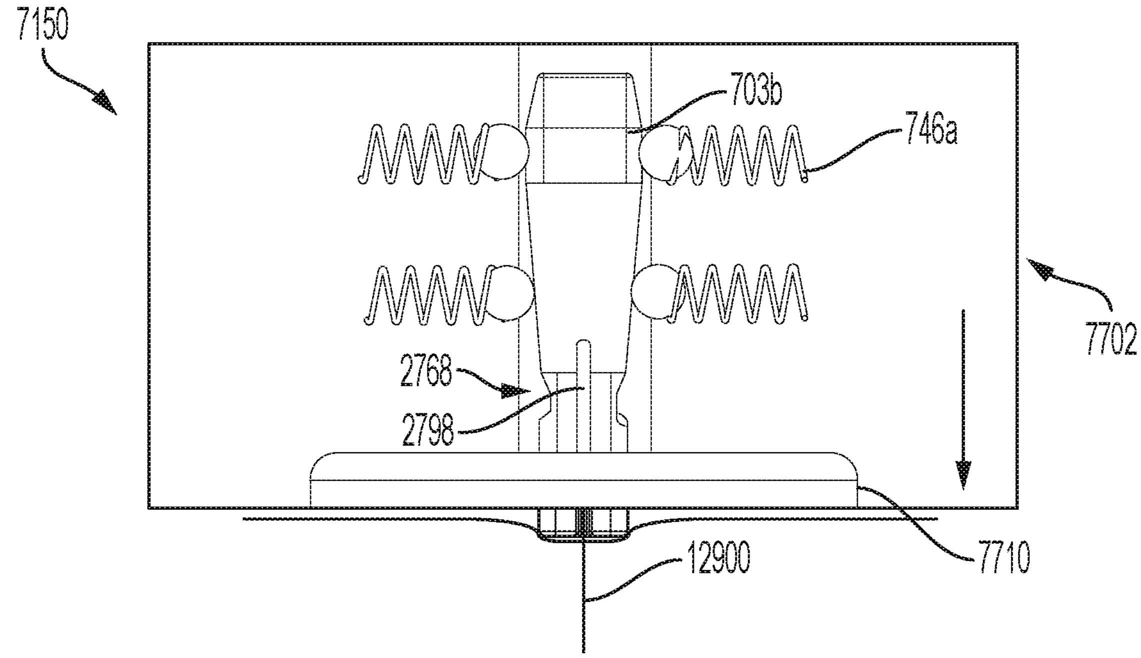

FIG. 16F shows the applicator assembly 7150 as it continues moving downward after sensor insertion. Guide 7102 continues to travel in a proximal direction into housing 7702 due to the counterforce generated by the skin. According to some embodiments, at this stage, sensor insertion can continue with more of the sensor length entering the skin of the subject. Further, at this stage, the upper ball-plunger set 746*a* sits in the guide grooves 703*b*. In this stage, the guide 7102 is still partially protruding from its distal end and is not fully retracted into the applicator 7150.

Figure 16G:
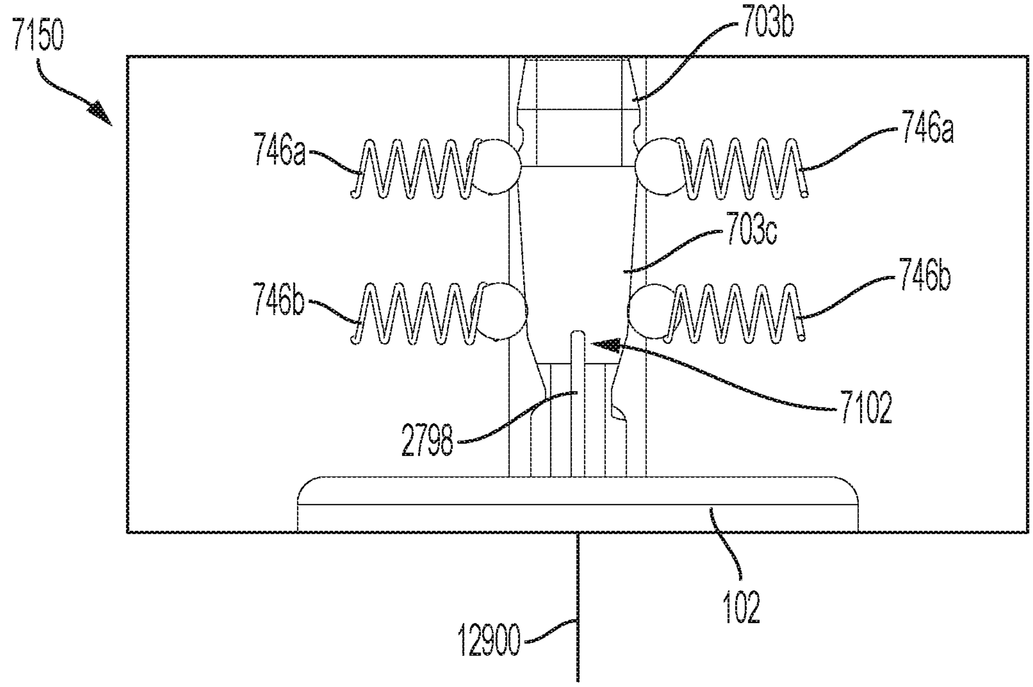

FIG. 16G illustrates sharpless applicator assembly 7150 in a sensor fully-inserted stage. In some embodiments, the motion of housing is slowed or stopped by sensor control device 102 contacting the skin. According to one aspect of the embodiments, at the stage depicted in FIG. 16G, analyte sensor 12900 has reached the desired insertion depth in the subject's skin. In some embodiments, distal end of guide 7102 can be flush with bottom surface of sensor control device 102. As shown in FIG. 16G, guide groove section 703*b* has now been advanced to a position proximal to the upper ball-plunger set 746*a*. As such, both ball-plunger sets 746*a*, 746*b* are in contact with the second ramp 703*c* of guide 7102. This can impart a force on guide 7102 in a proximal direction, thereby pushing guide 7102 further into the housing 7702 and away from device carrier 7710. With respect to the guide ramp shapes and ball-plunger forces, those of skill in the art will appreciate that certain embodiments of the guide ramps and ball-plungers can be dimensioned and configured to provide optimization for increased axial force in either a distal or proximal direction to ensure insertion and/or retraction. For example, if certain guide ramp surfaces are more sloped, this can cause an increase in insertion and/or retraction speed. Alternatively, certain guide ramp shapes may increase the initial acceleration.

Figure 16H:
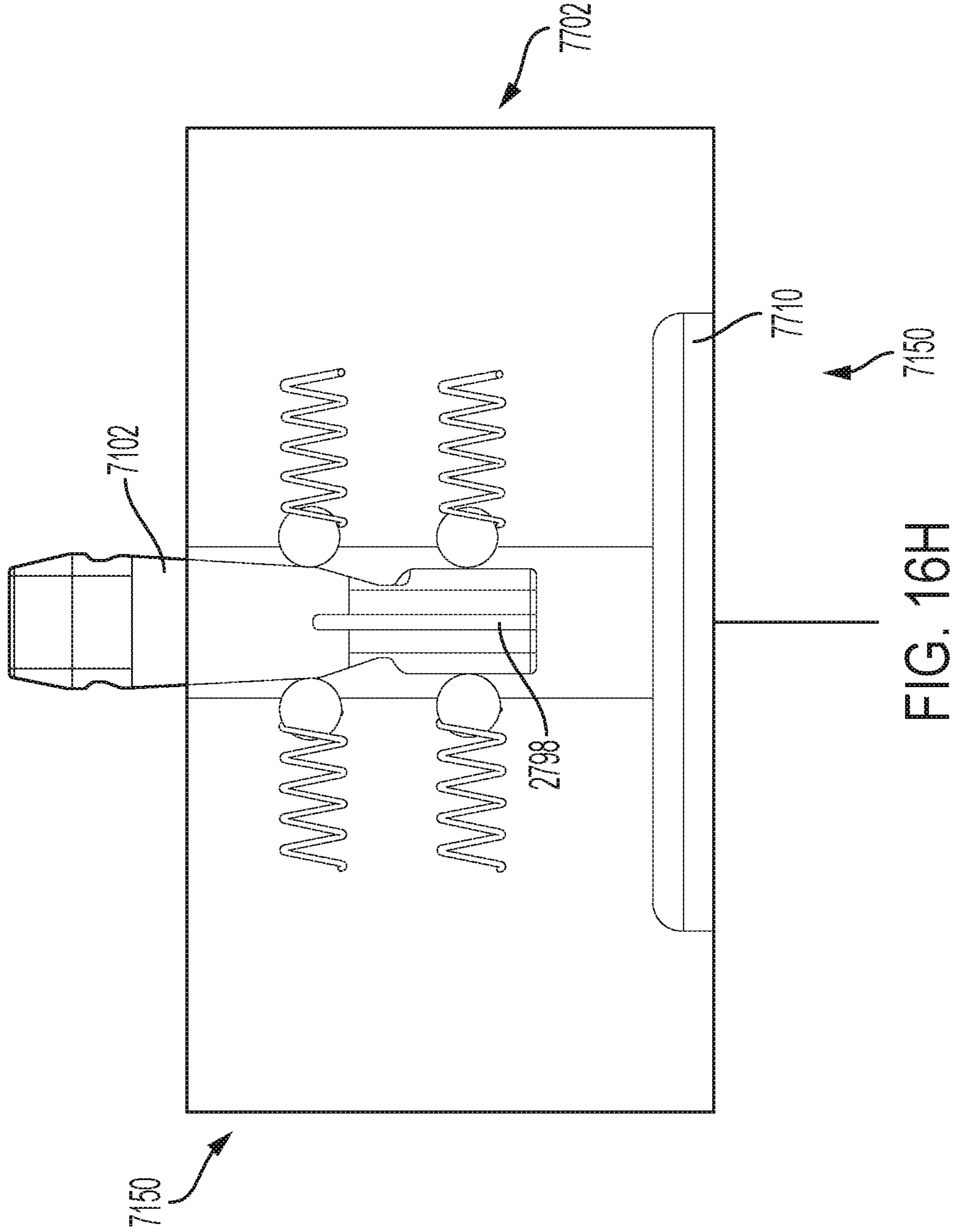

FIG. 16H is a cross-sectional view showing the sharpless applicator assembly 7150 in a retraction state. As depicted in FIG. 16H, sensor 12900 has been inserted into the subject's skin to the desired insertion depth, and guide 7102 has been retracted fully into the applicator 7150 and away from user access. The sharpless applicator assembly 7150 is further advantageous because it does not contain a sharp and is therefore not considered a biohazard.

Figure 16I:
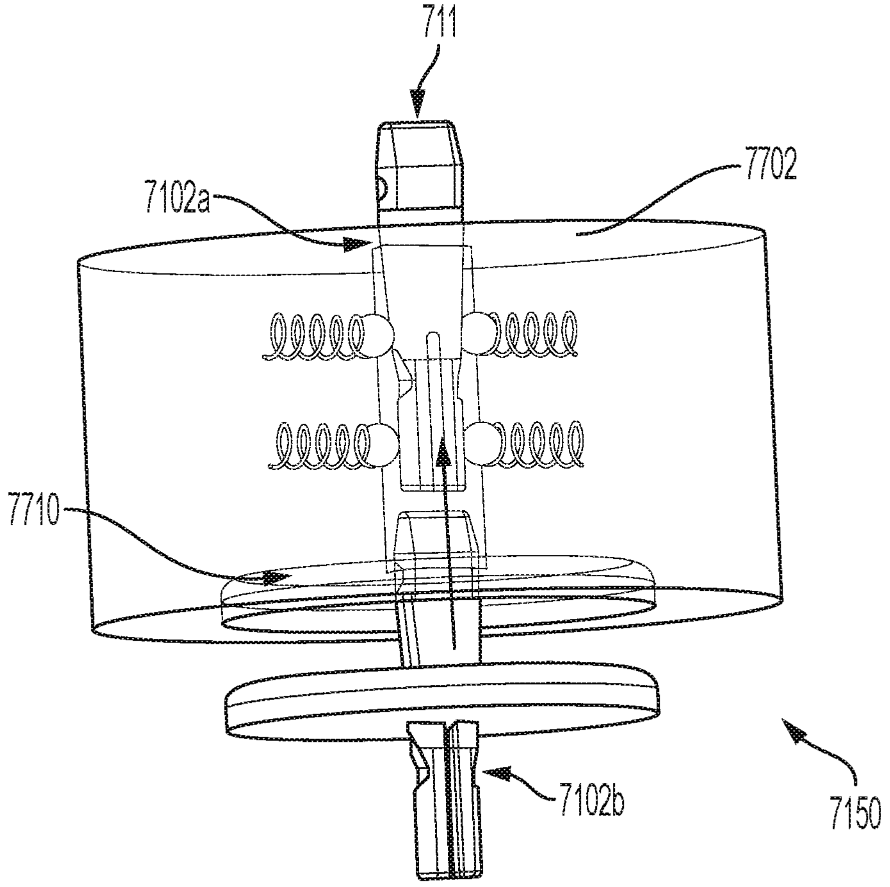
FIG. 16I is a cross-sectional view depicting an example embodiment of a sharpless applicator illustrated in FIG. 16A.

In addition, as seen in FIG. 16I, according to some embodiments, sharpless applicator assembly 7150 can include a container 711 either coupled with or inside applicator 7150. According to some embodiments, container 711 can be configured to collect used guides. In some embodiments where sharpless applicator assembly 7150 is reusable, the user may reload a new guide and sensor control device into the distal end of the applicator. By doing this, a force in the proximal direction is exerted on the used guide 7102*a*, causing it to push upwards into the applicator 7150 until it is collected in the container 711. In some embodiments, the container 711 is designed and configured to collect a plurality of used guides. Alternatively, the used guide 7102*a* may be ejected from an aperture at the proximal surface of the applicator 7150 every time a user loads a new guide 7102*b*.

Figures 1, 16J:
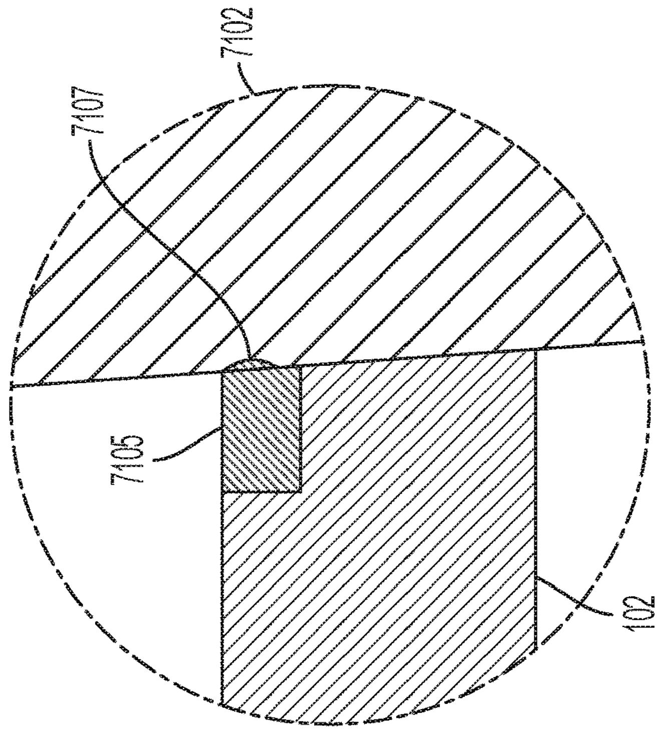
Figure 16J:
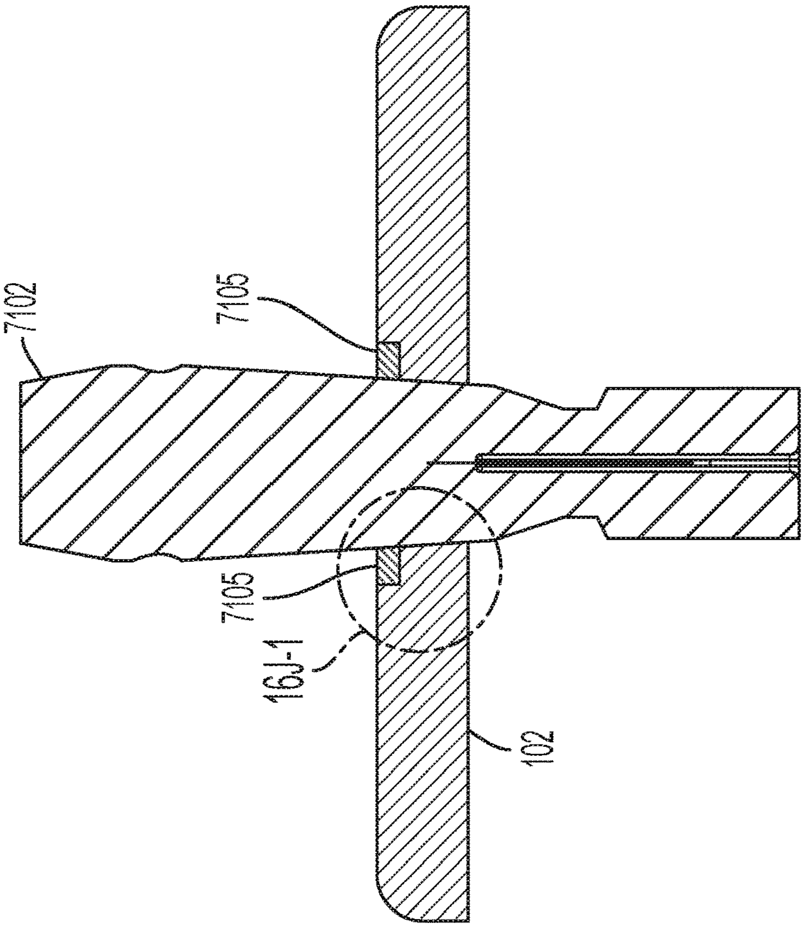

FIG. 16J depicts a guide-sensor control device assembly, which can be configured to be loaded into a reusable sharpless applicator, such as those depicted in FIGS. 16A to 16I. As can be seen in call-out FIG. 16J-1, to prevent contaminants from entering an interior of sensor control device 102, a seal 7105 can be disposed at an interface between guide 7102 and sensor control device 102. According to one aspect of the embodiments, seal 7105 can comprise an overmolded elastomeric material. In some embodiments, seal 7105 can comprise a single annular ring configured to interface with guide 7102. In other embodiments, seal 7105 can comprise a plurality of discrete elastomeric components configured to interface a corresponding plurality of locations along guide 7102. According to another aspect of some embodiments, seal 7105 can comprise at least one concave surface 7107 configured to interface with guide 7102. In some embodiments, sensor control device 102 can comprise a housing constructed from a hard plastic material different from the elastomeric material of seal 7105. In other embodiments, housing of sensor control device 102 can be constructed from the same material of seal 7105, such that the housing and seal have a unitary construction. Those of skill in the art will appreciate that guide 7102, or at least some portions thereof, can comprise an elastomeric material or have one or more concave surfaces to provide for a barrier against contaminants entering the interior of sensor control device 102.

Figure 16K:
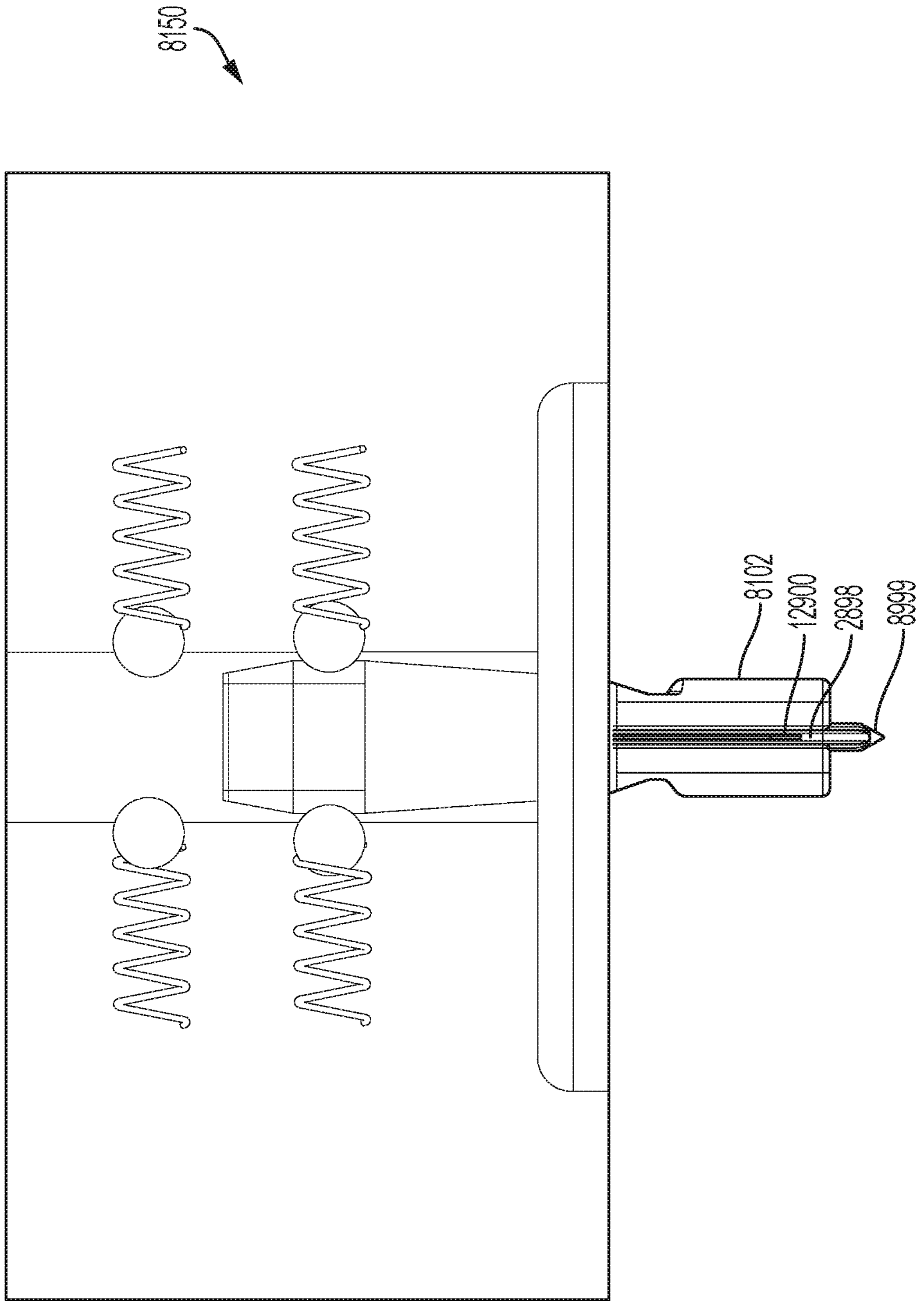
FIG. 16K is a cross-sectional view depicting an example embodiment of a sharpless applicator.

Further, FIG. 16K depicts a sharpless applicator assembly 8150, which is similar to the sharpless applicator assembly 7150 illustrated in FIGS. 16A-16I, except that sharpless applicator assembly 8150 further comprises guide 8102 having a short sharp distal end 8999. Specifically, guide 8102 comprises sharp distal end 8999 with sufficient sharpness to initiate skin penetration and facilitate insertion of the sensor 12900 to its fully-inserted stage or desired insertion depth. In some embodiments, a first end of sensor support channel 2898 extends into and terminates at the sharp distal end 8999 of guide 8102.

Figures 1, 2, 17A:
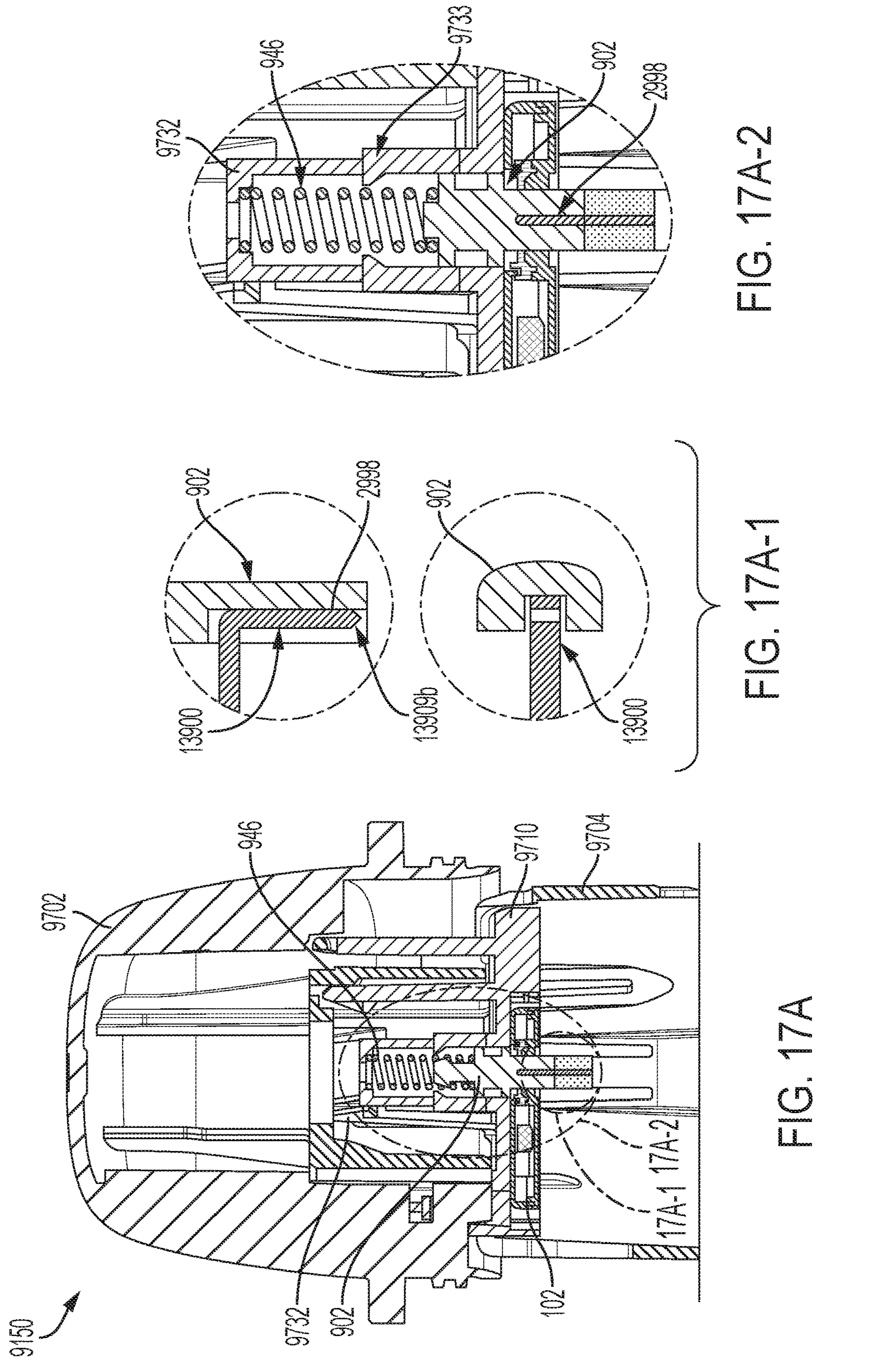
FIG. 17A-17A-2 are cross-sectional and callout views of an example embodiment of a sharpless applicator, in accordance with one embodiment of the disclosed subject matter.

Another example embodiment of a sharpless applicator 9150 is illustrated in cross-section in FIG. 17A. Referring to FIG. 17A, various components of sharpless applicator 9150 will now be described. In particular, FIG. 17A depicts a cross-sectional view of a sharpless applicator 9150 in an initial state, shown along with two call-out views (FIG. 17A-1 and FIG. 17A-2), wherein sharpless applicator 9150 can comprise the following components: housing 9702, sheath 9704, guide 902, retraction spring 946, and device carrier 9710. FIG. 17A also depicts sensor control device 102 and sensor 13900 disposed entirely within sharpless applicator 9150. Those of skill in the art will understand that sharpless applicator 9150 can include any of the embodiments of housings, sheaths, device carriers, and/or analyte sensors described herein, or in other publications which have been incorporated by reference.

FIG. 17A illustrates sharpless applicator 9150 in an initial state, prior to insertion, in which housing 9702 is in a proximal position with respect to sheath 9704. According to an aspect of the embodiments, sheath 9704 is slidably coupled with and partially positioned within housing 9702. Although sheath 9704 and housing 9702 are shown in FIG. 17A as having a generally cylindrical geometry, those of skill in the art will appreciate that other geometries can be utilized. According to another aspect of the embodiments, as best seen in call-out FIG. 17A-2, spring 946 can comprise a distal end of the spring 946 in contact with a proximal end of guide 902, and a proximal end of spring 946 in contact with a spring retention element 9732. In some embodiments, spring retention element 9732 can be a proximally extending arm that protrudes from device carrier 9710, as described in further detail below. In other embodiments (not shown), spring retention element 9732 can comprise a feature of sheath 9704.

Referring still to FIG. 17A, according to an aspect of some embodiments, in the initial configuration, the retraction spring 946 may be in a semi-compressed state, i.e., not fully compressed, nor fully expanded, and pre-loaded against the guide 902 while housing 9702 is disposed proximally from sheath 9704. In other embodiments, retraction spring 946 may be fully compressed.

According to another aspect of some embodiments, sheath 9704 generally encloses or defines a cavity within which guide 902 and device carrier 9710 are moveable from a proximal position entirely within the applicator to a distal position. In many of the embodiments, device carrier 9710 is configured to releasably retain a sensor control device 102 having a distal surface for placement on the skin of the subject. In some embodiments, a guide locating ring (not shown) which receives one end of the guide 902 can be provided. Furthermore, in some embodiments, device carrier 9710 can comprise a proximally-extending latch 9733 (seen in call-out FIG. 17A-2) configured to retain guide 902 in a retracted position after insertion is complete. At least a portion of guide 902 extends through and is engaged with device carrier 9710 and sensor control device 102, and movable therein during insertion (e.g., before retraction is completed). As described above, in some embodiments, device carrier 9710 can also include one or more deflectable arms 9732 for retaining the retraction spring 946 in a compressed or partially compressed state. In some embodiments, the one or more deflectable arms 9732 may also engage with an exterior surface or wall of guide 902. The one or more movable arms 9732 may be maintained in engagement with the guide 9732 when the device carrier 9710 is in the proximal position.

According to another aspect of the embodiments, guide 902 can have a hollow and/or substantially cylindrical shape, and can include a sensor support channel or slot 2998, at least a portion of which is located in a distal portion of guide 902. In some embodiments, sensor support channel or slot 2998 can include a distal end that does not extend beyond the distal portion of guide 902. The proximal portion of guide 902 can be hollow and include a conical or partially conical surface.

According to another aspect of some embodiments, analyte sensor 13900 is at least partially disposed within sensor support channel or slot 2998 and, as best seen in call-out FIG. 17A-1, supported by one or more supporting walls of guide 902. The sensor tail of the analyte sensor 13900 may be disposed in the sensor support channel 2998. Analyte sensor 13900 can comprises a tip portion 13909*b* with sufficient sharpness so as to initiate and complete insertion without the need for a separate sharp. In some embodiments, sensor 13900 comprises a sensor tail 13909*b* having a bottom end with a V-shaped tip portion. Additionally, analyte sensor 13900 further comprises sufficient free length so as to provide the necessary sensor stiffness to facilitate effective insertion into the subject's skin. Stiffness of the sensor is determined by free length of the sensor. For example, an analyte sensor with a shorter free length will be stiffer. Analyte sensor 13900 can include components similar to those of the embodiment described with respect to FIG. 14C.

Figure 17B:
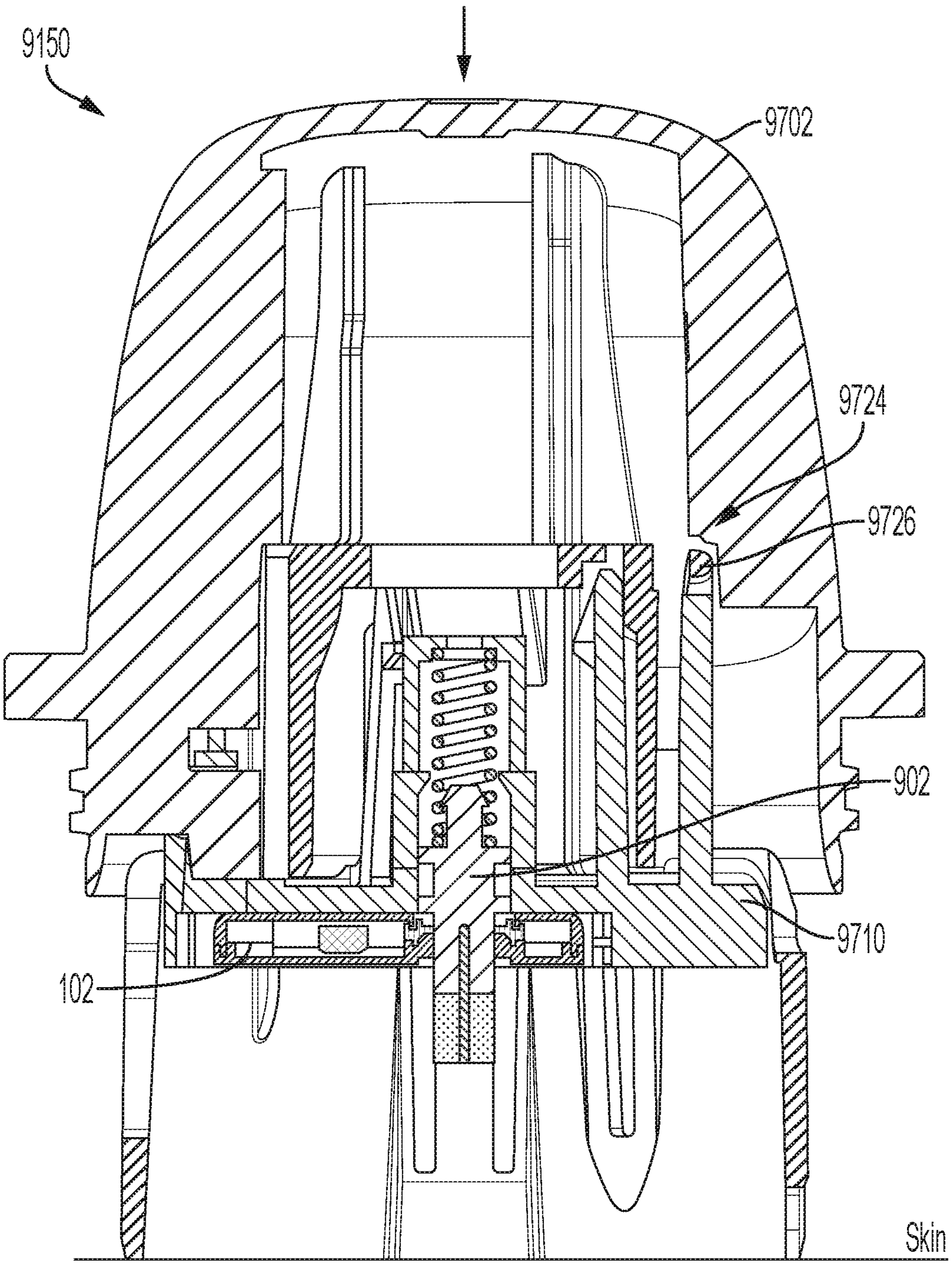
FIGS. 17B to 17D are cross-sectional views of the sharpless applicator depicted in FIG. 17A during various stages of operation.

FIG. 17B illustrates applicator 9150 in cross-section as a user applies a force in a distal direction to housing 9702 (as indicated by the downward arrow). In some embodiments, a predetermined minimum force must be used so that attachment snap 9726 advances past detent 9724. After detent 9724 has been overcome, e.g., snap 9726 is radially displaced, and further depression of housing 9702 with respect to sheath 9704 further causes guide 902, device carrier 9710, and sensor control device 102 to continue to advance from a proximal position towards a distal position towards the skin. In this stage, the distal end of the guide 902 is protruding further distally than the distal surface of sensor control device 102.

Figure 17C:
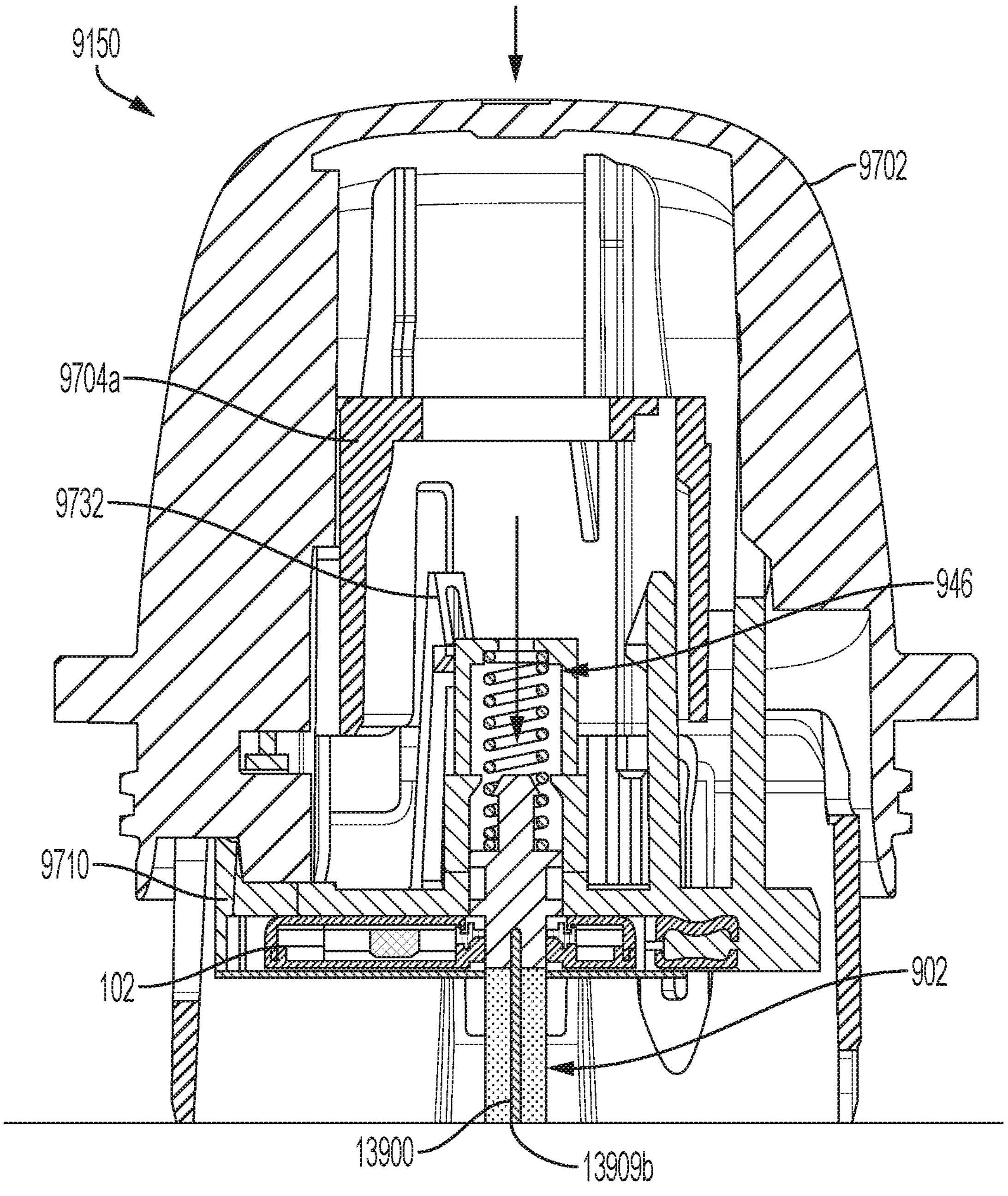

Referring next to FIG. 17C, applicator 9150 is depicted as the distal portion of guide 902 and sensor 13900 make contact with the subject's skin surface. Subsequently, the sensor's sharpened tip portion 13909*b* pierces the skin, while sensor 13900 is supported by guide 902, and inserts a sensor insertion portion of sensor 13900 into the subject's skin, S. In some embodiments, during this phase, the interior surface of proximal portion 9704*a* of the sheath 9704 remains engaged with the carrier arms 9732 to prevent radial displacement of the arms 9732, and thus maintains retraction spring 946 in a compressed or partially compressed state.

Figure 17D:
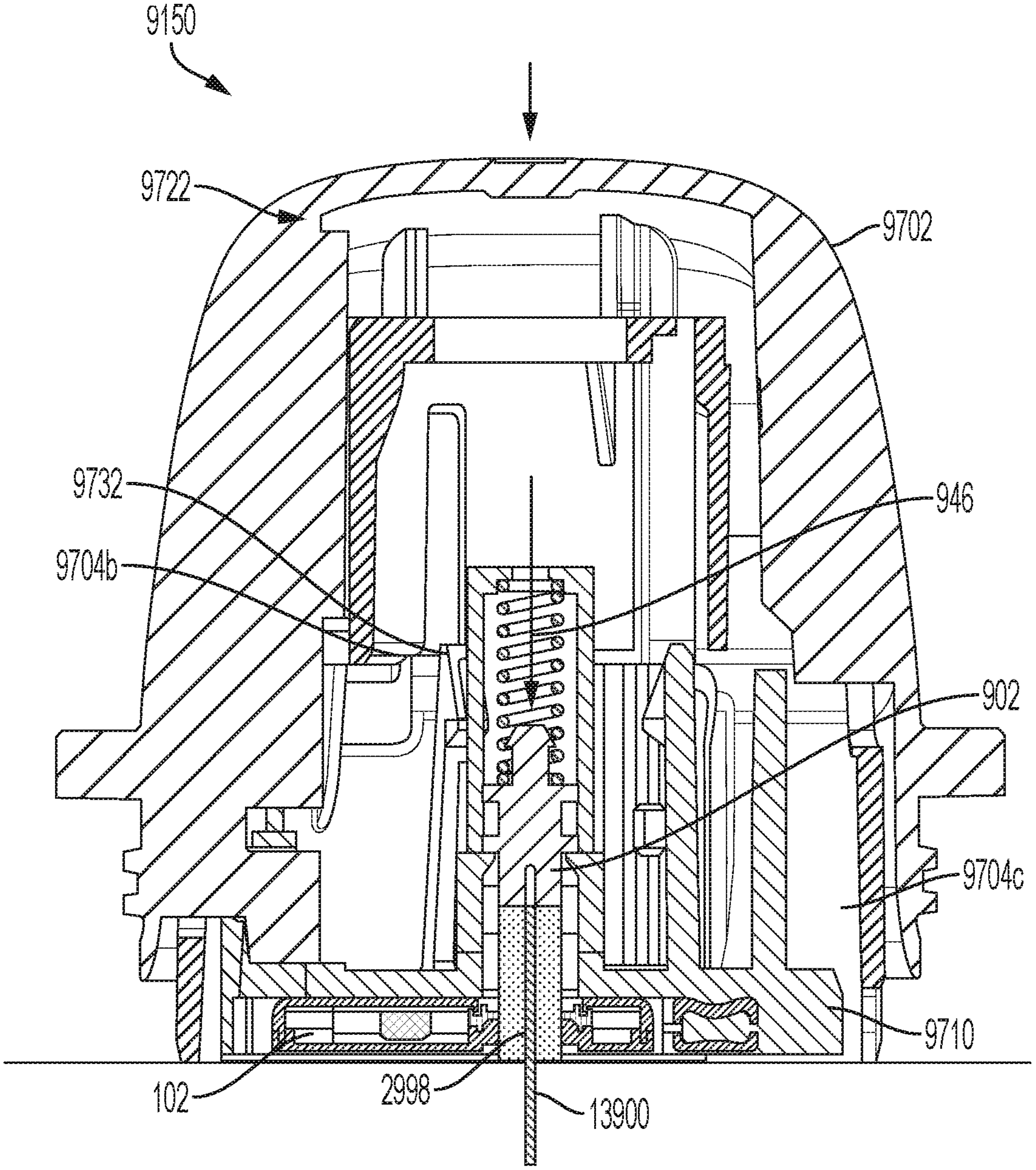

Referring next to FIG. 17D, applicator 9150 is depicted as sensor 13900 reaches its insertion depth, and device carrier 9710 and sensor control device 102 have reached the distal position. In some embodiments, sensor control device 102 includes an adhesive pad that engages the skin surface of the subject at this stage.

According to another aspect of the embodiments, spring retention element 9732 causes retraction spring 946 to expand and retract guide 902 to its retracted position. In some embodiments, for example, spring 946 is a passive element that, during retraction, expands and can return guide 902 to its initial position, or alternatively, be captured by a latch 9733 (FIG. 17A) at some point in between which would allow the guide 902 to be at a different position than its initial position. According to many of the embodiments, sensor 13900 is maintained in its inserted position and sensor control device 102 is left attached to the skin.

Referring still to FIG. 17D, in some embodiments, retraction can be activated when carrier arms 9732 are advanced distally beyond shelf 9704*b* of sheath and clear a support wall. This allows carrier arms 9732 to deflect radially outwardly into the larger diameter distal portion 9704*c* of the sheath 9704. When carrier arms 9732 deflect outwardly, shoulder portions of carrier arms 9732 are no longer in an interference relationship with the guide 902, which can be retracted in a proximal direction to its retracted position within applicator 9150. According to another aspect of some embodiments, the retraction step can also be aided by the counterforce created by the skin (and skin deformation), as described earlier with respect to FIG. 16A to 16J.

According to another aspect of some embodiments, housing 9702 is maintained in the distal position by a lock-out feature. In some embodiments, for example, a sheath snap of the sheath 9704 can move up to lock over feature 9722 of the housing 9702. Now the housing 9702 and the sheath 9704 can no longer slidably move with respect to each other, and provides an indication to a user that the inserter has been used.

With respect to retraction spring 946, it should be noted that although compression springs are shown in FIGS. 17A-17D, those of skill in the art will appreciate that other types of springs can be utilized in any of the embodiments described herein, including but not limited to torsion springs, disc springs, leaf springs and others. Furthermore, those of skill in the art will understand that insertion efficiency of the applicator embodiments described herein can be changed by changing insertion speed, sensor length, material or shape, and guide reaction force and fit with sensor during insertion. Additionally, insertion efficiency may be changed by pre-penetrating the skin, as well. Similarly, those of skill in the art will understand that insertion and retraction speeds of the applicator embodiments described herein can be changed by changing the stiffness or length of the retraction spring, and the insertion force and travel length of the sensor.

In some embodiments, the applicator may be a powered applicator and comprise an insertion spring to drive the sensor (and other elements) into the skin of the subject. In the powered applicator embodiment, the insertion spring can be compressed and pre-loaded before it is fired.

Figure 18A:
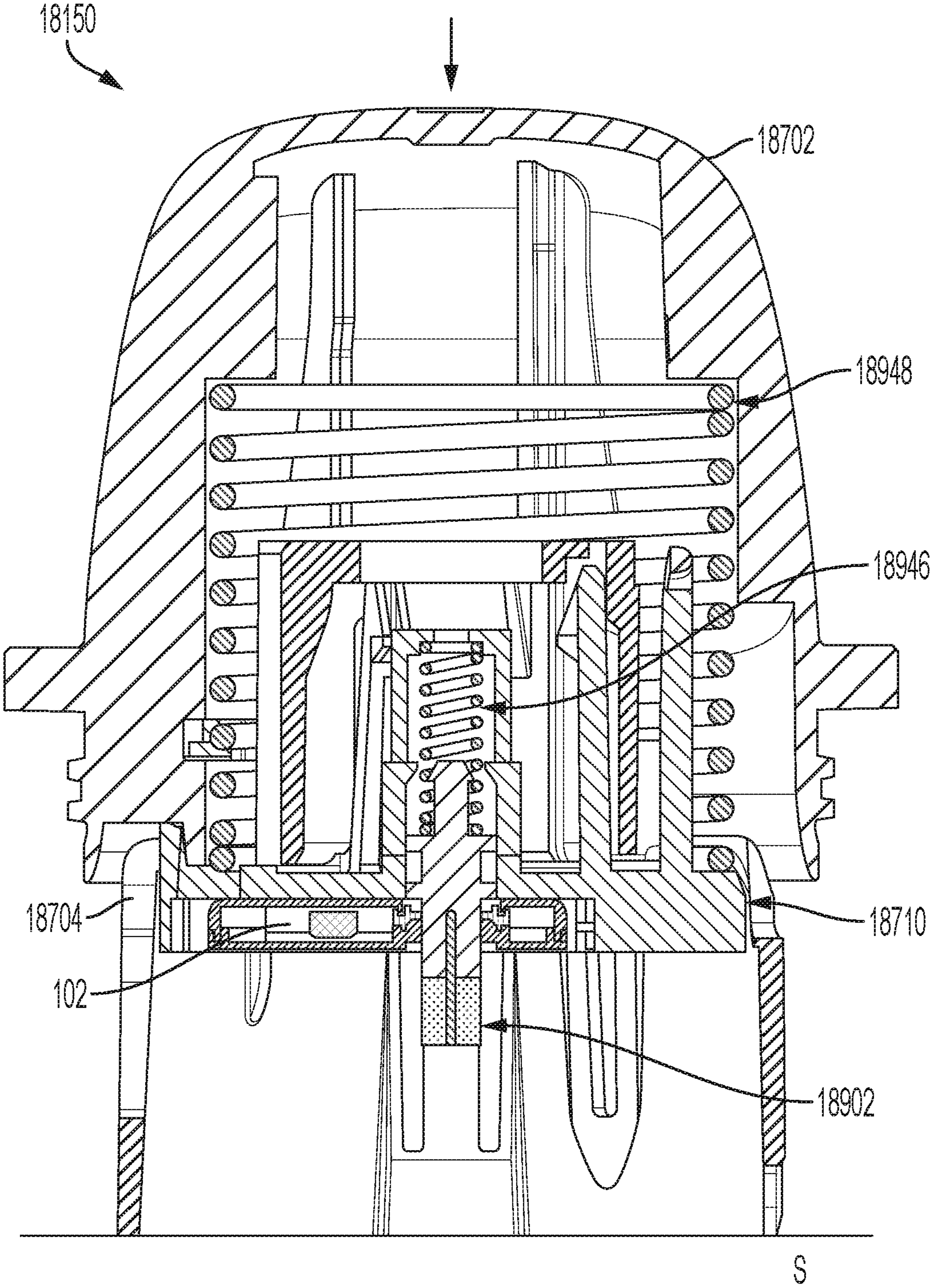
FIGS. 18A to 18C are cross-sectional views of a powered sharpless applicator during various stages of operation.
Figure 18B:
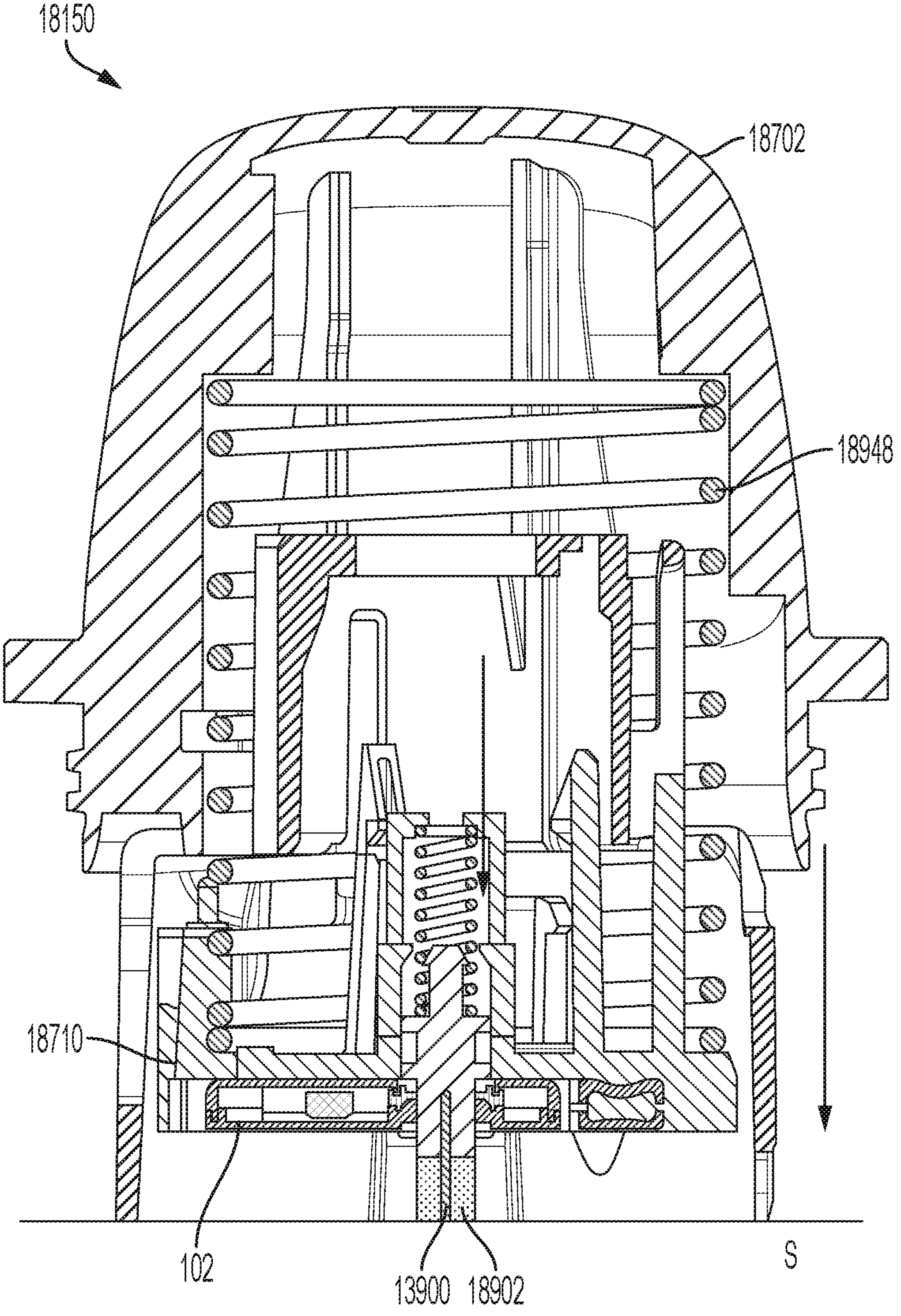
Figure 18C:
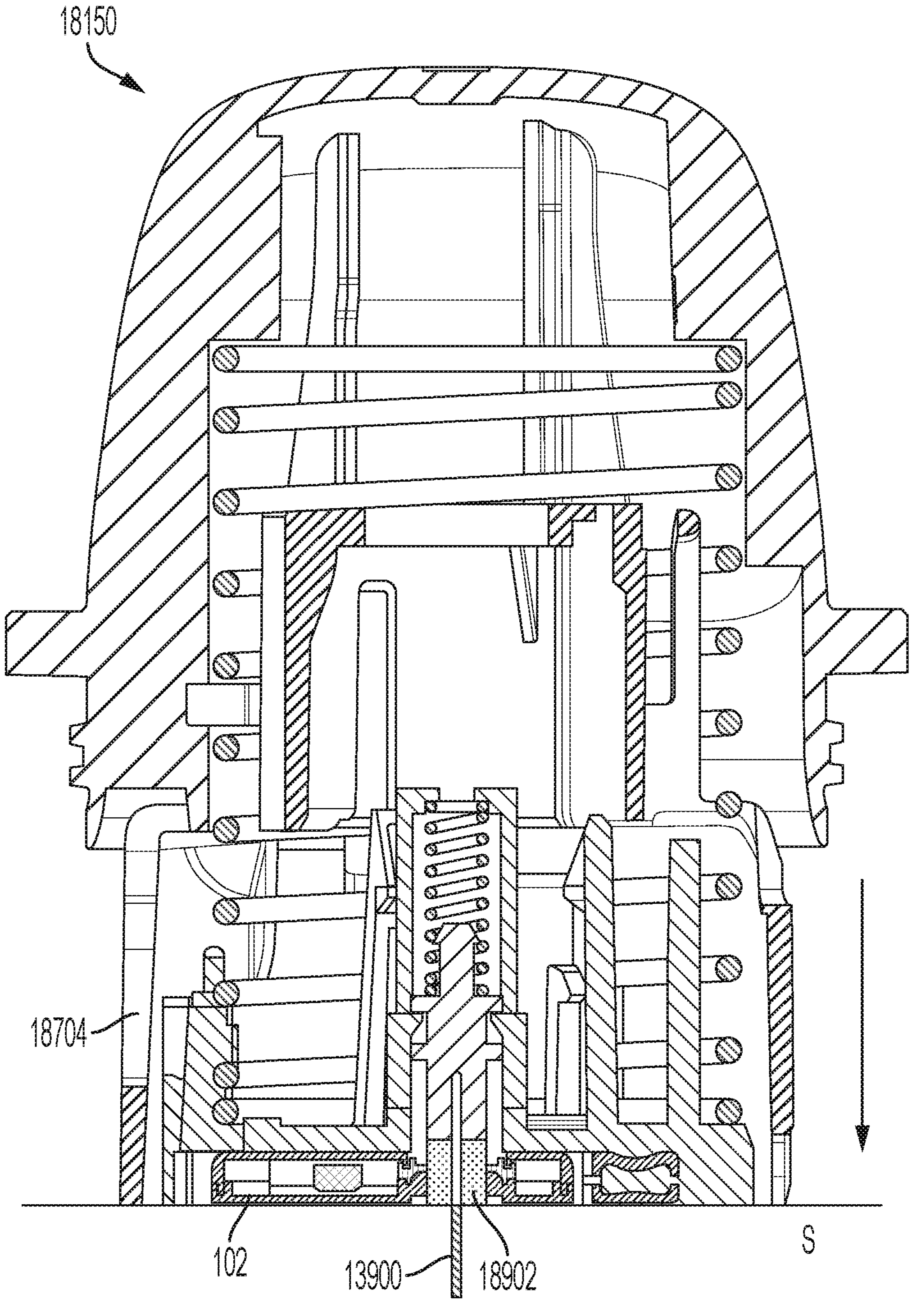

FIGS. 18A to 18C depict cross-sectional views of a powered and sharpless applicator 18150 in various stages of operation. In many respects, applicator 18150 operates in a similar manner to applicator 9150, as described with respect to FIGS. 17A to 17D. For example, applicator 18150 can include many of the same components to applicator 9150, including a housing 18702, sheath 18704, retraction spring 18946, device carrier 18710, and guide 18902, each of which operates in a substantially similar manner to its corresponding component in applicator 9150 (FIGS. 17A to 17D). According to one aspect of the embodiments, however, applicator 18150 further comprises an insertion spring 18948 configured to facilitate a powered (or partially powered) insertion of the sensor.

Referring first to FIG. 18A, applicator 18150 is depicted in an initial stage, where user begins to apply a force upon housing 18702 in a distal direction (as indicated by the downward arrow above applicator 18150). According to one aspect of the embodiments, before the force is applied, carrier 18710, guide 18902, and sensor control device 102 are in a proximal position entirely within applicator 18150. According to another aspect of the embodiments, both insertion spring 18948 and retraction spring 18946 are in a compressed or partially compressed state.

Referring next to FIG. 18B, insertion spring 18948 is shown in an activated state, which causes device carrier 18710, sensor control device 102, and guide 18902 to advance from the proximal position to a distal position (as indicated by the downward arrow to the right of applicator 18150). At this stage, guide 18902 is in contact with the subject's skin, S, and configured to support sensor 13900 during insertion. In some embodiments, insertion spring 18948 is triggered when housing 18702 is advanced a predetermined distance in the distal direction in response to the application of force in the distal direction. For example, housing 18702 can be configured to cause a retention element (not shown) to disengage from insertion spring 18948, causing insertion spring 18948 to expand. In some embodiments, insertion spring 18948 can be activated by a separate button, for example, that can only be depressed if the housing is advanced a predetermined distance in the distal direction. Those of skill in the art will appreciate that other mechanisms for activating insertion spring 18948 can be utilized and are within the scope of the present disclosure.

Referring next to FIG. 18C, sensor 13900 is depicted after it reached the insertion depth (FIG. 18C depicts sensor insertion portion of sensor 13900). At this stage, sensor control device 102 has also reached the distal position. In some embodiments, sensor control device 102 can include an adhesive patch or an adhesive distal-facing surface that is configured to adhere the sensor control device 102 to the subject's skin, S. According to another aspect of the embodiments, retraction spring 18946 has been activated and retracts guide 18902 in the proximal direction to a retracted position. In some embodiments, retracted position of guide 18902 is the same as the initial proximal position of guide 18902, as shown in FIG. 18A. In other embodiments, the retracted position of guide 18902 can be different from the initial proximal position of guide 18902, as shown in FIG. 18A. Subsequently, the applicator 18150 can be removed from the user's skin, S, leaving behind the sensor control device 102 and sensor 13900.

In some embodiments, either or both of sheath 18704 and/or guide 18902 can be locked into the retracted position. As described with respect to FIGS. 17A to 17D, applicator 18150 can include lock-out mechanisms to provide an indication to the user that the applicator has been used.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Thus, the foregoing description of specific embodiments of the disclosed subject matter has been presented for purposes of illustration and description. It is explicitly acknowledged that express recitation of every possible combination and substitution is overly burdensome, especially given that the permissibility of each and every such combination and substitution will be readily recognized by those of ordinary skill in the art.

While the embodiments are susceptible to various modifications and alternative forms, specific examples thereof have been shown in the drawings and are herein described in detail. It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents. Furthermore, any features, functions, steps, or elements of the embodiments may be recited in or added to the claims, as well as negative limitations that define the inventive scope of the claims by features, functions, steps, or elements that are not within that scope.

What is claimed is:

1. An insertion apparatus comprising:

a housing;

a sheath comprising a distal end configured to be placed on a subject's skin;

a device carrier configured to releasably retain a sensor control device;

the sensor control device comprising a sensor;

a guide configured to support at least a portion of the sensor; and a spring configured to retract the guide;

wherein the housing is configured to move between a proximal position and a distal position relative to the sheath, and to advance the device carrier, the sensor control device, and the guide in a distal direction towards the subject's skin, wherein the sensor comprises a sharp tip portion configured to pierce the subject's skin without the use of a sharp or a needle, and wherein the guide is configured to retract towards a retracted position.

2. The apparatus of claim 1, wherein at least a portion of the guide extends through a portion of the device carrier.

3. The apparatus of claim 1, wherein the device carrier comprises a guide locating ring, and wherein one end of the guide is received by the guide locating ring.

4. The apparatus of claim 1, wherein the guide further comprises a plurality of supporting walls, and wherein the plurality of supporting walls support the at least a portion of the sensor.

5. The apparatus of claim 4, wherein the plurality of supporting walls comprises three supporting walls.

6. The apparatus of claim 1, wherein the guide further comprises a sensor support channel disposed in a distal portion of the guide, wherein the sensor channel comprises a distal end that does not extend beyond the distal portion of the guide.

7. The apparatus of claim 6, wherein advancement of the device carrier, the sensor control device, and the guide in the distal direction causes a distal portion of the guide to contact the subject's skin.

8. The apparatus of claim 7, wherein advancement of the device carrier, the sensor control device, and the guide in the distal direction further causes the sensor control device to contact the subject's skin.

9. The apparatus of claim 7, wherein the contact between the guide and the subject's skin causes a skin deformation and creates a counterforce against the guide in a proximal direction.

10. The apparatus of claim 1, wherein the spring is a retraction spring, and wherein the retraction spring is in a semi-compressed state when the housing is in the proximal position.

11. The apparatus of claim 10, wherein the retraction spring is advanced in the distal direction when the housing is moved from the proximal position to the distal position.

12. The apparatus of claim 1, wherein the spring is a retraction spring, wherein the retraction spring is configured to expand in response to a deflection of a spring retention element.

13. The apparatus of claim 1, wherein the guide further comprises a proximal portion having a conical surface, and wherein at least one end of the spring is received by the proximal portion of the guide.

14. The apparatus of claim 1, wherein the spring is a retraction spring, and wherein the apparatus further comprises an insertion spring.

15. The apparatus of claim 14, wherein the insertion spring is in a compressed state when the housing is in the proximal position.

16. The apparatus of claim 1, wherein the device carrier comprises one or more deflectable arms.

17. The apparatus of claim 16, wherein the one or more deflectable arms are configured to retain the spring in a compressed or partially compressed state.

18. The apparatus of claim 1, wherein the sensor is an in vivo analyte sensor configured to measure an analyte level in a bodily fluid of the subject, and wherein the analyte sensor comprises a sensor tail having a V-shaped tip portion.

* * * * *